(12) United States Patent
Ricciardi et al.

(10) Patent No.: US 8,196,604 B1
(45) Date of Patent: Jun. 12, 2012

(54) DEPLOYABLE AUTOMATED VENT COVER DEVICE

(76) Inventors: Jonathan J. Ricciardi, Kennewick, WA (US); Carl L. Ricciardi, Tomahawk, WI (US); John D. Wolf, II, Edwardsburg, MI (US)

( * ) Notice: Subject to any disclaimer, the term of this patent is extended or adjusted under 35 U.S.C. 154(b) by 0 days.

(21) Appl. No.: 12/979,460

(22) Filed: Dec. 28, 2010

Related U.S. Application Data

(60) Provisional application No. 61/295,869, filed on Jan. 18, 2010.

(51) Int. Cl.
F16K 31/56 (2006.01)
F16K 35/14 (2006.01)
F16K 31/46 (2006.01)
F24F 13/15 (2006.01)

(52) U.S. Cl. ......... 137/601.11; 251/68; 251/74; 251/90; 251/116

(58) Field of Classification Search .......... 251/114, 251/116, 89, 90, 66, 68, 74, 144; 137/601.08, 137/601.11
See application file for complete search history.

(56) References Cited

U.S. PATENT DOCUMENTS

| | | | | |
|---|---|---|---|---|
| 1,241,209 A * | 9/1917 | Grinnell | | 169/20 |
| 2,342,589 A * | 2/1944 | Lewis | | 169/19 |
| 2,389,817 A * | 11/1945 | Rider | | 169/19 |
| 3,307,633 A * | 3/1967 | Newall | | 169/22 |
| 3,433,461 A | 3/1969 | Scarpa | | |
| 3,729,138 A | 4/1973 | Tysk | | |
| 4,109,863 A | 8/1978 | Olson et al. | | |
| 4,366,125 A | 12/1982 | Kodera et al. | | |
| 4,512,951 A | 4/1985 | Koubek | | |
| 4,952,370 A | 8/1990 | Cummings et al. | | |
| 4,976,259 A | 12/1990 | Higson et al. | | |
| 5,300,260 A | 4/1994 | Kehset et al. | | |
| 5,878,355 A | 3/1999 | Berg et al. | | |
| 5,925,966 A | 7/1999 | Riftin et al. | | |
| 6,102,992 A | 8/2000 | Berg et al. | | |
| 6,708,771 B2 * | 3/2004 | Reilly | | 169/16 |
| 2005/0042130 A1 | 2/2005 | Lin et al. | | |
| 2007/0053789 A1 | 3/2007 | Ricciardi et al. | | |

FOREIGN PATENT DOCUMENTS

FR  2860721  4/2005
GB  1128245  9/1968

OTHER PUBLICATIONS

William C. Hinds, Aerosol Technology, 1999 by John Wiley & Sons, Inc.

* cited by examiner

*Primary Examiner* — John Rivell
*Assistant Examiner* — Atif Chaudry
(74) *Attorney, Agent, or Firm* — Donald J. Ersler

(57) ABSTRACT

A deployable automated vent cover device includes a vent cover and a telescopic pole. The vent cover includes a vent base, a first vent door, a second vent door and a release mechanism. The release mechanism includes a solenoid, a pivot release, a first latch device and a second latch device. The vent base preferably includes a base plate with two openings, and a vent seal. The first and second vent doors are pivotal attached to the base plate. The first latch device is retained on the base plate and the second latch device is retained on the base plate. The first and second latch devices retain the first and second vent doors in a closed orientation. The pivot release is pivotally connected to the solenoid and to the first and second latch devices. The solenoid is actuated to open the first and second vent doors through the pivot release.

18 Claims, 68 Drawing Sheets

DEPLOYABLE AUTOMATED VENT COVER DEVICE

CROSS-REFERENCES TO RELATED APPLICATIONS

This is a non-provisional patent application, which takes priority from provisional patent application No. 61/295,869, filed on Jan. 18, 2010.

TECHNICAL FIELD OF THE INVENTION

The present invention relates to improved apparatuses and methods for the generation and application of an ultrasonically generated aerosol for uses including but not limited to the sanitization, detoxification, disinfection, high-level disinfection, or sterilization of one or more areas and the surfaces in those areas, as well as the delivery of other types of liquid agents, for various

BACKGROUND OF THE INVENTION

The apparatus described in U.S. Pat. No. 4,366,125, which is incorporated herein by reference in its entirety, including any references cited therein, generates a hydrogen peroxide mist by an ultrasonic wave vibrator. The mist adheres to the surface of materials being sterilized and is then irradiated with ultraviolet-ray lamps. U.S. Pat. Nos. 5,878,355 and 6,102,992, each of which is incorporated herein by reference in its entirety, including any references cited therein, disclose a method and device for decontamination of a contaminated process area whereby a fine aerosol of an encapsulant is generated to encapsulate contaminants within a contaminated environment. The aerosol is generated by one or more ultrasonic transducers located below the surface of a reservoir containing a liquid. The output of the transducers is focused to either a point and/or directed toward an area near the surface of the liquid to cause a surface disturbance, which results in the formation of an aerosol from the liquid. The transducers used in these apparatuses are made from lead-zirconate-titanate-four (PZT-4) or other piezoelectric materials. This material is coated with a conductive coating (electrode material) that enables an electrical signal to energize the transducer and causes it to emit high frequency pressure (energy).

While operating these prior art apparatuses and similar apparatuses, it has been found that certain liquids, especially acidic solutions, chemically react with the electrode materials of the transducers that generate the aerosol. The result is a noticeable deterioration of both the transducers and their performance. For example, acidic solutions of hydrogen peroxide and peroxyacetic acid have caused noticeable deterioration of the transducers within minutes of operation.

An attempt was made to prevent transducer degradation by coating the face of the transducers with a thin coating of different materials. None of these efforts have been successful. For example, U.S. Pat. No. 4,109,863, which is incorporated herein by reference in its entirety, including any references cited therein, discloses similar findings. The protective coating on the transducer deteriorated to a point where the transducer failed to be energized. It was initially believed that this deterioration was caused by transducer induced cavitation within the tank; however, the aforementioned coatings were also shown to fail in simple immersion tests, conducted over time in an acidic solution, with unpowered transducers. For example, laboratory work indicated that PZT material coated with an electroless nickel plating, or a glaze, were both found to be incompatible with a 4% solution of hydrogen peroxide and peroxyacetic acid, after being exposed to the solution for two weeks at 160° F.

In addition, it was found that various materials used to construct the transducer housing and assembly experienced deterioration after being subjected to a simulated long-term exposure to an acid solution of hydrogen peroxide and peroxyacetic acid. This was observed with an accelerated aging test. This test consisted of placing components constructed of various material types in vessels containing the hydrogen peroxide and peroxyacetic acid solution and subjecting them to increased temperature over a course of time. Without being limited to the theory, this test is based on the theory recognized in the art that at higher temperatures chemical or physical reactions will proceed faster due to the increased probability that two molecules will collide and chemically react.

Without being limited to a particular mechanism, method, or chemical, it is believed that chemically reactive liquids are necessary in sterilization processes to contact contaminants including but not limited to toxins, bacteria, virus, fungus, and spores (both fungal and bacterial), prions or protein structures, within a target area(s) either killing the bacteria, fungus, or spores, neutralizing or destroying toxins, or rendering a protein structure incapable of replication or otherwise interfering with the target's cellular physiology. These chemically reactive liquids may be provided as an aerosol. For example, U.S. Pat. No. 4,512,951, which is incorporated herein by reference in its entirety, including any references cited therein, teaches using hydrogen peroxide to sterilize medical devices by condensing hydrogen peroxide-water vapors to deposit a film of liquid on the devices. The liquid film is then evaporated.

While the prior art attempted to coat the transducer with a protective substance, there were problems with these coatings. U.S. Pat. Nos. 3,729,138; 4,109,863; and 4,976,259, each of which is incorporated herein by reference in its entirety, including any references cited therein, teach that the optimum thickness of a glass barrier, which may be used as a protective plate and/or cover, on a transducer should be any multiple of one-half (½) the wavelength of the transmitted pressure (energy). The thicknesses of protective barriers have been calculated using wave transmission theories and their respective mathematical formulas known to those skilled in the art. It is estimated that twenty percent (20%) of the energy emitted from the transducers is being transmitted into the liquid beyond the protective barrier. The prior art does not include techniques for further increasing the energy emitted from the transducer with a protective plate and/or cover.

U.S. Pat. Nos. 3,433,461; 3,729,138; 4,109,863; and 4,976,259, each of which is incorporated herein by reference in its entirety, including any references cited therein, teach that an effective thickness of a protective barrier material "interfaced with" a transducer can be approximately any multiple of one-half (½) the wavelength of the transmitted pressure (energy) from the transducer. Prior art has taught that barriers having a thickness equal to or about one-half (½) wavelength constructed from non-conductive and/or insulating type materials like glass, could be effectively coupled with an ultrasonic transducer for generating aerosol, as long as they included a special design consideration for cooling the transducer, or the transducer was separated from the glass barrier with a layer of liquid. U.S. Pat. No. 3,433,461 teaches utilizing a 1.5 inch diameter transducer bonded to a metal barrier that is a one-half wavelength thick. A problem associated with using metal barriers is corrosion, which was acknowledged in U.S. Pat. No. 3,729,138. In addition, U.S. Pat. No. 3,433,461 discloses that heat has a detrimental effect associated with the operation of a transducer and that a metal barrier interfaced with a transducer permitted the use of much higher driving powers than in prior art devices, since it provided more heat dissipation. Further, the driving power supplied to the transducers is limited by the heat dissipation in the device, which is a function, in each case, of the total area of the generator.

According to U.S. Pat. No. 4,976,259, an attempt was made to bond a glass barrier to a piezoelectric crystal with an adhesive, but such an attempt did not improve on the prior art and resulted in a major loss of acoustic coupling of the ultrasonic energy into the glass cover as the adhesive bond deteriorated. The deterioration was due to high localized temperatures caused by reflected energy resulting from mismatched acoustical impedances.

The prior art does not currently include commercially effective techniques for constructing and operating a high frequency and high power aerosol producing transducer assembly consisting of one or more transducers bonded or adhered to a protective barrier constructed from non-metallic and/or insulative type materials, such as glass, with a thickness that is not one-half (½) of a wavelength. Furthermore, the prior art does not currently include high frequency and high power aerosol producing glass barrier and transducer assemblies that are capable of operating without additional liquid layers or liquid cooling means incorporated into the transducer assembly design.

Therefore, the need for a protective barrier for the aerosol producing transducer that is highly resistant to degradation caused by chemically reactive solutions exists. The protective barrier should withstand the heat generated by a transducer and should function effectively with the transducer to produce a fine aerosol at high output levels (which requires high energy emitted by the transducer). This heat is due to the high frequency and energy that is needed to achieve a high output of aerosolized liquid per hour with the aerosol droplets being less than about 10 microns in size. In general, within the effective frequency band, the higher the power at the effective aerosol producing frequencies, the larger the quantity of aerosol produced; and the higher the effective frequency the smaller the droplet size in the aerosol.

The complete and assured sanitization, disinfection, high-level disinfection, or sterilization of devices, tools, machinery, or other objects or surfaces, within enclosed or unenclosed targeted areas or surfaces, related to industries including, but not limited to, health care, food production, medical device or products, clean rooms, and pharmaceutical, has always been a challenge in terms of overall effectiveness, processing time, cost, and engineering tradeoffs. In addition, the applied agents must have limited toxicity, be reasonably safe, as well as non-harmful to the materials or substances to which they are applied.

The prior art has extensively taught that relatively quick disinfection and sterilization of surfaces can be achieved by exposing them to an aerosol of a disinfectant/sterilizing agent created by ultrasonic nebulization. The apparatus described in U.S. Pat. No. 4,366,125 (Kodera et al., 1980), which is incorporated herein by reference in its entirety, including any references cited therein, generates a hydrogen peroxide mist by an ultrasonic waves vibrator. The aqueous hydrogen peroxide is heated as it travels from a tank into a basin (col. 4, line 6-8) where it is turned into a fog or mist as the surface of the germicidal liquid in the basin is acted upon by ultrasonic waves. The fog or mist will adhere to the surface of materials being sterilized or disinfected. The surface is then irradiated with ultraviolet-ray lamps.

G.B. Patent No. 1,128,245, (Rosdahl et al., 1968) which is incorporated herein by reference in its entirety, including any references cited therein, describes a device for disinfecting apparatuses and instruments, including medical instruments. This apparatus also generates a mist of disinfectant, including hydrogen peroxide, by means of an ultrasonic aerosol generator. According to Rosdahl et al., this patent was "primarily adapted for the disinfection of small medical instruments such as scalpels, tongs, syringes, or the like, positioned on a grid in a container" (pg. 3 col. 23-30). However, another separate intended use for a second described apparatus was to disinfect the interior surfaces of objects such as hollow tubing used for "breathing apparatuses" and "heart lung machines" (pg. 1 line 30-36 and pg 2 line 95-101). Rosdahl et al. also taught the use of the germicidal fogging technology to disinfect rooms, apartments and the like (pg. 2 col. 28-30). The pressurized air in Rosdahl et al. is supplied by way of a fan etc. or carrier gas, (pg. 2 line 48-49) and is used to move the generated aerosol as well as to dry objects placed within the enclosed area of the described apparatus. Rosdahl et al. also incorporated "a heating element in the flow path of the carrier gas, to increase drying efficiency" (pg. 3 line 123-127).

Ultrasonic nebulizers have a unique advantage in that they can create aerosol droplets less than 10 microns in size depending on the power and frequency used in their operation. The small size of the droplets enables them to penetrate small cracks and crevices and to behave like a gas due to Brownian movement and diffusion. In addition, the dense cloud of small droplets is able to form a very thin coating or film over surfaces. The thin coating or film of disinfectant or sterilization agent is able to dry much faster than coatings created by aerosols consisting of larger diameter droplets. It is also theorized that even partial contact of the aerosol droplets with the targeted contaminate(s), can contribute to the overall efficacy of the process. U.S. Pat. No. 4,366,125, (Kodera et al., 1980) taught that heated H2O2 was more efficacious than H2O2 used at room temperature (col. 1, line 19-25). In other words, (Kodera et al., 1980) taught that the efficacious nature of a liquid agent can be increased as it is heated to temperatures higher than ambient temperature. This is desired, without limitation, in the present invention. The text entitled, "Aerosol Technology" by William C. Hinds (1982), which is incorporated herein by reference in its entirety, including any references cited therein, also taught that the size of the aerosol particles produced by ultrasounic means is not only affected by the frequency of the transducer operation, but also by the surface tension and density of the liquid as shown by the following mathematical expression (page 382):

$$CMD=((y)/(pL)(f^2))^{1/3}$$ Equation 1:

where: CMD=particle size produced; y=surface tension; pL=liquid density; and f=frequency It is commonly known that heating a liquid to point less than its boiling point will reduce its surface tension. Therefore, according to Equation 1 above, a direct relationship was established by William C. Hinds (1982) where one skilled in the art can ascertain that the higher the temperature of the liquid, the lower the liquid's surface tension, which will result in smaller sized aerosol particles. This principal is incorporated without limitation, in the present invention. William C. Hinds (1982) also taught in the same text that smaller diameter particles demonstrate characteristics such as but not limited to, a lower settling velocity, a higher diffusion coefficient, and a higher Brownian displacement (movement), which is desired, without limitation, in the present invention. William C. Hinds (1982) further taught that ultrasonic aerosol generating transducers can heat the surrounding liquid (page 382). This is also desired in the present invention.

Despite the plethora of advancements shown in the current art, limitations exist in many areas that reduce the effectiveness or viability of the ultrasonic aerosol generator technology in actual commercial applications. The methods and apparatuses of the present invention address the need for an ultrasonic aerosol generator that is, without limitation: (a) designed so that the apparatus can be quickly and easily set up and operated in a reproducible manner on uneven or angled surfaces(s), (b) designed so that the transducers can quickly heat the liquid and liquid surface above and/or around them, (c) designed to prevent or limit dust and debris contamination inside the pressurized air channels or pipes of the apparatus or in the tank in which one or more transducer(s) are located, (d) designed so that if a valve of a liquid storage, holding tank, or reservoir, breaks the tank(s) or reservoir(s) in which the transducer(s) is located is not flooded, (e) designed so that excess, leaked, or spilled liquid can be transferred to a separate containment tank or basin from sources such as but not limited to the fill pipe(s), blower housing(s), internal catch pan(s), transducer tank(s) or basin(s), (f) designed so that the liquid in the tank in which the transducers are located does not drop below the minimum or exceed the maximum operating temperature for that liquid or particular process, coupled with one or more sensor(s) that can determine when an effective or sufficient amount of aerosol has been applied or administered to the targeted area and/or surfaces, (g) designed so that a partially empty apparatus can be easily and effectively refilled, (h) designed to prevent expired liquid that has been added or is otherwise available to the apparatus from being administered by or deployed from the apparatus, (i) designed so that the stream of aerosol deployed from the apparatus can be simultaneously delivered to one or more separate areas.

It is obvious to those skilled in the art that an apparatus can automatically shut down if an insufficient amount of inventory or product is available with which to complete its defined operational cycle. This activity is also mentioned in French Patent No. FR2860721 (Schwal et al.), which is incorporated herein by reference in its entirety, including any references cited therein. This patent claims the use, by any aerosol generator, of single-use liquid refill/fill cartridges that are associated with specific identifiers, and a reader integrated into the aerosol generator apparatus that can read the said identifiers, all of which is dependently combined with a system of defined steps to establish a set process whereby the apparatus will not generate aerosol if there are any non-conformances related to the entire process, and each cycle of use is terminated with a recording of various information pertaining to the process as a whole. However, according to patent No. FR2860721, the apparatus only notifies the operator if an insufficient liquid quantity is available (pg. 6 line 15-25 and pg. 10 line 10-25) and when it is necessary to replace a filler cartridge (pg. 10 line 15-25). Patent No. FR2860721, does not teach or describe an aerosol generator apparatus that can communicate, by any means, to the apparatus operator the quantity of liquid or at least the exact minimum quantity of liquid, expressed in units of measurement, that is necessary to add or make available to the apparatus so that it may successfully complete its desired or chosen operational time or run cycle. The methods and apparatuses of the present invention address the need to provide this information.

French Patent No. FR2860721 also fails to address the issue of preventing the apparatus from using expired or outdated liquid that is available to the apparatus from, without limitation, one or more tanks or reservoirs inside or attached to the apparatus that have been fed, supplied, or filled by a refill/fill cartridge or other means. This is critical since some liquid agents have a defined period of time of efficacious use once they have undergone, without limitation, dilution from a concentrate or exposure to air. The methods and apparatuses of the present invention address the need to prevent the use or deployment of a liquid agent that is available to the apparatus, but has expired, is unusable, or undesired.

The need for an ultrasonic aerosol generator that can be positioned and operated from within the area in which the aerosol is being dispersed so as to, without limitation, eliminate or reduce the effects of increased air pressure within the targeted area and operate without damage to its internal and external structures and components is also addressed in the present invention and includes, without limitation, methods and apparatuses such as: (a) means for cooling the various motors, electronics, and other components; (b) properly housing various motors, electronics, and other components to prevent their exposure to the environment surrounding the apparatus; (c) the remote control of and remote communication with the apparatus; (d) preventing any parts of the apparatus that are exposed to the aerosol from becoming higher in temperature than the temperature of the atmosphere surrounding the apparatus.

There is also a continued need in the market place to increase efficacy and effectiveness from the aerosol and the process of its administration, as well as a system that offers shortened cycle times. The present invention addresses these issues. One such means in the present invention is the utilization of thermal forces and their resultant effects, by cooling or decreasing the temperature of the objects, the atmosphere in which they reside, or the targeted area for the administration of an aerosol as well any surfaces in that area, before the administration of the aerosol to the targeted area or surfaces. Prior art has taught the step of cooling an enclosed area and its surfaces before the administration of a hydrogen peroxide disinfectant, however the hydrogen peroxide was first vaporized into a gaseous state before its administration, and the cooling step was intended to condense the vaporized hydrogen peroxide gas out of the atmosphere in which it was administered and onto the intended surfaces, as taught in U.S. Pat. No. 4,512,951 (Koubek et al., 1983), which is incorporated herein by reference in its entirety, including any references cited therein. More specifically, Koubek et al., teaches a method of sterilization where a liquid of aqueous hydrogen peroxide is vaporized, and the uniformly vaporized mixed hydrogen peroxide-water vapors are delivered into an evacuated sterilizer chamber. The articles to be sterilized are cooled if necessary prior to the introduction of the vapor (or are cooled by the evacuation of air from the sterilizing zone) to a temperature below the dew point of the entering vapors and the condensing vapor deposits a film of liquid on all such cool surfaces (col 2, line 40-51). Koubek et al., also mentions in claim 2 that the result of vaporization was a mixed "gaseous vapor" consisting of hydrogen peroxide and water vapor free of solid contaminants.

U.S. Pat. No. 4,952,370 (Cummings et al., 1988), which is incorporated herein by reference in its entirety, including any references cited therein, teaches a similar method of sterilization where a liquid of aqueous hydrogen peroxide is also vaporized into a gaseous state before its administration into an evacuated sterilizer chamber. However, Cummings et al., teaches improvements to the art where the hydrogen peroxide-water vapor is applied under vacuum to surfaces that are below 10 degree centigrade, or surfaces in an environment that are both below 10 degree centigrade and above 10 degree centigrade. The cold surfaces mentioned in Cummings et al., were not cooled to accentuate or enhance the process, but were surfaces of components that were inherently cold for their own operational purposes. This is mentioned in sections such as (col 2, line 4-9), (col 2, line 29-33), and (col 4, line 67 to col 5, line 2).

U.S. Patent Application No. 2005/0042130 A1 (Lin et al., 2003), which is incorporated herein by reference in its entirety, including any references cited therein, claims the use of an applied vacuum to move an ultrasonically derived aerosol, consisting of a sterilant, throughout the area of an enclosed chamber. The use of various vacuum pressures below atmospheric pressure was also mentioned as well as the possibility that vacuum pressures lower than 5 ton lower than atmospheric pressure would likely "enhance the results", and that using a vacuum pressure low enough to vaporize the sterilant generally enhances sterilization (pg. 2, paragraph 28). However, Lin et al, was silent with respect to how the lower vacuum pressures would "enhance the results" other than any enhancement that vaporization of the aerosol might bring. Lin et al, was also silent with respect to the amount of time that is needed to elapse between lowering the pressure within the enclosed chamber and the application of an aerosol, in order to obtain the needed or desired level of efficacy. (Lin et al., 2003) was silent with respect to cooling any surfaces within the sterilization chamber or applying the aerosol to any cooled surfaces.

It is important to note that Lin et al, did not mention any process or method to heat the liquid of the aerosol or cool the surfaces in the sterilization chamber before or during the delivery of the aerosol, or any means to incur condensation if the liquid was vaporized. In fact, the 5 ton negative pressure that was used by Lin et al. to generate their findings was reported to be sufficient enough to disperse the mist within the sterilization chamber (pg. 2, paragraph 28), but was never mentioned to have cooled the surfaces within the sterilization chamber or to have that intended effect.

In addition, it is important to note that the cooling of a targeted environment(s) and/or the surfaces contained therein addressed by the present invention is intended, without limitation, for a completely different application and purpose. The present invention utilizes the principals of aerosol behavior to increase the performance of the process of the present invention, and not the condensation of a gas as taught in the prior art. This is further addressed in the present invention.

By comparison, the current invention utilizes, without limitation, the cooling of the targeted environment(s) and its surfaces to enhance the performance and efficacy of the aerosol administration process and not to condense a gas as taught by the prior art. The methods and apparatuses of the present invention also address the need to apply an aerosol to surfaces that are without limitation, difficult, impossible, time consuming, or not cost effective to enclose.

SUMMARY OF THE INVENTION

In view of the need for improvements in the current art, the present invention includes improved apparatuses and methods for the generation and application of an ultrasonically generated aerosol for uses including, but not limited to, the sanitization, disinfection, high-level disinfection, or sterilization of one or more areas and the surfaces in those areas, as well as the delivery of other types of liquid agents, for various purposes, to one or more areas, and the surfaces found therein.

It is preferred, without limitation, that the aerosol is generated within the apparatus and administered into a targeted area and/or onto targeted surfaces by pressurized air or the movement of air or gas. The generated aerosol can be of various sizes, mass concentration or density, and number concentration. It is preferred without limitation that the aerosol is a submicron droplet fog or aerosol of an anti-pathogen, toxin, fungal, sterilization, disinfection, or sporicidal agent(s) or mixtures thereof (herein collectively "agent(s)"). However, any liquid agent(s) may be used in the present invention for various purposes. The fog or aerosol can, without limitation, consist substantially of ten micron to submicron size aerosolized droplets. It is preferred, without limitation, that the aerosol has a higher rather than lower mass concentration or density of droplets. It is also preferred, without limitation, that the aerosol has a higher rather than lower number concentration of droplets.

The apparatus and methods described in the present invention can pertain to any ultrasonic aerosol producing apparatus. They can also pertain to an aerosol producing apparatus as described in the present invention. This apparatus, briefly described, has one or more piezoelectric transducers that are operated in parallel or series. The transducers are submerged in one or more tanks or reservoirs, and cause a surface disturbance, which results in the formation of an aerosol of the liquid in the tanks or reservoir(s). The one or more tanks or reservoirs in which the transducers are located can be connected to one or more additional tanks or reservoirs that hold the liquid agent. The liquid level in the tank(s) or reservoir(s) in which the transducers are located is controlled by one or more valves which are actuated when the liquid level drops to a certain level causing the valves to open and allows additional liquid to flow in. The tanks or reservoirs also have a means to sense if they are under or overfilled, and can cause the apparatus to shut down if this occurs. The tank(s) or reservoir(s) in which the transducers are located, can be positioned in a chamber that can have a flow of pressurized air/gas, or can be constructed in such a way so that pressurized air/gas can flow through or over them. The pressurized air/gas is intended to move the generated aerosol from the apparatus to the targeted areas or surfaces. The pressurized air/gas can be supplied from sources such as, but not limited to, one or more, fan(s), blower(s), or supply of pressurized air or gas. The apparatus in the present invention can be operated either from inside or outside of the targeted area.

An apparatus and method of an embodiment of the present invention, briefly summarized, comprises constructing the apparatus so that the aerosol producing transducer(s) and/or their liquid facing surfaces, are able to, without limitation, automatically align themselves with, match the angle of, or remain level with, the surface of the liquid above them. This allows the apparatus to be quickly and easily set up and operated, in a reproducible manner, on uneven or angled surfaces. It also eliminates, without limitation, the need to operate the apparatus on level surfaces. This embodiment includes placing, positioning, or mounting the transducers to or with a gimbal or other similar means known in the art, where the transducers are located at an effective range or depth below the surface of the liquid during their operation. However, it is preferred without limitation that the transducer(s) and their associated parts and housing(s) are designed so that they can be suspended, positioned, held, or maintained, in numerous ways at an effective range or depth below the surface of the liquid during their operation. Without being limited, the transducer(s) and their housing(s) can be suspended, positioned, held, or maintained, at an effective range or depth below the surface of the liquid from an object or component that is floating on the surface of the liquid, partially submerged in the liquid, or completely submerged in the liquid.

An apparatus and method of an embodiment of the present invention, briefly summarized, comprises interfacing the transducer(s) with a protective barrier that is ground and polished on one or more sides. Polishing the side of the barrier that interfaces with the liquid in the reservoir(s) offers advantages including, but not limited to, ease of cleaning, increased resistance to mineral or foreign object debris deposition or buildup, efficient and effective movement of liquid off of the barrier. In addition, polishing the side of the barrier that interfaces with the adhesive and transducer(s), offers advantages including, but not limited to, reduced variability in adhesive thickness due to diminished variability in the protective barrier's surface features, which can without limitation, reduce variability in transmission related issues.

An apparatus and method of an embodiment of the present invention, briefly summarized, comprises constructing the enclosing glass plate to have approximately a thickness of about ¼ the wavelength in glass or other material forming the barrier of the transmitted pressure wave generated by the transducer at the natural resonant frequency of the transducer. When the barrier thickness has been calculated, the transducer can be operated at an operational frequency up to 60% percent greater than the natural resonant frequency to achieve a much more efficient operation for the transducer in forming the aerosol. Alternatively, the thickness of the barrier can be varied from the optimal thickness in the range of −0.010 inches to +0.024 inches to increase the efficiency of operation of the transducer. Further, it has been found that the glass or other material barrier thickness may be increased to around various odd multiples of ¼ wavelength and still operate effectively to provide a high volume small aerosol particle output.

An apparatus and method of an embodiment of the present invention, briefly summarized, comprises enclosing or encircling aerosol producing transducers with one or more wall(s) or barrier(s), that can be, without limitation, continuous or discontinuous, sealed, partially sealed, or unsealed, of various heights including, but not limited to, above the surface of the liquid above the transducers. The purpose of the wall(s) or barrier(s) is to contain the liquid above and around the transducers and use the heat from the transducers to heat that liquid above and around the transducers, and without limitation, the liquid surface above the transducers. The wall(s) or barrier(s) can be perforated or have holes or notches in various orientations or locations in order to allow liquid of various temperatures to flow in and out of the enclosed or encircled areas.

An apparatus and method of an embodiment of the present invention, briefly summarized, comprises filtering the pressurized air before it enters the apparatus, or at least before entering the aerosol generation chamber. Without limitation, it is preferred that one or more filter(s) is located where the air is drawn or pulled into the apparatus by a blower or fan. The filter(s) can be located either on the inside or outside of the apparatus. The addition of one or more filter(s) prevents or limits dust and debris contamination inside the pressurized air channels or pipes of the apparatus or in the tank or area in which the transducer(s) are located. Various types of filters can be used in the present invention and is dependent on the application. The filter(s), are not used in any configuration(s) or application(s) where aerosol is pulled or pushed from the area in which it was administered, back through the aerosol generator and filtered before it is exhausted out from the targeted or treated area.

An apparatus and method of an embodiment of the present invention, briefly summarized, comprises connecting one or more tanks between the main tank(s) in which the liquid is stored in the apparatus, and the tank(s) in which the transducer(s) are located, and without limitation, each of the aforementioned tanks have one or more inline valve(s) or float valve(s) that controls the flow of liquid. Without limitation, these connecting tank(s) and valve(s) system(s) act as a check or failsafe mechanism to ensure that the tank(s) or basin(s) in which the transducer(s) are located is not over filled or flooded.

An apparatus and method of an embodiment of the present invention, briefly summarized, comprises connecting, without limitation, the fill pipe(s) or their spill over tray(s) or basin(s), blower or fan housing(s), internal catch pan(s) or basin(s), transducer tank(s) or basin(s), to one or more liquid containment tank(s). Without limitation, the liquid containment tank(s) are designed to collect excess, spilled, leaked, gathered, or coalesced liquid. This collection system can be connected to the pipe(s) and valve(s) used to drain the apparatus, or it can also have its own drain pipe(s) and valve(s).

An apparatus and method of an embodiment of the present invention, briefly summarized, comprises the incorporation of a means to control or prevent the temperature of the liquid in the tank or basin in which the transducer(s) are located from exceeding the maximum desired, established, or required operating temperature for that liquid or particular process. The prior art has taught that the transducers impart heat into the liquid during their operation. The air that is used to transfer the aerosol from the basin or tank in which the transducer(s) are located to the targeted area(s), can function as a heat removal system. However this pressurized air flow can only remove a certain or calculated number of BTUs or watts of heat due to factors including, but not limited to, the surface area of the liquid in the basin or tank, and the volume and velocity of air that moves over that surface area. If more heat is imparted into the liquid than is removed or dissipated over time, the temperature of the liquid will continue to rise. The means to control or prevent the temperature of the liquid in the tank(s) or basin(s) in which the transducers are located from exceeding the aforementioned maximum desired, established, or required operating temperature, includes without limitation, pumping or otherwise moving the liquid that is in the basin(s) or tank(s) in which the transducer(s) are located, or any other liquid that could possibly have contact with that liquid, through one or more heat exchanger, cooling fins, cooling plate, cooling block, chiller, chilling or cooling apparatus, or other means to remove heat from the liquid. Without limitation, the liquid from the basin(s) or tank(s) in which the transducer(s) are located, can be pumped or moved through one or more cooling fins, chill block, or heat exchanger that is located in the path of the pressurized air that is used to move the generated aerosol out from the apparatus.

An apparatus and method of an embodiment of the present invention, briefly summarized, comprises the remote control of and communication with the apparatus in the present invention. This improvement in the present invention offers many advantages such as, but not limited to, reducing or eliminating the chance of the operator having an accidental exposure to the aerosol from an apparatus that is operated from within the same environment in which the aerosol is applied. The remote control of and communication with the apparatus can be accomplished by means such as, but not limited to, any radio frequency, any light frequency, or directly or indirectly connected wires, or any combination of the said means. Various information, data, and commands can be communicated between the apparatus and a separate means to send and receive information, data, or commands.

An apparatus and method of an embodiment of the present invention, briefly summarized, comprises the apparatus having one or more sensors or the communication with one or more sensors to determine when an effective or sufficient amount of aerosol has been applied to the targeted area and/or surfaces. The sensor(s) consists of a means of varying intensity to project one or more beams of light or a light source, and one or more means to sense the beam(s) of light or light source(s) and indicate its absence or presence. Without limitation, the means to sense the light can vary widely in its sensitivity, and can indicate the presence or absence of the beam or light with a signal such as but not limited to any electrical, fiber optic, or radio frequency signal. It is preferred, without limitation, the sensor consists of a laser and a photoelectric sensor. The means to sense the beam of light communicates with a programmable logic circuit, computer, control mechanism or device, or other electronics that control or operate the apparatus (herein called "PLC"), and the presence or absence of a signal or communication causes or results in the apparatus to take actions or undergo activities, such as but not limited to, ceasing the production of aerosol, ceasing the operation of the blower or fan, or even shutting down. It is the intent of the present invention to generate and deliver aerosol into an area until a sufficient amount or density of aerosol is present which will, disrupt, diminish, or completely prevent, the light, beams of light, or light source, from reaching the means to sense the light. The amount of this applied aerosol can vary depending on the application.

An apparatus and method of an embodiment of the present invention, briefly summarized, comprises the apparatus alerting or communicating with the operator if he/she programs the apparatus or otherwise undertakes an activity that would cause the apparatus to operate and generate aerosol for a specific period of time or to fill a specific volume of space with aerosol, and there is an insufficient amount of liquid available in or available to the apparatus for the chosen operating time or volume of space to fill with aerosol, and communicating to the operator the quantity of liquid or at least the exact minimum quantity of liquid, expressed in units of measurement, that is necessary to add or make available to the apparatus so that it may successfully complete its desired or chosen operational time or run cycle. The actual number of needed fill/refill cartridges can also be communicated to the operator. This embodiment includes without limitation, the apparatus having the ability to sense or detect the liquid level or amount of liquid available to the apparatus, or calculating the total amount of liquid available in one or more reservoir(s) that are, without limitation, inside, attached, or otherwise connected to the apparatus. In addition, the means to alert and communicate information to the operator can include but is not limited to any alphanumeric image shown on a screen, monitor, or human-machine-interface (herein called "HMI"), any graphic-user-interface (GUI) shown on a screen, monitor, or human-machine-interface (HMI), lights, lights with associated text, voice commands or directions, or any audible signal.

An apparatus and method of an embodiment of the present invention, briefly summarized, comprises the apparatus having the ability to prevent the liquid agent from being dispersed, that is available to the apparatus from, without limitation, one or more tanks or reservoirs inside, attached, or connected, to the apparatus, which has exceeded its time or date of expiration, exceeded the time or date in which it can be efficaciously used, or has reached a point of time or date where it has degraded or aged to a point where its use is unacceptable. This embodiment does not encompass refill/fill cartridges. The apparatus in this embodiment possesses a means known in the art for measuring, comparing, calculating, or otherwise keeping track of the time between when the apparatus is initially charged or filled with the liquid agent, or the last purge of the apparatus of undesired or unusable liquid, and when the time has been reached when that liquid agent cannot be used and must be disposed of. Once the usable time for the liquid agent has expired, the apparatus can prevent the liquid agent from being dispersed with means including, but is not limited to, using a programmable logic circuit (PLC), control mechanism or device, or other electronics that control or operate the apparatus, to take action(s) that result in stopping the apparatus from generating aerosol. In addition, the apparatus can alert or communicate to the operator that the liquid agent has expired. The means to alert and communicate information to the operator can include but is not limited to any alphanumeric image shown on a screen, monitor, or human-machine-interface (HMI), any graphic-user-interface (GUI) shown on a screen, monitor, or human-machine-interface (HMI), lights, lights with associated text, voice commands or directions, any audible signal.

An apparatus and method of an embodiment of the present invention, briefly summarized, addresses the cooling of components that can heat up inside of the apparatus when it is being operated in areas such as, but not limited to, the area in which the aerosol is being applied. This situation presents engineering challenges because as the apparatus is operated, its components such as, but not limited to, motors or electronics heat up over time. They cannot be cooled by blowing air from outside of the apparatus past or onto them to remove heat if they are in an aerosol filled environment. This air would contain the administered aerosol and be wet. This condition could pose a risk for unwanted chemical reactions with the components depending on the chemical agent that is present in the aerosol. In one part of this embodiment, the electronics that are used to operate or power the transducer(s) are located in a sealed enclosure and cooled with a means that transfers the heat generated from the electronics into a pressurized air stream. It is preferred, without limitation, that this pressurized air stream is the same air stream that is used to move the generated aerosol out of the apparatus. This helps, without limitation, to minimize the total amperage that is utilized or needed for proper or effective function of the apparatus, which is a critical issue with regard to aerosol generators of this complexity. The one or more heat transfer point(s) can be located before or after the fan(s) or blower(s) that create the pressurized air stream. It is also preferred, without limitation, that the heat generated from the electronics is transferred in various ways known in the art to a heat sink that has fins or other cooling enhancements also known in the art, and the heat sink is positioned in the pressurized air stream. In another part of this embodiment, the components other than the electronics that are used to operate or power the transducer(s), including but not limited to motors or electronics, or the atmosphere in their enclosure(s), are also cooled with a means that transfers the heat generated from the components into a pressurized air stream.

An apparatus and method of an embodiment of the present invention, briefly summarized, comprises constructing the apparatus in a way that prevents any exterior parts of the apparatus that are exposed to the aerosol from becoming higher in temperature than the temperature of the atmosphere surrounding the apparatus. Generally speaking, this is important because aerosol particles experience a force in the direction of decreasing temperature. This embodiment is applicable and especially beneficial for applications where the apparatus is operated from within the same environment in which the aerosol is applied, and it is desired or required that all of the exterior surfaces of the apparatus have interaction or contact with the administered aerosol. Without this improvement to the current art, the exterior surfaces of the apparatus could become warmer in temperature than the surrounding atmosphere and repel the aerosol, which would prevent the exterior surfaces from having interaction or contact with the administered aerosol if it is desired or required. The apparatus can be constructed in ways that include, but are not limited to, enclosing the components or parts that can heat up in a sealed enclosure and then placing that enclosure inside of another closure that is sealed or unsealed, or insulating the outer skin of the apparatus.

An apparatus and method of an embodiment of the present invention, briefly summarized, comprises cooling or decreasing the temperature of the objects, the atmosphere in which they reside, or the targeted area for the administration of an aerosol as well any surfaces in that area with refrigerated or chilled air, before the administration of the aerosol to the targeted area or surfaces. This cooling activity or process enables the present invention to utilize the principals of aerosol behavior to increase the efficacy or performance of the process of the present invention. Aerosol particles experience a force in the direction of decreasing temperature. By decreasing the surface temperature of the targeted surfaces, the administered aerosol, and especially an aerosol where the liquid was heated, is drawn towards the cooled surfaces in the targeted area or environment where they interact, interface, or coat the said surfaces with the liquid agent.

An apparatus and method of an embodiment of the present invention, briefly summarized, comprises utilizing a means to administer the mixture of aerosol and gas or air that is ejected or moved out of the apparatus to one or more separate enclosed rooms or areas. This embodiment does not encompass applications where the areas are within the same room, since this is already known in the art. The said means can include but is not limited to connecting one or more tubes to the apparatus, or splitting the flow from these tube(s) so that they can connect, interface, or otherwise empty into the one or more separate enclosed areas. The said means can also have a means to close off the flow of the air/gas and aerosol to one or more of the said tube(s).

An apparatus and method of an embodiment of the present invention, briefly summarized, comprises designing the apparatus so that the electronics that operate or energize the transducer(s) may be able to adjust the frequency or frequency range of the signal that is sent to the transducer(s) multiple times during the lifespan of the transducer(s) so that the transducer(s) are able to be consistently operated at a frequency or within frequency range in which the they are able to have an effective or functional output and/or operate at their maximum performance or aerosol output.

An apparatus and method of an embodiment of the present invention, briefly summarized, comprises connecting, interfacing, or attaching, the aerosol generating apparatus in the present invention to one or more sealed, semi-sealed, or semi-open enclosures or areas. The enclosure(s) has at least five distinguishing features: a) the enclosure(s) is designed to fit over or under various things such as, but not limited to, equipment, objects, or architectural features, etc., b) any walls can have various openings through which any objects may be moved or accessed, c) the enclosure can hang from hooks or other means of attachment that connect to the ceiling or other locations of the area in which the enclosure(s) is located, d) the floors of the enclosure(s) can be constructed with or utilize a surface design or accessory(s) so as to reduce any potential for slip hazards inside the enclosure(s), e) the enclosure can be interfaced with one or means for fire suppression inside or outside of the enclosure.

An apparatus and method of an embodiment of the present invention, briefly summarized, comprises administering an aerosol into an enclosed area where the floor of that enclosed area is removed, and the surface(s) which the walls of the enclosed area interfaces forms the floor of the enclosed area. This interface can be fully sealed, semi sealed, or unsealed. In addition, one or more holes for access to the enclosed area can also be present in the walls of the enclosed area and the holes can be covered in a matter so that they are sealed or semi-sealed closed, or they can be open and unsealed.

An apparatus and method of an embodiment of the present invention, briefly summarized, comprises the utilization of one or more means or holder to prop or hold any items such as, but not limited to, any hose(s), wire(s), cord(s) that are present in the area in which the aerosol is administered or lead to or from the aerosol generator(s), so that they are prevented from touching or contacting any floor or surface on which the holder is placed. The use of the holder(s) helps to reduce or eliminate an incomplete treatment or administration of the aerosol to all of the desired or needed surfaces in a targeted area. The holder(s) can, without limitation, have absorbent material placed between the holder and any surface(s) on which the holder is placed or interfaces. Absorbent material can also, without limitation, be placed between the holder(s) and any object(s) that it holds or supports. The absorbent material may, without limitation, be soaked, saturated, or contacted with any liquid or substance for various purposes before, during, or after the holder is interfaced with an object(s) or placed on a surface(s) or floor.

In view of the need for further improvements in the current art, the present invention also includes additional improved apparatuses and methods.

An apparatus and method of an embodiment of the present invention, briefly summarized, comprises the incorporation of a means to add or remove one or more sources of weight or mass from various locations on any of the floated parts of the apparatus including, but not limited to, transducer housing(s), the buoyant objects or components, and/or any of the parts that are directly or indirectly connected to the buoyant objects or components, in order to position or maintain the position of each of the transducer(s) and/or their housing(s) at an effective range or depth below the surface of the liquid.

An apparatus and method of an embodiment of the present invention, briefly summarized, comprises without limitation, allowing the buoyant objects or components, and/or any of the parts that are directly or indirectly connected to the buoyant objects or components, as well as the transducers and their housing(s), to freely float in any tank(s) or reservoir(s), where the only anchor point(s) for these parts is the location where the transducer electrical cable(s) and any tubing through which they travel connect either directly or indirectly to the walls of the tank(s) or reservoir(s).

An apparatus and method of an embodiment of the present invention, briefly summarized, comprises locating the inlet for the inbound air opposite from the air outlet of the fog tank or reservoir in which the transducers are located, and directing or moving the inbound air downward into the one or more reservoir(s) in which the transducer(s) are located. This is coupled with locating one or more openings of various sizes and shapes in the roof of the reservoir opposite from the air outlet. This means can reduce the number of larger droplets in the exiting air stream.

An apparatus and method of an embodiment of the present invention, briefly summarized, comprises using one or more means to distribute the inbound air to more than one location in the fog tank(s) or reservoir(s) for purposes including, but not limited to eliminating or diminishing any, uneven airflow, uneven air distribution, turbulent air, or vortices, within the interior air space of the fog tank or reservoir. This means to move the air can also be perforated in various orientations with one or more orifices of various sizes and shapes.

An apparatus and method of an embodiment of the present invention, briefly summarized, comprises reducing the feet per second output of the air exiting from the fog tank(s) or reservoir(s) in which the transducers are located, or otherwise the aerosol generating apparatus, any time near the end of the aerosol generation and delivery cycle. This procedure will promote faster accumulation of the aerosol cloud in the immediate vicinity of the aerosol generating apparatus.

An apparatus and method of an embodiment of the present invention, briefly summarized, comprises equipping the aerosol generating apparatus with one or more sensors to determine when an effective or sufficient amount of aerosol has been applied to the targeted area and/or its targeted surfaces. The sensor(s) may be directly or indirectly attached to the apparatus, or they may be remotely located in any location where the aerosol is applied or administered. The sensor(s) can be positioned in any orientation and communicate with the aerosol generating apparatus in various ways such as, but not limited to, radio, sound, fiber optics, or wires, all in a manner known to those skilled in the art.

An apparatus and method of an embodiment of the present invention, briefly summarized, comprises the operation of a means to dehumidify the area in which the aerosol was administered, any time after the aerosol deployment cycle has finished, or the aerosol generating apparatus was shut down for any reason(s). In one embodiment, a dehumidifier is used as an independent apparatus "not" connected to the aerosol generating apparatus. It may be remotely controlled or programmed by the operator all in a manner all known to those skilled in the art. In another embodiment, an independent dehumidifier is used, but in this particular embodiment it is controlled by, and electrically connected to, the aerosol generating apparatus. The operation of the dehumidifying apparatus is controlled by the software or computer program that operates or controls the aerosol generating apparatus. In an additional embodiment, the means to dehumidify the area in which the aerosol was administered, is enhanced so that it contains one or more filter media to filter the aerosol before, during, or after it passes over the chill coils.

Filtering the deployed aerosol was initially demonstrated by the inventors of the present invention in a public area at the Richland, Wash. Municipal Airport on Oct. 9, 2003. Staff from Washington State University, observed aerosol created by the aerosol generating apparatus described in the present invention, pass through a long tortuous path created with 150 feet of six inch diameter flex ducting, that terminated with various filter media including a HEPA filter and a furnace filter. This same system was used to dehumidify and dry the system of ductwork, after the aerosol was deployed.

In an embodiment, the dehumidifier can also incorporate a means to receive any type of signal from various sources including, but not limited to, the aerosol generating apparatus, or any means for remote control, to not only signal the dehumidifier to dehumidify a targeted area or environment, but also to complete or terminate the dehumidification process by moving, switching, or directing the air flow through a separate filter, such as, but not limited to, an activated carbon filter, or any filter that can remove various gases or vapor(s) from the treated area(s).

An apparatus and method of an embodiment of the present invention, briefly summarized, comprises the construction and use of a means to effectively cover and/or seal the various types of vents that can be found in treated areas including, but not limited to, inbound and outbound air vents for a building HVAC system. These air vents are commonly found in facilities such as, hospitals, schools, clinics, factories, laboratories, and clean rooms. Many times these vents have one or more protruding metal geometries, which makes sealing the vents difficult or impossible with current means. In addition, sealing these vents can be time consuming as well as dangerous because ladders are often necessitated to reach the ceiling mounted vents. The improved means to effectively cover or seal the various types of vents, includes parts such as but not limited to, a vent cover with sealing material to seal it to the vent or any surrounding or connected areas or materials, any pole which can, without limitation, be adjusted or modified for length, and a means to directly or indirectly connect the pole to the vent cover. In another embodiment, the pole with adjustable length can be constructed so that its one or more ends that are opposite from the vent cover has a means to swivel or articulate so that the base(s) of the pole can articulate at any angle with the floor or any other surface that it contacts. In an additional embodiment, any surfaces of the end(s) of the pole that is compressed or pushed down onto any surface that results in the compression of the vent cover or its seal material can be, without limitation, formed from, coated with, adhered with, or consist of any absorbent material. This material can be, without limitation, treated or saturated with any liquid, at any time, consisting of any anti-pathogen, toxin, fungal, sterilization, disinfection, or sporicidal agent(s) or mixtures thereof (herein collectively "agent(s)"). However, any liquid agent(s) may be used in the present invention for various purposes.

An apparatus and method of an embodiment of the present invention, briefly summarized, comprises modifying a magnetic vent cover so that it has one or more attachment points where a means, such as, but not limited to, rope, cord, thread, wire, cable, twine, tube, or hose, can be attached to the vent cover so that it may be easily removed from a ceiling or ceiling vent eliminating the need to use a ladder. The magnetic vent cover is known to those skilled in the art, and is commonly found in the form of a flexible sheet that is embedded with one or magnets, or coated or laminated with one or more magnetic materials.

An apparatus and method of an embodiment of the present invention provides a deployable automated vent cover device. This device is intended to effectively cover or seal the various types of one or more vents, so that it has, without limitation, one or more of any door(s), gill(s), shudder(s), valuer(s), grate(s), or other opening(s), that can open and allow the passage of any air, gas, vapor, or aerosol. Furthermore, these opening(s) are able to open upon receiving one or more of any command(s) or signal(s) at any time and for any reason. This command(s) or signal(s) can be, in various forms including, but not limited to, light, sound, radio, or electrical signal, and can be sent via either direct or indirect connection.

The deployable vent cover device preferably includes a vent cover and a telescopic pole. The vent cover preferably includes a vent base, a first vent door, a second vent door and a release mechanism. The release mechanism preferably includes a solenoid, a pivot release, a first latch device and a second latch device. The vent base preferably includes a base plate, a tubular boss and a vent seal. At least two vent openings are formed through the base plate. A pole boss is attached to a bottom of the base plate. The vent seal makes contact with a vent. The first vent door is pivotal attached to one end of the base plate and the second vent door is pivotally attached to the other end of the base. The first latch device is retained on the base plate and includes at least two first latches. The second latch device is retained on the base plate and includes at least two second latches. The first latches retain the first vent door in a closed orientation and the second latches retain the second vent door in a closed orientation. The first latch device further includes a first lever arm and the second latch device further includes a second lever arm. Ends of the first and second lever arms are pivotally secured to each other. The pivot release supports the pivotal connection between the first and second lever arms. The pivot release is also pivotally retained by an end of an actuation rod of the solenoid. However, the vent cover may also include only one vent door. At least one vent opening would be formed through the base plate, and the second latch device and second vent door would be eliminated.

In use, a telescopic pole is inserted into the pole boss. The pole is raised, until the vent cover seals the vents. One or more cables, wires, lines, or other means known to those skilled in the art, are directly or indirectly connected to a PLC that communicates and/or controls the aerosol generating system. The aerosol generating system is activated and treats an enclosed area. When the treatment is finished, the PLC allows or controls the supply of electrical power to the solenoid, which results in the actuation rod being retracted into the solenoid. The retraction of the actuation rod causes the pivot release to stop support of the first lever arm, which results in the first and second lever arms moving toward the base plate. The inward movement of the first and second lever arms causes the first and second latches to release the first and second vent doors, such that they fall open. After use, the pivotal connection of the first and second extension legs is manually pulled away from the base plate, such that the pivot release supports the first lever arm.

The following embodiments are intended to augment current methods utilized in the surgical suite to further reduce the continued prevalence and threat of nonsocial infections. Despite the use of directed air flow, ultra violet light and sterile site preparation, MRSA and other serious infection causing pathogens continue to directly cause the deaths of over 102,000 individuals per year.

An apparatus and method of an embodiment of the present invention, briefly summarized, comprises administering an aerosol and/or vapor into one or more enclosed area(s) where the enclosed area(s) can have, without limitation, one or more opening(s) or orifice(s), and one or more object(s) can be positioned or inserted through these opening(s) or orifice(s), and the direct or indirect contact or interface of the object(s) with these opening(s) or orifice(s) results or causes the enclosed area(s) to become, without limitation, effectively sealed. The object(s) can, without limitation, be positioned or inserted completely through the enclosed area in any orientation, through the one or more opening(s) or orifice(s). The direct or indirect interface(s) between the object(s) or surface(s) and the one or more wall(s) of the enclosed area can be, without limitation, sealed or semi sealed. This further clarifies the initial submission for the present invention. The enclosed area can also incorporate various means for the introduction or supply of one or more sources of pressurized air or gas, or any vacuum, into any location of the enclosed area, as well as across or over any of these one or more door(s) or opening(s) to the enclosed area(s). This enclosed system combined with a pressurized air flow and vacuum near the door(s) opening(s), allows work, such as but not limited to, surgical procedures, to be performed in an environment where all of the targeted surfaces are treated, and the air traveling over, under, or across the door(s) allows that sterile environment to be effectively maintained.

An apparatus and method of an embodiment of the present invention, briefly summarized, comprises generating and then injecting, directing or administering an aerosol, comprised of a treatment agent known to those skilled in the art, into or onto a wound, body cavity, or surgical incision, via a means such as, but not limited to one or more, tube, pipe, or conduit. It is preferred, without limitation, that the means to generate the aerosol is an ultrasonic aerosol generator described in the present invention.

Numerous other features, aspects and advantages of the present invention will be made apparent from the following detailed description taken together with the drawing figures.

BRIEF DESCRIPTION OF THE DRAWINGS

The methods and devices for the present invention, is best understood with reference to the following detailed description of the invention and the drawings in which.

DETAILED DESCRIPTION

Figure 1:
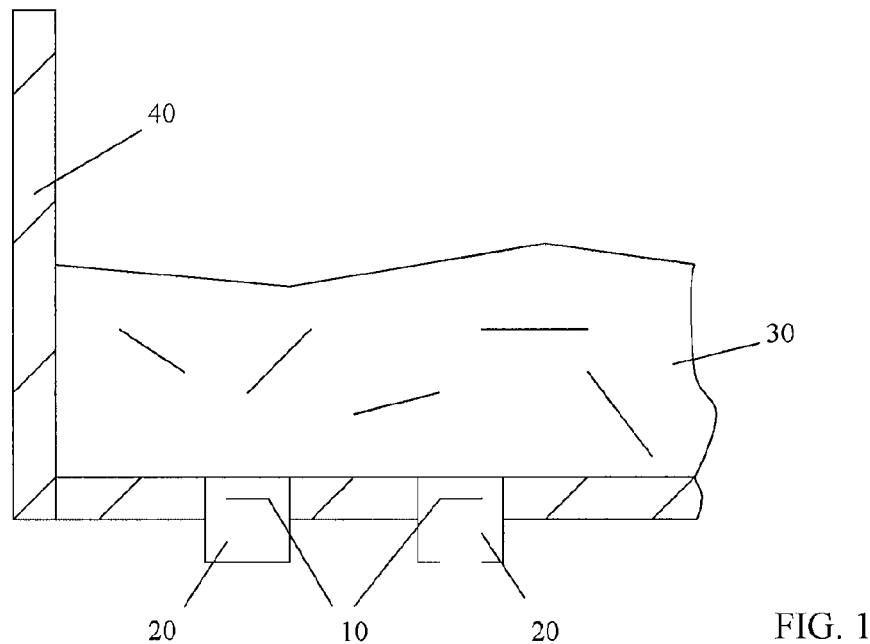
FIG. 1 is a schematic view of an embodiment of a reservoir where one or more aerosol generating ultrasonic transducers are located below the surface of a liquid held within the reservoir.

Detailed references to the embodiments of the invention, are illustrated in the accompanying drawings that serve as examples. While the invention will be described in conjunction with the embodiments, it is understood that they are not intended to limit the invention to those embodiments. On the contrary, the invention is intended to cover alternatives, modifications, and equivalents, which may be included within the spirit and scope of the invention as defined by the appended claims.

As illustrated in FIGS. 1-5B, an embodiment of the invention includes a method and apparatus for protecting and enhancing the performance of one or more aerosol generating ultrasonic transducer(s) (10) by adhering one or more protective barrier(s) (60) to a transducer(s) (10). Unless otherwise stated, adhering in this specification includes, but is not limited to adhering, coupling, gluing, attaching, cementing, cohering, fastening, pasting, depositing, applying, melting onto or melting together, and chemically, thermally, or physically bonding. According to an embodiment the transducer(s) (10) may be made of a piezoelectric material, preferably a lead-zirconate-titanate (PZT) material, and more preferably lead-zirconate-titanate-four (PZT-4). According to an embodiment, the protective barrier (60) may be any material that has an effective or high chemical resistance to a liquid (30); however any material that has an effective coefficient of conductivity for pressure (energy) could also be used. Further, the protective barrier (60) may be a pane, sheet, or plate, and may be made of materials such as glass, ceramic, or a polymer. According to an embodiment, the thickness of the protective barrier(s) (60) can range from about 0.001 inches to about 0.125 inches, wherein the thickness is not equal to or about n/2 of a wavelength of sound or pressure (energy), preferably in the form of a wave, generated by the transducer(s) (10) at a frequency, wherein n is any integer. In an embodiment, the liquid (30) may be, but is not limited to one or more of any chemical, compound, mixture, or substance, which is a liquid, preferably a solution, and may optionally include but is not limited to water, medicines, fertilizers, pesticides, fuels, chemical neutralizers, or anti-pathogen/toxin/fungal/sporicidal agents, substances, combinations thereof, and the like. According to an embodiment, the liquid (30) may also be heated to achieve a desired aerosol (200) output.

According to an embodiment, a protective barrier (60) is adhered to the side of the transducer(s) 10 that faces the liquid (30), preferably hydrogen peroxide and peroxyacetic acid in solution, to separate the transducer(s) (10) from the liquid (30). In an embodiment, the protective barrier (60) is quartz glass and is adhered to the transducer(s) (10) by an adhesive (70) whose performance is unaffected and/or not adversely affected by heat. No liquid or other medium, other than the adhesive (70) (and optionally, a conductive coating (50)), is necessary between the transducer(s) (10) and the protective barrier (60) for the transducer(s) (10) to function properly. According to an embodiment, the thickness of the protective barrier (60) ranges from about 0.001 inches to about 0.125 inches, wherein the thickness is not equal to or about n/2 of a wavelength of pressure generated by the transducer(s) (10) at a frequency between about 0.025 MHz and about 10 MHz, wherein n is any integer, preferably a thickness between about 0.026 inches and about 0.070 inches at a frequency between about 0.5 MHz and about 2.5 MHz, more preferably a thickness between about 0.030 inches and about 0.060 inches at a frequency between about 1.2 MHz and about 2.2 MHz, and even more preferably a thickness between about 0.029 inches and about 0.042 inches at a frequency between about 1.2 MHz and about 2.2 MHz.

Referring to FIGS. 1 and 2, an embodiment of the invention includes one or more aerosol generating ultrasonic transducer(s) (10) (and their housings (20), if utilized) located below the surface of a solution, fluid, or liquid (herein collectively "liquid") (30) in a reservoir (40). According to an embodiment, the liquid (30) can be, but is not limited to one or more of any chemical, compound, mixture, or substance, which is a liquid, preferably a solution, and may optionally include but is not limited to water, medicines, fertilizers, pesticides, fuels, chemical neutralizers, or anti-pathogen/toxin/fungal/sporicidal agents, substances, combinations thereof, and the like.

According to a preferred embodiment, a preferred liquid (30) is hydrogen peroxide and peroxyacetic acid in an aqueous solution, which may be effective in sanitization, disinfection, high-level disinfection, and sterilization, and other applications, preferably approximately 2.2% hydrogen peroxide and approximately 0.45% peroxyacetic acid in solution, more preferably approximately 1% hydrogen peroxide and approximately 0.25% peroxyacetic acid in an aqueous solution. Other liquids (30) that may be used include, but are not limited to chlorine dioxide in solution and ozone in solution.

The tank or reservoir (40) may be made of any suitable material that is not affected by the chemical action of the liquid (30). Suitable materials of the reservoir (40) may include PVC, polypropylene, and stainless steel, but other suitable materials may be used. The aerosol (200) generated by operation of the transducer(s) (10) forms above the surface of the liquid (30) in the reservoir (40) and may be transferred from the reservoir (40) to the space to be treated by a blower (180) or other source of pressurized air, as will be described in greater detail below.

The output of the protected transducer(s) (10) may be focused or directed to a point and/or an area near the surface of the liquid (30) to cause a surface disturbance, which results in the formation of an aerosol (200) of the liquid (30) in the reservoir (40). The aerosol (200) is then blown or otherwise moved with pressurized air, into one or more targeted areas or chambers.

According to an embodiment, the transducer(s) (10) may be made of a piezoelectric material, preferably a lead-zirconate-titanate (PZT) material, and more preferably lead-zirconate-titanate-four (PZT-4). With reference to FIG. 2, the transducer(s) (10) is coated with a conductive coating (50) that enables an electrical signal to energize or drive the transducer(s) (10) causing it to emit pressure (energy) of a desired character. When a protective barrier (60) is adhered or otherwise coupled to a transducer(s) (10) it is understood to mean herein that a conductive coating (50) may exist between the protective barrier (60) and the transducer(s) (10). According to an embodiment, some or all of the conductive coating (50) may be removed from the back of the transducer(s) (10) to allow it to receive the radio frequency (RF) output from the amplifier. Moreover, according to an embodiment, an electrically conductive material (i.e., metal wire, conductive tab or spring, etc.) interfaces or is connected to the conductive coating (50) on the transducer(s) (10), and is then either electrically grounded or electrically connected back to the power amplifier to complete the circuit. This circuit is not polarity sensitive. The electrically conductive material can be attached in their reverse manner.

According to an embodiment, the transducer(s) (10) may be manufactured into various shapes and sizes according to a desired application, preferably circular in shape. Also, according to an embodiment, the transducer(s) (10) may have a diameter of various lengths, preferably about one (1) inch. By using a protective barrier (60) of the present invention, the transducer(s) (10) may have a smaller diameter and smaller surface area than that taught in the prior art without the problems of overheating and/or failing during operation, the need for a cooling mechanism to prevent the transducer(s) (10) from overheating and/or failing, and/or putting space between the protective barrier (60) and the transducer(s) (10) and/or filling that space with various cooling fluids.

Examples of electronic equipment and methods for operating or driving the transducer(s) (10) are discussed in U.S. Pat. Nos. 5,878,355 and 6,102,992 (both of which are incorporated herein by reference in its entirety, including any references cited therein). U.S. Pat. No. 5,925,966, which is incorporated herein by reference in its entirety, including any references cited therein, also provides details of the hardware necessary to operate the transducer(s) (10). Additional electronic equipment, tolerances, and methods for operating or driving the transducer(s) (10) known in the art may also be used. A variable frequency oscillator or signal generator is used to generate a high frequency wave, preferably a sine or square wave.

According to an embodiment, a preferred oscillator is a digital function generator/counter capable of producing sine, square, triangle, pulse and ramp waves. A preferred oscillator has an adjustable frequency range from about 0.025 MHz to about 12 MHz, and may be set or designed for a particular need or requirement. It preferably has variable output amplitude from 5 mV to 20 Vp-p (Volts peak to peak) being delivered to the amplifier, variable symmetry/duty cycle from 5% to 95% in the ramp or pulse mode, continuous or externally controlled outputs. This signal can then be optionally amplified using a power amplifier to increase the power to the optimum aerosol producing power. The volts peak to peak is a measure of power that is supplied to the transducer(s) (10). A direct current (D.C.) offset between −10 v to +10 v can be added to any of the output waveforms.

In one embodiment, the amplifier is a solid-state amplifier that provides up to 2500 watts of linear power with low harmonic and intermodulation distortion and peak to peak voltages of about 20 volts to about 300 volts; however the number of watts could also be increased in order to provide enough power to drive a desired number of transducers and the peak to peak voltages could also be increased, preferably about 100 watts of linear power per transducer(s) (10) with about 190 to about 230 Vp-p. The amplified signal from the amplifier is used to operate or drive one or a plurality of transducer(s) (10), where in an embodiment each transducer(s) (10) is operated at a frequency range between about 0.025 MHz to about 10 MHz or higher, preferably between about 0.5 MHz to about 2.5 MHz, more preferably between about 1.2 MHz and about 2.2 MHz. Moreover, in such an embodiment each transducer(s) (10) has a resonant frequency between about 0.025 and about 10.0 MHz or higher. The operating frequency is the frequency at which the transducer(s) (10) is being driven or operated. The resonant frequency is the frequency of the transducer(s) (10), unloaded in air, without being adhered to the protective barrier (60) or other parts of the transducer assembly (100).

Optionally, in one embodiment, the conductive coating (50) may be applied to the entirety of the surface of each transducer(s) (10) so that it can be energized. According to an embodiment, some or all of the conductive coating (50) may be removed from the side (5) that faces away from the liquid (30) in the reservoir (40). The side (5) of the transducer(s) (10) is also the side that receives the radio frequency (RF) output from the amplifier. According to an embodiment, an electrically conductive material (i.e., metal wire, conductive tab or spring, etc.) interfaces or is connected to the conductive coating (50) on the transducer(s) (10), and is then either electrically grounded or electrically connected back to the power amplifier to complete the circuit. This circuit is not polarity sensitive. The electrically conductive material can be attached in their reverse manner.

The transducer(s) (10) is protected from chemical interaction with a liquid (30), as well as any erosion that could be caused by cavitation, by utilizing a protective barrier (60). In an embodiment, referring to FIG. 2, applying a protective barrier (60) onto the side of the transducer(s) (10) that faces the liquid (30); where the protective barrier (60) is first heated to a pliable or molten state and then applied to the transducer(s) (10). In another embodiment, referring to FIG. 3, adhering, or bonding the surface of one or more transducer(s) (10) that faces the liquid (30) with a protective barrier (60). According to an embodiment, the protective barrier (60) may be a pane or plate, and/or be made of materials such as glass, ceramic, or a polymer. Preferably the protective barrier (60) is a sheet of quartz glass. The material of a protective barrier (60) should have an effective or high chemical resistance to the liquid (30) used. The thickness of a protective barrier (60) is held to specific tolerances. In one embodiment, an adhesive, cement, epoxy, or bonding agent/compound, etc. (herein, collectively "adhesive" (70)), whose performance is unaffected and/or not adversely affected by heat, is utilized for adhering, or otherwise connecting a protective barrier (60) with a transducer(s) (10). An interface and/or connection between a protective barrier (60) and a transducer(s) (10) may also be established by other means known to those skilled in the art. Further, no liquid or other medium, other than the adhesive (70) (and optionally, a conductive coating (50)), is necessary between a transducer(s) (10) and a protective barrier (60) for the transducer(s) (10) to function properly. According to an embodiment, glass was chosen due to attributes including, but not limited to its physical and/or mechanical properties, and ability to withstand the heat generated by a transducer(s) (10) and its general ability to withstand chemical attack. The technique of adhering a transducer to a glass barrier material is taught in U.S. Pat. Nos. 4,109,863; 3,433,461; 3,729,138; and 4,976,259, each of which is incorporated herein by reference in its entirety, including the references cited therein.

According to a preferred embodiment, a transducer(s) (10) and/or a transducer assembly (100) are placed in a chemically resistant housing (20) or other chemically resistant means to hold, holdfast, secure, and/or protect the transducer(s) (10). Certain metals and plastics have demonstrated high chemical resistance to various liquids. A chemical resistant seal or O-ring (herein "O-ring") (80) serves as a seal between the transducer assembly (100), and the liquid (30) in the reservoir (40). According to an embodiment, the O-ring (80) may be made of any chemically resistant material depending upon the composition of the liquid (30) utilized, preferably Viton®. The preferred material has the highest chemical resistance to the liquid used.

In each of the embodiments shown in FIGS. 2-5, the transducer assembly (100), including the transducer(s) (10) and the protective barrier (60), is enclosed or packaged in, assembled with, or coupled with, a housing (20). According to an embodiment, the housing (20) may be a hermetically or non-hermetically sealed or unsealed housing, or other hermetically or non-hermetically sealed or unsealed means to hold, holdfast, secure, and/or protect transducer(s) 10, that is either interfaced with the reservoir (40), or mounted to or in the reservoir (40), or positioned within the reservoir (40), or preferably coupled or attached to the bottom wall of the reservoir (40). According to an embodiment, a sealed interface exists between the protective barrier (60) and/or the housing (20) or means to hold, holdfast, secure, and/or protect the transducer(s) (10).

Figure 2:
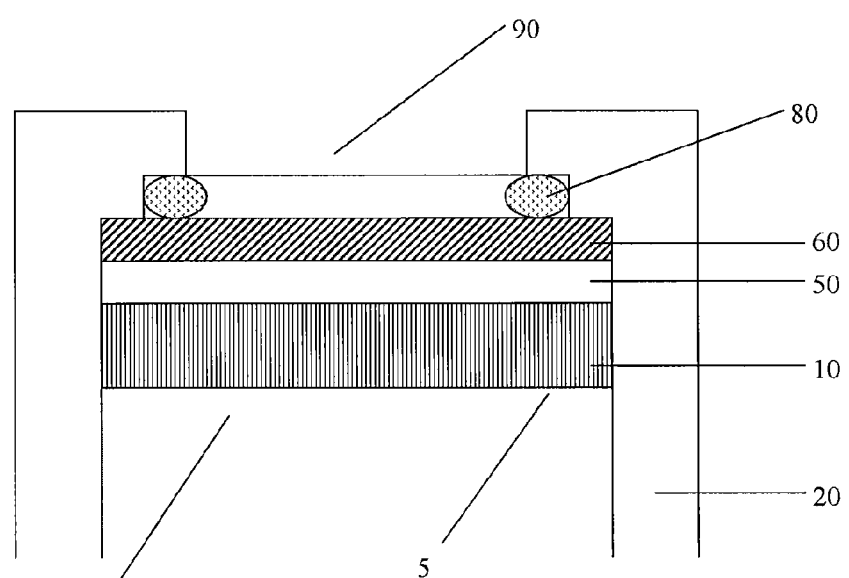
FIG. 2 is a schematic view of an embodiment of a transducer assembly comprising a housing, a transducer, and a protective O-ring interface, wherein a protective barrier is applied to the side of a transducer that faces a liquid.
Figure 3:
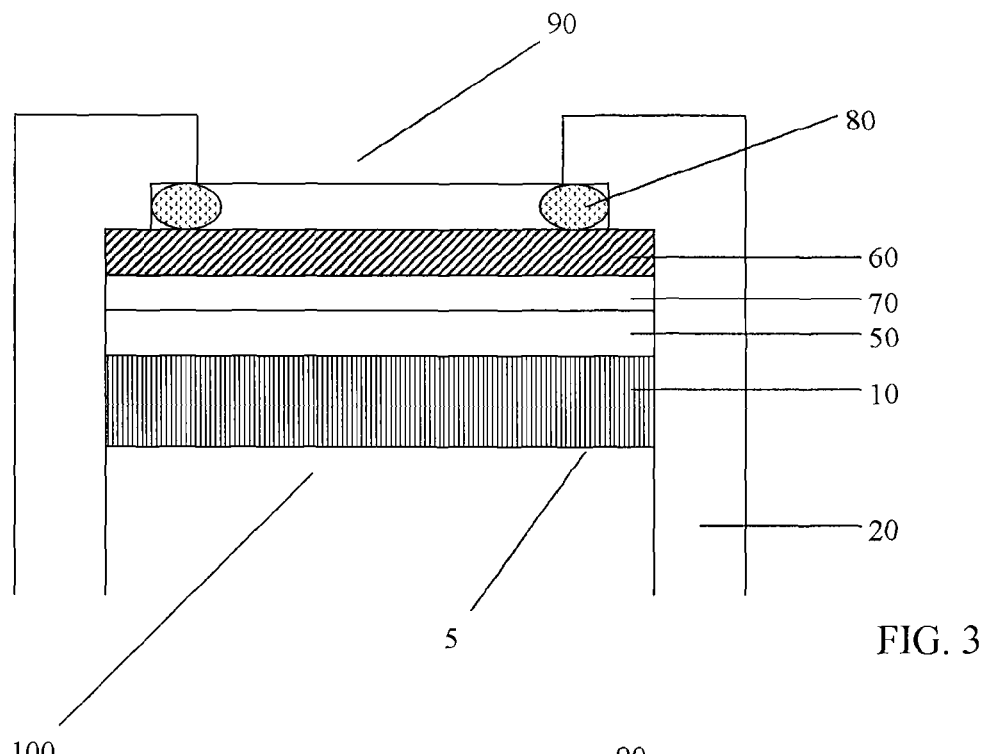
FIG. 3 is a schematic view of an embodiment of a transducer assembly comprising a housing, a transducer coupled with a protective barrier such as a pane, plate, or sheet of glass or other material, and a protective interface above the protective barrier.
Figure 4:
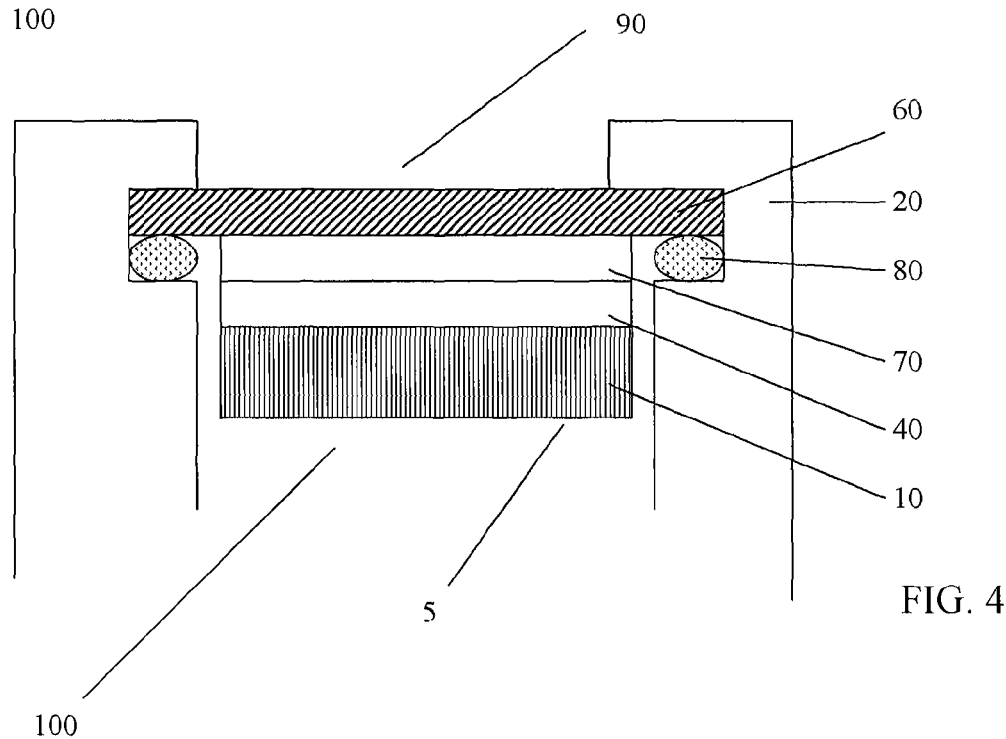
FIG. 4 is a schematic view of an embodiment of a transducer assembly comprising a housing, a transducer coupled with a protective barrier, and a protective seal below the protective barrier.

In one embodiment, see FIGS. 2 and 3, the O-ring seal (80) seals the interface between the protective barrier (60) and the open upper end (90) of the housing (20). In FIG. 4, the O-ring seal (80) is positioned below the protective barrier (60).

Figure 5A:
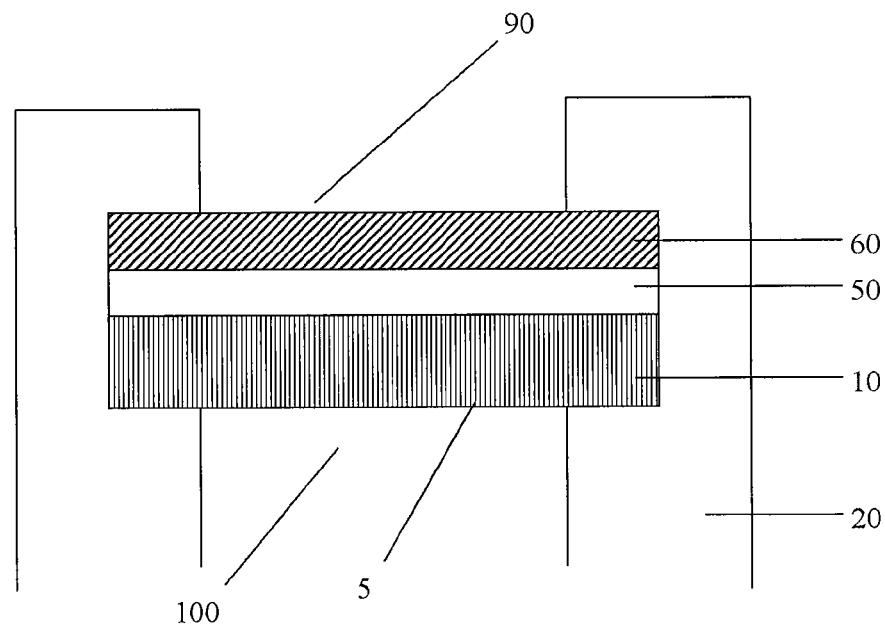
FIG. 5a and b are a schematic views of embodiments of a transducer assembly according to the present invention.
Figure 5B:
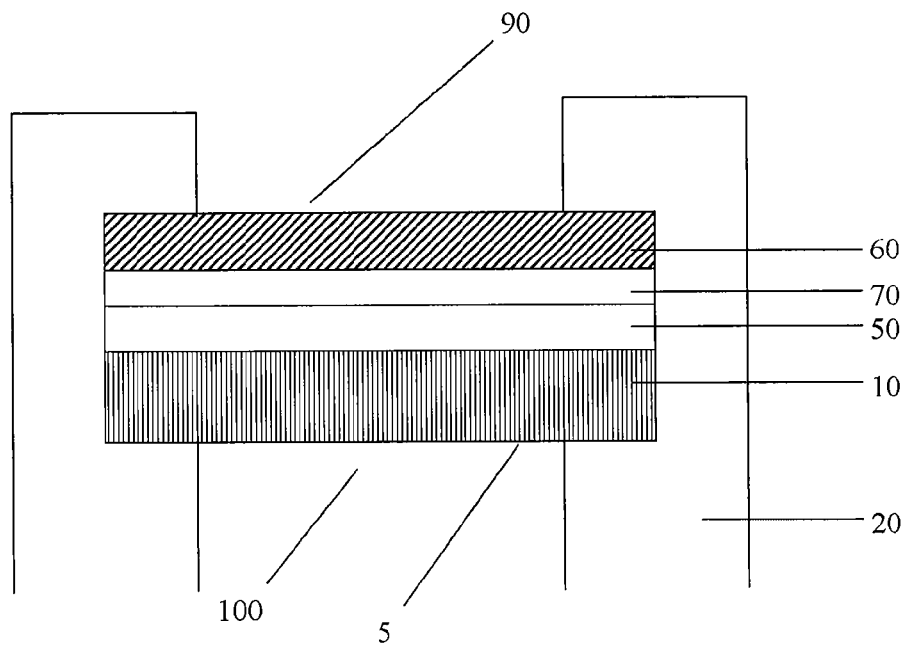
Figure 6:
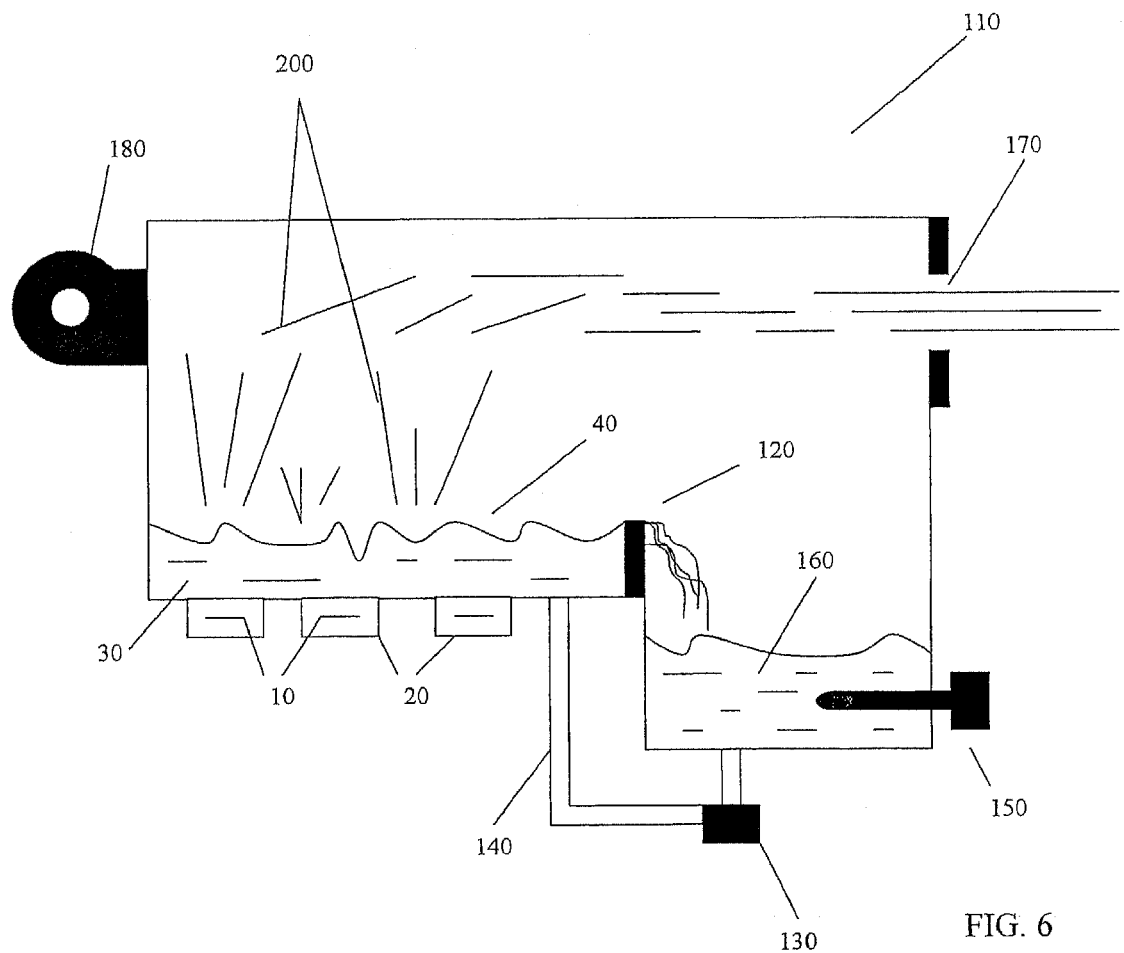
FIG. 6 is a schematic view of an embodiment of an aerosol generator according to the present invention.

In FIGS. 5a and 5b, the transducer(s) 10 and the protective barrier (60), where the protective barrier (60) is formed and/or assembled by method (1) or (2), is molded, thermoformed, cemented, adhered, or otherwise interfaced with/to the reservoir (40), or the housing (20) or other means to hold, holdfast, secure, and/or protect the transducer(s) (10), which establishes an effective seal between the interfacing materials. Other methods known in the art can also be used to establish this interface. In an another embodiment, the surfaces within the reservoir (40), or other surfaces to which the transducer assembly (100) is coupled, interfaced, connected, or mounted, may also act or function as the housing (20) and FIGS. 2-4 are also applicable in this capacity. Finally, a sealed interface may also exist between the housing (20) or the means to hold, holdfast, secure, and/or protect the transducer(s) (10), and a wall of the reservoir (40), or other surface(s) with which it interfaces.

According to an embodiment, it is preferred that with both protective barrier (60) methods (1) and (2), when glass is used, the glass type used may be of any acid and/or alkaline resistant glass such as, for example, quartz, or Type I (borosilicate glass or Pyrex) or Type II glass as defined by the United States Pharmacopoeia. The protective barrier (60) may be any chemically resistant material. Preferably, the protective barrier (60) has a high chemical resistance to the liquid (30) used.

The selection of a material for either of the two protective barrier (60) assemblies and methods is further determined by the material's impedance properties according to known wave transmission theories. In other words, some materials are better at transmitting pressure (energy) than others. This correlates directly with the efficiency and effectiveness of the transducer(s) (10) and is represented by the maximum amount of aerosol (200) generated by the aerosol generating system (110) per unit of time. In order to maximize the energy transfer into the liquid (30), transmission coefficients for various protective barrier (60) materials are calculated by means of known mathematical formulas pertaining to the various theories of wave transmission known to those of skill in the art. The transmission coefficients are calculated and then compared and the highest transmission coefficient is chosen. Generally, the higher the energy transmitted through the protective barrier (60), the higher the aerosol (200) output. In addition, the higher the frequency, the smaller the particles. According to an embodiment, good wave transmission is achieved through the use of a quartz glass or a borosilicate glass protective barrier (60).

The thickness of the material of the protective barrier (60) is another factor that influences the efficiency and effectiveness of the transducer(s) (10) or the total amount of or size of aerosol (200) the transducer(s) (10) is able to generate. This relates to the fact that operational frequencies will dictate selected glass thicknesses, thinner glass being selected with higher frequencies. These higher operational frequencies produce smaller droplet sizes. In the first protective barrier method, the protective barrier (60) is either formed or applied to the proper thickness. If the thickness of the protective barrier (60) is not within specifications, the protective barrier (60) may be further processed or machined to achieve the proper thickness. The second protective barrier method involves adhering, or otherwise connecting the protective barrier (60), which may be processed or machined to the proper thickness, with the transducer(s) (10). In both methods, the thickness of the protective barrier (60) is controlled to tight tolerances in order to control its transmission coefficient.

It was thought in the prior art that the optimum protective barrier thickness was equal to or about one-half (½) or any multiple of one-half (½) of the wavelength of the transmitted pressure (energy) wave. According to the prior art, at this thickness, the protective barrier material looks acoustically invisible and roughly twenty percent (20%) of the energy emitted from the transducers is being transmitted into the liquid beyond the protective barrier.

However, according to an embodiment of the present invention, it has been found that the transmission of energy through a material can be further optimized or enhanced if the thickness of that material, is between about 0.001 inches and about 0.125 inches, wherein the thickness is not n/2 or about n/2 of the wavelength of a transmitted pressure (energy) that is generated by the transducer(s) (10), wherein n is any integer. Without being limited to the mechanism, it is believed that roughly seventy percent (70%) of the energy emitted from the transducers (10) may be transmitted into the liquid (30) beyond the protective barrier (60) with the thicknesses of the present invention, which is significantly higher than the 20% emitted from the protective barrier (60) with a prior art thickness of one-half (½) or any multiple of ½ the wavelength. Without being limited to the mechanism of action, the material of the protective barrier (60) may actually maximize the transmission coefficient of the pressure (energy) and thus increase the efficiency and effectiveness of the aerosol (200) output of the transducer(s) (10), in addition to protecting the electrode material. A preferred material of the protective barrier (60) may be glass, more preferably quartz glass.

Based upon an embodiment, the invention gave rise to unexpected results, including, but not limited to a significant increase in aerosol (200) output, smaller aerosol (200) particle size, and more energy being transferred to the liquid (30). Additionally, in an embodiment of the apparatus and methods of protecting a transducer(s) (10), a cooling system to prevent the transducer(s) (10) from burning or otherwise failing at various operating frequencies is not necessary. For example, U.S. Pat. No. 4,109,863, which is incorporated herein by reference in its entirety, including the references cited therein, requires a means for circulating a fluid over the transducer and glass for cooling and stabilizing a transducer. However, according to U.S. Pat. No. 4,976,259, this method has the undesirable effect of acoustically dampening the back side of the transducer which reduces the efficiency of the nebulizer system.

When calculating the optimum thickness of the protective barrier (60) in an embodiment of the present invention, the following are considered: (1) operating frequency; (2) the specific natural frequency of the transducer(s) (10); (3) the type of protective barrier (60) material; (4) the thickness of the protective barrier (60); (5) optionally, a suitable adhesive/bonding agent (70); and (6) an acceptable and optimum level of aerosol (200) by sweeping the transducer assembly (100) with a range of frequencies and power to find the desired aerosol (200) output.

According to an embodiment, once the transducer assembly (100) is assembled it can be operated at a range of frequencies. The thickness of the protective barrier (60) may range depending upon the operating frequency of the transducer(s) (10). According to an embodiment, the thickness of the protective barrier (60) ranges from about 0.001 inches to about 0.125 inches, wherein the thickness is not equal to or about n/2 of the wavelength of pressure (energy) generated by the transducer(s) (10) at a frequency between about 0.025 MHz and about 10 MHz, wherein n is any integer, preferably a thickness between about 0.026 inches and about 0.070 inches at a frequency between about 0.5 MHz and about 2.5 MHz, more preferably a thickness between about 0.030 inches and about 0.060 inches at a frequency between about 1.2 MHz and about 2.2 MHz, and even more preferably a thickness between about 0.029 inches and about 0.042 inches at a frequency between about 1.2 MHz and about 2.2 MHz.

Empirical testing for hydrogen peroxide and peroxyacetic acid in solution; and water determined that the transducer(s) (10) generated the greatest amount of aerosol (200) when the liquid (30) above them was maintained at a temperature above about 80° F., preferably about 105° F. This is most likely due to the reduction of the surface tension of the liquid (30) as its temperature increases.

According to an embodiment, the liquid (30) may not have to be at least 80° F. for effective performance in certain circumstances where high aerosol output is not necessary, or the liquid already has a low enough surface tension to achieve a desired result. Further, according to an embodiment, any variations in the temperature may be made to optimize the aerosol (200) output based upon the type of liquid (30) used and the results desired by the user.

According to an embodiment, a protective barrier (60) for an aerosol (200) producing transducer(s) (10) has a thickness between about 0.001 inches and 0.125 inches, wherein the thickness is other than equal to or about n/2 of the wavelength of the transmitted pressure (energy) waves that are generated by the transducer(s) (10), wherein n is any integer. Thus, the thickness of the protective barrier (60) as described above permits the transducer(s) (10) to operate effectively to provide a high volume small aerosol (200) particle output, which is preferred, or any other desired output without the need for space between the transducer(s) (10) and the protective barrier (60) or a cooling mechanism.

Most preferably, in accordance with one aspect of the present invention, it has been found that the transmission of energy through a material can also be optimized if the thickness of that material, in this case glass, is about one quarter (¼) or any multiple of one quarter (¼) of the wavelength of the transmitted pressure waves generated at the natural resonant frequency of the transducer. The barrier material in this case will not only look acoustically invisible but will also maximize the transmission coefficient of the pressure waves and thus increase the efficiency and effectiveness of the transducer's aerosol output. The gain in power transmission for a particular transducer can, without limitation, increase from approximately 20%, for a barrier sized at one half (½) of the wavelength of the transmitted pressure waves generated by the transducer at the natural resonant frequency of the transducer, to approximately 71% for a barrier sized at one quarter (¼) of the wavelength of the transmitted pressure waves generated by the same transducer at the natural resonant frequency of that transducer.

Testing was conducted in the laboratory to determine what glass thickness when adhered to the transducer would generate the maximum amount of aerosol. Transducers with an adhered quartz glass thickness of 0.096 inch and 0.125 inch were tested first, and both suffered damage when the heat from operating the transducer burned the epoxy, which is used to adhere the glass to the transducer. This was evidence that a thinner glass material was needed in order to, without limitation, more effectively transmit the energy and heat produced by the transducer into the liquid above the glass. A quartz glass barrier of about ¼ wave length of the propagated pressure wave for a 1.5 Mhz transducer, or 0.036 inch, was manufactured, and its output greatly exceeded the target of 800 milliliters of aerosolized liquid per hour with an average output of 1500 milliliters per hour, as shown in the data in Table 1, along with data illustrating the effectiveness of barriers having other thicknesses with the 1.5 Mhz transducer.

TABLE 1

Experimental Data

| Frequency (Mhz) | Wavelength | Protective Barrier Thickness (inches) | Aerosol Results: Output Observations/Volumes (ml/hr) |
|---|---|---|---|
| 1.87 | 0.311 | 0.036 | 2138 ml per hr |
| 1.85 | 0.308 | 0.036 | 1769 ml per hr |
| 1.86 | 0.309 | 0.036 | 2064 ml per hr |
| 1.89 | 0.314 | 0.036 | 1622 ml per hr |
| 1.89 | 0.314 | 0.036 | 1843 ml per hr |
| 1.88 | 0.313 | 0.036 | 0 ml per hr; transducer burned |
| 1.90 | 0.316 | 0.036 | 1460 ml per hr |
| 1.84 | 0.306 | 0.036 | 1695 ml per hr |
| 1.85 | 0.308 | 0.036 | 1500 ml per hr |

TABLE 1-continued

Experimental Data

| Frequency (Mhz) | Wavelength | Protective Barrier Thickness (inches) | Aerosol Results: Output Observations/Volumes (ml/hr) |
|---|---|---|---|
| 1.86 | 0.309 | 0.036 | 1825 ml per hr |
| 1.89 | 0.314 | 0.036 | 1870 ml per hr |
| 1.90 | 0.316 | 0.036 | 1550 ml per hr |
| 1.90 | 0.316 | 0.036 | 1550 ml per hr |
| 2.11 | 0.283 | 0.029 | Est. <500 ml per hr |
| 1.83 | 0.338 | 0.040 | 1971 ml per hr |
| 1.81 | 0.334 | 0.040 | 2138 ml per hr |
| 1.83 | 0.338 | 0.040 | 2005 ml per hr |
| 1.68 | 0.388 | 0.050 | 1769 ml per hr |
| 1.91 | 0.847 | 0.096 | 0 ml per hr; transducer burned |
| 1.58 | 0.912 | 0.125 | 0 ml per hr |
| 1.59 | 0.918 | 0.125 | 0 ml per hr |
| 1.88 | 0.313 | 0.036 | 0 ml per hr; transducer burned |
| 1.90 | 0.316 | 0.036 | 1900 ml per hr; amplifier issue - ran hot |
| 1.80 | 0.299 | 0.036 | 0 ml per hr; transducer burned |
| 1.82 | 0.303 | 0.036 | 0 ml per hr; lens may have been cracked |
| 1.71 | 0.355 | 0.045 | 0 ml per hr |
| 1.74 | 0.362 | 0.045 | 0 ml per hr |

As a result of this testing, it has recently been determined that the transducer incorporating the barrier provides the best results when the thickness is calculated as a multiple of about n/4 of the wavelength of the natural resonant frequency (unloaded in air) of the transducer. The transducer including the barrier having this calculated thickness must also be operated at an operational frequency that is greater than the natural resonant frequency of the transducer by between about 4% and about 60% of the natural resonant frequency of the transducer. This calculation of the barrier thickness and the resulting operational frequency to optimize the aerosol generation by the transducer can be utilized for transducers having natural resonant frequencies in the range of 0.5 Mhz to 8.0 Mhz.

Further empirical testing in the laboratory for a particular transducer also determined that the actual effective range of glass thickness for aerosol output of a transducer having a natural resonant frequency of 1.5 Mhz was minus 0.010 inches and plus 0.024 inches, from 0.036 inches, or the calculated barrier thickness of one quarter (¼) of the wavelength of the transmitted pressure waves from the 1.5 Mhz transducer. It was also found that this asymmetrical range is, without limitation, strongly correlated with the admittance vs. frequency sweeps for transducers with glass barriers of this type. These sweeps include, but are not limited to, showing two distinct and separate peaks or amplitudes that both exhibit a curve that has a pronounced or sharp drop to the right of each amplitude. Thus, the operation and effectiveness of the aerosol generator including the transducer (10) including the barrier (60) can also be increased by utilizing a barrier having a thickness in this range above and below the calculated barrier thickness at approximately n/4 for the wavelength of the transducer at its natural resonant frequency.

Also, empirical testing determined that the transducers generated the greatest amount of aerosol when the liquid above them was maintained at a temperature above 80 degree Fahrenheit. This is most likely due to the reduction of the liquid's surface tension as its temperature increases.

Therefore, in the present invention the optimum glass barrier thickness for the aerosol producing transducer, is approximately one quarter (¼) or approximately any multiple of one quarter (e.g., 0.5/4, 1/4, 1.5/4, 2.5/4, 3/4, 3.5/4, 5/4 ... or n/4 where n=about any odd number, or the result of any mathematical operation) but not equal or about equal to any multiple of n/2 of the wavelength of the transmitted pressure waves from the transducer as calculated by the formula:

$$\lambda(\text{wavelength}) = \frac{c(\text{speed of sound in the selected material})}{f(\text{natural resonance frequency})}$$

when the transducer is operated at an operation frequency of up to 60% above, preferably between 4% and 60% above, more preferably between 9% and 50% above or about 10% to about 45% above, and most preferably between about 18% and 27% above the natural resonant frequency of the transducer.

Additionally, the transducer can be constructed with a barrier within a range of minus 0.010 inches (−0.010 inches) and plus 0.024 inches (+0.024 inches) from the calculated optimum barrier thickness, where the n/4 multiple of the wavelength is not equal to or approximately equal to any multiple of one half (½) of a wavelength. These methods in their entirety can be used with any transducer with a natural resonant frequency, unloaded in air, between 0.5 MHz to 8.0 MHz.

Specifically, maximum aerosol output is achieved with a glass thickness within the range of minus (−) 0.010 inches and plus (+) 0.024 inches, from the optimum thickness calculated as the multiple of n/4 of the wavelength of the transmitted pressure waves, with this multiple more preferably being a multiple where n=an odd number (i.e., 1, 3, 5, 7, 9, etc.) and where n/4 is not equal to any multiple of n/2. More preferably, n is from 1 to 9. In a particularly preferred embodiment, the calculated glass barrier thickness is 0.036 inches (0.036-0.010 to 0.036+0.024 inches).

In a preferred embodiment, the transducers utilized with the barriers having these thicknesses have a natural resonant frequency, unloaded in air, between 1.25 to 1.65 MHz and their operating frequency range in liquid is between 1.71 to 2.00 MHz.

In one embodiment, the liquid depth above the transducers can range from 0.5 to 5.0 inches. In addition the liquid in the tank above the transducers should be maintained at a temperature of 80 degree Fahrenheit or greater in order to maximize the amount of aerosol that is generated.

When utilizing a barrier (60) having a thickness in this calculated range, the transmission of energy from the transducer (10) through the barrier (60) to the liquid (30) is increased from around 20% to around 70%. This increased transmission percentage greatly reduces the degradation of the bond formed by the adhesive (70) binding the barrier (60) to the transducer (10), allowing the adhesive (70) to hold the barrier (60) in place during operation of the transducer (10).

According to an embodiment, many depths of the liquid (30) above the transducer(s) (10) may be used; preferably the depth of the liquid (30) above the transducer(s) (10) is from about 0.25 inches to about 8.0 inches, and more preferably a depth of about 1.25 inches. However, it may be possible to operate the invention at levels below 0.25 inches if lower power and/or frequencies are used. Moreover, according to an embodiment, the liquid (30) may be maintained at any temperature necessary to achieve the desired results based upon the preferences of the user or the type of liquid used. Preferably any liquid (30), such as peroxyacetic acid and hydrogen peroxide, in the reservoir (40) may be maintained at a temperature of about 80° F. or greater in order to maximize the amount of aerosol (200) that is generated. However, the temperature of the liquid (30) may vary depending upon such parameters as the desired aerosol (200) output, the type of liquid (30) used, and the surface tension of the liquid (30).

Referring to FIGS. 6-15, there are shown embodiments of an aerosol generator (110) according to the present invention. The reservoir (40) contains a volume of liquid (30), the level of which is controlled by a dam (or weir gate) (120) operatively associated with a supply pump (130) and a supply line (140) to maintain the level of the liquid (30) at a preferred level above the transducer(s) (10) mounted on the bottom wall of the reservoir (40). The transducer(s) (10) may be individually mounted in separate housings (20), as shown in one of the embodiments of FIGS. 2-4, or they may all be coupled to a common protective barrier (60) wall and appropriately sealed from contact with the liquid (30). It has been found that efficiency of aerosol (200) generation is enhanced by heating the liquid (30) to at least 20° F. above ambient, preferably to at least about 80° F.; however the temperature may vary depending upon the type of liquid (30) used. A heater element (150) is coupled with a liquid supply sump (160) to control the temperature of the liquid (30). The aerosolized liquid (200) is delivered to the space to be treated via an exit orifice (170) of the aerosol generator (110) to which suitable piping (not shown) may be attached for delivery. A blower (180), fan, or other source of pressurized air generates the air flow necessary to deliver the aerosol (200), all in a manner well-known in the art.

According to an embodiment, the transducer(s) (10) and the protective barrier (60) may be sized to provide an optimized resonant frequency that is operative when driven or operated at an operating frequency in the range of about 0.5 MHz to about 2.5 MHz. This large range is due to the appearance of two separate operating ranges that are apparently unique to the transducer assembly (100). For example, using a transducer(s) (10) having a resonant frequency of about 1.40 MHz to about 1.48 MHz with a protective barrier (60) thickness of about 0.036 inches, driven at an operating frequency ranging from about 1.78 MHz to about 1.98 MHz will most commonly show a maximized aerosol (200) output of at least about 1,000 ml per hour of the liquid (30). A second effective operating frequency with lower output is noted at about 1.2 MHz. According to an embodiment, for certain applications where the volume of the space to be treated is small, an output of at least 1,000 ml/hr may not be necessary. In such a situation, the transducer(s) (10) may be operated or driven with various combinations of power or volts peak to peak, and frequencies that result in the generation of lower aerosolized (200) liquid output. For example, in the treatment of a space the size of about a small glove box or the like, an output of 10 ml/hr or less may be adequate.

The apparatus and methods of the present invention may yield aerosol (200) droplets of various sizes. According to an embodiment, they may yield aerosol (200) droplets with a defined size distribution of mostly less than about one (1) microns in diameter, without being limited to a mechanism it is believed this allows the droplets to behave more like a gas with respect to Brownian movement and diffusion. The size of the aerosol (200) droplets may be adjusted upward or downward according to the desired results. The small aerosol (200) droplet size enables the drops to penetrate small cracks and crevices, and apply very thin films on surfaces. In addition, the aerosol (200) may effectively reach and disinfect areas of contamination and areas of otherwise limited accessibility. Any means to create an aerosol (200) with droplets less than about 10 microns in size could be used in the present invention. Larger particles will by their nature cause less penetration and decrease the effectiveness for many but not all possible application. Thus, the present invention may generate predominantly submicron size droplets or sizes may be controlled for a desired result. According to an embodiment, the average particle size may range from less than one micron to about 10 microns, preferably less than about 5 microns, more preferably less than one micron, and even more preferably about 0.68 microns.

According to an embodiment, multiple transducer(s) (10) are typically used to provide an output volume of aerosolized liquid (200) sufficient to rapidly treat a large enclosed space. In such a case, the transducer(s) (10) may be mounted individually, or a plurality of transducer(s) (10) may be coupled to a single protective barrier (60), with one or more of the protective barrier (60) being coupled, mounted on or in a reservoir (40), or positioned within a reservoir (40) with an appropriate coupling device. Multiple transducer(s) (10) may be coupled to a single protective barrier (60) at varying distances apart, preferably between at least about 0.25 inches apart, more preferably about 0.75 inches apart.

Figure 7:
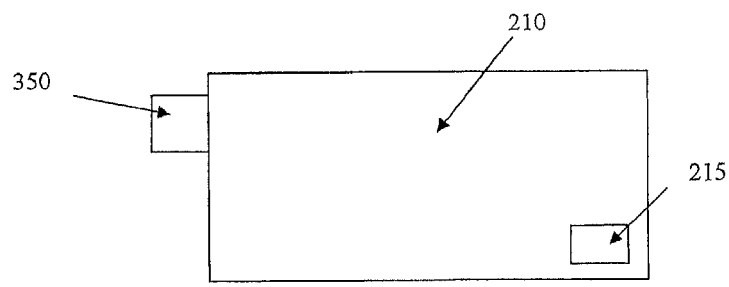
FIG. 7 is a schematic view of an embodiment of a targeted area(s) for administering the aerosol from the aerosol generating apparatus.
Figure 8:
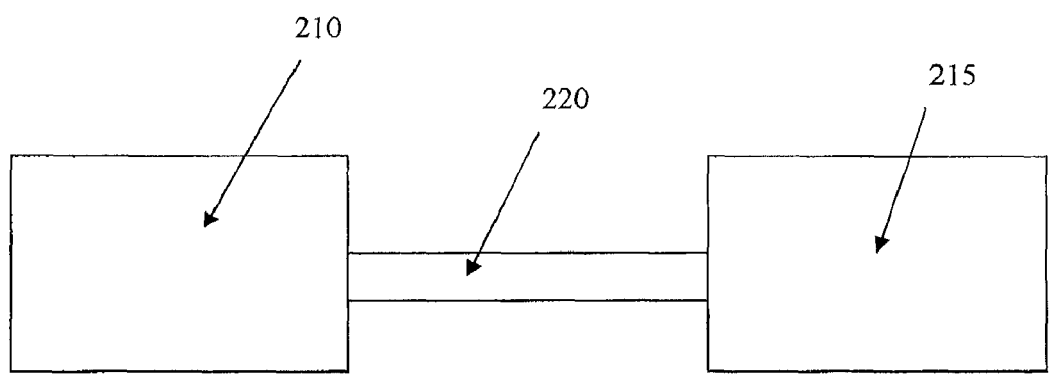
FIG. 8 is a schematic view of an embodiment of an aerosol generating apparatus connected to a targeted area(s) with a pipe through which aerosol can be administered.
Figure 9:
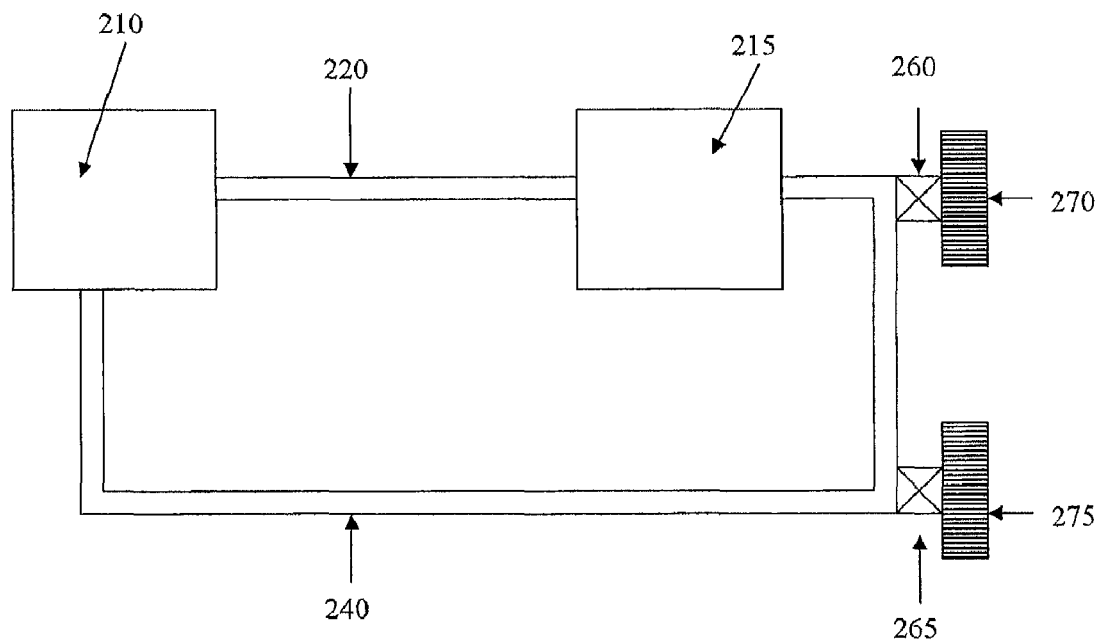
FIG. 9 is a schematic view of an embodiment of an aerosol generating apparatus connected to the targeted area(s) in a closed loop system.

The present invention includes apparatuses and methods related to the generation and delivery or application of an aerosol (200) of liquid (30) that is created with ultrasound or piezoelectric transducers (10), for a wide range of uses including but not limited to: (a) the sanitization, disinfection, high-level disinfection, or sterilization of one or more areas and the surfaces in those areas, (b) the delivery of other types of liquid (30) in the form of an aerosol (200) for various purposes, such as, but not limited to, the application of pesticides, moisture, medication, particles, or nano sized or smaller machines, to one or more areas and surfaces within those area(s). The attributes of the area to which the aerosol (200) is delivered or applied can vary and can include, but is not limited to: spaces that are open, enclosed, semi-enclosed, unsealed, sealed, or partially sealed. It is preferred, without limitation, that the area in which the aerosol is administered in the present invention is enclosed and effectively sealed to prevent the leakage of the aerosol from the enclosed area. Referring initially to FIGS. 7-9, the apparatus (215) can be operated either outside, partially inside and partially outside, or within the area in which the aerosol is deployed or administered.

Preferably and without limitation, an aerosol (200) of a liquid is first generated and/or administered in or into the intended or targeted area (210). This area can also, without limitation, contain one or more objects and surfaces. The aerosol (200) may have various mass concentrations, which is the mass of particulate matter in a unit volume of aerosol. The number concentration of the aerosol (200) may also vary. The number concentration is the number of particles per unit volume of aerosol. It is preferred without limitation, that the aerosol (200) has a higher rather than lower mass concentration of droplets. It is preferred without limitation, that the aerosol (200) has a higher rather than lower number concentration of droplets. The aerosol (200) droplets may be of various sizes. The aerosol may be created from any liquid containing one or more chemical(s) of any kind, or a combination of liquids each containing one or more of any kind of chemical(s).

According to an embodiment, it is preferred, without limitation, that the aerosol (200) is a ten micron to submicron size droplet. The fog or aerosol can, without limitation, consist substantially of submicron aerosolized droplets. The fog or aerosol can, without limitation, have characteristics that include but are not limited to (1) a faster anti-pathogen, toxin, fungal, sterilization, disinfection, or sporicidal effect than the non-aerosolized liquid; (2) the ability to penetrate and disinfect, high-level disinfect or sterilize, areas and surfaces where aerosols comprised of droplets greater than two microns may not work; (3) resists coalescence and condensation typical of larger size droplets; and/or (4) dense packing of small particles provides an unprecedented droplet surface area per volume of gas.

The apparatus and methods described in the present invention can pertain to any aerosol generator or aerosol generator that uses ultrasound or piezoelectric transducers (10). They may also pertain to an aerosol producing apparatus as described in the present invention, including the specifics of the present invention hereto mentioned. This apparatus is further described with the attributes discussed below. Referring to FIGS. 11-13, 16-32 and 35-36, which shows the preferred apparatus (215) in the present invention, the apparatus (215) generates aerosol (200) by operating one or more piezoelectric transducers (10), in parallel or series. One or more amplifiers (230) may be used. It is preferred, without limitation, that the transducer(s) (10) receive signal or power from at least one amplifier(s) (230), and that multiple transducers are operated in parallel. One or more transducers (10) are located under the surface of the liquid (30) in one or more reservoirs, chambers, basins, or tanks (40) (herein referred to as reservoir(s)) at an effective depth and orientation. The reservoir(s) (40) may be made from any material that is compatible, and suitable for use with the liquid (30). The aerosol (200) generated by operation of the transducer(s) (10) forms above the surface of the liquid (30) in the reservoir(s) (40) and may be transferred from the reservoir(s) (40) to one or more targeted area(s) or chamber(s) by one or more fan(s) or blower(s) or other source of pressurized air or gas (herein referred to as blower(s)) (180).

The air and aerosol (200) can, without limitation, flow from the aerosol generator (110) to the one or more targeted area(s) (210) through one or more pipe(s) (220). It is preferred, without limitation, that only one reservoir (40) in which the transducer(s) are located is utilized in the apparatus (215) of the present invention. The reservoir(s) (40) can be, without limitation, unenclosed, semi-enclosed, or enclosed. It is preferred, without limitation that an enclosed reservoir(s) is utilized, and is built in a manner known in the art so that air from a fan or blower can flow through it and carry the generated aerosol out of the reservoir and away from the apparatus (215).

The air and aerosol can flow through a zig-zag path or be directed around one or more baffle plates (250), positioned anywhere in the path of the air/aerosol as it moves from the reservoirs in which the transducers are located to the exterior of the apparatus (215). The use of the aforementioned baffle plate(s) is taught at (col. 4, line 18-22) of U.S. Pat. No. 4,366,125 (Kodera et al., 1980), which is incorporated herein by reference in its entirety, including any references cited therein.

If needed or desired, the apparatus (215) in the present invention can be connected in a closed loop or system as shown in FIG. 9, to the targeted area(s) or chamber(s) (210), as taught at (pg. 3 col. 23-34) of G.B. Patent No. 1,128,245, (Rosdahl et al., 1968), which is incorporated herein by reference in its entirety, including any references cited therein. The air and aerosol (200) discharged from the apparatus (215) in the present invention, can be delivered with one or more pipe(s) or conduit(s) (220). The air and aerosol (200) may also be recirculated through one or more return pipe(s) or conduit(s) (240) from the targeted area(s) or chamber(s) (210), back to the air/gas intake(s) (255) for the fan(s) or blower(s) (180). Throughout the present invention, the terms "pipe", "pipes", or "piping" includes pipes, ducts, conduits, tunnels, and the like. In addition, the aforementioned closed loop or system can have, without limitation, one or more air/gas valve(s) (260) that can allow non-filtered or filtered inbound air/gas into the said closed loop or system, as well as one or more air/gas valve(s) (265) that can allow non-filtered or filtered inbound air/gas out of the said closed loop or system. The air/gas that is supplied via the inbound air/gas valve(s) (260) can be supplied, without limitation, from the atmosphere surrounding the apparatus (215) and the air/gas that passes through the outbound air/gas valve can be, without limitation, vented into the atmosphere surrounding the apparatus (215). The filter(s) (265) can be or consist of any filter design, material, or other effective means for the intended application. The filter or its application can include, without limitation, what is taught in U.S. Pat. No. 4,512,951 (Koubek et al., 1983), and incorporated herein by reference in its entirety, including any references cited therein. The said air/gas valves (260) or (265) can, without limitation, be electronically or electrically opened and closed in a manner known to those skilled in the art, and can be positioned or interfaced in numerous places in the closed loop or system. The outbound air or aerosol can, without limitation, be filtered with one or more filters (270) to prevent any employees or operators from being exposed to any vented aerosol, and to comply with any worker safety or environmental safety guidelines or regulations.

The liquid capacity of the reservoir(s) (40) in which the transducer(s) (10) are located can vary, but the liquid level is at least at a suitable depth or level so that the transducer(s) (10) can effectively and safely operate. The reservoir(s) (40) in which the transducer(s) (10) are located is connected to one or more tanks(s) (280) that are connected and feed liquid to the reservoir(s) (40). The tank(s) (280) that feeds or supplies the liquid (30) can be of any size, geometry, shape, and capacity, and may be made from any material that is compatible, and suitable for use with the liquid (30). The tank(s) (280) may be non-ventilated, or ventilated in one or more places in a way know to those skilled in the art, and the means to ventilate the tank(s) (280) can incorporate a suitable filter. The filter(s) are any suitable filter for the intended application, and are known to those skilled in the art. It is preferred, without limitation, that the apparatus (215) in the present invention has only one tank (280) that feeds or supplies liquid to the reservoir (40) in which the transducer(s) (10) are located. However, a means known to those skilled in the art can be provided so that additional tanks (280) can be attached to or interfaced with the apparatus (215) and feed liquid to either the main feed or supply tank (280) or the reservoir(s) (40) in which the transducers (10) are located.

The one or more tank(s) (280), that feeds or supplies the liquid (30) to the reservoir(s) (40) in which the transducer(s) (10) are located, can be filled in various ways, including, but not limited to, directly pouring a liquid that is either mixed or unmixed into one or more feed interface(s) (285) or pipe(s) (295) that are connected to the said tank(s) (280). Without limitation, the feed interface(s) (285) or pipe(s) (295) orifices can have: (a) a funnel or be shaped like a funnel to make pouring the liquid (30) into the feed interface(s) (285) or pipe(s) orifices (295) easier, (b) a tray or bowl located under or around the outer edges of the feed interface(s) (285) or pipe(s) orifices (295) to catch any spilled liquid (30) in a manner known in the art. Without limitation, the apparatus (215) in the present invention can also be designed and constructed, in a manner that is known to those skilled in the art, so that it can interface with one or more disposable or reusable containers or cartridges (herein referred to as "cartridge", "cartridges", or "cartridge(s)") (290) used to supply, fill, or refill the apparatus (215) with liquid (30). Without being limited, the cartridges (290) and apparatus (215) can be designed in a manner known in the art, so that only unique, special, or proprietary cartridges (290) may be used. The means to interface the cartridge(s)s with the apparatus (215) so that the liquid is effectively and safely transferred from the cartridges (290) into the said reservoir(s) (40), is known to those skilled in the art.

The reservoir(s) (40) in which the transducer(s) (10) are located can also have one or more valves (300) that can, without limitation, control the flow of liquid (30) from the tank(s) (280) that feed or supply the said reservoir(s) (40). Without limitation, the valve(s) (300) can be connected to one or more sensor(s) (305) or PLC(s) (315) which are known to those skilled in the art, that can cause the valve(s) (300) to close or open and allow liquid (30) to flow into the reservoir(s) (40) in which the transducer(s) (10) are located when the liquid (30) level or depth in the reservoir(s) (40) reaches a specified level. The depth or level of the liquid (30) causing the valve (300) to open can vary. The sensor (305) can include, but is not limited to a float switch. The valve (300) can include, but is not limited to, a solenoid valve. However, it is preferred in the present invention that at least one float-valve is used, which consists of a valve (300) that is mechanically or electrically opened or closed by the movement of a float which acts as the sensor (305).

The reservoir(s) (40) in which the transducer(s) (10) are located, can have one or more float switch(s) or other sensor(s) (305) that can cause the apparatus (215), the PLC, (315), HMI (320), or any other parts or components, to enter a fault/error mode or completely shut down if the depth of the liquid (30) exceeds a certain specified depth or level. The float switch or other sensor(s) (305) is actuated and communicates or is connected to suitable circuitry, all in a way known to those skilled in the art, to cause the apparatus (215), the PLC, (315), HMI (320), or any other parts or components to shut down or enter a fault or error mode when the depth or level of liquid (30) exceeds a specified depth. The positioning of the float switch(s) or other sensor(s) (305) can vary inside the reservoir(s) (40). It is preferred in the present invention that at least one float switch (305) is utilized for this purpose.

A float switch or other liquid level sensor(s) (305) can also be used to detect and communicate or is connected to suitable circuitry, all in a way known to those skilled in the art, to cause the apparatus (215), the PLC, (315), HMI (320), or any other parts or components to shut down or enter a fault or error mode when the depth or level of liquid (30) drops below a certain point or depth in the reservoir(s) (40) in which the transducer(s) (10) are located. This can, without limitation, prevent the liquid (30) in the reservoir(s) (40) from dropping to an ineffective or unsafe depth or level. This condition may occur from situations including, but not limited to, a valve (300) that is stuck closed from a tank (280) that supplies the liquid, or a leaking tank. The positioning of the float switch(s) or other sensor(s) (305) can vary inside the reservoir(s) (40). It is preferred in the present invention that at least one float switch or liquid level sensor (305) is utilized for this purpose.

The fan or blower (180), or other source of pressurized air or gas, may also be constructed from any suitable material that is not affected by the chemical action of the liquid (30). Suitable materials may include PVC, polypropylene, and stainless steel, but other suitable materials may also be used. The blower(s) can either push or pull the air or gas, as well as aerosol, through, or across, the chamber, reservoir, or other area in which the aerosol is generated to remove it from the apparatus (215). The blower(s) (180) or other source of pressurized air or gas can move any quantity of air at any speed sufficient for the intended application. The blower(s) (180) can also be chosen, without limitation, to meet the following variables that include, but are not limited to: (a) the quantity of aerosol that is being generated, (b) the amount of surface disruption that it might create and its effect on aerosol production, (c) the desired quantity of aerosol that is evacuated from the apparatus (215), (d) the geometry and volume of the targeted area, (e) the geometry and volume of any conduit or piping that may be used to deliver the aerosol, (f) the manner and effectiveness in which the targeted area is sealed, (g) and uniformity of the aerosol (200) deployment or administration in or into the targeted area. Without limitation, the blower(s) (180) can be controlled by the PLC (315) in a manner known in the art.

Certain applications will require lower airflows, while other applications will require higher airflows. It is preferred, without limitation, that the blower (180) used in the present invention is a centrifugal fan or blower and that it is constructed using polypropylene for a housing and impeller, and 316L stainless steel for its drive shaft. It is further preferred, without limitation, that the fan or blower (180) pushes air/gas and aerosol out of the chamber, reservoir, or other area in which the aerosol is generated. The housing or enclosure for the blower(s) (180) can be plumbed to remove any excess liquid that may collect as the blower is operated. It is preferred, without limitation, that the housing or enclosure for the blower(s) (180) is plumbed in the present invention.

According to the prior art established by U.S. Pat. No. 4,366,125 (Kodera et al., 1980), and the book titled, "Aerosol Technology" by William C. Hinds (1982), the liquid (30) utilized in the present invention can be heated by using three different means, or a combination of one or more of the three different means. First, the liquid (30) can be heated inside the reservoir(s) (40) in which the transducers (10) are located, by utilizing one or more means to provide heat (150) that is either in direct contact with the liquid or interface with the walls of the reservoir(s) (40), or both. Second, the liquid (30) in the reservoir(s) in which the transducer(s) (10) are located can also be heated by circulating it through one or more means to heat (310) the liquid, and back into the reservoir(s) (40). Third, the liquid can be heated as it flows from one or more tank(s) (280), that feeds or supplies the liquid (30) to the reservoir(s) (40) in which the transducers (10) are located.

In addition, and without limitation, the one or more valves (300) that control the flow of the liquid (30) can be electrically or electronically signaled to open, close, or semi-open, in a manner known in the art. A pump or other means (130) can move the liquid (30) intermittently or can continuously circulate the liquid (30) from the reservoir(s) (40) in which the transducers (10) are located, back to the aforementioned tank(s) that feeds or supplies the liquid (30) to the reservoir(s) (40). Without being limited, the valves (300) in this situation can be maintained in a semi-open or open position unless signaled or caused by some other means including, but not limited to, an electrical signal from an electronic controller or programmable logic circuit (315), to close, for various reasons including, but not limited to, a pump (130) failure that would cause the reservoir(s) (40) in which the transducers (10) are located to overflow.

It is preferred, without limitation, that one or more means (150) for heating the liquid (30) is located inside or partially inside the reservoir(s) (40) in which the transducers (10) are located, and is installed into or interfaced with the said reservoir(s) (40) in a way that is known to those skilled in the art. It is further preferred, without limitation, that the said means for heating (150) the liquid (30) is a cartridge heater.

The three aforementioned means to heat the liquid (30) are known to those skilled in the art, and are sufficiently designed and built for their intended purpose, and may be constructed from any material that is compatible, and suitable for use with the liquid (30). Properly heating the liquid (30) to the desired, or efficacious temperature can involve issues such as, but not limited to, the type of heater(s) that would be effective, the number of heater(s) used, the heat output of each heater, the duration and timing of operation for each heater, the intensity of the heat generated, the materials of construction, and are known to those skilled in the art. In addition, the pump or other means (130) used to circulate the liquid (30) provides the necessary flow rate or pumping capacity, which can vary, for the intended application and may be constructed from any material that is compatible, and suitable for use with the liquid (30).

Figure 10:
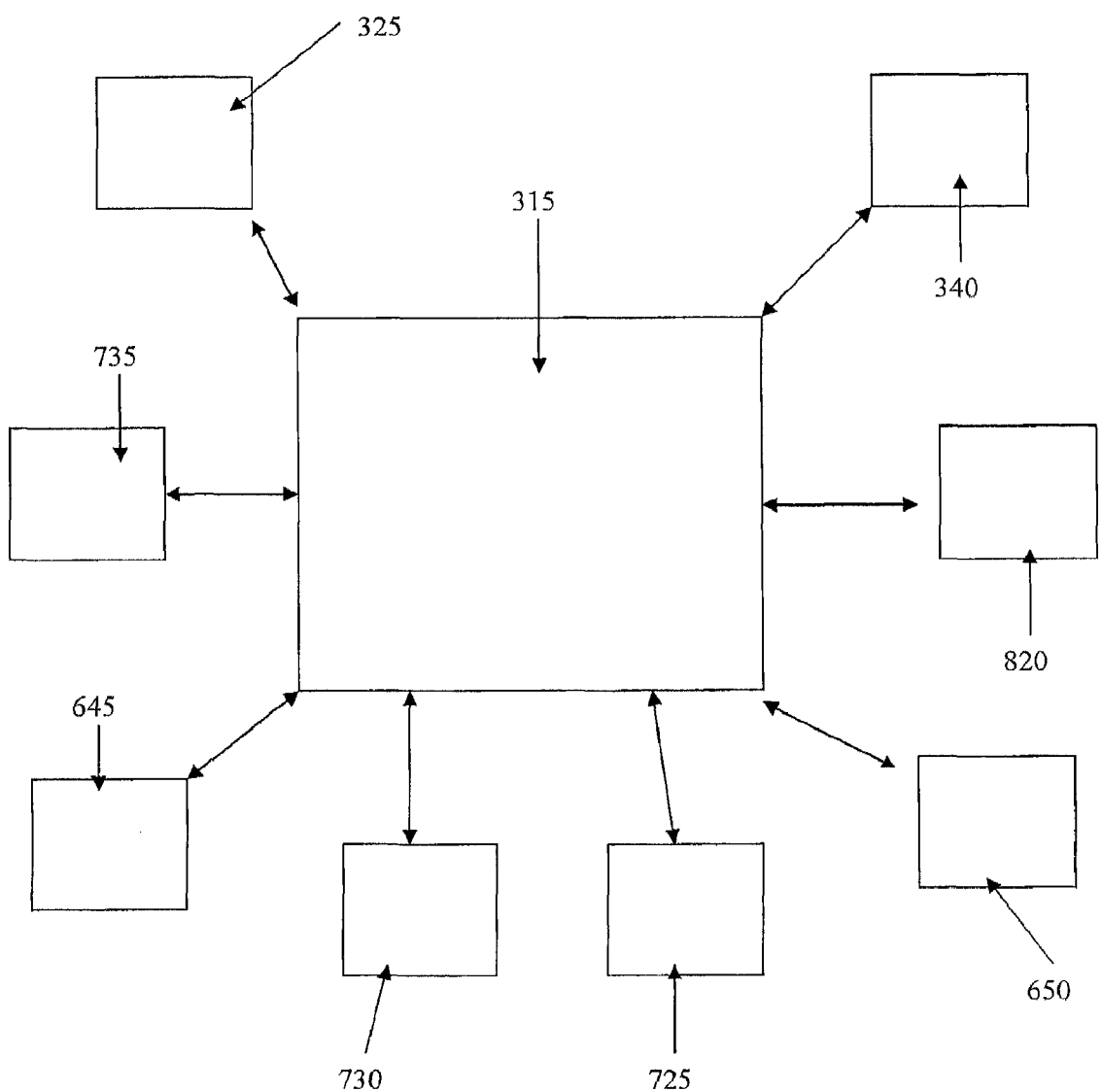
FIG. 10 is a schematic view of an embodiment of a PLC connected to various components of the aerosol generating apparatus.
Figure 11:
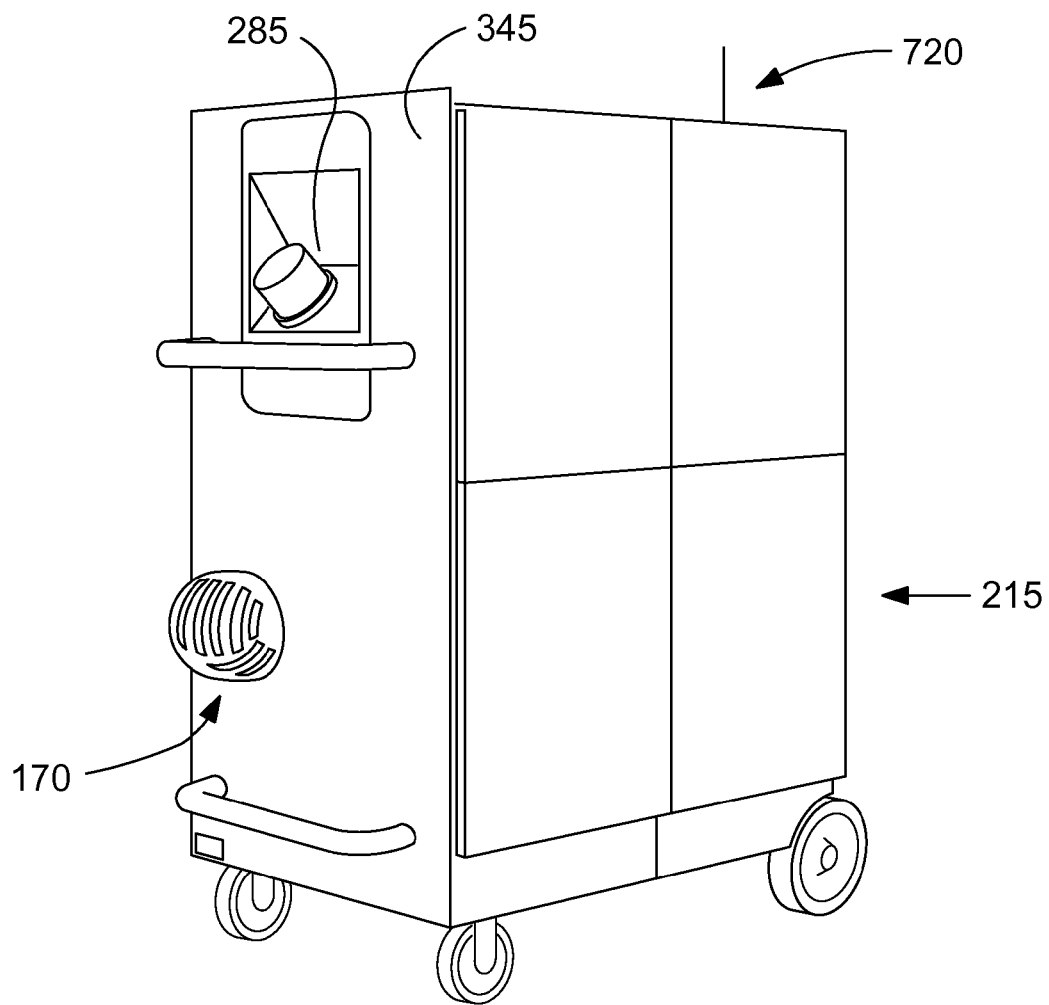
FIG. 11 is an isometric view of an embodiment of an aerosol generating apparatus according to the present invention.
Figure 12:
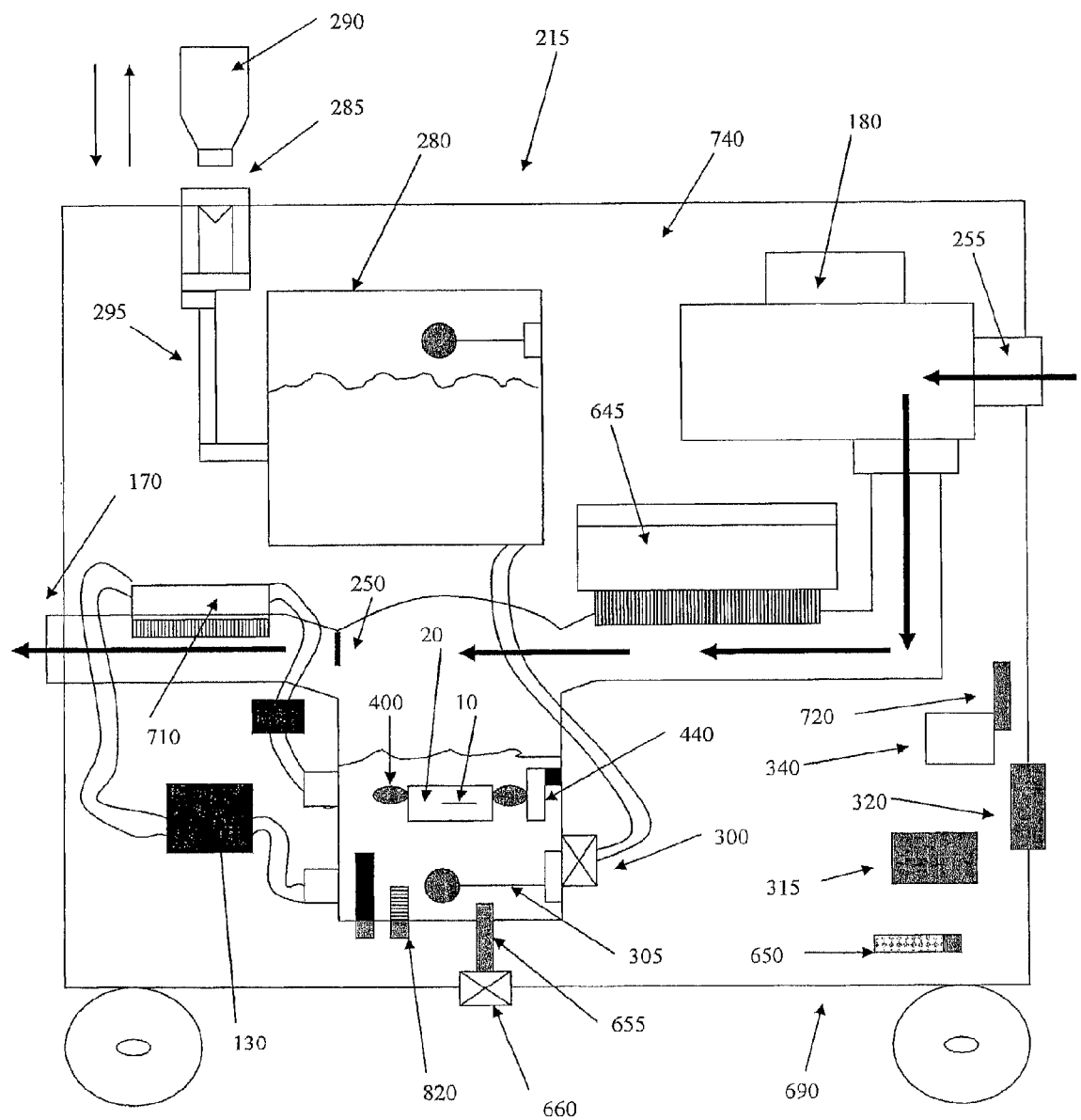
FIG. 12 is a schematic view of an embodiment of an aerosol generating apparatus according to the present invention.
Figure 13:
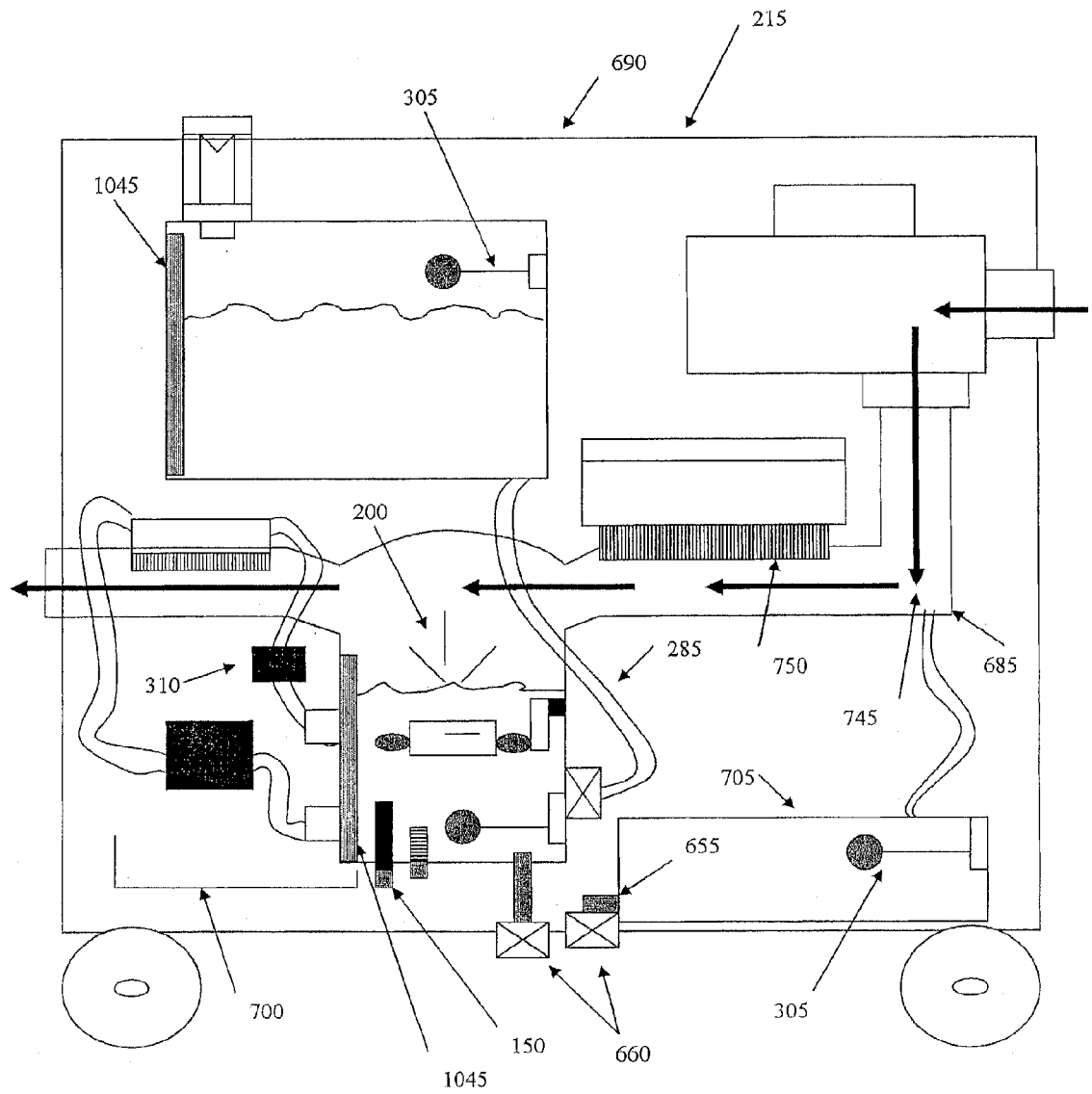
FIG. 13 is a schematic view of an embodiment of an aerosol generating apparatus according to the present invention.
Figure 14:
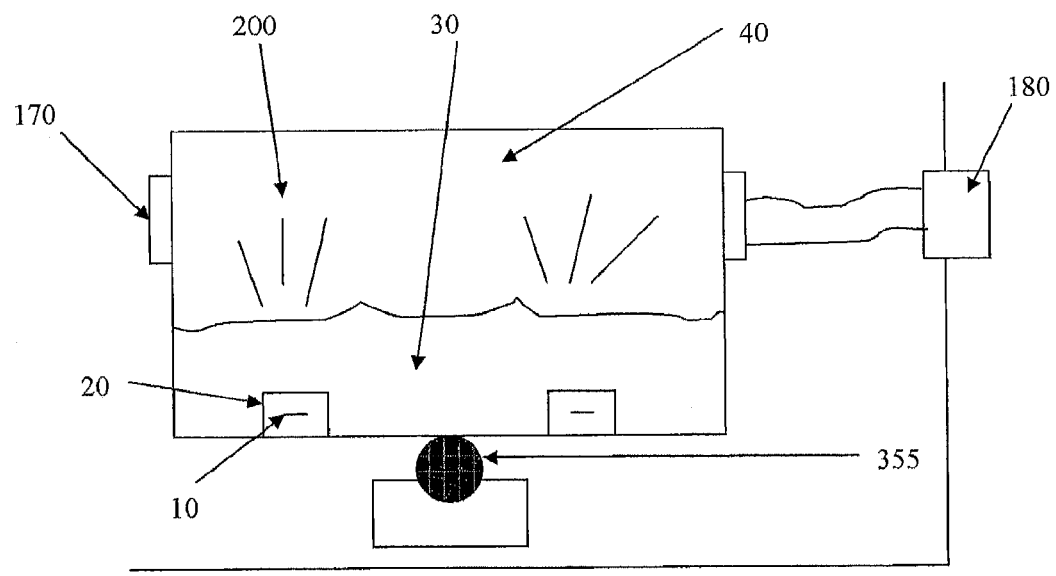
FIG. 14 is a schematic view of an embodiment of aerosol generating transducers attached to a reservoir that is connected to a means that can enable the transducers and/or their liquid facing surfaces to match the angle of or remain aligned with, the surface of the liquid above them.
Figure 15:
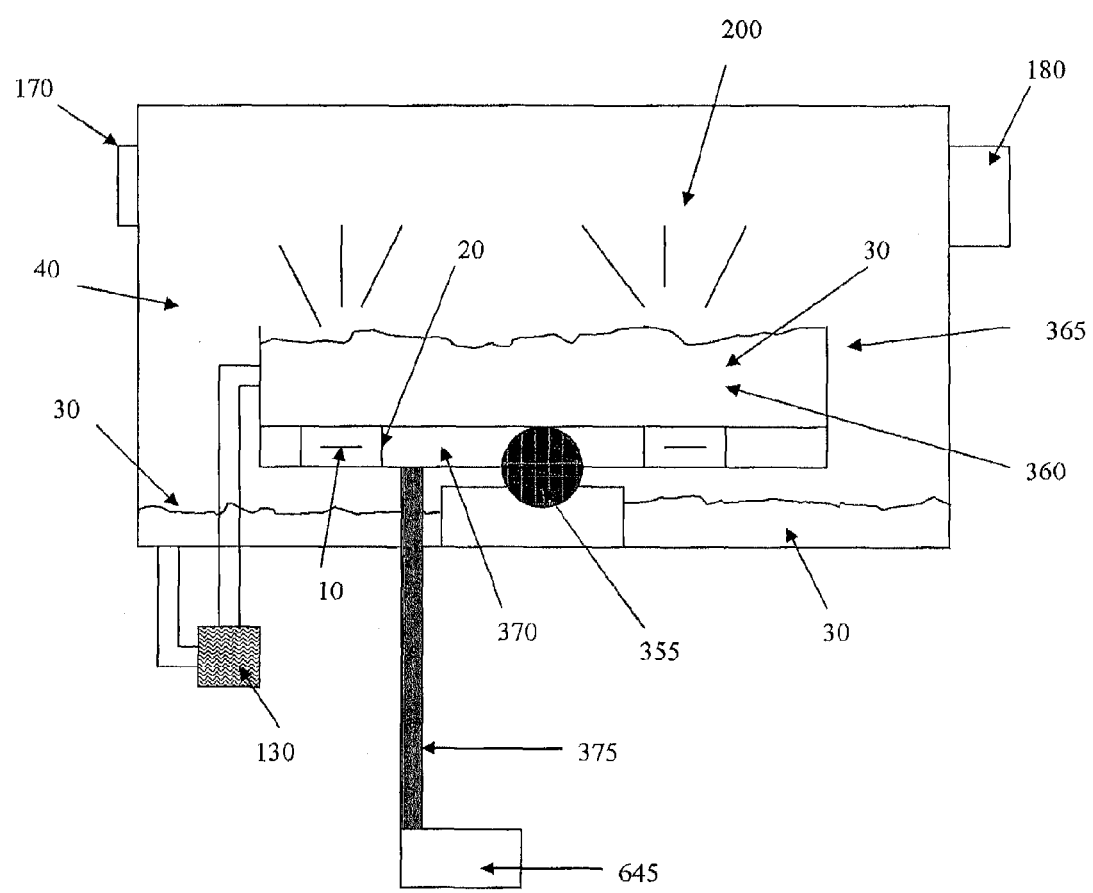
FIG. 15 is a schematic view of an embodiment of aerosol generating transducers attached to a secondary reservoir inside of a main reservoir and that is connected to a means that can enable the transducers and/or their liquid facing surfaces to match the angle of or remain aligned with, the surface of the liquid above them.
Figure 16:
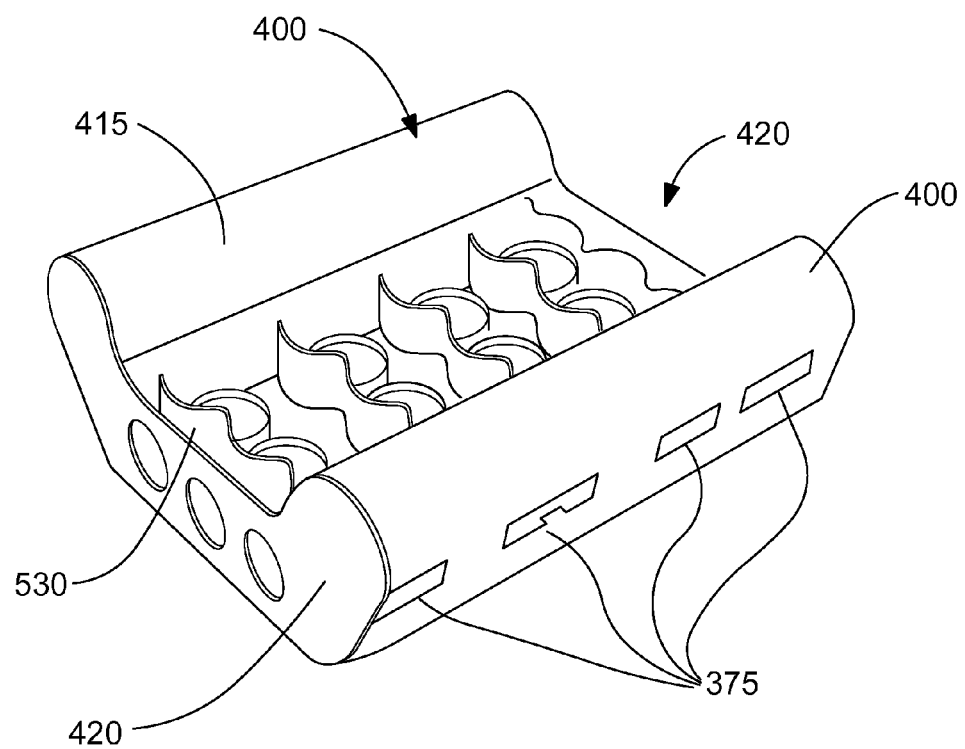
FIG. 16 is an isometric view of an embodiment of multiple transducers interfaced with multiple housings, and the housings are attached to multiple buoyant objects.
Figure 17:
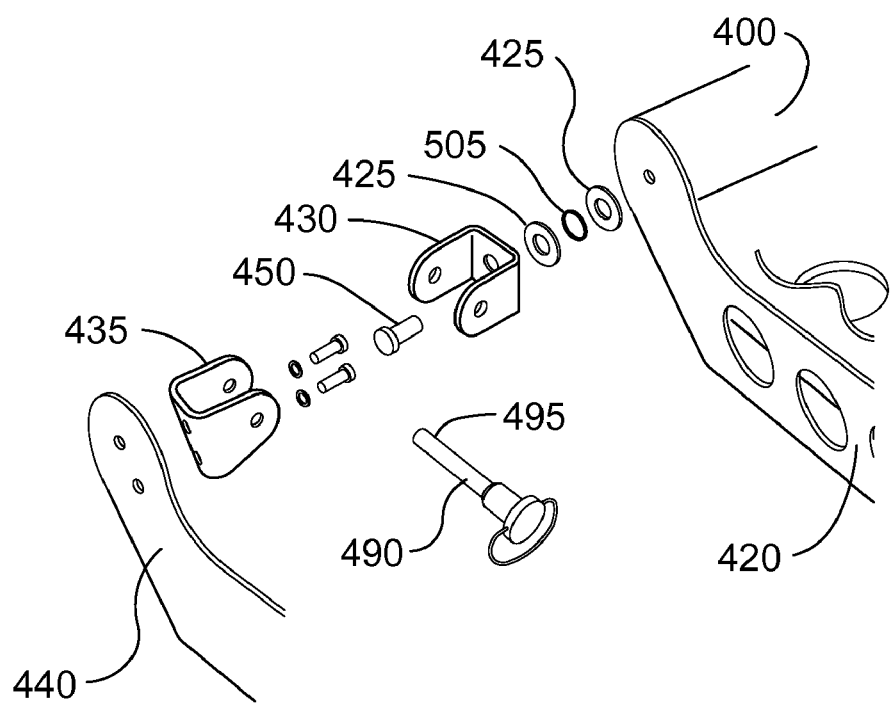
FIG. 17 is a partially broken away, exploded isometric view of an embodiment of more than one clevis assembly that allows various ranges of motion for various parts and components such as, the transducers, housings, and buoyant objects according to the present invention.
Figure 18:
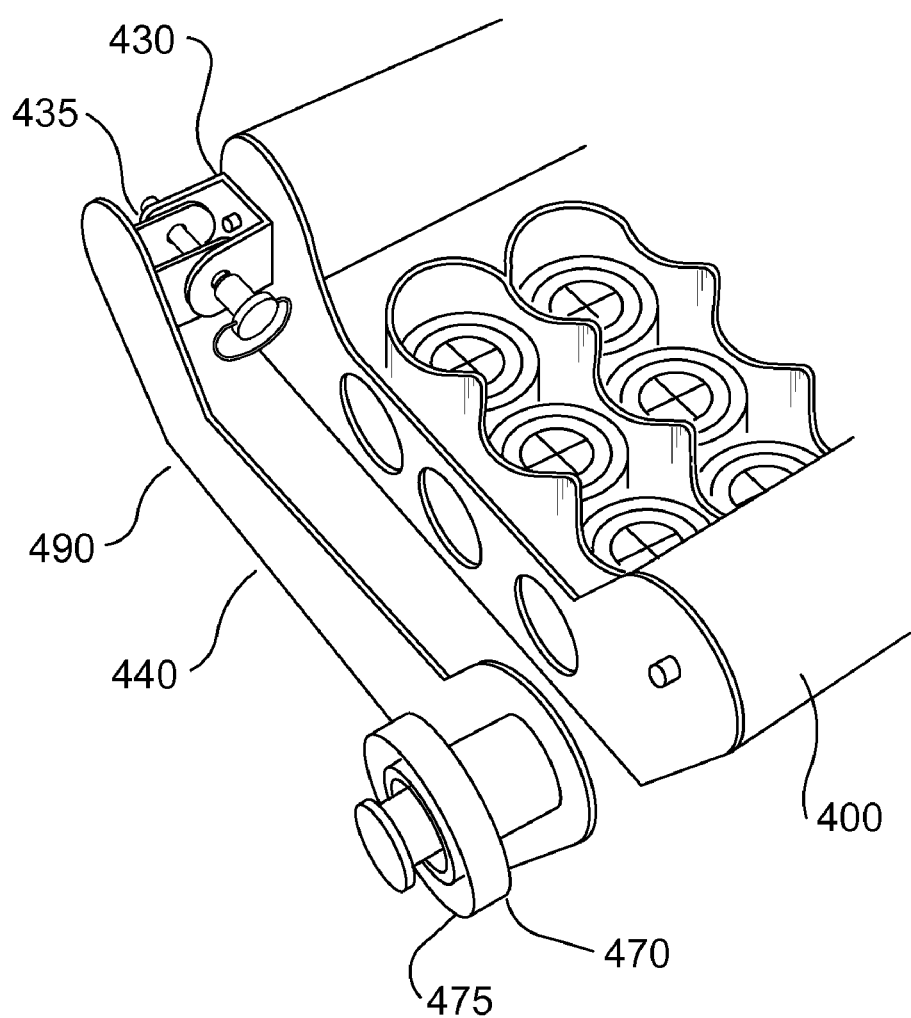
FIG. 18 is a partially broken away isometric view of an embodiment of the pivot arm assembly that allows various ranges of motion for various parts and components such as, the transducers, housings, and buoyant objects, according to the present invention.
Figure 19:
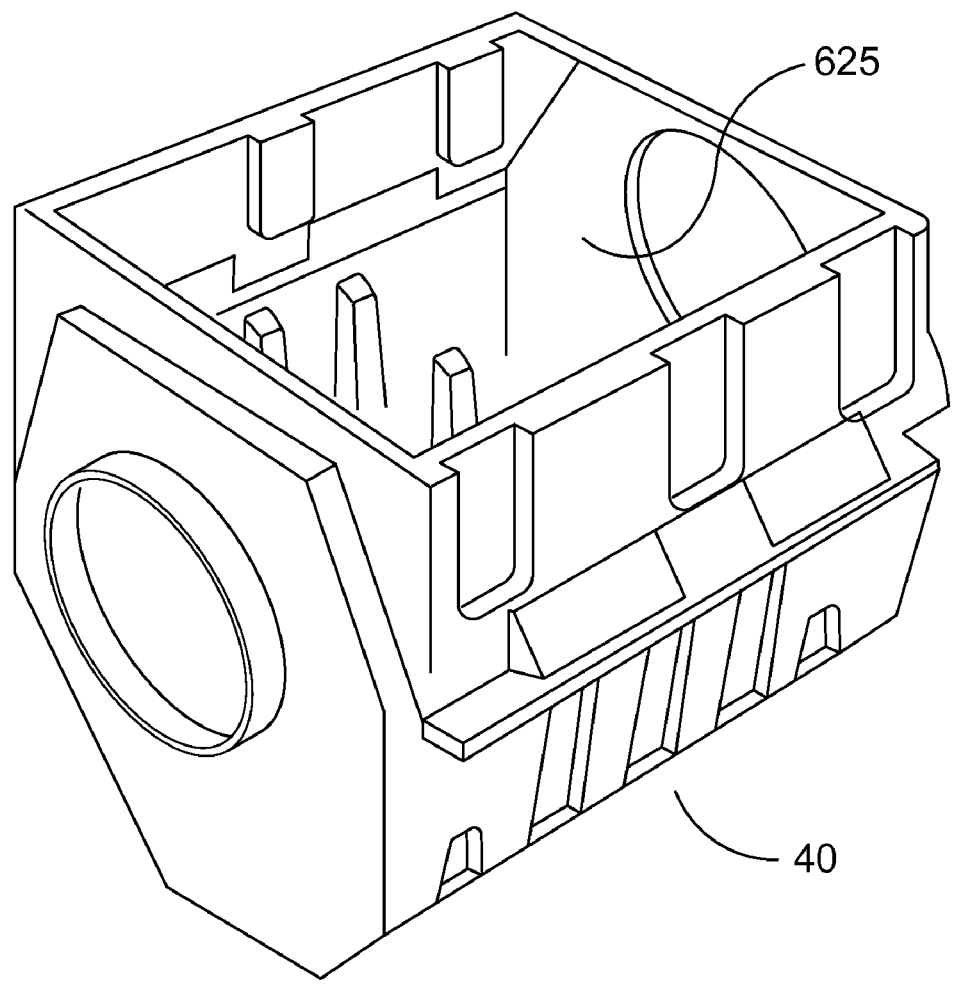
FIG. 19 is a schematic view of an embodiment of the reservoir in which the transducers are located according to the present invention.
Figure 20:
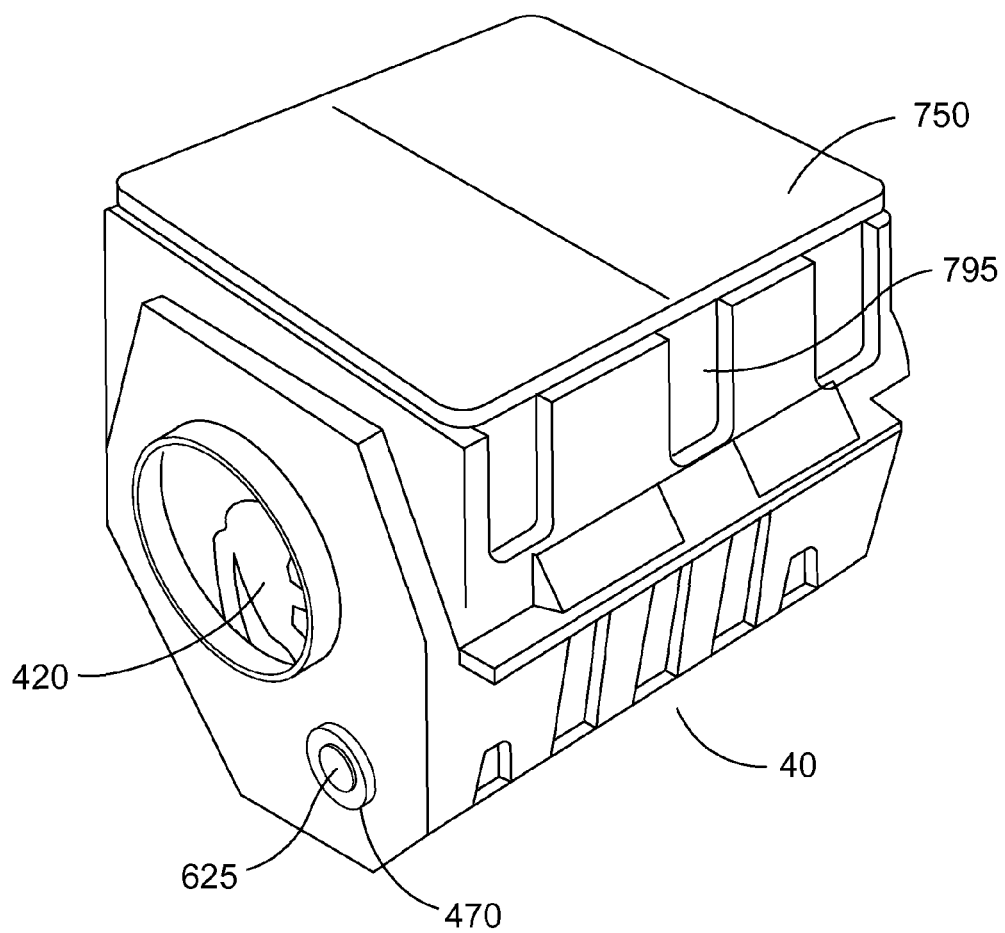
FIG. 20 is an isometric view of an embodiment of a heat sink interfacing with the reservoir in which the transducers are located with the cooling fins of the heat sink effectively positioned within the air stream that passes through the reservoir, in addition a hole which interfaces with the pivot arm is positioned within the wall of the reservoir.
Figure 21:
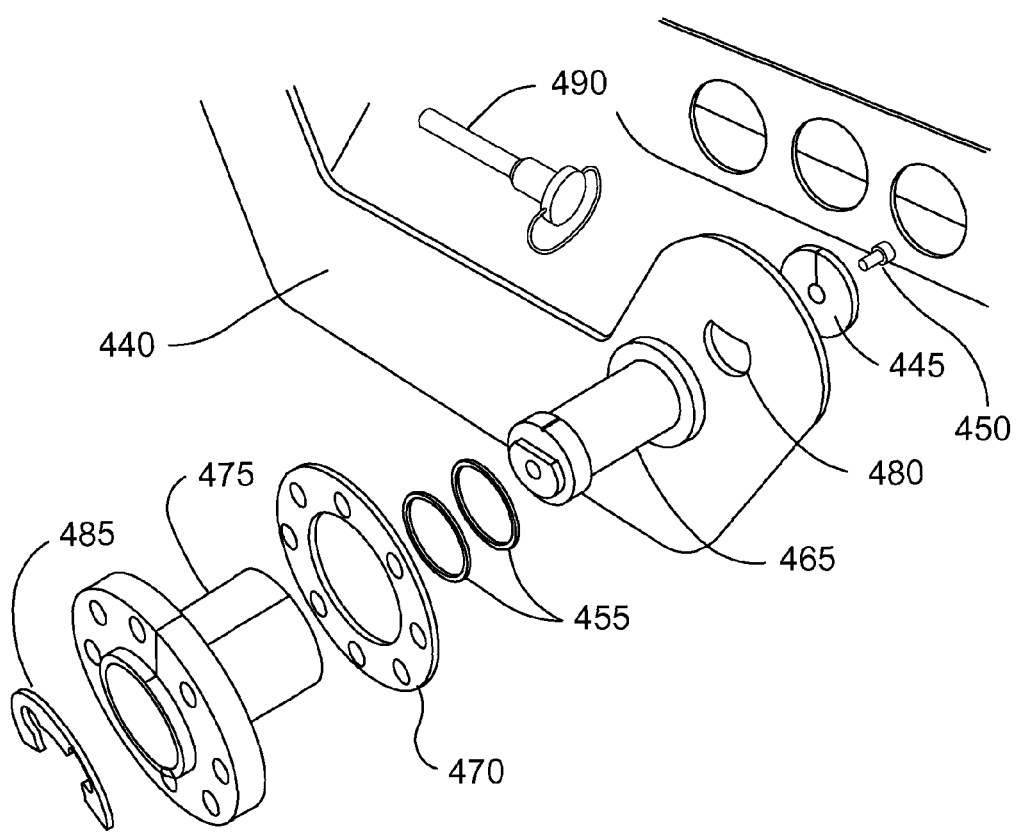
FIG. 21 is a partially broken away, exploded isometric view of an embodiment of the pivot arm assembly that consists of various parts and components according to the present invention.
Figure 22:
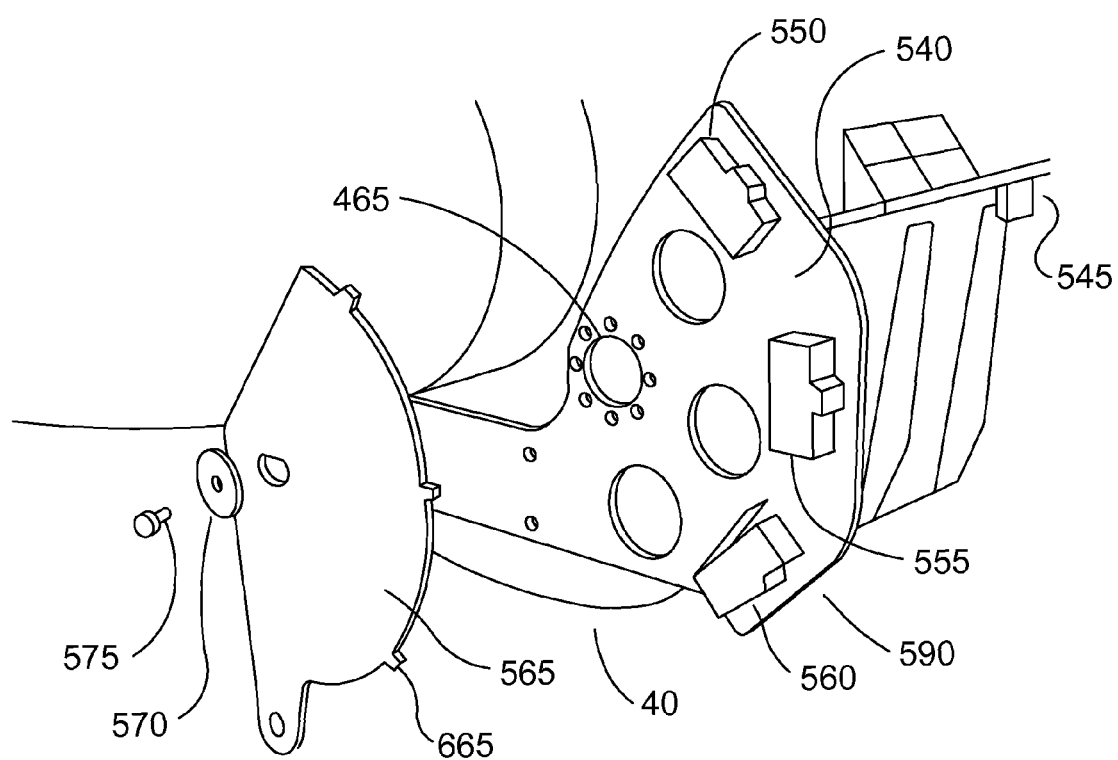
FIG. 22 is a partially broken away, exploded isometric view of an embodiment of the means used to actuate the various switches to communicate any information or status related to the reservoir or within the reservoir to the PLC, and consists of components such as, switches, switch actuator plate, protrusions, torque tube, and base plate.
Figure 23:
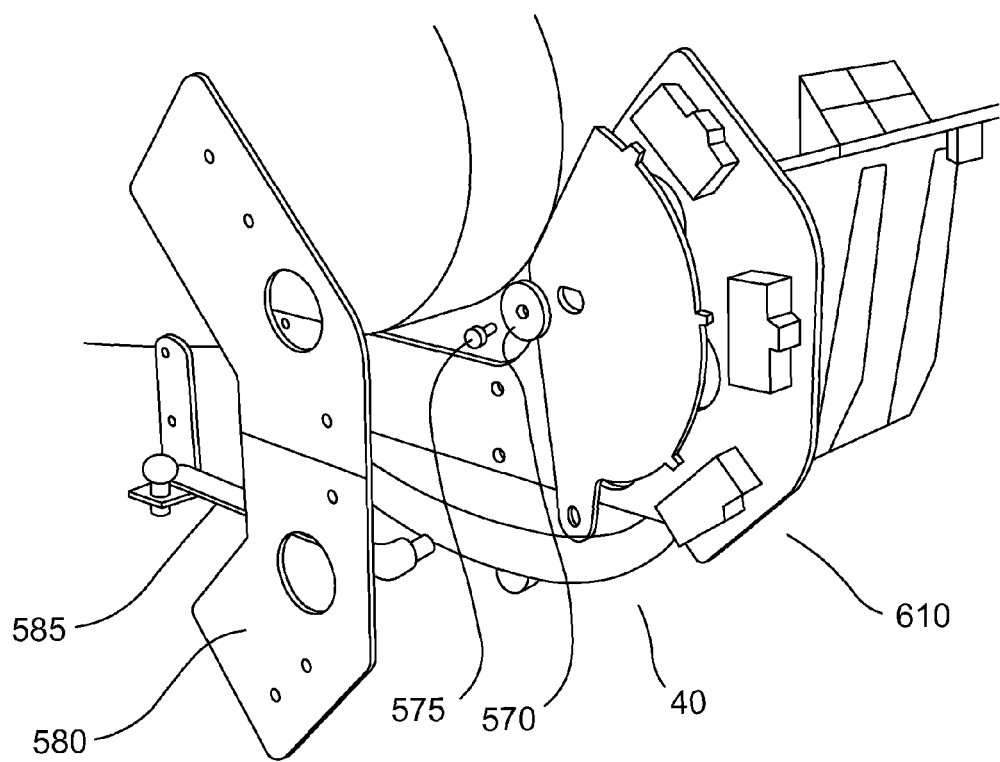
FIG. 23 is a partially broken away, exploded isometric view of an embodiment of the means used to actuate the various switches to communicate any information or status related to the reservoir or within the reservoir to the PLC, and consists of components such as, switches, switch actuator plate, protrusions, torque tube, base plate, cover plate, and hydraulic dampener.
Figure 24:
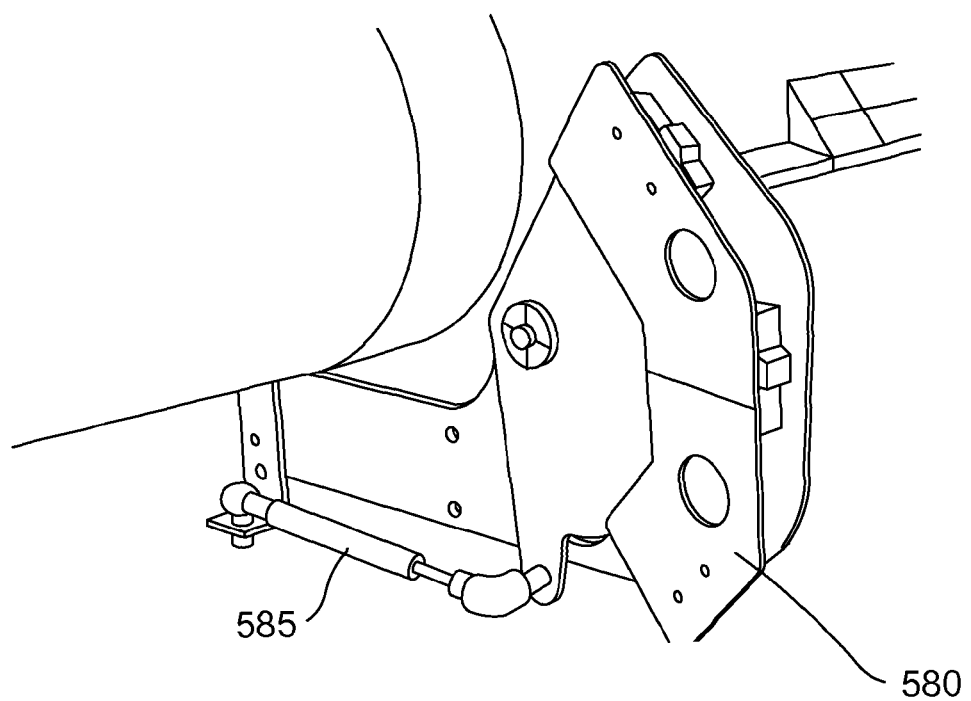
FIG. 24 is a partially broken away isometric view of an embodiment of the means used to actuate the various switches to communicate any information or status related to the reservoir or within the reservoir to the PLC, and consists of components such as, switches, switch actuator plate, protrusions, torque tube, base plate, cover plate, and hydraulic dampener.
Figure 25:
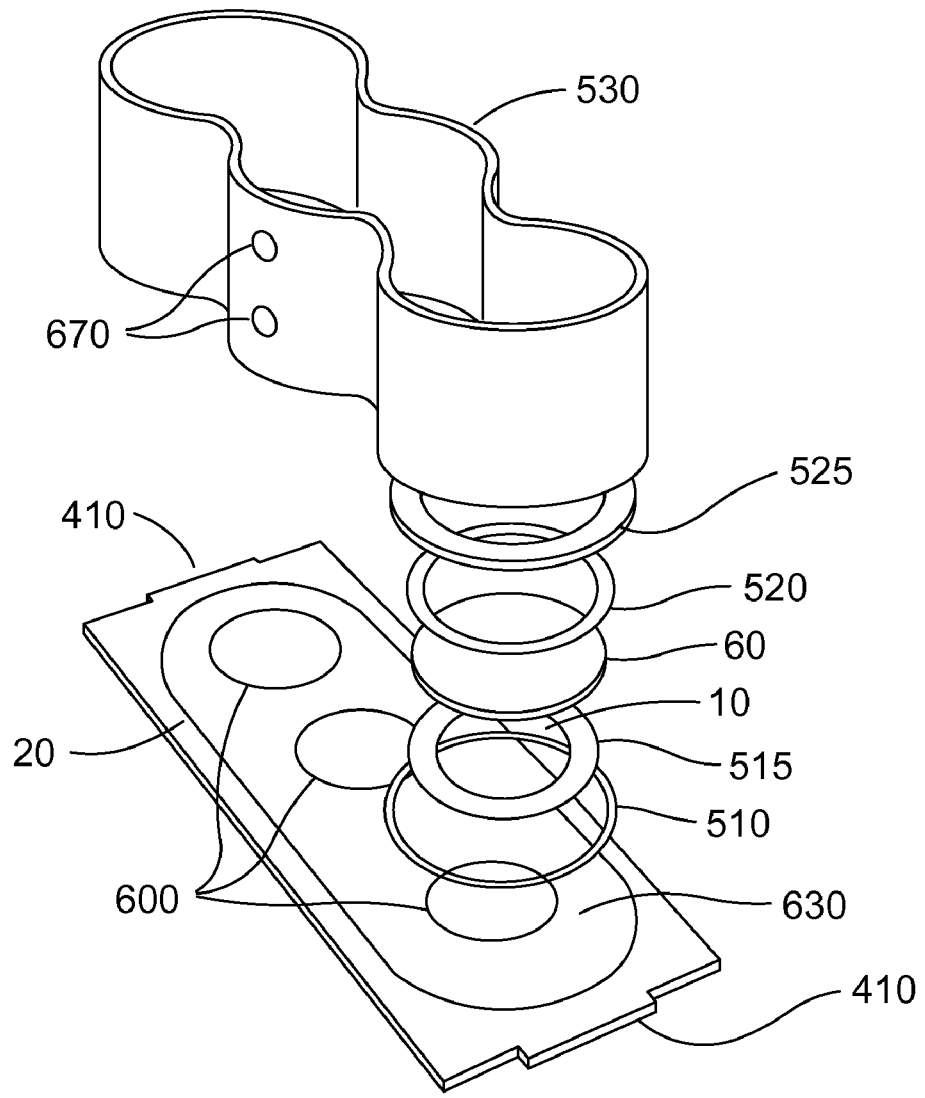
FIG. 25 is an exploded isometric view of an embodiment of an enhanced design for interfacing one or more transducers or transducer assemblies with their housing, consisting of various features, parts, and components according to the present invention.
Figure 26:
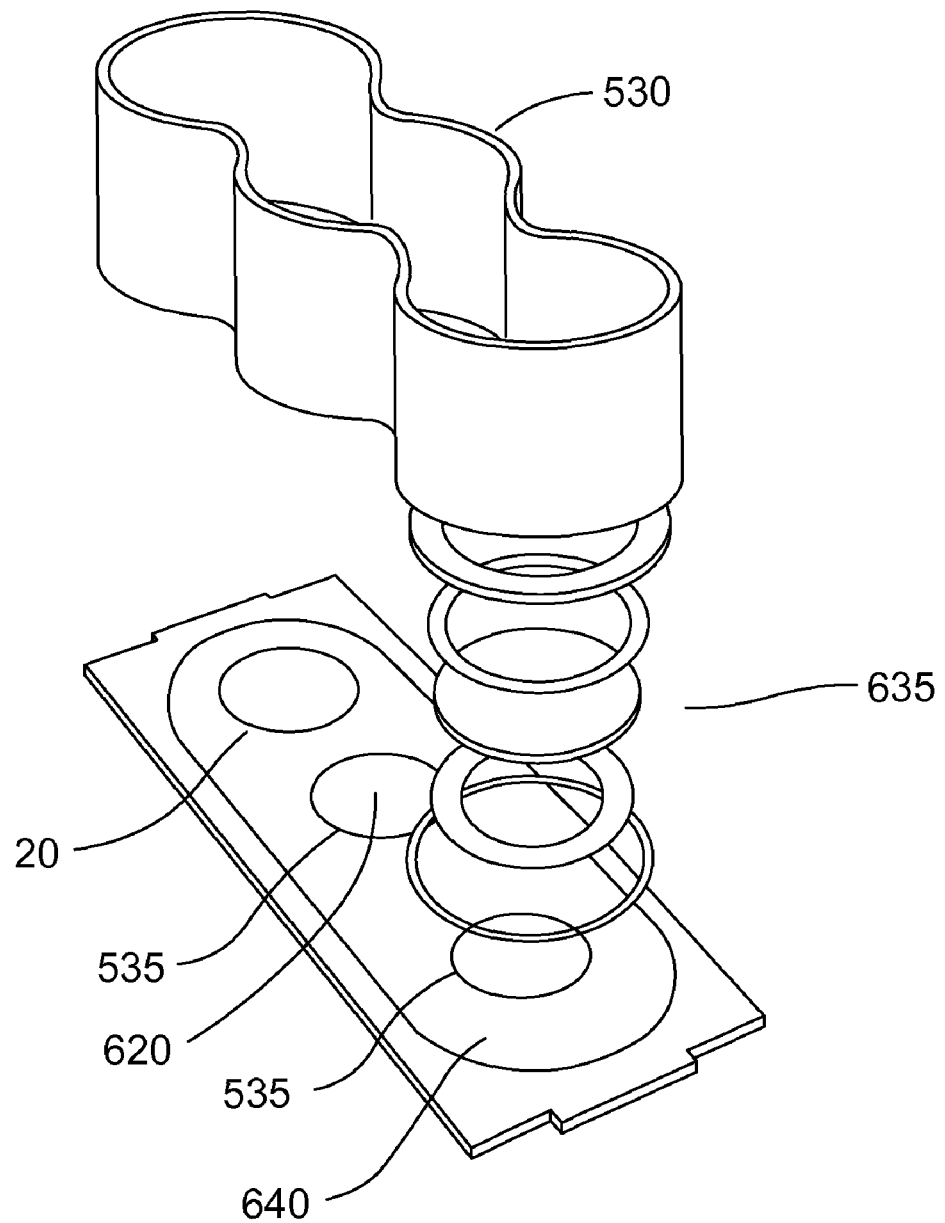
FIG. 26 is an exploded isometric view of an embodiment of an enhanced design for interfacing one or more transducers or transducer assemblies with their housing, consisting of various features, parts, and components according to the present invention.
Figure 27:
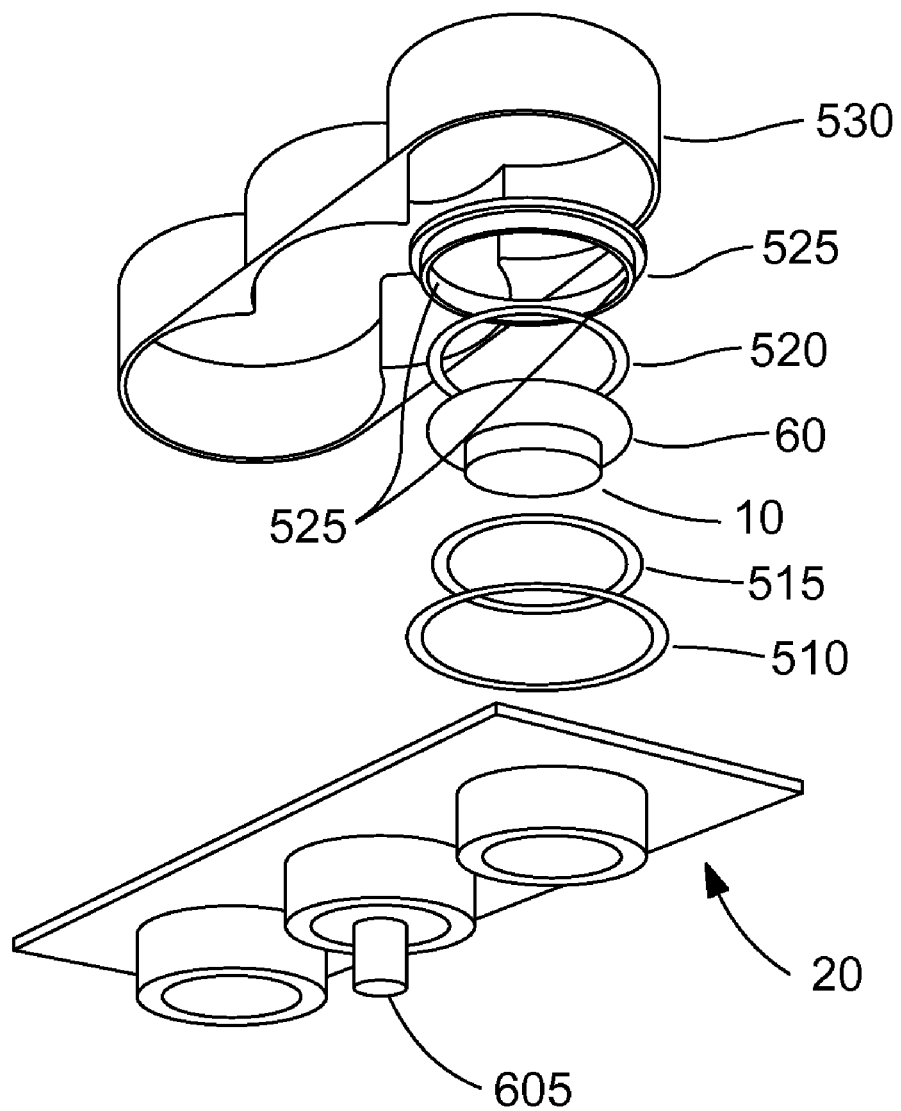
FIG. 27 is an isometric view of an embodiment of an enhanced design for interfacing one or more transducers with their housing, consisting of various features, parts, and components according to the present invention.
Figure 28:
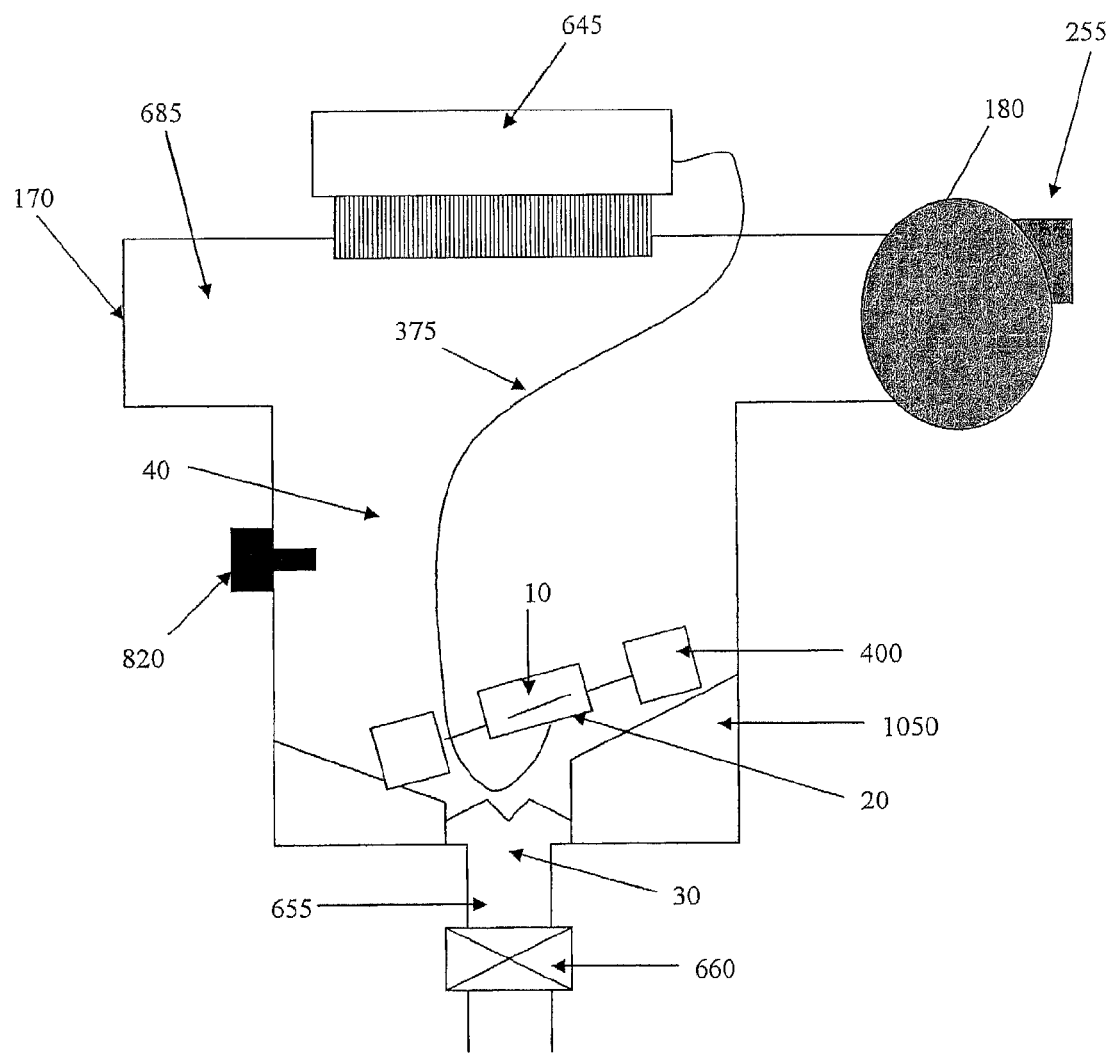
FIG. 28 is a schematic view of an embodiment of a means for the transducer housing, buoyant objects, or other parts and components to interact with any means so that the transducers or transducer assemblies are angled when the liquid in the reservoir is at a specified level or is drained.
Figure 29:
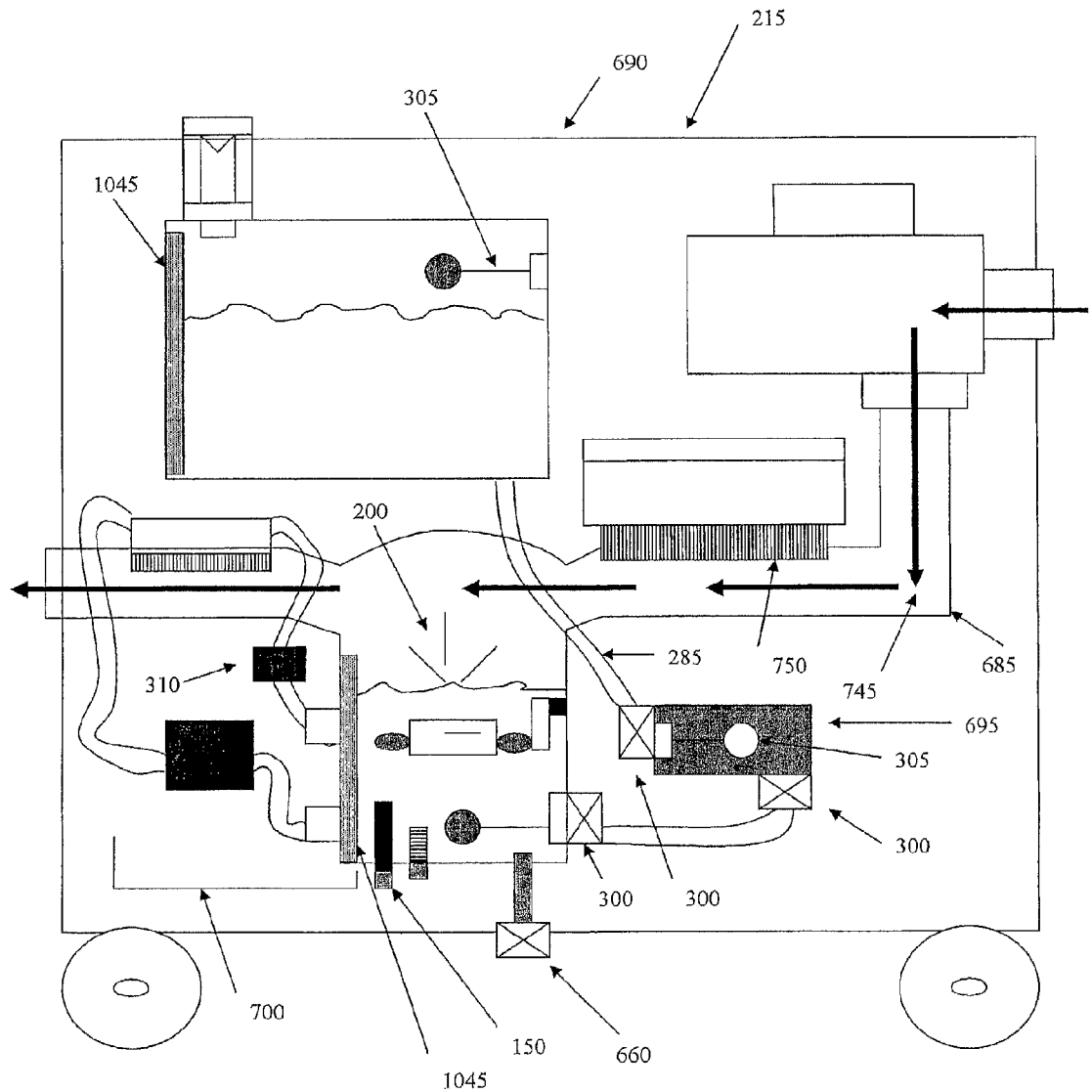
FIG. 29 is a schematic view of an embodiment of an aerosol generating apparatus according to the present invention.
Figure 30:
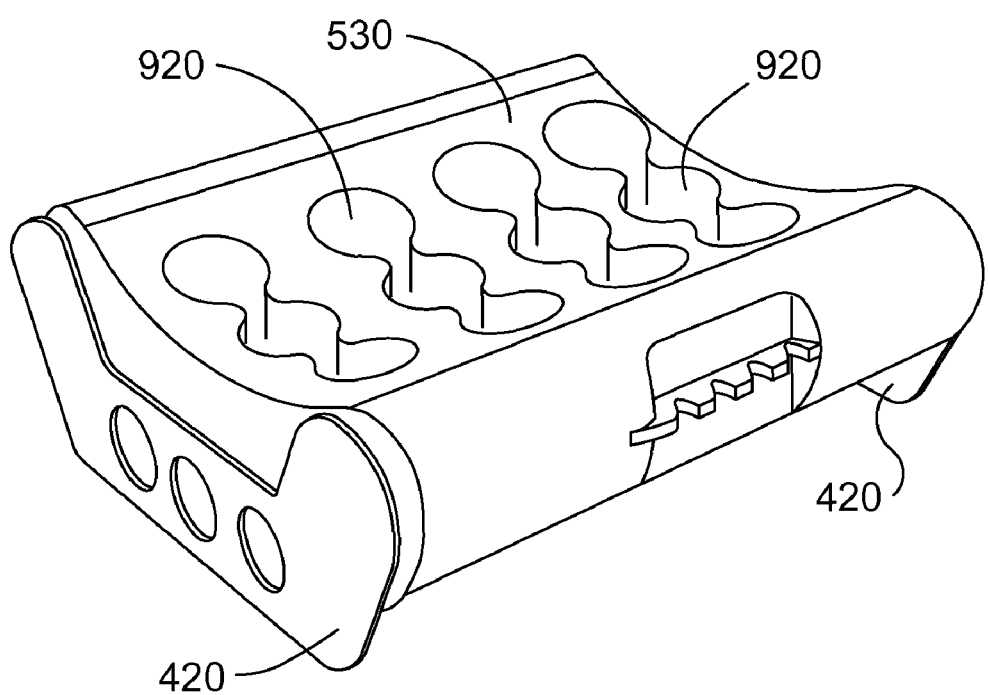
FIG. 30 is an isometric view of an embodiment of a buoyant object interfaced with multiple transducer assemblies and end plates, according to the present invention.
Figure 31:
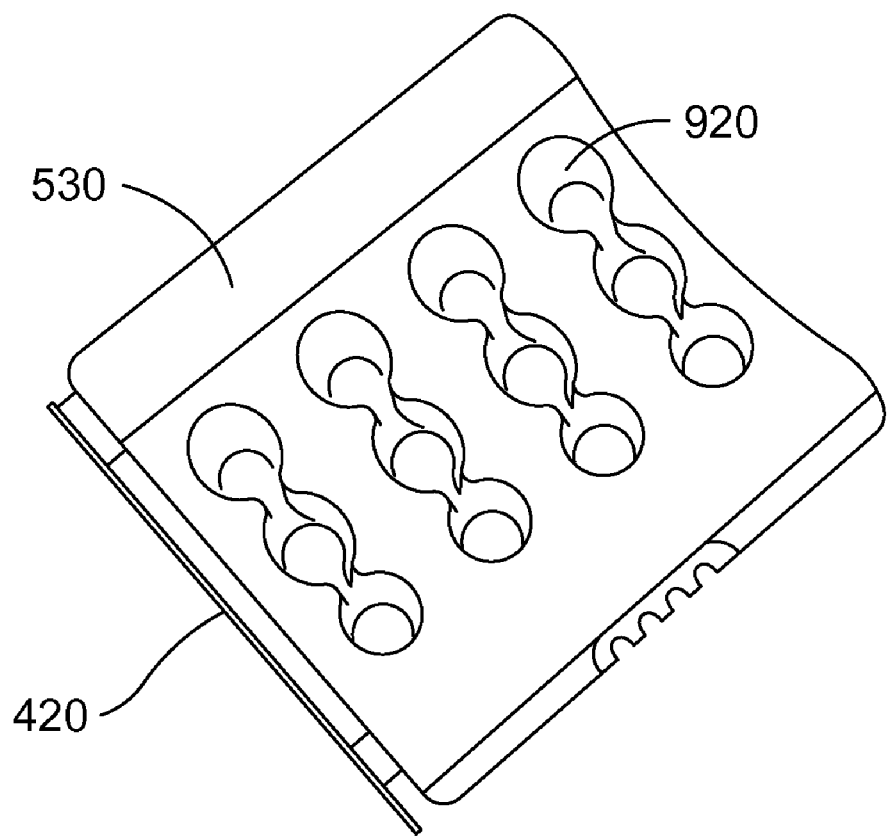
FIG. 31 is a top plan view of an embodiment of a buoyant object interfaced with multiple transducer assemblies and end plates, according to the present invention.
Figure 32:
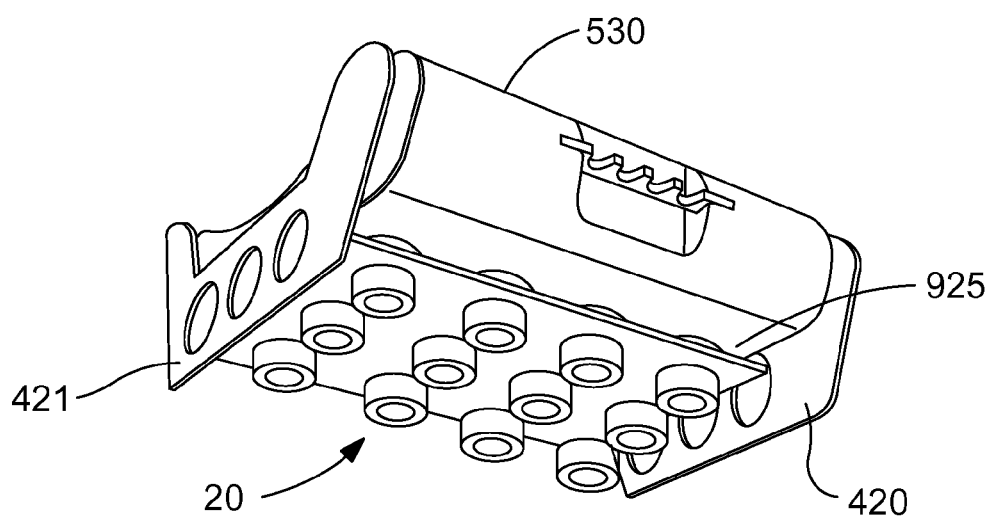
FIG. 32 is an isometric view of an embodiment of a buoyant object interfaced with multiple transducer assemblies and end plates, and spaces or gaps exist, especially above the transducers, between the housing and the buoyant object that is positioned above the transducers, according to the present invention.
Figure 33:
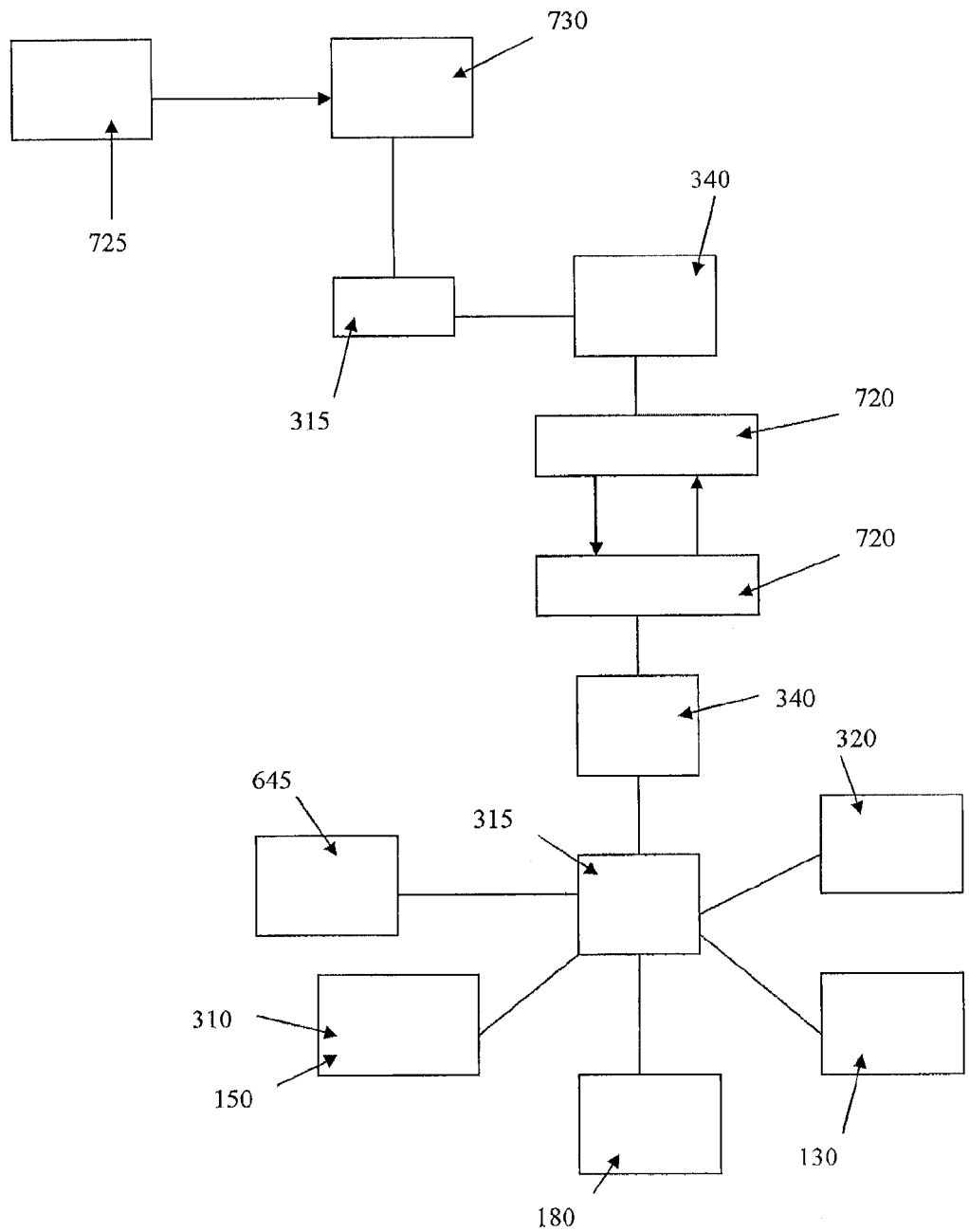
FIG. 33 is a schematic view of an embodiment of a light source and light sensor that communicates with a PLC that communicates with various parts and components of an aerosol generating apparatus, according to the present invention.
Figure 34:
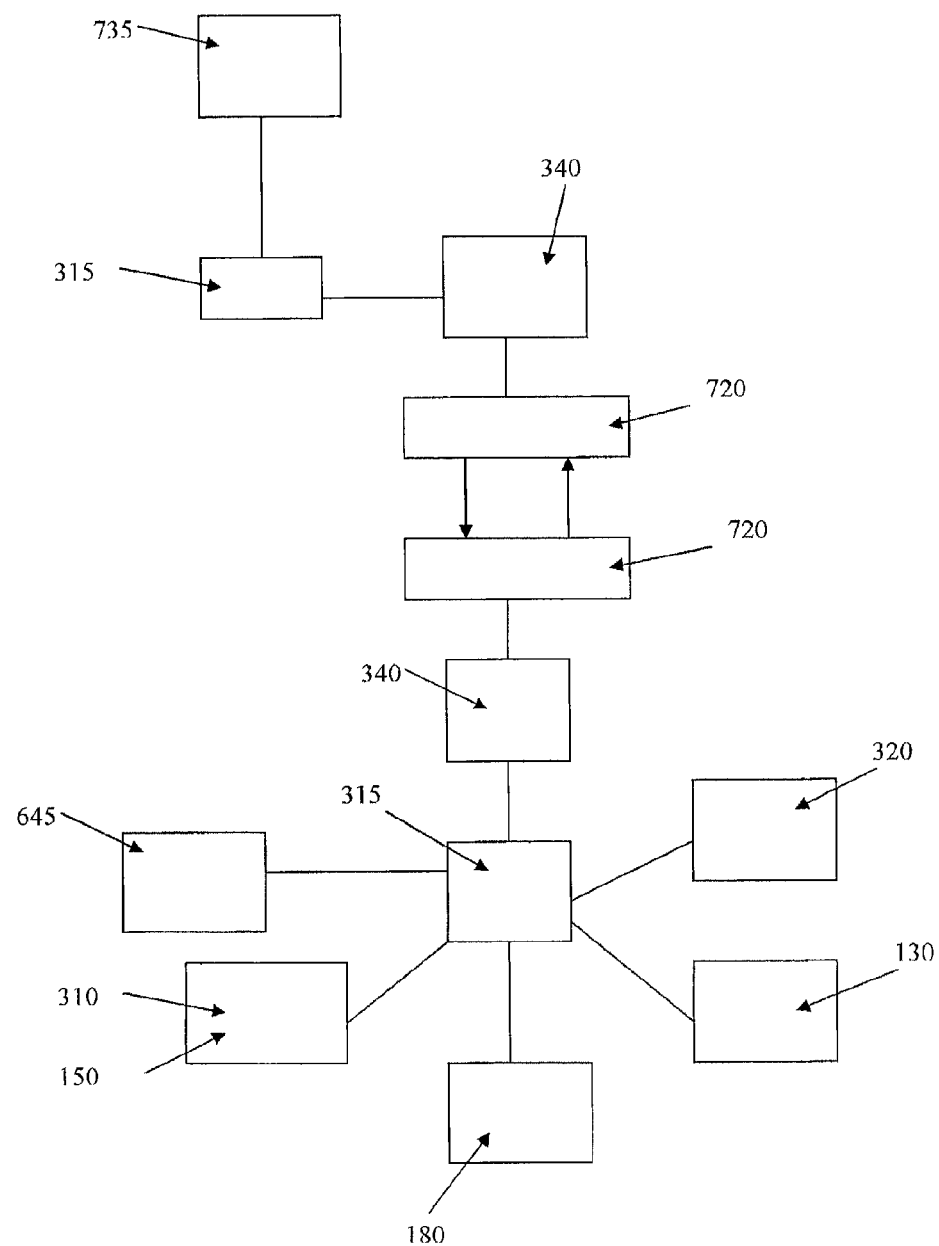
FIG. 34 is a schematic view of an embodiment of a relative humidity sensor that communicates with a PLC that communicates with a transceiver that communicates with various parts and components of an aerosol generating apparatus, according to the present invention.
Figure 35:
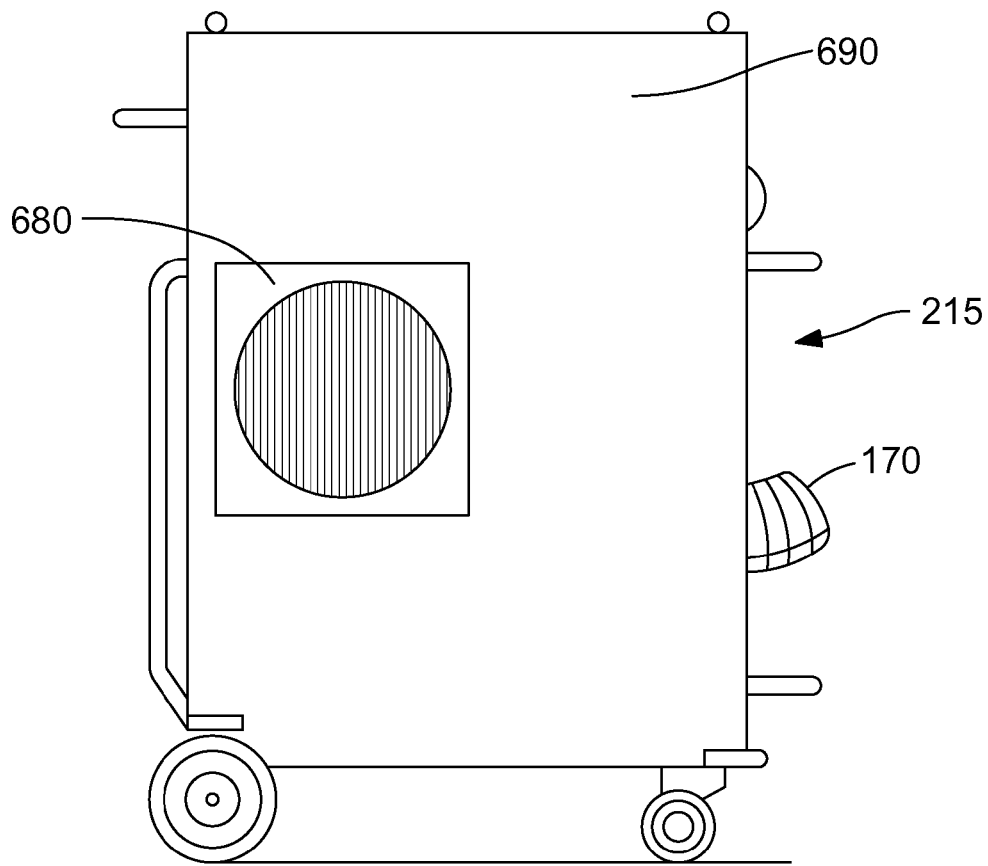
FIG. 35 is a side plan view of an embodiment of an aerosol generating apparatus according to the present invention.
Figure 36:
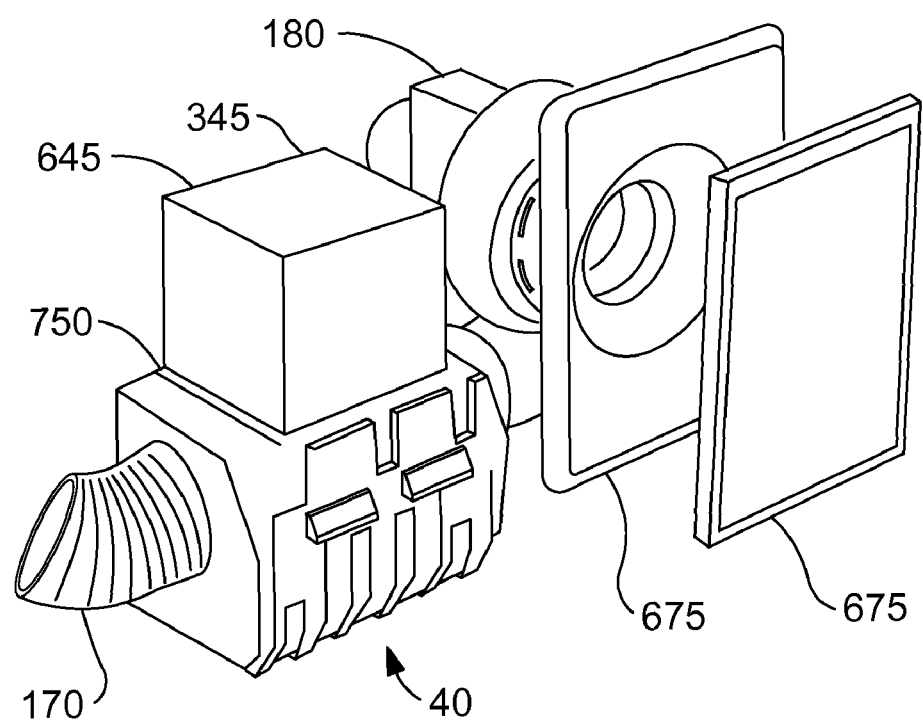
FIG. 36 is a partially broken away, exploded isometric view of an embodiment of various parts and components of the aerosol generating apparatus such as, fil frequency range for the transducer(s), and this can be performed multiple times for a plurality of transducers, according to the present invention.
Figure 37:
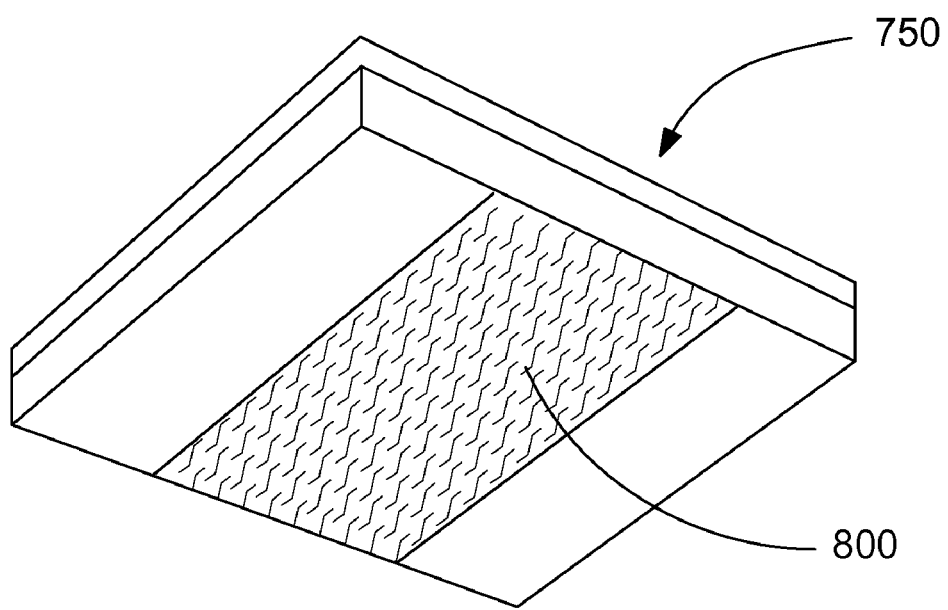
Figure 38:
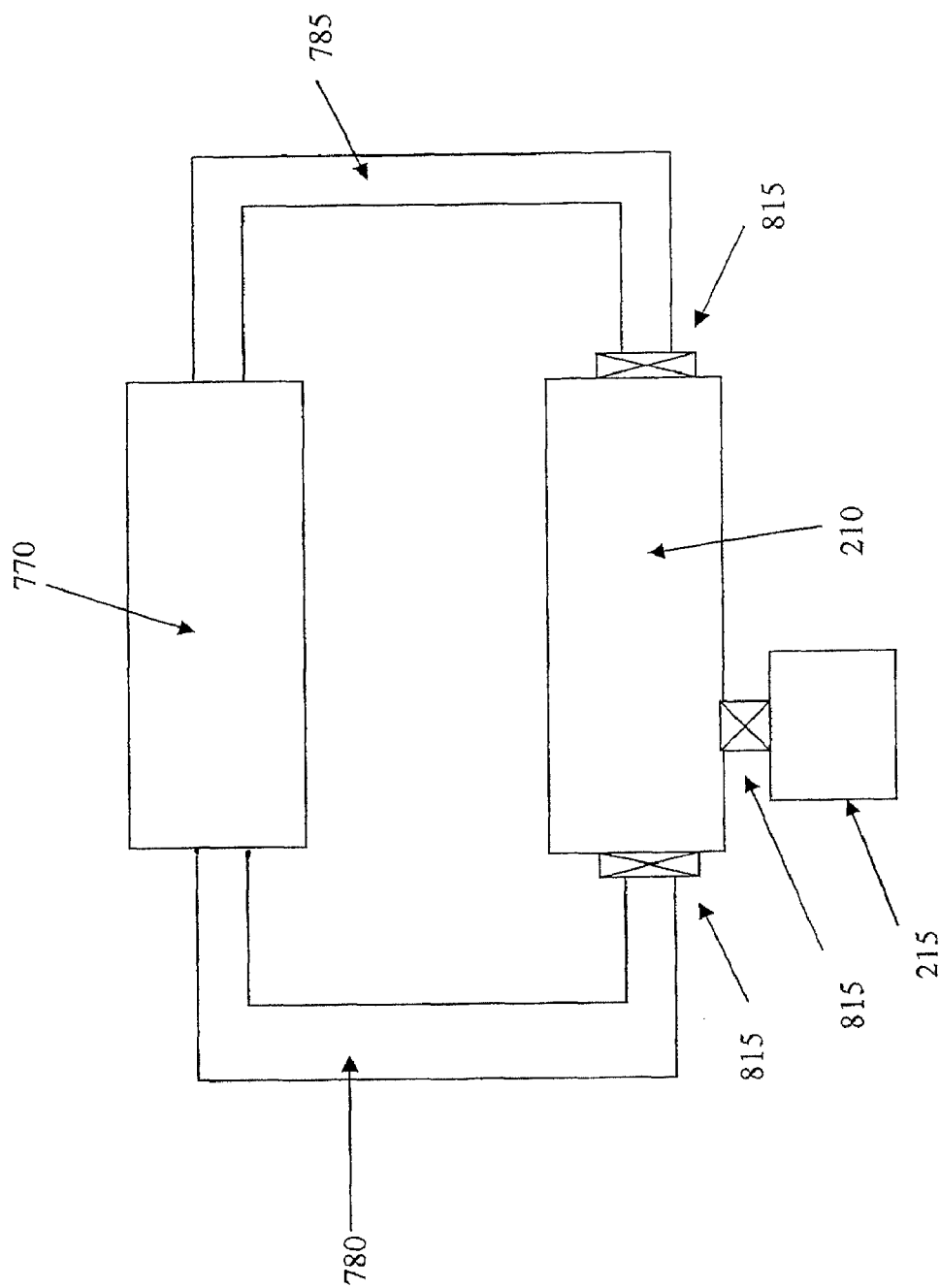
Figure 39:
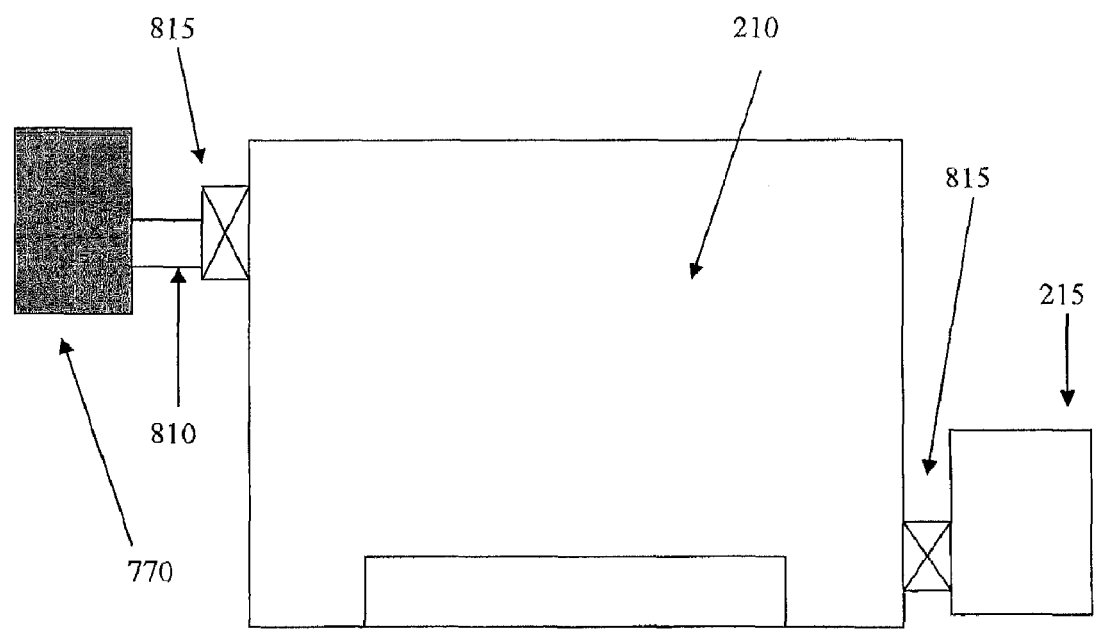
Figure 40:
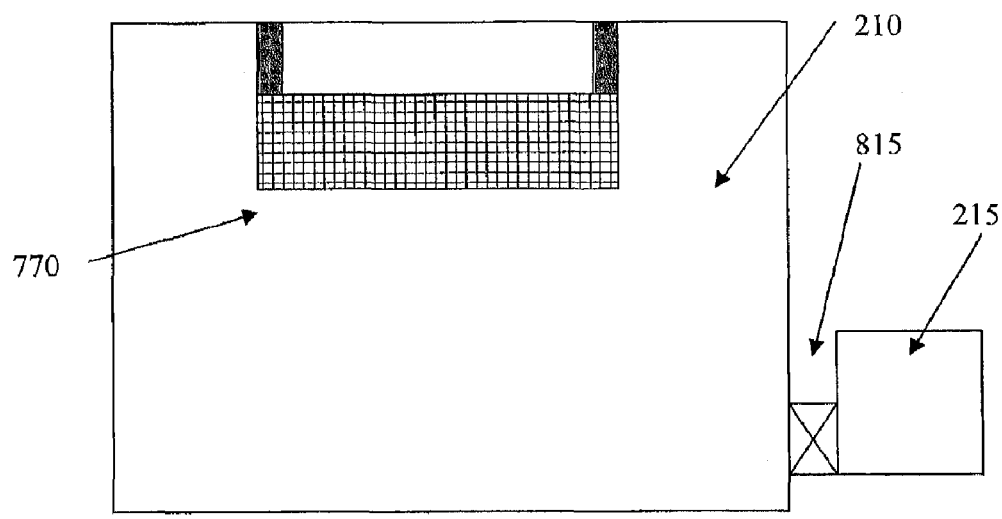
Figure 41:
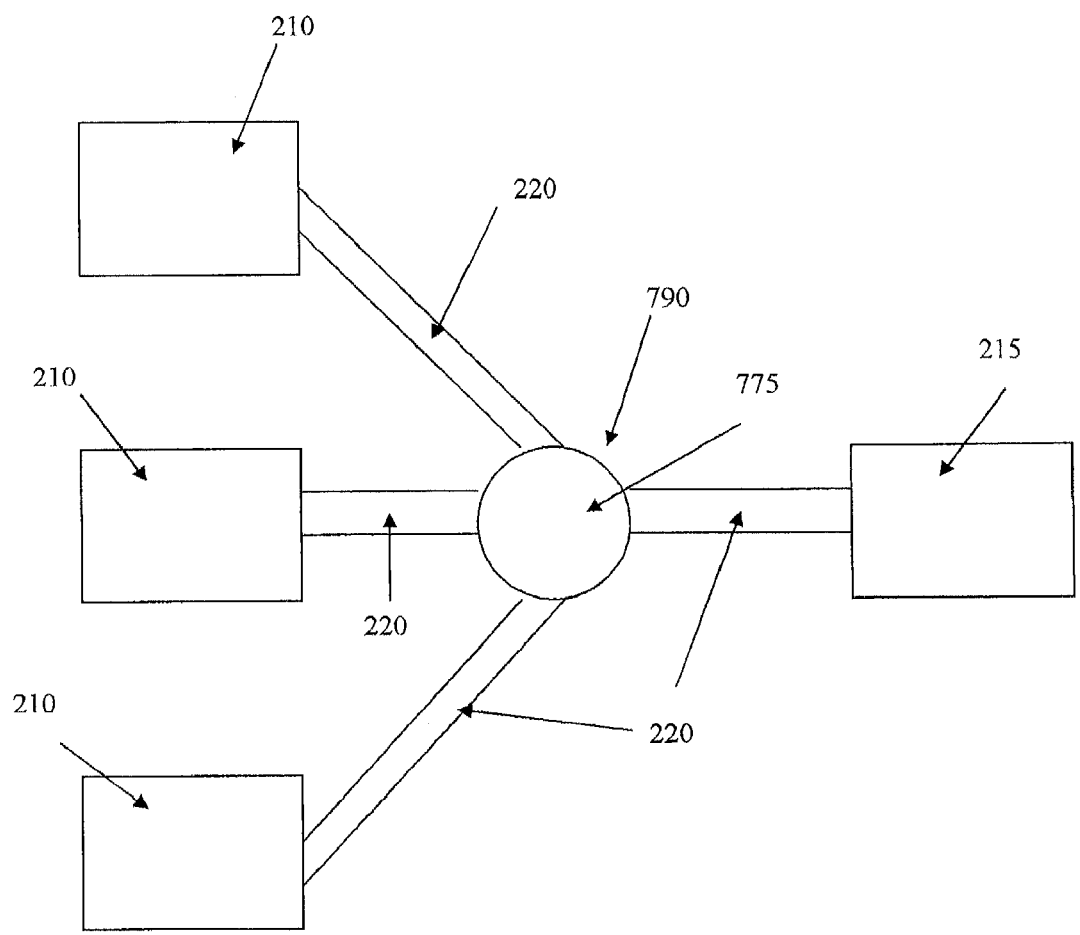
Figure 42:
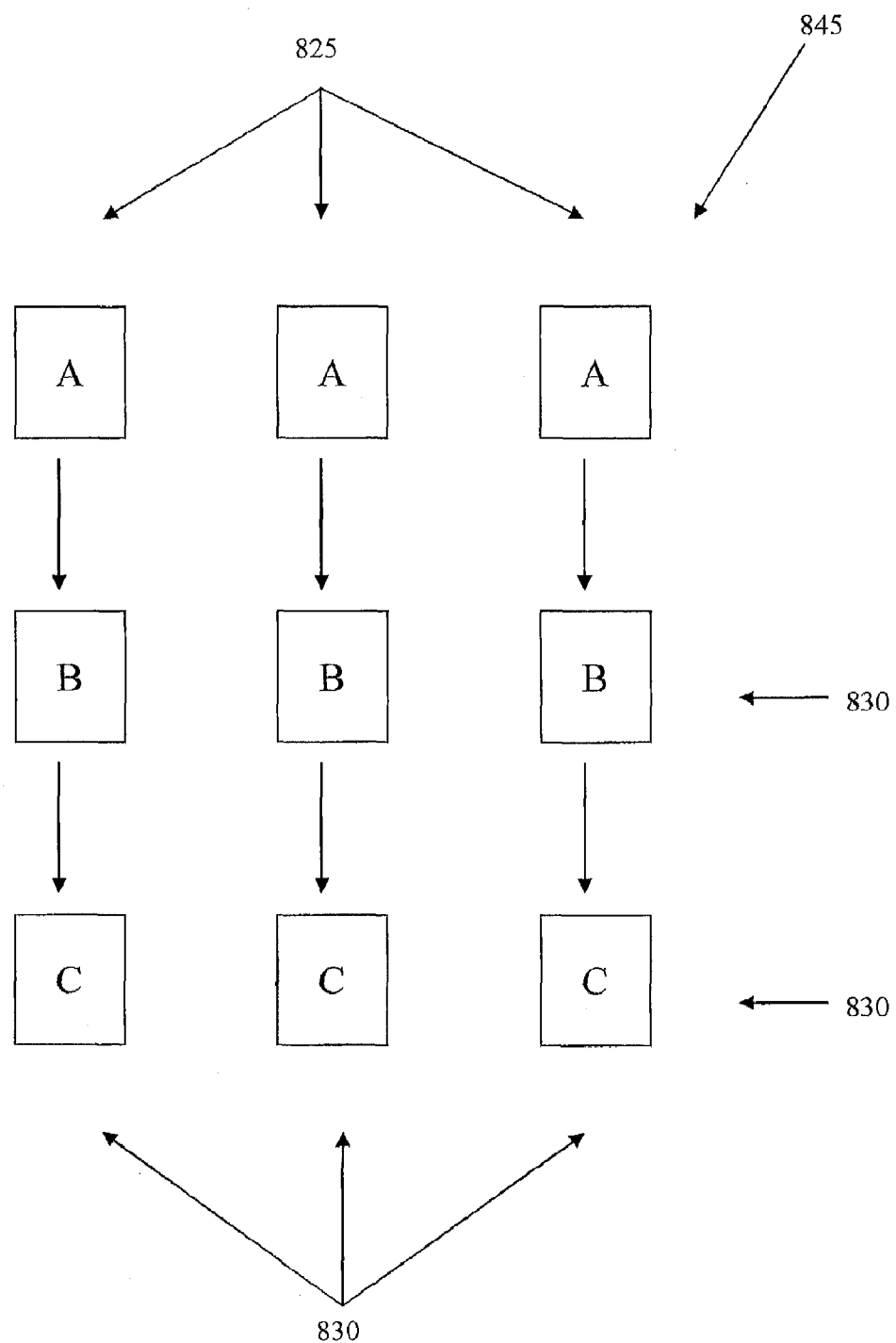
Figure 43:
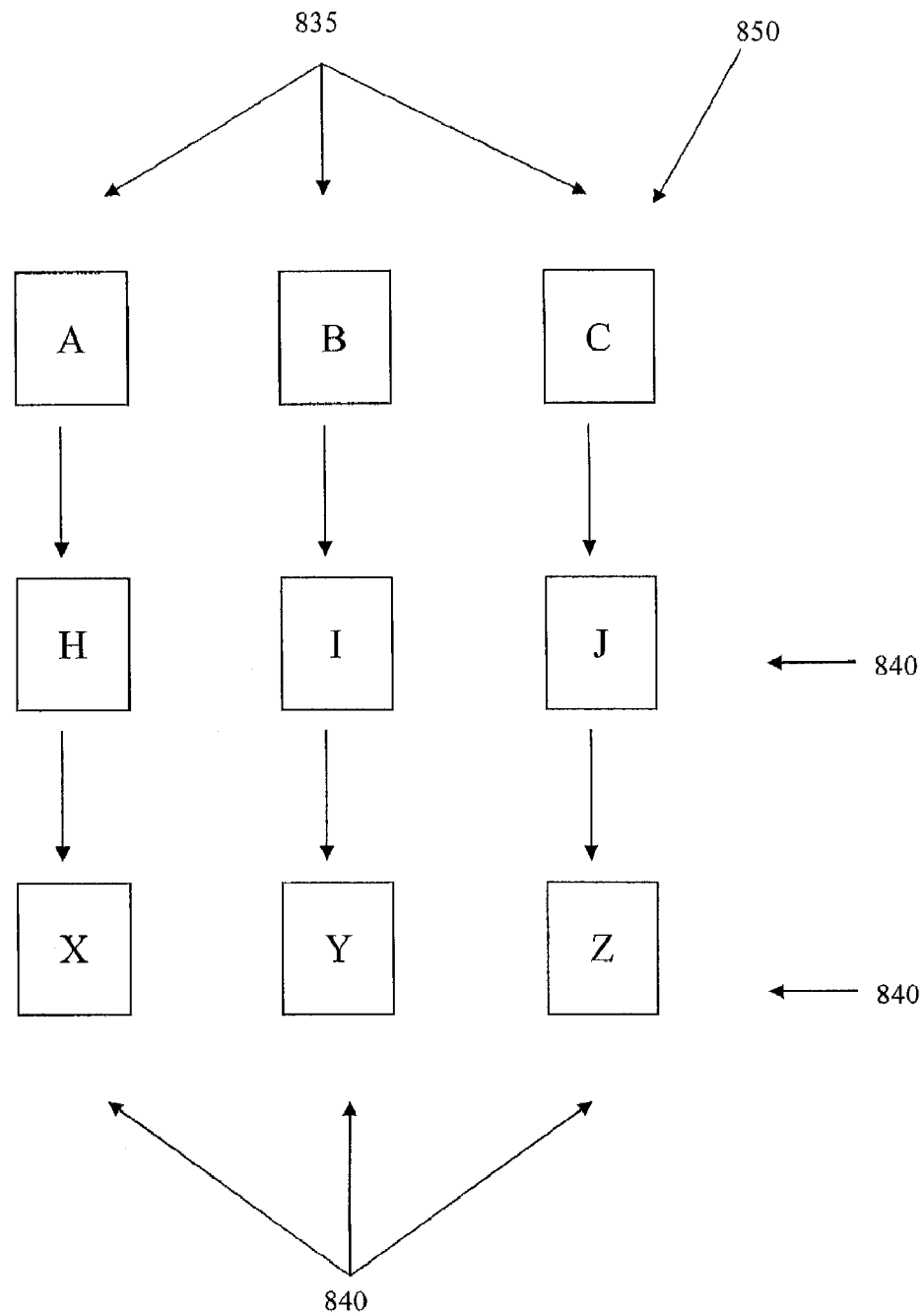
Figure 44:
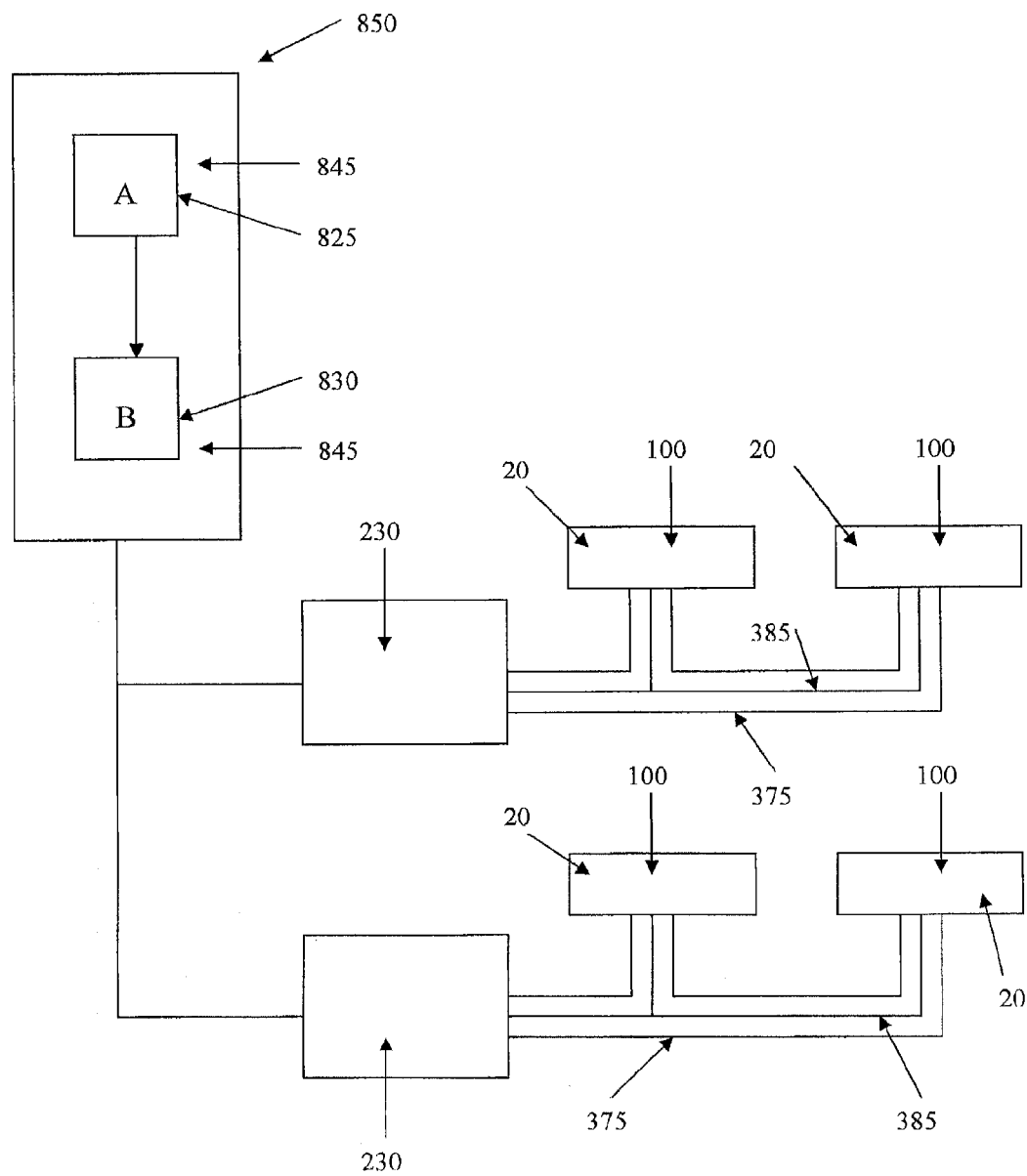
FIG. 44 is a schematic view of an embodiment of a means to compensate for any shifting of transducer frequencies, where a crystal that is a part or component of a signal generator is initially used to generate one specific frequency or specific frequency range for a transducer(s), is then switched to a different crystal that is a part or component of the same signal generator, and is used to generate another specific frequency or specific frequency range for the transducer(s), and the signal generated from the activated crystal is sent via the signal generator to an amplifier(s) that is connected to one or more transducers, according to the present invention.
Figure 45:
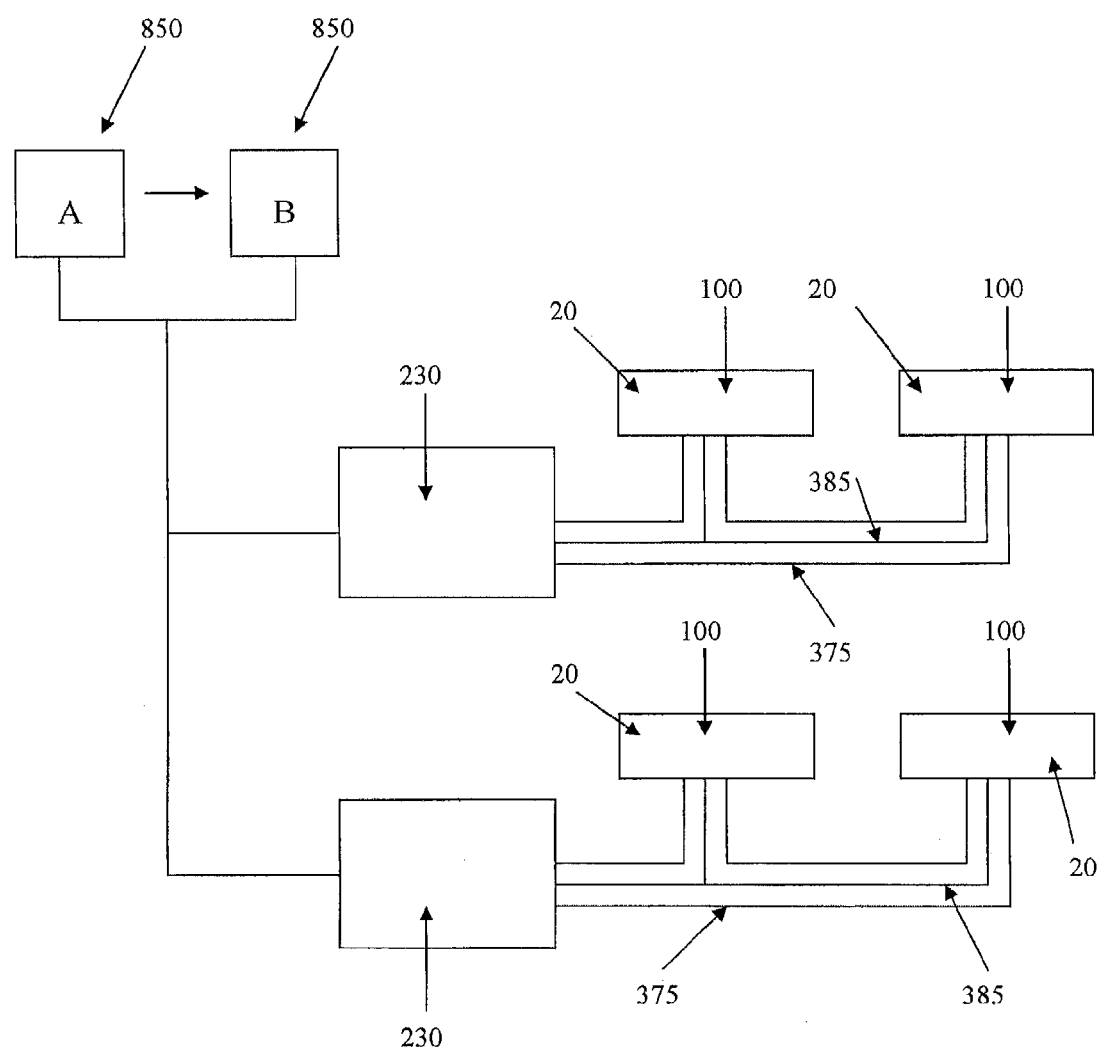
FIG. 45 is a schematic view of an embodiment of a means to compensate for any shifting of transducer frequencies, where a signal generator is initially used to generate one specific frequency or specific frequency range for a transducer(s), is then switched to a different signal generator, that is used to generate another specific frequency or specific frequency range for the transducer(s), and the signal generated from the activated signal generator is sent to an amplifier(s) that is connected to one or more transducers, according to the present invention.

As best shown in FIG. 10, the apparatus (215) in the present invention can be controlled, without limitation, by one or more programmable logic circuit(s) (PLC) or other suitable circuitry, computer, electrical system, or electronics (herein called "PLC or PLC(s)") (315), and related software and program(s), known to those skilled in the art. Without limitation, one or more human machine interface(s) (HMI), screen, or other means to interact with the operator (herein called "HMI or HMI(s)") (320), and related software and program(s), known to those skilled in the art, can be used, without limitation, to convey information as well as allow the operator to set parameters or enter commands. The PLC (315) and HMI (320) can be configured or programmed to enable the operator to, without limitation, enter information into the HMI (320) or PLC (315), program the HMI (320) or PLC (315), or execute command(s). The HMI (320) or PLC (315) can also provide a means, without limitation, for the operator to choose a specific volume or area for the apparatus (215) to administer or deploy the generated aerosol, or choose a specific aerosol deployment time. The HMI (320) or PLC (315) can be programmed to associate one or more values for volumes or areas chosen by the operator with specific aerosol deployment time(s). The menus, software, and programming for the HMI (320) or PLC (315) can be customized for each customer's needs and may include, without limitation, providing the operator with one or more menus that presents a plurality of room numbers or other attributes that the operator can choose, and each room number or attribute is associated with operational parameters and variables such as, but not limited to, liquid temperature(s), volume of the room or targeted area, and the total cycle time that the apparatus (215) would need to operate in order to efficaciously and effectively deploy the aerosol into the chosen room or targeted area. In addition, and without limitation, the HMI (320) or PLC (315) can have a provision in its program(s) or software to change the operational parameters that effect the performance of the apparatus (215) or process due to temperature and humidity values that are either reported to the HMI (320) or PLC (315) by the operator or by automated means known to those skilled in the art. The PLC (315) can, without limitation, include any PID, PID tuning, or PID auto tuning, functions, attributes, or activities. The PLC (315) can, without limitation, control and maintain the temperature of any liquid (30) to any desired or necessary temperature in any reservoir(s), including, but not limited to, the reservoir(s) (40) in which the transducers (10) are located. Without limitation, the PLC (315) can control liquid (30) temperature, by controlling one or more part(s) and component(s) of the apparatus (215) such as, but not limited to any: (a) blower(s), (b) valve(s), (c) heater(s), (d) pump(s), (e) amplifier(s) or other means to power or control the transducer(s) (10), or (f) any means used to cool the liquid (30). Without limitation, the PLC (315) can control liquid (30) temperature, by controlling or communicating with one or more part(s) and component(s) of the apparatus (215) such as, but not limited to any: (a) any thermostat or temperature controlling device (b) blower(s), (c) valve(s), (d) heater(s), (e) pump(s), (f) amplifier(s) or other means to power or control the transducer(s) (10), or (g) any means used to cool the liquid (30).

The PLC (315) can also, without limitation, send or receive or detect any signal, current, or other modes of communication, or their absence, from various components or parts of the apparatus (215) or components or parts related to effective operation of the apparatus (215). These signals, current, or other modes of communication, or their absence, can without limitation, be used by the PLC (315) to, control the apparatus (215) or its components and functions, or monitor the function or status of components or parts of the apparatus (215). Without limitation, the signals, current, or other modes of communication, or their absence, sent by the PLC or to the PLC, can result from the direct or indirect connection and communication of the PLC (315) with components such as, but not limited to, any: (a) current sensor(s) (325), (b) liquid level sensor(s) (305), (c) electronics that power, operate, or control, the transducer(s) (10) (herein referred to as "drive electronics") (645), (d) air/gas temperature sensing thermocouple(s) (650) or other means to sense air/gas temperature, (e) liquid temperature sensing thermocouple(s) (820) or other means to sense liquid temperature, (f) humidity sensor(s) (335), (g) valve(s) (300) (660) that control the flow of liquid, (h) valve(s) (260) (265) (210) (815) (775) that control the flow of any air/gas or aerosol that can flow into or out of a targeted area, (i) wireless transceiver(s) (340) or other signal transmitter(s)/receiver(s).

One or more air/gas temperature sensor(s) (650) can be placed in various locations inside or outside of the apparatus(s) (215). It is preferred, without limitation, that at least one air/gas temperature sensor is positioned in any enclosure or NEMA or IP rated sealed enclosure (345) that has the potential for its internal atmosphere (740) to increase in temperature due to the operation of the apparatus(s) (215). The PLC(s) (315) can, without limitation, use the input from any sensors including, but not limited to, liquid temperature, air/gas temperature, or any other temperature sensor(s), to control activities such as, but not limited to, heating of any liquid and any related activities (30), cooling of any liquid and any related activities (30), or cooling of any part(s), component(s), or atmosphere(s) (740) in any enclosed space(s) found in the apparatus(s) (215) and any related activities. Any valve(s) utilized in the present invention can also, without limitation, be manually controlled and operated, or electronically controlled and operated by one or more PLC(s) (315) in a manner known to those skilled in the art. It is preferred, without limitation, that any electrically or electronically controlled valve(s) that can be utilized for various purposes and at various locations, are solenoid valve(s).

The drive electronics (645) can include, but is not limited to, the following parts or components: (a) one or more power supply(s), (b) one or more signal or waveform generator(s) (herein referred to as "signal generator(s)") (c) one or more amplifier(s), or (d) other electronic equipment, components, parts, and methods for operating or driving the transducer(s) (10) known in the art may also be used. In addition, one or more sensors or means (1045) for determining the liquid level or the amount of liquid in the reservoir(s) (40) in which the transducers (10) are located or in the tank(s) (280) that feeds or supplies liquid (30) to the said reservoir(s) (40), can also be connected or communicate with the PLC (315), in a manner known in the art, and can enable the PLC (315) to determine if a sufficient quantity of liquid is available for any application time or volume of space chosen by the operator.

More specifically, the various signals, current, or other modes of communication, or their absence, received or detected by the PLC (315) can be used, without limitation to determine if the apparatus is functioning or operating within acceptable operational parameters. If the apparatus (215) is not operating within acceptable operational parameters, the PLC (315) can shut down, without limitation, the aerosol generation activity, any blower(s) (180), any means to heat the liquid (30), any means to cool the liquid (30), or any fluid pumps (130). The PLC (315) can also cause the apparatus (215) to shut down and enter a fault or error mode if the apparatus (215) is not functioning or operating within acceptable parameters. These can include, without limitation, the apparatus (215) shutting down all components and displaying a fault or error message on the HMI (320) communicating the source of the fault or error. Faults or errors can result from sources or situations including, but not limited to, insufficient liquid (30) availability to start or complete a cycle, failure to heat the liquid (30) to effective temperatures, overheating of the liquid (30) or components, failure of one or more components evidenced by the lack of current detected by a current sensor, under filling or over filling of the tank(s) (280) or reservoir(s) (40), failure of any drive electronics (645), failure of a transceiver(s) (340). If the apparatus (215) is not functioning or operating within acceptable operational parameters, the PLC (315) can also cause the apparatus (215) to emit an audible as well as visual warning. Without limitation, an audible as well as visual signal can also be communicated to the operator after the apparatus (215) has successfully completed administering the aerosol. The HMI (320) can be located inside, outside, or partially inside and outside of the apparatus (215).

At the end of the operational cycle, or upon a premature shut down of the apparatus (215) due to a failure of the apparatus (215) to function or operate within acceptable operational parameters, the apparatus (215) can create a record or report that can include, but is not limited to, whether or not there were any faults or errors during operation, the source of any faults or errors if they transpired, the lowest and highest recorded liquid (30) temperature that is in the reservoir(s) (40), the total time the aerosol was administered, the date and time the cycle was started, the date and time the cycle was completed, the room number or name if applicable, operator descriptor. The record or report may be stored, without limitation, in the memory of the PLC (315) or HMI (320), or on removable memory media, or other means known to those skilled in the art. The record or data may also be made available for printing or download via a USB port or other means known to those skilled in the art.

The PLC (315) can, without limitation, operate, energize, shut down, suspend, idle, or deactivate, one or more parts or components including, but not limited to any, (a) heater(s), (b) pump(s), (c) transceiver(s), (d) blower(s), (e) valve(s), (f) HMI(s), or (g) drive electronics, numerous times of various duration during the operation of the apparatus (215). This is particularly useful in situations that include, but are not limited to: (a) an insufficient amount of power is available to the apparatus(s) (215) to operate one or more of its parts or components simultaneously, necessitating that one or more parts and components such as, but not limited to, the blower(s) (180) and/or drive electronics (645) are temporarily idled, shut down, turned off, or suspended, to provide or make sufficient power available to the heater(s) (150) or (310), or other parts and components, (b) an insufficient amount of power is available to the apparatus(s) (215) to operate one or more of its parts or components simultaneously, necessitating that one or more parts and components such as, but not limited to, the heater(s) (150) or (310) is temporarily idled, shut down, turned off, or suspended, to provide or make sufficient power available to the drive electronics (645), or other parts or components.

The apparatus (215) can be designed, without limitation, so that all of the components or parts are mounted inside the skin or covering of the machine. For applications where the apparatus (215) is operated from within the area in which the aerosol is deployed or administered, the components or parts can be housed inside a suitable and effective NEMA or IP rated enclosure (345) that can keep any liquid, aerosol, or humidity from reaching or contacting any parts or components, and is accomplished in a manner known to those skilled in the art. The components can be independently or collectively housed in the aforementioned enclosure(s). The exterior or outside walls (755) (the term "wall(s)" can also refer to ceilings and floors in the present invention) of the apparatus (215) can, without limitation, form the NEMA or IP rated enclosure.

The apparatus (215) can, without limitation, be designed so that it can be mobile and easy to move. Without being limited, the apparatus (215) can have features including, but not limited to, a robust frame, robust wheels, bumpers, multiple grab and hoist points, and other design features known to those skilled in the art for designing a mobile apparatus (215) that can be of variable weight and size. The apparatus (215) may be constructed from any material that is compatible, and suitable for use with the liquid (30).

Without limitation, the administered or applied aerosol (200) can be removed from the area(s) in which it is applied during or after the application of the aerosol and can be accomplished with various means know to those skilled in the art. It is preferred, without limitation, that one or more ventilation or exhaust blower(s) (350) be used to pull or push air or gas and aerosol (200) out of the area(s) (210) in which the aerosol is administered or deployed. The said ventilation or exhaust blower(s) (350) can be controlled with one or more PLC(s) either not connected or connected directly or indirectly to the PLC(s) (315) of the apparatus of the present invention. The ventilation or exhaust blower(s) (350) can move any quantity of air/gas at any speed, but should have effective attributes and design for the intended application, all which is known by those skilled in the art. Anything that is removed from the area(s) (210) with the ventilation or exhaust blower(s) (350) can be done so in a manner known to those skilled in the art.

The ventilation or exhaust blower(s) (350) can also be used to bring fresh air into the area(s) in which the aerosol is applied either during or after the administration or deployment of the aerosol. The air or gas that is either removed or brought into the process area(s) can be accomplished in a manner known to those skilled in the art. The blower(s) (350) and related parts may be constructed from any material that is compatible, and suitable for use with the liquid (30).

The liquid (30) in any tank(s) or reservoir(s) (40) can be removed from the apparatus via one or more drain (655) in a manner known in the art. The movement of any liquid (30) out of the apparatus (215) can be controlled with one or more valve(s) (660). It is preferred, without limitation, that the valve(s) (660) is a solenoid valve and can communicate or send signal to one or more PLC(s) (315).

According to an embodiment, the apparatus is designed and constructed so that the aerosol producing transducer(s) (10) and/or their liquid facing surfaces or the surfaces from which there is aerosol-producing output, are able to match the angle of or remain level or parallel with, the surface of the liquid (30) above them. This is made possible by means including, but not limited to, a float assembly that holds, houses, or otherwise positions the transducers, and a gimbaled or articulating arm or holding assembly, as best shown in FIGS. 16-32. This embodiment is important for reasons including, but not limited to, the need to cover the transducers (10) with an effective amount or depth of liquid (30) to prevent the transducers (10) from being damaged due to being covered with an insufficient amount or depth of liquid (30), or to prevent the transducers (10) from being damaged by being operated without liquid above them. (30). This embodiment permits the present invention to be operated on or interfaced with surfaces that are without limitation, flat, semi-angled, angled, sloped, not sloped, or have various orientations. This embodiment does not claim, or attempt to claim, leveling the apparatus (215) by utilizing height adjustable legs or wheels that extend from the apparatus (215) and interface with a floor(s), a table top(s), or other surface(s) on which the apparatus (215) is placed or otherwise resting on, since this feature is taught in (col. 8, line 42-51) by U.S. Pat. No. 5,878,355 (Berg et al. 1996), and in (col. 8, line 50-58) by U.S. Pat. No. 6,102,992 (Berg et al. 1998). This embodiment includes interfacing, connecting, positioning, placing, or mounting, the transducers (10) to a means, or a material or object that is connected to a means, that can enable the transducer(s) (10) and/or their liquid facing surfaces or the surfaces from which there is aerosol-producing output, to match the angle of or remain aligned, level, or parallel with, the surface of the liquid (30) above them.

The first aspect of this embodiment includes, without limitation, mounting, interfacing, or connecting the aerosol generating transducers (10) to a reservoir (40) or into a reservoir (40), or to a means such as, but not limited to, one or more float(s) or float assembly(s) positioned or located in a reservoir (40), and the transducers (10) or reservoir(s) (40) is interfaced, connected, positioned, placed, or mounted, to a means (355), or a material or object that is connected to a means, that can enable the transducer(s) (10) and/or their liquid (30) facing surfaces or the surfaces from which there is aerosol (200) producing output, to match the angle of or remain aligned, level, or parallel with, the surface of the liquid (30) above them. The said means can include, but is not limited to, a ball joint, gimbal, or other means known to those skilled in the art. The components are designed and assembled in a manner known to those skilled in the art, but at least, without limitation, addresses design and assembly issues such that design considerations or variables like center of gravity and balance of the total system are sufficiently addressed and results in an effective apparatus (215). The transducers (10) in this first aspect can be, without limitation, mounted or interfaced with the reservoir(s) (40) through openings in the reservoir(s) in a way that is known to those skilled in the art, or they can be mounted, interfaced, or connected to the reservoir(s) either inside or outside of the reservoir. Without limitation, the reservoir(s) (40) can be fixed in position, free floated, or allowed to freely move. Without limitation, the reservoir(s) (40) can be enclosed, not enclosed, or semi-enclosed, so that air/gas can flow through it and carry the generated aerosol (200) away from the apparatus (215). The said means can also include, but is not limited to, hanging or suspending the entire nebulizing apparatus(s), or at least one or more of the reservoirs (40) in which the aerosol (200) is generated, from any means that would allow them to be freely hung or suspended in air or in a liquid, and have an effective free range of motion so that the transducer(s)

Figure 51:
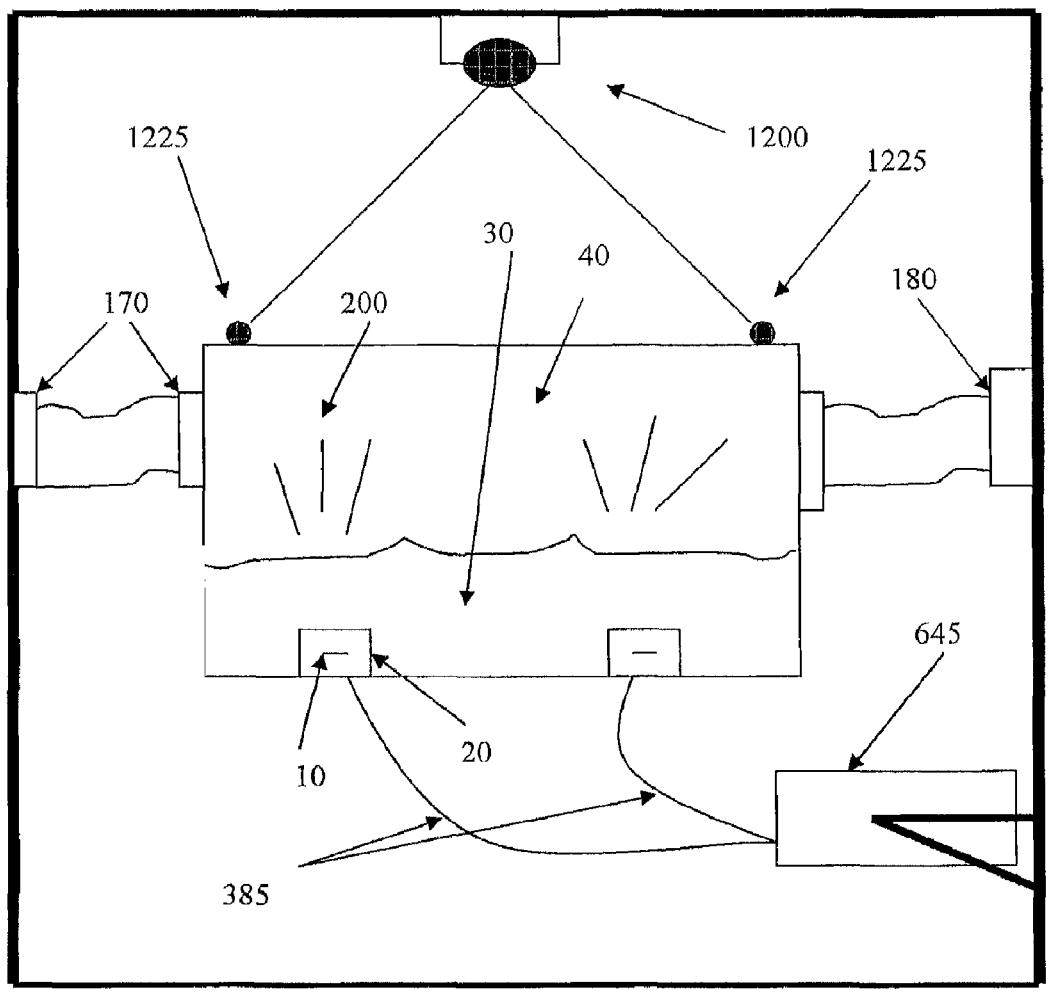
FIG. 51 is a schematic view of an embodiment of the aerosol generator that suspends the tank or reservoir including the transducers from a vertically-elevated support surface.

(10) are covered with a sufficient or effective amount of liquid (30). It is preferred, without limitation, that if more than one transducer (10) is utilized, they are not only effectively covered with liquid, but that they are covered with an equal depth or amount of liquid (30). This may, without limitation, include suspending or hanging the entire nebulizing apparatus(s) or one or more of the reservoir(s) (40) in which the aerosol (200) is generated, from one or more of any pivot point, swivel, ball joint, gimbal, or other means known to those skilled in the art (1200), as shown in FIG. 51. The one or more attachment points that enable the entire nebulizing apparatus(s), reservoir(s), or chambers to be suspended or hung, are effectively positioned. The means to hang (1200) the reservoir(s) (40) or chambers may also, without limitation, attach to one or more of any pivot point, swivel, ball joint, gimbal, or other similar means known to those skilled in the art (1225), that may also be effectively connected or otherwise directly or indirectly attached to the entire nebulizing apparatus(s), or reservoir(s) (40). The nebulizing apparatus(s), reservoir(s) (40), or any related parts or components in the present invention may be attached to any material or components including, but not limited to, wiring, tubing, piping, or conduits, and they may be, without limitation, flexible. They may also, without limitation, have sufficient flexibility to enable the entire nebulizing apparatus(s) or reservoir(s) (40) to freely hang, suspend, or have an effective free range of motion.

The second aspect of this embodiment includes, without limitation, placing one or more reservoir(s) (herein referred to as "secondary reservoir(s)") (360) inside of another reservoir(s) (herein referred to as "primary reservoir(s)") (40). Transducer(s) (10) are mounted or interfaced to or with the secondary reservoir(s) (360) in a way that is effective and is known in the art, or they can be mounted, interfaced, or connected to the secondary reservoir(s) (360) either inside or outside of that reservoir(s) (360), in a way that is effective and known to those skilled in the art. The secondary reservoir(s) (360) may also be interfaced, connected, positioned, placed, or mounted, to a means (355), or a material or object that is connected to a means, that can enable the transducer(s) (10) and/or their liquid facing surfaces or the surfaces from which there is aerosol (200) producing output, to match the angle of or remain aligned, level, or parallel with, the surface of the liquid (30) above them. The said means can include, but is not limited to a spherical ball joint or gimbal. Without limitation, the secondary reservoir(s) (40) can be free floated or allowed to freely move. Again, the components are designed and assembled in a manner known to those skilled in the art, but at least, without limitation, addresses design and assembly issues such that the center of gravity and balance of the total system are effectively or sufficiently accommodated.

Liquid (30) from the primary reservoir(s) (40) may be pumped into the secondary reservoir(s) (360) in various ways and fill the secondary reservoir(s) (360) so that it an effective depth or amount of liquid (30) is maintained. The walls (365) of the secondary reservoir(s) (360) can be of various heights, including, but not limited to, a height that allows the liquid (30) in the secondary reservoir(s) (360) to attain at least an effective depth. More specifically, the effective liquid (30) depth in the secondary reservoir(s) (360) may be attained by means including, but not limited to, positioning one or more openings or notches in the walls (365) of the secondary reservoir(s) (360) so that a sufficient amount of liquid (30) is able to drain out into the primary reservoir(s) (40) to maintain an effective depth of liquid in the secondary reservoir(s) (360). However, it is preferred, without limitation, that the walls (365) of the secondary reservoir(s) (360) are of a height so that the liquid (30) crests and spills over the walls (365) and back into the primary reservoir(s) (40), to ensure that an effective depth of liquid (30) is maintained. The height of the walls (365) of the secondary reservoir(s) (360) can also be adjusted to compensate for any drain holes that may be present to ensure that the secondary reservoir(s) (360) may effectively drain into the primary reservoir(s) (40) once the apparatus (215) has shut down.

Without limitation, the secondary reservoir(s) (360) can be designed so that a hermitically sealed area or compartment(s) (370) with a sufficient airspace known to those skilled in the art, can connect to or is extended from at least the floor or bottom of the secondary reservoir(s) (360), or even its walls (365), to facilitate the mounting or interface of the transducers (10) and provide an environment where the transducers (10) can safely and effectively operate. Without limitation, the hermitically sealed compartment(s) (370) can extend with flexible wall material and interface with the floor, bottom, or wall(s), of the primary reservoir(s) (40), or even extend through the floor, bottom, or wall(s), of the primary reservoir(s) (40). The flexible wall material is sufficiently flexible to allow the secondary reservoir(s) (360) to effectively move. However, it is preferred without limitation that flexible tubing (375) connect the aforementioned hermitically sealed compartment(s) (370) with any airspace in which the drive electronics (645) or amplifier(s) (230) is located. Wiring from the drive electronics (645) or amplifier(s) (230) can travel through this tubing to the transducer(s) (10). The secondary reservoir(s) (360) and related components, hermitically sealed area(s) or compartment(s) (370), flexible wall material, and tubing, are constructed from any material that is compatible, and suitable for use with the liquid (30). The secondary reservoir(s) (360) can also have sensor(s) to determine if the liquid (30) is either above or below what is desired or needed. In addition, any reference made in the present invention, to any reservoir(s) (40) in which the transducer(s) (10) are located, can also apply to the reservoir(s) (360) and (40) referenced in this second aspect of the embodiment.

The third aspect of this embodiment is preferred, and it includes, without limitation, locating or suspending one or more transducer(s) (10), their wiring, and housing(s) (20), where the housing (20) can be shared or used independently with the one or more transducer(s) (10), with the transducer(s) (10) being independently, interchangeably or collectively mounted to the housing (20), and other associated circuitry, parts and components, (herein referred to as "transducer assembly(s)") (100), at an effective orientation, depth, or distance below the surface of the liquid (30) in the reservoir(s) (40) during their operation. The transducer(s) (10) are a part of the transducer assembly(s) (100) and the transducer assembly(s) (100) may consist of one or more transducers (10). The transducer assembly(s) (100) consists of one or more transducer(s) (10) and their related parts, which are hermitically sealed in a housing (100). One or more transducers (10) and its associated parts may be located in or with a housing (20). There are numerous ways to effectively locate, position, or suspend the transducer assembly(s) (100) in the liquid (30) and includes, but is not limited to locating or suspending the transducer assembly(s) (100) at an effective distance, range, or depth, below the surface of the liquid (30), from one or more, wire(s), cable(s), tube(s), conduit(s), beam(s), or other means, that interfaces with or is attached to various locations, including, but not limited to, the walls or roof of the reservoir(s) (40), or secondary reservoir(s) (360) if it is used, or the walls or roof of the targeted area or sterilization chamber (210). The wire(s) (385) that connects from the transducer(s) (10) or transducer assembly(s) (100) to any drive electronics (645) or amplifier(s) (230) that sends signal to or operates the transducer(s) (10), can be, without limitation, protected from the liquid (30) or aerosol (200) in various ways including, but not limited to, placing, positioning, or running the wire(s) (385) inside or through tubing, pipes, conduit, beams, or other means to contain or embed the wire(s) (375) (herein referred to as "tubing"), and keep the wire(s) (385) separated from any aerosol (200) or any liquid (30). The tubing (375) may be constructed from any material that is compatible and suitable for use with the liquid (30). The wire(s) (385) may also be constructed from any material that is compatible, and suitable for use with the liquid (30). It is even more preferred that flexible tubing (375) connect the hermitically sealed transducer assembly(s) (100) with any airspace, that is hermitically or not hermitically sealed, in which the drive electronics (645) or amplifier(s) (230) is located. The flexible tubing (375) can also, without limitation, connect the environments of the transducer assembly(s) (100) and the drive electronics (645) or amplifier(s) (230) in a manner that is effective and safe, and known to those skilled in the art.

It is also preferred, without limitation, that the said tubing (375) or wire(s) (385) can connect with a suitable, effective, and usable, interface at various locations underneath the transducer assembly(s) (100). The wire(s) (385) and tubing (375) can also connect at other locations of the transducer assembly(s) (100) and in various ways known to those skilled in the art. It is further preferred that the wire(s) (385) or tubing (375) connects or interfaces with the underside of the transducer assembly(s) (100) with a watertight seal in a manner known to those skilled in the art. The wire(s) (385) or tubing (375) and wire(s) (385) can then travel through the wall(s) of the transducers assembly(s) (100) into its interior and connect to the transducer(s) (10). Without limitation, any clamp (390) made of a material that is compatible with the liquid (30), can help to create an effective seal between the tubing (375), and the housing (20) or transducer assembly(s) (100). It is even further preferred, without limitation, that the interface of the wire(s) (385) or tubing (375) with the transducer assembly(s) (100) is effectively or hermitically sealed from at least the inside of the transducer assembly(s) (100) with a means that includes, but is not limited to any, caulk, glue, sealant, or other means known to those skilled in the art, that is compatible and suitable for use with the liquid (30).

It is also preferred, without limitation, that the transducer(s) (10) or transducer assembly(s) (100), is located or suspended at an effective distance, range, or depth, below the surface of the liquid (30) by being directly or indirectly attached to or suspended from, without limitation, one or more buoyant object(s) (400), an interconnection or system of buoyant object(s) (400), or one or more components or parts that are connected or interconnected to one or more buoyant object(s) (400), where the said buoyant object(s) (400): (a) has buoyancy or neutral buoyancy but is completely submerged in the liquid (30), (b) has the ability to float partially submerged in the liquid (30), or (c) have the ability to float on the surface of the liquid (30). Without limitation, the transducer assembly(s) (100) can also be designed so that it can independently, have buoyancy or neutral buoyancy but is completely submerged in the liquid (30), have the ability to float partially submerged in the liquid (30), or have the ability to float on the surface of the liquid (30).

The transducer assembly(s) (100) and the said buoyant object(s) (400) can be designed to rise and fall in the reservoir(s) (40) to match any fluctuations in the depth of the liquid (30) in the reservoir(s) (40) so that an effective orientation and effective depth or distance below the surface of the liquid (30) in the reservoir(s) (40) is constantly maintained during the operation of the transducer(s) (10). It is also preferred, without limitation, that the transducer assembly(s) (100), as well as buoyant object(s) (400) if they are used, in the preferred aspect, be maintained in the proper, designated, or desired position(s), in an X-Y-Z coordinate plane or desired area(s) in the reservoir(s) (40), especially if the liquid (30) level fluctuates. This can be accomplished, without limitation, by connecting the transducer assembly(s) (100) or buoyant object(s) (400) with one or more control arm(s) (440) or other means, which is directly or indirectly connected to or interfaced with the walls, floors, roof, or any surfaces, of the reservoir(s) (40). The control arm(s) (440) or other means can, without limitation, be connected to any buoyant object (400). It is further preferred, without limitation that the control arm(s) (440) be designed in a manner known to those skilled in the art, so it can pivot or move in various directions or orientations. The control arm(s) (440) can also, without limitation, have one or more additional means to allow the transducer assembly(s) to freely pivot or move in various directions or orientations, and without limitation, directly or indirectly interface with the transducer assembly(s) (100). The control arm(s) (440) can be designed to keep the transducer assembly(s) (100) from inadvertently contacting any walls or surfaces of the reservoir(s) (40). The various components and parts that interface with the transducer housing(s) (20), or assist in holding or positioning the transducer housing(s) (20), are constructed from any material that is compatible and suitable for use with the liquid (30).

The control arm(s) (405) or other similar means, can also, without limitation, incorporate sensors into their design or the design of direct or indirectly connected parts and components, or in the design of the walls or ceiling of the reservoir(s) (40) so that the apparatus (215) will shut down or enter a fault or error mode if the control arm(s) (405) or related parts or components rises beyond a predetermined point due to a rise in the depth of the liquid (30) in the reservoir(s) (40), or drops below a predetermined point due to a drop in the depth of the liquid (30) in the reservoir. The type of sensors and their incorporation into the design of the apparatus (215), as well as their communication with the PLC (315) can vary. The various components utilized in this embodiment can be, without limitation, designed and assembled to address issues such as center of gravity and balance of the total system.

It is more preferred, without limitation, that one or more transducer assembly(s) (100) are effectively positioned within the reservoir(s) (40) using a combination of one or more, but not limited to, the following features or attributes: First, the transducer housing(s) (20) is located between or connected to one or more buoyant object(s) (400) of various size, shape, material, and buoyancy. Second, one or more spring clip(s) (415) are attached or connected to each buoyant object(s) (400) and interface, hold, or support the transducer housing(s) (20). Other means may also be used to connect or interface the transducer housing(s) (20) with the buoyant object(s) (400). The spring clip(s) (415) can interface with the transducer housing(s) (20) in various ways. It is preferred, without limitation, that one or more protrusions (410) from the transducer housing(s) (20) engage one or more trough(s), hole(s), or grove(s) of any shape and size present in the spring clip(s) (415). This supports or holds the transducer assembly(s) (100). Third, one or more end plates (420) connect with the buoyant object(s) (400). Fourth, one or more buoyant object(s) (400) or end plate(s) (420) connects with a spacer washer (425), which is connected to a wave washer (505) that also connects with another spacer washer (425). Fifth, a rotating clevis (430) connects to the spacer washer (425) furthest from the buoyant object(s) (400) or end plate(s) (420). Sixth, a shoulder bolt (500) connects with the rotating clevis (430), spacer washer (425), wave washer (505), another spacer washer (425), and end plate(s) (420) or buoyant object(s) (400). Seventh, the interface or connection of the shoulder bolt (500), spacer washers (425), and the wave washer (505), enables the transducer housing(s) (20) and buoyant object(s) (400) to have a free range of motion about the longitudinal axis of the shoulder bolt (500).

Eighth, a second clevis (435) is attached or connected to a pivot arm (herein referred to as "control arm") (440). The second clevis (435) can either move or be fixed in position. Ninth, the second clevis (435) can move by being connected or attached to the control arm (440) in the same manner that the rotating clevis (430) connects to the buoyant object(s) (400) or end plate(s) (420). Tenth, it is preferred, without limitation, that the fixed clevis (435) is held in place to the control arm (440) with bolts or screws. Eleventh, the fixed clevis (435) and rotating clevis (430) are connected and held together with a bolt, pin, or quick release pin (herein referred to as "pin") (490). The pin (490) can have a locking mechanism (495). Twelfth, the interface of the fixed clevis (435), rotating clevis (430), and pin (490), enable the transducer housing(s) (20) to have a free range of motion about the longitudinal axis of the pin (490).

Thirteenth, the control arm (440) has a hole (480) into or through which a torque tube (465) is positioned or connected. Fourteenth, the torque tube (465) interfaces with a washer (445) and bolt (450) from the interior side of the reservoir (40). Fifteenth, the torque tube (465) can have one or more notches or grooves located at any effective location where at least one, but preferably two or more o-rings (455) are seated. Sixteenth, the flange plate (470) fits over and interfaces with the bearing (475). Both the o-rings (455) and flange plate (470) are made of any suitable, effective, and chemically compatible material, and their hardness can vary. Seventeenth, the bearing (475) fits over and interfaces with the torque tube (465). Eighteenth, it is preferred, without limitation, that the torque tube (465) and bearing (475) are interfaced by inserting the torque tube (465) through a pivot hole (625) in the wall of the reservoir(s) (40), from the interior side of the reservoir(s) (40), and inserting the bearing (475) into the same hole (625) from outside of the reservoir(s) (40). Nineteenth, it is further preferred, without limitation, that the flange plate (470) interfaces with the bearing (475) outside of the reservoir(s) (40). Twentieth, the retaining spring plate (485) interfaces with the bearing (475). Twenty-first, the bearing (475) can also, without limitation, be connected or attached to the control arm (440), and the torque tube (465) and bearing (475) can be interfaced by inserting the bearing (475) and related components, through a hole (625) in the wall of the reservoir(s) (40), from the interior side of the reservoir(s) (40), and inserting the torque tube (465) and related components, into the same hole (480) from outside of the reservoir(s) (40). In this situation, the flange plate (470) would interface with the bearing (475) inside of the reservoir(s) (40).

Twenty-second, one or more control arm(s) (440) and any direct or indirectly connected parts or components can be used. The control arm(s) may have any range, angle, or degree of motion or movement. It is preferred, without limitation, that the control arm(s) (440) can have up to thirteen degrees in vertical, arc, or semi-vertical motion. Twenty-third, in essence, the control arm(s) (440) is connected to a torsional tube (445) that transfers motion from the inside of the reservoir(s) (40) through the reservoir(s) (40) walls, to the switch actuator plate (565).

Twenty-fourth, one or more switch actuator plates (565) is interfaced with the torsional tube (445) or bearing (475) and is located at the exterior of the reservoir(s) (40). It is preferred, without limitation, that the switch actuator plate(s) (565) is interfaced with the torsional tube (445). Twenty-fifth, the movement of the control arm(s) (440) directly or indirectly causes the switch actuator plate(s) (565) to move. Twenty-sixth, the switch actuator plate(s) (565) is designed so that its movement causes the actuation of one or more various switch(s) (590). The switch actuator plate(s) (565) can be of many different shapes, sizes, and geometries. Twenty-seventh, any type and number of switch(s) (590) may be used to indicate or communicate any condition(s) or situation (s) in the reservoir(s) (40). Twenty-eighth, the switch(s) (590) may be located anywhere around, in front of, or at any effective proximity to the switch actuator plate(s) (565). It is preferred, without limitation, that the switch actuator plate(s) (565) has one or more protrusion(s), groove(s), or indentation(s) (665), which can interface with and contact or actuate one or more switch(s) (590). Twenty-ninth, one or more switch(s) (590) are interfaced with or connected to one or more base plate(s) (540) which is interfaced with the exterior wall(s) of the reservoir(s) (40) or other surfaces. Thirtieth, the position and meaning of each switch (590) connected to a base plate(s) (540) can vary and be interchanged. It is preferred, without limitation, that three switches (590) are used to indicate or communicate to the PLC(s) (315) the various liquid levels in the reservoir(s) (40). The first switch is the tank full switch (550). Without limitation, the interaction or lack of interaction of the switch actuator plate(s) (565) with this switch (550) can indicate or communicate to the PLC(s) (315) that the liquid (30) level in the reservoir(s) (40) is at or above a designated or specified level. This can, without limitation, cause one or more valves (300) that control the flow of liquid (30) into the reservoir(s) (40) to close. The second switch is the tank refill switch (555). Without limitation, the interaction or lack of interaction of the switch actuator plate(s) (565) with this switch (555) can indicate or communicate to the PLC(s) (315) that the liquid (30) level in the reservoir(s) (40) is at or below a designated or specified level and the reservoir(s) (40) needs refilling. This can, without limitation, cause one or more valves (300) that control the flow of liquid (30) into the reservoir(s) (40) to open or semi-open. The third switch is the tank low level switch (560). Without limitation, the interaction or lack of interaction of the switch actuator plate(s) (565) with this switch (560) can indicate or communicate to the PLC(s) (315) that the liquid (30) level in the reservoir(s) (40) is at or below a designated or specified level. This can, without limitation, cause various components of the apparatus (215) to shut down such as, but not limited to any, pump(s) (130), blower(s) (180), heater(s) (150) or (310), or any drive electronics (645) or amplifier(s) (230).

Thirty-first, one or more cover plate(s) (580) fit over the switch(s) (590). The cover plate(s) can, without limitation, provide rigidity to the various connected components (610) and prevent damage to the switches (590) resulting from possible contact with any objects. The cover plate(s) (580) can also prevent certain shock hazards as well as act as a passive terminal protection for the various switch(s) (590).

Thirty-second, one or more hydraulic dampener(s) are connected to the switch actuator plate(s) (565) or any other components that directly or indirectly connect to the transducer assembly(s) (100), buoyant objects (400), or control/control arm (440). The hydraulic dampener(s) (585) is a push or pull hydraulic mechanism whose design and function is known in the art. The hydraulic dampener(s) (585) can, without limitation, dampen any rotation or movement of the control arm (440), transducer housing(s) (20), switch actuator plate (565), or other related components, resulting from any shock and vibration that the apparatus (215) may encounter.

It is further preferred, without limitation, that an enhanced design for interfacing one or more transducer(s) (10) with one or more housing(s) (20) in various and modifiable configurations is utilized in the present invention. This design includes, without limitation, the following features. First, each housing (20) that is utilized is constructed so that it has one or more space(s) or recess(s) (600) that interface with one or more transducer(s) (10) as desired. The housing(s) may be made of any suitable material that is not affected by the chemical action of the liquid (30). Suitable materials for the housing(s) (20) may include PVC, polypropylene, and stainless steel, but other suitable materials may be used. It is preferred without limitation that the housing(s) (20) is made from stainless steel. It is preferred, without limitation, that three spaces or recesses (600) are utilized per transducer housing (20), and the center space or recess (620) connects with the other spaces or recesses (600) through one or more hole(s), opening(s), pipe(s), channel(s), or conduit(s) (herein referred to as "holes") (535). The wire(s) (385) that connect the amplifier(s) (230) to the transducer(s) (10), enter the housing(s) (20) through one or more hole(s), opening(s), pipe(s), channel(s), or conduit(s) (605) located anywhere on the side of the housing (20) that faces opposite from the surface of the liquid (30) in the reservoir(s) (40). The wire(s) (385) can, without limitation, enter the center space(s) or recess(s) (620) and travel through the hole(s) (535) to connect with their respective transducer(s) (10). The wire(s) (385) connect with the transducer(s) in a manner known to those skilled in the art.

Each space(s) or recess(s) (600) or their surrounding surfaces (640) can interface with one or more o-rings (635). It is preferred, without limitation, that each space(s) or recess(s) (600) interfaces directly or indirectly with at least three different o-rings and various other parts or components. The first o-ring is the secondary o-ring (515), and it interfaces with a concentric shelf (630) that is built into each space or recess (600). The second o-ring is the outside o-ring (510), and it interfaces with the outside circumference of the compression ring (525). Without limitation, any surface of each housing (20) can have groves or indentations of various construction in which the o-rings can be seated, and the groves are designed and constructed in a manner known to those skilled in the art. The transducer (10) is interfaced or adhered to the barrier (60). It is preferred, without limitation, that the barrier (60) is constructed from glass. The barrier (60) is interfaced with, seated into, or nested on top of the secondary o-ring (515). The third o-ring is the primary o-ring (520), and it interfaces with the liquid (30) facing side of the barrier (60) and any of the inside surfaces (525) of the compression ring (525). The compression ring (525) can be constructed from any suitable material that is not affected by the chemical action of the liquid (30). Suitable materials of the compression ring (525) may include PVC, polypropylene, and stainless steel, but other suitable materials may be used. It is preferred, without limitation that the compression ring (525) is made from stainless steel. Any o-rings, including the secondary o-ring (515), outside o-ring (510), and primary o-ring (520), can have any cross section shape, or hardness, and are constructed from any suitable material that is not affected by the chemical action of the liquid (30). It is preferred, without limitation, that the primary o-ring (520) and secondary o-ring (515) have a double seal cross-section shape, and the outside o-ring (510) has a round cross-section shape, and these various o-rings are constructed from Viton material. The various components, except for the transducer (10) and barrier (60) are assembled and compressed together to form a watertight seal in various ways known to those skilled in the art. Without limitation, tub walls (530) may also interface with any housing(s) (20).

The control arm(s) (405), transducer assembly(s) (100), reservoir(s) (40), and other related component(s), can be designed, so that when the reservoir(s) (40) is drained, the buoyant object(s) (400), transducer assembly(s) (100), control arm(s) (405), or other connected parts or components will move down into or onto, one or more of any means to sufficiently and effectively prop, position, stabilize, or hold, the buoyant object(s) (400), transducer assembly(s) (100), control arm(s) (405), or other connected parts or components, at any angle or orientation, within the reservoir(s) (40). This may include, without limitation, any mechanism(s), apparatus(s), structure(s), inset mold(s), nest(s), groove(s), indentation(s), or protrusion(s) (herein referred to as "structure") (1050) that can, interface with the buoyant object(s) (400), transducer assembly(s) (100), control arm(s) (405), or other connected parts or components, or without limitation, partially, generally, roughly, or exactly, mirror or generally mirror, at least a sufficient amount of the contours or geometry of the buoyant object(s) (400), transducer assembly(s) (100), control arm(s) (405), or other connected parts or components, to be effective. The said mold(s), inset(s), nest(s), groove(s), indentation(s), or other structures can be designed to drain if necessary or when desired, in a manner known to those skilled in the art. When the reservoir(s) (40) is drained the buoyant object(s) (400), transducer assembly(s) (100), control arm(s) (405), or other connected parts or components, can rest, without limitation, at any angle or orientation to provide an angle that is steep enough for any deposited liquid to move off or drain from any surfaces of the transducer assembly(s) (100), including any surfaces above or interfaced with the transducers(s) (10), into the reservoir(s)'s (40) drain(s) (655).

According to an embodiment, the protective barrier (60) that interfaces with the transducer(s) (10) can be polished on one or more sides. When a protective barrier (60) is ground to a specific thickness, its ground sides may have an appearance or characteristics that can include, but is not limited to, unpolished, rough, hazy, or frosted due to the grinding process. This is, without limitation, especially true with protective barriers (60) that are constructed from any type of glass that is ground. The prior art has taught the use of protective barriers (60), including glass, in U.S. Pat. No. 3,433,461 (Scarpa et al.), U.S. Pat. No. 3,729,138 (Tysk), U.S. Pat. No. 4,109,863 (Olson et al.), and U.S. Pat. No. 4,976,259 (Higson et al.), which are incorporated herein by reference in their entirety, including any references cited therein. However, the prior art is silent with respect to the use of a polished barrier(s). It can be assumed that the protective barriers (60) mentioned in the prior art were ground to their specific thicknesses but not polished after being ground. Polishing the liquid side of the protective barrier (60) can, without limitation: (a) reduce or eliminate the texture or surface features that can catch or hold undesirable foreign objects or debris, (b) provide a surface that easier to clean and/or be more effectively cleaned, (c) reduce the amount of texture or surface features that may promote the build up of mineral deposits, (d) promote easier movement of liquid (30), foreign objects, or debris, off of the protective barrier (60) surface(s) when the reservoir(s) (40) is emptied. Polishing the side of the protective barrier (60) that is not in contact with the liquid can, without limitation: (a) reduce surface variability on the side of the protective barrier (60) that interfaces with any adhesive (70), which can reduce the variability in the thickness of the adhesive (70) between the protective barrier (60) and transducer(s) (10) which may in turn, without being limited, reduce variability in certain energy transmission characteristics or other transmission related issues. An unpolished protective barrier (60) surface that interfaces with an adhesive (70) can enhance the bonding between the protective barrier (60) and the transducer(s) (10) for reasons known to those skilled in the art. The protective barrier (60) in the present invention can, without limitation, be polished or unpolished on both the liquid (30) and transducer (10) facing sides. However, it is preferred, without limitation, that the protective barrier (60) is polished on the side that faces the liquid (30) and remain unpolished on the side that faces the transducer(s) (10). Polishing in this embodiment can vary in ways including, but not limited to its, depth, completeness, precision, quality, and accuracy.

According to an embodiment, the apparatus can be designed and constructed so that more than one aerosol producing transducer (10) is surrounded, enclosed, or encircled by one or more walls or barriers (herein referred to as "tub walls") (530). However, if only one transducer (10) is used in the present invention, it may also be surrounded, enclosed, or encircled by one or more tub walls (530). This embodiment should not be confused with what is taught in U.S. Pat. No. 5,300,260 (Keshet et al., 1993) in (col. 3, line 15-21) and (col. 3, line 50-51), which is incorporated herein by reference in its entirety, including any references cited therein. Keshet et al., taught the positioning of baffles between each aerosol producing transducer as a means to suppress waves. The tub walls (530) in this embodiment are not positioned between individual transducers (10) so as to not conflict with U.S. Pat. No. 5,300,260. The performance of the transducers (10) in the present invention was found in the laboratory not to be adversely effected by waves created by neighboring, or even closely positioned transducers (10). The art taught by Keshet et al. is inapplicable to the present invention. The walls (10) in the present invention are intended to contain the liquid (30) above and around the transducers (10) and use the heat generated by the transducer(s) (10) to heat the liquid (30) above and around the transducer(s) (10), as well as the liquid (30) at the liquid (30) surface above the transducers (10). This embodiment may, without limitation, eliminate the need for any additional means to heat the liquid in certain circumstances known to those skilled in the art. This embodiment utilizes teachings from the book titled, "Aerosol Technology" by William C. Hinds (1982), which is incorporated herein by reference in its entirety, including any references cited therein, where it is taught that ultrasonic aerosol generating transducers can heat the surrounding liquid (page 382). This embodiment can without limitation, offer the added benefit of enabling the transducers (10) to quickly heat the surrounding liquid (30) and liquid (30) surface above them. The tub walls (530) can also, without limitation, be designed or modified in a manner known to those skilled in the art so that the liquid (30) contained within the tub walls (530) is able to reach or experience an effective exchange with the surrounding liquid (30) outside of the tub walls (530), so that the liquid (30) within the tub walls (530) is not able to either exceed a given temperature or drop below a given temperature. Without limitation, the tub walls (530) can be continuous or non-continuous, and they can have one or more openings (670) of various size, shape, and in various locations. The tub walls (530) can, without limitation, be sealed or partially sealed, interfaced or not interfaced, interlocked either tightly or loosely, or be unsealed. The tub walls (530) can without limitation, interface completely or intermittently, or not interface, with the surfaces of the transducer assembly(s) (100) or the housing (20), and the height of the tub walls (530) can also vary. Any gap or distance (925) may exist between the tub walls (530) and any surfaces of the transducer assembly(s) (100) or the housing (20). It is preferred without limitation, that the tub walls (530) extend to an effective height above the surface of the liquid (30). Without being limited, one or more notches can also be cut into the top of the walls and can be of various size, shape, and in various locations. The tub walls (530) and associated parts may be constructed from any material that is compatible, and suitable for use with the liquid (30). The tub wall(s) (530) can also be designed and constructed to perform the same function(s) as the buoyant object(s) (400), or share any of the same features of the buoyant object(s) (400). The tub wall(s) (530) can, without limitation, have any density, buoyancy, air space, thickness, size, shape, and can be injection or blow molded. Without limitation, the tub wall(s) can be directly or indirectly positioned or interfaced anywhere with and in any orientation to the transducer assembly(s) (100) or housing(s) (20). The tub wall(s) (530) can have any number of vertical or angled voids, holes or openings (herein referred to as "openings") (920) above the transducer(s) (10) or transducer assembly(s) (100). The openings (920) can, without limitation, allow any emitted pressure (energy) resulting from the operation of the transducer(s) (10), to reach the surface of the liquid (30) in the reservoir(s) (40). The openings (920) can be any size, shape, or have any angle or cant.

According to an embodiment shown in FIGS. 53 and 36, the apparatus can be designed and constructed so that air/gas that surrounds the apparatus (215) or outside air/gas that is pulled into the apparatus (215) for purposes including, without limitation, removing the aerosol (200) that is generated by the transducer(s) (10), from the apparatus (215) and into the intended or targeted area (210), is filtered before it enters the apparatus (215), or at least before the air/gas reaches the aerosol generation chamber (40). One or more filters (675) of various kinds and function, may be used, but should be at least sufficient for the intended amount or degree of filtering that is desired or needed, and the correct filter (675) that is used for a specific application is known to those skilled in the art. It is preferred, without limitation that the filter(s) (675) is located at any location where the air/gas is drawn or pulled into the apparatus (215) by a blower or fan or other means (180) to move the air/gas or aerosol (200). It can be located either on the inside or outside of the apparatus (215) and sufficiently interfaced with the apparatus (215) in a manner that is known to those skilled in the art. The filter(s) (675) can, without limitation, prevent or limit dust or debris contamination inside of, on, or in: (a) any liquid (30), (b) any pipe(s) (685) that are used to construct the aerosol generating apparatus (215) through which the air/gas is moved, (c) the fan or blower or other source of pressurized air (180), (d) the chamber (40) in which the transducer(s) (10) are located, or (e) the introduction of various types of contaminates into the intended or targeted area (210) in which the aerosol (200) is deployed. The filter(s) (535) are not used in any configuration(s) or application(s) involving a "closed loop system" where the air/gas or aerosol (200) that is deployed from the apparatus (215) is then recirculated back to the apparatus (215) through one or more return conduit(s) or pipe(s) (240). This avoids any conflict with: (a) (col. 3, line 19-24), (col. 11, line 14-17) and (claim #21) of U.S. Pat. No. 5,878,355 (Berg et al. 1996), and (b) (col. 3 line 26-31), (col. 11, line 20-23) and (claim #8) of U.S. Pat. No. 6,102,992 (Berg et al. 1998), both of which are incorporated herein by reference in its entirety, including any references cited therein. The filter(s) (675) can be, without limitation, disposable. One or more protective covers (680) may also be directly or indirectly connected to the filters (535). The protective covers (680) may be positioned, or installed anywhere in the air/gas stream before the air/gas enters the filter(s). One or more protective cover(s) (680) may also be integrated into any external walls (755) of the apparatus and may be constructed from any material that is compatible, and suitable for use with the liquid (30).

According to an embodiment, the apparatus (215) can be designed and constructed so that one or more tank(s) (herein referred to as "intermediate tank(s)") (695), are connected between the one or more tank(s) (280) in which liquid (30) is stored and the reservoir(s) (40) they feed or supply, in which transducer(s) (10) are located. The intermediate tank(s) (280) can, without limitation, perform the function of a check or failsafe device or design, and prevent the reservoir(s) (40) in which the transducers (10) are located from being overfilled with liquid (30) if one or more valve(s) (300) from the tank(s) (280) that feed or supplies the reservoir(s) (40) fail in an open or semi-open position. The intermediate tanks (695) can have one or more of various types of valves (300) that include, but are not limited to, float valves, or solenoid valves. The valve(s) (300) can control the flow of either inbound or outbound liquid (30). The said valve(s) (300) can, without limitation, be actuated by a PLC (315), or by one or more sensor(s) (305) located in the intermediate tank(s) (695) or reservoir(s) (40) in which the transducer(s) (10) are located, and is accomplished in a manner known in the art. The valve(s) (300) are also installed, and connected to a PLC (315), if applicable, in a manner known to those skilled in the art. The valve(s), immediate tank(s), and associated parts may be constructed from any material that is compatible, and suitable for use with the liquid (30).

According to an embodiment, the apparatus (215) can be designed and constructed so that one or more liquid containment tank(s) (705) is connected to various parts, components, or areas of the apparatus including, but not limited to, the fill pipe(s) (295), blower or fan housing(s) (180), internal catch pan(s) or basin(s) (700), reservoir(s) (40) in which the transducers (10) are located, or pressurized air pipe(s) or conduit(s) (685). Without limitation, the aforementioned liquid containment tank(s) (705) is designed to collect excess, spilled, leaked, coalesced, or other undesired liquid (30). It can be connected to the main drain (655) and valve (660) used to drain the apparatus, or it can have its own drain pipe and valve. The positioning of the liquid containment tank(s) (705) as well as its shape and capacity can vary. A liquid level sensor (305) may be used to detect the presence of any liquid (30) or the depth of the liquid (30) in the containment tank(s) (705). The said liquid level sensor (305) may communicate with a PLC (315) and cause the apparatus to shut down or enter a fault or error mode if the if the liquid level (30) exceeds a defined depth. The liquid containment tank(s) (705) and associated parts may be constructed from any material that is compatible, and suitable for use with the liquid (30). Without limitation, any pipe(s) (685) carrying inbound or outbound air or aerosol, as well as the blower(s) (180) and the pipe(s) (685) that connect it to the reservoir(s) (40) in which the transducers (10) are located, can be canted or angled back toward the reservoir(s) (40) in which the transducer(s) (10) are located to carry out various functions such as, but not limited to, helping collect any liquid (30) from those areas.

According to an embodiment, the apparatus can be designed and constructed so that it has one or more means to control the temperature of the liquid (30) in the various reservoir(s), which includes, but is not limited to, preventing the temperature of the liquid (30) in the reservoir(s) (40) in which the transducers (10) are located, from exceeding the maximum desired, established, or required operating temperature for that liquid (30) or particular process in which the liquid (30) is being used.

As previously discussed, the prior art has taught the heating of the liquid (30) in various ways including, but not limited to, heating the liquid (30) from the heat that is imparted into the liquid (30) during the operation of the transducers (10). It is obvious to one skilled in the art, that the air or gas that is used to remove the generated aerosol (200) from the reservoir(s) (40) in which the transducers (10) are located, can contribute to the removal of heat from the liquid (30). However, this pressurized air/gas flow can only remove a certain quantity of heat and is affected by factors including, but not limited to, the surface area of the liquid (30) in the reservoir(s) (40), and the volume and velocity of air/gas that moves over that surface area. If more heat is imparted into the liquid (30) than is removed over time, the liquid (30) will continue to rise in temperature.

The means to control or prevent the temperature of the liquid (30) in the reservoir(s) (40) in which the transducers (10) are located, from exceeding the aforementioned maximum desired, established, or required operating temperature, includes without limitation, a means to cool the liquid (30) by pumping or otherwise moving the liquid (30) that is in the reservoir(s) (40) in which the transducer(s) (10) are located, or any other liquid (30) that could possibly have contact with the liquid (30) in the reservoir(s) (40) in which the transducer(s) (10) are located, through a heat exchanger, cooling fins, cooling plate, cooling block, chiller, chilling or cooling apparatus, or other means known in the art (710), to remove heat from the liquid (30). It is preferred that this means includes pumping or moving the liquid (30) from the reservoir(s) (40) in which the transducers (10) are located, through cooling fins, chill block, or heat exchanger that is located in the path of the pressurized air/gas that is used to move the generated aerosol (200) away from the apparatus. The means to cool the liquid (30) can also interface or directly interface with the reservoir(s) (40) in which the transducers (10) are located and can include, but is not limited to, the interface or insertion of chill coil(s) or chill block(s) directly into the reservoir(s) (40) in which the transducers (10) are located. The means mentioned in this embodiment to cool the liquid (30) and associated parts may be constructed from any material that is compatible, and suitable for use with the liquid (30). The PLC(s) (315) can monitor the temperature of the liquid (30) in the reservoir(s) (40) with input from one or more liquid temperature sensing device(s) (820). The PLC(s) (315) can activate whatever means necessary to start, maintain, or stop any liquid (30) cooling activities or actions, to maintain any desired or necessary temperature.

An additional aspect of this embodiment includes, without limitation, insulating the reservoir(s) (40) in which the transducer(s) (10) are located, in various ways including, but not limited to, interfacing or applying any type of insulation material (760) to any surfaces of the reservoir(s) (40), or using a double wall construction (765) for the reservoir (40) where the said walls are separated with a layer of air, or other means known to those skilled in the art. Without limitation, insulating the reservoir(s) (40) can be useful in environments where it is important to increase heating efficiency or capacity and diminish heat loss from the system.

According to an embodiment illustrated in FIGS. 33 and 34, the apparatus can be designed and constructed so that it can be remotely communicated with and controlled, by anyone or any means. Without being limited, one or more PLC(s) (315) that control one or more parts of the apparatus can also communicate with or be controlled by any other apparatus and their PLC(s). More specifically, and without limitation, the remote control and communication with the apparatus can be accomplished by means such as, but not limited to, any radio frequency or amplitude, any electrical frequency or amplitude, any light frequency or amplitude, any digital or analog data packet, or by any directly or indirectly connected wire(s), which includes fiber optic wire(s), or any combination of the of the said means. Without limitation, any data, commands, or information can be sent and received by the apparatus and communicated between the apparatus and one or more additional means to send and receive any data, commands, or information. Commands, can include, but are not limited to, a command for the apparatus to start or to end an aerosol generation or deployment cycle. Communicated information or data can include, but is not limited to, the apparatus communicating its current operational status or condition, as well as liquid (30) level and temperature. It is preferred, without limitation, that the apparatus communicates by using one or more radio transceiver(s) (340) that is connected to one or more PLC(s) (315), that is connected to one or more HMI(s) (320), and communicates with one or more remote radio transceiver(s) (315) that is connected to one or more remote PLC(s) (315) which are attached to one or more remote HMI(s) (320) or other parts or components. The one or more antenna(s) (720) connected to the radio transceiver(s) (340), can be located anywhere on or in the apparatus (215), and can be constructed from various materials. The antenna(s) (720) and any related parts may be constructed from any material that is compatible, and suitable for use with the liquid (30). It is preferred, without limitation, that the radio transceiver(s) (340) and antenna(s) (720) be located within any NEMA or IP rated or hermitically sealed container(s) (345) that is constructed from polymer that is compatible, and suitable for use with the liquid (30). Within this embodiment, and without limitation, a plurality of apparatuses, including, but not limited to, apparatuses that are similar in process, or apparatuses that are similar or identical to the apparatus (215) of the present invention, can operate in the same, connected, or shared volume of space, and communicate information including, but not limited to their condition or status of their systems or the apparatus in general, to all of these apparatuses, so that if one apparatus has a problem, or enters into a fault or error condition or state, all of the other apparatuses can also shut down, or at least relay the incident to one or more remote PLC(s) (315), HMI(s) (320) which the operator can monitor. This embodiment also offers many advantages including, but not limited to, reducing or eliminating the chance of accidental exposure to the aerosol (200) from an apparatus (215) that is operating within the same environment (210) in which the aerosol (200) is applied.

According to an embodiment, the apparatus (215) can be designed and constructed so that it has one or more sensors, or the means for indirect or direct communication with one or more sensor(s) or PLC(s) (315) which are connected to one or more sensor(s), to determine if an effective or sufficient amount of aerosol (200) has been applied to the targeted area (210) and/or surfaces.

In the first aspect of this embodiment, each sensor consists of at least two parts including, but not limited to, a light source (725) and a light sensor (730), known to those skilled in the art. The light source (725) and light sensor (730) can be directly or indirectly connected, or they can be placed or positioned independent from one another. The distance between the light source (725) and light sensor (730) can vary. It is preferred without limitation, that the light source (725) and light sensor (730) are at separated by at least one foot. It is more preferred, without limitation, that the light source (725) and light sensor (730) be separated by at least four feet. It is even more preferred, without limitation, that the light source (725) and light sensor (730) be separated by at least seven feet. It is preferred, without limitation, that each sensor(s) consists of at least one laser of any power or class type for a light source (725), and at least one photoelectric sensor of any type and sensitivity (730) for a light sensor (730). The emitted light or energy, or light source (725) can have, without limitation, various: (a) intensity(s), (b) brightness, (c) period(s), (d) frequency(s), and (e) wavelength(s). The light source (725) can be controlled via a PLC (315), the light sensor(s) (730), or other means known in the art. The means to sense the light (730) can, without limitation, vary widely in its sensitivity and ability to sense light of various: (a) intensity(s), (b) brightness, (c) period(s), (d) frequency(s), and (e) wavelength(s). The means to sense the light (730) can also have various capabilities known in the art, including, without limitation, the ability to have adjustable sensitivity and trigger level(s), or the ability to communicate with a PLC(s) (315) or other components. The light sensor(s) (730) can, without limitation, indicate or communicate to a PLC(s) (315) if it either receives or ceases to receive a desired or set level of light stimulus, and the said communication can be accomplished in various ways known in the art. It is preferred, without limitation that the PLC(s) (315) is indicated or receives information by either an electrical signal or lack of an electrical signal from the light sensor(s) (730). This communication can result in various actions such as, but not limited to: (a) shutting down any drive electronics (645) or amplifier(s) (230), (b) shutting down the blower (180) or flow of pressurized air, or (c) shutting down the apparatus (215).

Without limitation, an effective or sufficient amount of administered aerosol (200) in this embodiment is indicated by its causing the disruption, diminishment, or cessation, of the light that is emitted from the light source(s) (725) before it reaches the photoelectric sensor (730). The effective, sufficient amount, or specified quantity, of administered aerosol (200) can vary for intended or unintended reasons or designs, and the trigger or sensitivity levels for the light sensor(s) (730) can, without limitation, be varied, calibrated, or adjusted, for each situational circumstance.

In the second aspect of this embodiment each sensor can sense or measure relative humidity in a manner known to those skilled in the art. Without limitation, the relative humidity sensor(s) (735) can have various capabilities and attributes including, without limitation, varying sensitivity, the ability to have adjustable trigger level(s), or the ability to communicate with a PLC(s) (315) or other components. The humidity sensor(s) (735) can, without limitation, indicate or communicate to a PLC(s) (315) the relative humidity data it collects, which can be accomplished in ways known in the art. The relative humidity sensor(s) (735) can receive or send any signal of any kind to or from any other components. It is preferred, without limitation, that the PLC(s) (315) receive humidity data or indications of various humidity detection events by either an electrical, optical, or radio signal, or lack of these signals from the relative humidity sensor(s) (735) or any components connected to the relative humidity sensor(s) (735). It is preferred, without limitation that the PLC(s) (315) is indicated by either an electrical signal or lack of an electrical signal from the relative humidity sensor(s) (735) when a certain humidity level is detected. This communication can result in various actions such as, but not limited to: (a) shutting down any drive electronics (645) or amplifier(s) (230), (b) shutting down the blower (180) or flow of pressurized air, or (c) shutting down the apparatus (215).

Also, without limitation, the PLC(s) (315) can be programmed to have delays of various length of time after receiving any data, communication, or signal, to initiate actions such as, but not limited to: (a) shutting down any drive electronics (645) or amplifier(s) (230), (b) shutting down the blower (180) or flow of pressurized air, or (c) shutting down the apparatus (215), after receiving any signal(s), data, or communication from any sensor(s) such as the light sensor (730) or the relative humidity sensor(s) (735) or related components.

According to an embodiment, the apparatus can be designed and constructed so that it can without limitation, measure, determine, or sense, the amount of liquid (30) that is in any tank or reservoir. Without limitation, this information or data may be used, in concert with or without a PLC (315), to: (a) communicate to the operator whether there is either a sufficient or insufficient amount of liquid (30) to execute a chosen operational cycle time, (b) communicate to the operator whether there is either a sufficient or insufficient amount of liquid (30) to execute an operational cycle time associated with a specific volume of space or other attribute(s) chosen by the operator, (c) communicate to the operator the quantity of liquid (30) or at least the minimum quantity of liquid (30), expressed in units of measure, which may be necessary to add or make available to the apparatus so that it may effectively or successfully complete a chosen or desired operational cycle. It is preferred, without limitation, that the units of measure in the present invention include, but are not limited to, any liquid (30) volume quantities expressed in, standard units of measure, imperial units of measure, English units of measure, units of measure according to the metric system, or units of measure according to System International (SI) units. French Patent No. FR2860721 (Schwal et al.), which is incorporated herein by reference in its entirety, including any references cited therein, taught that a fogging apparatus can notify the operator if an insufficient liquid (30) quantity is available (pg. 6 line 15-25 and pg. 10 line 10-25) and when it is necessary to replace a cartridge (290) (pg. 10 line 15-25). However, FR2860721 (Schwal et al.), only mentioned that an indication would be made by the fogging apparatus to the operator to replace an interfaced cartridge (290) (pg. 10 line 15-25), or additional possibly interfaced cartridges (290) (pg. 7 line 3-10), but it was silent with respect to the apparatus itself determining the amount of liquid (30) that is needed to properly or effectively fill the apparatus, and communicating the exact number of a plurality of cartridges (290) that may be needed to fill the apparatus with liquid (30) either partially or to full capacity so that it can successfully and effectively complete a predetermined operational cycle. Therefore, it is more preferred, without limitation, that the units of measure communicated can also include more than one or a plurality of cartridges (290) with a known quantity of liquid (30) that is needed to provide the apparatus with a sufficient quantity of liquid (30) for it to effectively or successfully complete its operational cycle time. It is even more preferred, without limitation, that the units of measure include, any units of measure, including any number of cartridges (290) as long as it is a plurality of cartridges. The apparatus can, without limitation, communicate to the operator the minimum quantity of liquid (30) needed to complete an operational cycle, as well as the quantity of liquid (30) that would be needed to fill the apparatus to capacity. Again, the quantity of liquid (30) may be expressed in any units of measure including, but not limited to, the number of cartridges (290). Information or data can be communicated to or from the apparatus with any means known to those skilled in the art including, but not limited to, human-machine-interface(s) (HMI) (320), terminal(s), remote terminal(s), any button(s) and associated light(s), screen(s), or audible signal(s). The apparatus can, without limitation, require the operator to acknowledge one or more prompts to add a certain amount of liquid (30) or a certain number of cartridges (290) as well as one or more prompts to verify if the action was undertaken. This can be accomplished with an HMI (320) or other means known to those skilled in the art. More specifically, this embodiment includes without limitation, the apparatus having the ability to sense, detect, or determine, with one or more sensor(s) or other effective means, any: (a) liquid (30) level, (b) liquid (30) depth, or (c) amount of liquid (30) in any tank(s), reservoir(s) (40), or other places where liquid (30) is held and available to the apparatus, and communicate that information to a PLC(s) (315). This may be accomplished in a manner known to those skilled in the art. It is preferred, without limitation, that one or more float sensor(s) (305), which can be located in various locations in the apparatus, be utilized for this purpose. They can be constructed from any material that is compatible, and suitable for use with the liquid (30), and their use and configuration are known to those skilled in the art. Any data, information, or signals, can be sent from the said means to sense, detect, or determine the liquid (30) level, liquid (30) depth, or amount of liquid (30) available, and can be sent or communicated, without limitation, to various places or means including, but not limited to, one or more PLC(s) (315) or HMI(s) (320). The PLC(s) (315) or HMI(s) (320) can be programmed in a manner known in the art to use the inbound information, data, or communication to control or interact with the apparatus, as well as communicate information to or from the operator. The PLC(s) (315) can, without limitation, be programmed so that the apparatus (215) will enter into a fault or error condition, or shut down one or more functions, and communicate an audible or visual signal to the operator, as well as communicate with any other PLC(s) (315), if the apparatus receives a command to operate for a certain amount of time or apply aerosol (200) to a certain volume and the PLC(s) (315) determines that an insufficient amount of liquid (30) is available.

According to an embodiment, the apparatus (215) can be designed and constructed so that it will not, without limitation, generate, create, or deploy aerosol (200), when the liquid (30) that is in or available to the reservoir(s) (40) in which the transducer(s) (10) are located cannot be used, administered, or deployed, for reasons including but not limited to: (a) the fluid (30) has exceeded the time or date within which it can be efficaciously used, or (b) the fluid (30) has reached a point in time or date where it has degraded or aged to a point where its use or application would be ineffective, unaccepted, unauthorized, or illegal. The present embodiment does not encompass what is taught in French Patent No. FR2860721 (Schwal et al.), which is incorporated herein by reference in its entirety, including any references cited therein. That patent includes placing or fitting a container(s) or cartridge(s) (290) of single use that is filled with the liquid (30) to be fogged or diffused, on or with an aerosol (200) dispensing device, and reading an identifier on the said container(s) with a reader (pg. 2, line 33-36) to determine its year/date (pg. 9 line 15-20) and suspending the operation of the apparatus if there is non-conformance, or in other words, the identifier(s) is determined to be associated with a container(s) that has expired. However, this embodiment, without limitation, also encompasses the liquid (30) that is in any cartridge(s) (290) (FIG. 12) that interfaces with the apparatus after the cartridge(s) (290) has been read and its use is approved, and the cartridge(s) (290) is opened or its seal is compromised, allowing the liquid (30) to be used or made available to the apparatus. This is important for reasons including, but not limited to, the liquid (30) can have a certain shelf life or period of effectiveness while in a closed container/cartridge (290), but once the container/cartridge (290) is opened, and exposed to its surrounding environment, or diluted, the shelf life or effective period of use is diminished or shortened. This can, without limitation, necessitate the monitoring, measuring, tracking, calculating, comparing, (herein "measuring"), the time that the liquid (30) can be utilized in the present invention until it cannot be used for various reasons known to those skilled in the art. Measuring the time that the liquid (30) can or cannot be used or its useful lifespan, can be accomplished by using a PLC(s) (315), or other mechanism or device known to those skilled in the art. The apparatus (215) in this embodiment can possesses various means to determine the useful lifespan of a liquid (30) or the length of time a liquid (30) can be effectively utilized by the apparatus, and such means may include, but is not limited to, the following or combination of the following: (a) measuring the time between when an empty apparatus (215) is initially filled with liquid (30) and the time when it should be drained of the liquid (30), which is preferred in this embodiment, (b) measuring the time between when the apparatus (215) was last drained of liquid (30) and when it should be drained again, (c) measuring the time between when an empty apparatus (215) is interfaced with the first cartridge(s) (290) to begin filling the apparatus with liquid (30) and the time when it should be drained of the liquid (30). Draining the liquid (30) in these instances pertains to draining all of the liquid (30) from the apparatus (215). This embodiment includes without limitation, the apparatus (215) having the ability to sense, detect, interpret, or determine, with one or more sensor(s) known to those skilled in the art, various activities, status, or conditions such as, but are not limited to, (a) the interface of one or more cartridge(s) (290) or other means to hold liquid (30), with the apparatus (215), (b) the liquid (30) level(s) in any reservoir(s) (40), (c) the opening or closing, or any position or state, of one or more valve(s) (660) to empty the apparatus of any liquid (30) that could be used to generate aerosol (200), (d) the movement or presence of any liquid (30), object, or mechanism, resulting from the emptying of the apparatus (215). The sensor(s) can communicate information with a PLC(s) (315) in a manner known in the art, and the PLC(s) (315) can use that information to help determine the length of time the liquid (30) may be utilized until it must be drained or discarded. The PLC(s) (315) can be programmed to accomplish these tasks in a manner known to those skilled in the art. The PLC(s) (315) can, without limitation, be programmed so that the apparatus will enter into a fault or error condition, or shut down one or more functions, and communicate an audible or visual signal to the operator, as well as communicate with other PLC(s), if a period of time has elapsed where the liquid (30) should have been fully drained but was not. This feature prevents the use of liquid (30) that has, without limitation, exceeded its usefulness for various reasons known to those skilled in the art. All communication between either the PLC(s) or the operator can transpire in a manner known in the art. In addition, any information or data can be communicated to or from the apparatus (215) by means such as, but not limited to, any human-machine-interface (HMI) (320), any terminal and its images, any buttons, any buttons and associated lights, any voice command(s) and directions, or any audible signal. The apparatus (215) can, without limitation, also require the operator to acknowledge any error or fault messages, apparatus status queries, or if any action was taken by the operator. The proper, necessary or effective period of time in which the liquid (30) can be used before it needs to be fully drained, is entered into the PLC'(s)' (315) programming in a manner known to those skilled in the art.

According to an embodiment illustrated in FIGS. 12, 13, 20, 29 and 37, the apparatus (215) can be designed and constructed so that any of its part(s), component(s) or space(s) that will increase in temperature from the operation of the apparatus (215) may be cooled, or any heat that is generated by one or more part(s) or component(s) or any related part(s) can be removed or displaced from the apparatus (215) either collectively or individually. The apparatus (215) in the present invention can be operated from various locations including, but not limited to, within the same area (210) in which the aerosol (200) is administered or applied. The operation of the apparatus (215) in an environment in which the aerosol (200) is applied can introduce various engineering challenges, including, but not limited to, cooling the aforementioned part(s) or component(s) and their related part(s), or surrounding atmosphere(s) (740) in a way that does not: (a) damage the apparatus, (b) damage any part(s) or component(s) of the apparatus (215), or (c) introduce a safety hazard. Cooling the aforementioned part(s) or component(s) and their related part(s), or surrounding atmosphere(s) (740) while utilizing as little or no amperage as possible is also, without limitation, another engineering challenge addressed in the current invention. Without limitation, many component(s) of the apparatus (215), including but not limited to, any electrical or electronic parts, may not be cooled by aerosol (200) laden air from outside of the apparatus (215). Aerosol (200) laden air/gas may cause electrical problems, electrical hazards, or cause damage to the apparatus (215) or its component(s) or part(s).

Without being limited, the various component(s) or part(s) of the apparatus (215) including, but not limited to any, electrical system(s), drive electronic(s) (645), blower(s) (180), pump(s) (130), or other part(s) or component(s) of the apparatus (215), and their related part(s), can be located in various ways including, but not limited to, locating the components individually or collectively in an enclosure(s) (345) that is impervious to things such as, but not limited to, humidity, dust, liquid, and aerosol. In addition, and without limitation, the atmosphere or various component(s) or part(s) of the apparatus (215) including, but not limited to any, electrical system(s), drive electronic(s) (645), blower(s) (180), pump(s) (130), or other part(s) or component(s) of the apparatus (215), and their related part(s), inside of the enclosure(s) (345), can be directly or indirectly cooled by means known to those skilled in the art. This means for cooling can include, but is not limited to, the use of, circulated coolant liquid, or refrigerated air. Any heat that is generated in the creation of the refrigerated air or that is removed from the enclosure(s) (345), the atmosphere inside of the enclosure(s) (345), or any part(s) or component(s) inside of the enclosure(s) (345), can be transferred to any air stream or direct to the atmosphere surrounding the apparatus (215).

Without limitation, the PLC(s) (315) can monitor the temperature of any surface(s) or atmosphere(s) (740) within the apparatus (215) with input from one or more of any temperature sensing devices or air/gas temperature sensing device(s) (650). The PLC(s) (315) can activate whatever means necessary to start, maintain, or stop any cooling activities or actions for any part(s), component(s), or atmosphere(s) of the apparatus (215), to maintain any desired or necessary temperature.

It is preferred, without limitation that the heat is transferred to an air/gas stream and this air/gas stream is the same air/gas stream (745) that is used to move the generated aerosol (200) out of the apparatus (215). The heat can be transferred to the air/gas stream (745) in one or more locations of the apparatus (215) including, but not limited to, inside any reservoir(s) (40), or inside any pipe(s) (685) before or after the blower(s) (180) that create the air/gas stream (745) that moves the aerosol (200) from the apparatus (215). It is also preferred, without limitation, that the heat generated by the various component(s) or part(s), especially any drive electronics (645) that operate the transducer(s) (10), be transferred to one or more heat sink(s) (750) having one or more fin(s) or other means known in the art to enhance cooling. Without limitation, the heat sink(s) can also interface and transfer heat from any coolant liquid or circulated coolant liquid that is used to cool any part(s), component(s), or atmosphere in a manner known in the art. The heat sink(s) (750) can be positioned anywhere in the air stream (745), before or after the blower(s) (180), so that at least the fin(s) or other cooling enhancement(s) (800) is placed or positioned in the air stream (745). The interface between any heat sinks or other means to transmit heat into the air stream (745) can be sealed in a manner known in the art. It is also preferred without limitation, that the heat sink(s) (750) that interfaces with the drive electronics (645) is interfaced with the top of the reservoir(s) (40) in which the transducers(s) (10) is located, and the heat sink(s) (750) is effectively positioned and sealed in place with one or more clasps (795). Without limitation, the various part(s) and component(s) of the apparatus (215) can interface with any heat sink(s) (750) in any orientation(s), layout(s), and with any methods known to those skilled in the art.

According to an embodiment, the apparatus (215) can be designed and constructed so that any of its exterior skin, walls, or surfaces (755) that can be exposed to the administered or deployed aerosol (200), are prevented from becoming warmer in temperature than the temperature of the atmosphere surrounding the apparatus or other surfaces surrounding the apparatus (215). This is important considering the potential operating environments of the apparatus (215). The book entitled, "Aerosol Technology" by William C. Hinds (1982), which is incorporated herein by reference in its entirety, including any references cited therein, teaches that, "When a temperature gradient is established in a gas, the aerosol particles in that gas experience a force in the direction of decreasing temperature. The motion of the aerosol particle that results from this force is called thermophoresis (page 153)." William C. Hinds (1982), also taught, "The earliest studies of thermophoresis were empirical studies of the dust-free layer observed around a heated object, such as a metal rod immersed in smoke. The smoke particles appear to be repelled by the heated object and form a particle free layer usually less than 1 mm thick, with a well-defined boundary (page 153)." This embodiment is advantageous for reasons including, but not limited to, it can prevent the aerosol (200) from being repelled from the exterior skin, walls, or surfaces (755) of the apparatus (215) in situations where the apparatus (215) is operating within the area (210) in which the aerosol (200) is administered or deployed and where it is needed or required that the exterior skin, walls, or surfaces (755) of the apparatus have contact with the aerosol (200). This embodiment includes, without limitation, constructing the apparatus (215) so that the exterior skin, walls, or surfaces (755) of the apparatus (215) are insulated from heat in various ways, including, but not limited to, applying one or more layers of insulating material (760) to the inside or outside of the exterior skin, walls, or surfaces (755) of the apparatus (215), constructing the exterior skin, walls, or surfaces (755) of the apparatus (215) so that they are double walled with a layer of insulation (765), including air/gas, in the middle of the said walls, or enclosing the components or parts that can increase in temperature, inside a sealed, insulated, or both insulated and sealed, enclosure, and then placing that enclosure inside of another sealed or unsealed enclosure that can also be insulated or not insulated.

According to an embodiment, object(s), the atmosphere(s) in which they reside, or any surfaces in the area targeted (210) for the administration or deployment of an aerosol (200), can be cooled or have their/its temperature decreased, before, or during the time when, the aerosol (200) is administered. This embodiment should not be confused with what was taught by U.S. Pat. No. 4,512,951 (Koubek at al., 1983), which is incorporated herein by reference in its entirety, including any references cited therein. Koubek et al., 1983, taught a method of sterilization where a liquid of aqueous hydrogen peroxide is vaporized, and the uniformly vaporized mixed hydrogen peroxide-water vapors are delivered into an evacuated sterilizer chamber, and the articles to be sterilized are cooled prior to the introduction of the vapor (or are cooled by the evacuation of air from the sterilizing zone) to a temperature below the dew point of the entering vapors. The condensing vapor deposits a film of liquid on all such cool surfaces (col 2, line 40-51). Koubek et al., 1983, also mentions in claim 2 that the result of vaporization was a mixed "gaseous vapor" consisting of hydrogen peroxide and water vapor free of solid contaminants. The present embodiment is intended for a completely different application and purpose since it is related to using principals of aerosol (200) behavior to, without limitation, increase the efficacy or performance of the process of the present invention, and not the condensation of a gas as taught in the prior art.

Basic principles applied in this embodiment are taught in the book entitled, "Aerosol Technology" by William C. Hinds (1982), which is incorporated herein by reference in its entirety, including any references cited therein. Without limitation, the cooling of the said object(s), surfaces, or environment or atmosphere, within the targeted area (210), in the present invention, can accentuate the performance or efficacy of the aerosol (200) generated by the apparatus (215) in the present invention. In addition, and without being limited to a mechanism or method, the aforementioned principles taught by William C. Hinds (1982), show that the efficacy, efficiency, and performance of the process in the present invention can be further increased by introducing an aerosol (200), consisting of a heated liquid (30), into an environment or targeted area(s) (210) with cooled surfaces.

The cooling of object(s), surface(s), space(s), environment(s), or atmosphere(s), within a targeted area(s) (210), can be accomplished with any means except by decreasing the pressure or pulling a vacuum on an enclosed area that is sufficient enough to decrease the temperature of the surfaces or atmosphere within that enclosed area. Creating a vacuum in an enclosed area and applying an aerosol was taught in the prior art by U.S. Patent Application No. 2005/0042130 A1 (Lin et al., 2003). However, Lin et al., was silent with respect to cooling any surfaces within the sterilization chamber or targeted area, and only mentioned the vaporization of the applied aerosol as being any enhancement or advantage that further vacuum past 5 torr would provide (pg. 2 paragraph 28). The vacuum utilized by Lin et al., (pg. 2 paragraph 28) to obtain data, was intended to move the aerosol through the sterilization chamber. In addition, using a vacuum to cool object(s), surfaces, or environment or atmosphere, within a enclosed area, would not be desired in this embodiment due to the complexity and expense involved in designing a chamber for the necessary vacuum and the expense of acquiring the necessary pump, which is all known to those skilled in the art. It is desired that another means for cooling object(s), surfaces, or environment or atmosphere, within a targeted area(s) (210), other than utilizing a vacuum, be utilized.

As shown in FIGS. 38-41, it is preferred, without limitation, that the targeted area(s) (210)) and its atmosphere, environment, objects, or any of the surfaces within the targeted area(s) (210), be cooled with air or gas that is cooled or chilled in a manner known to those skilled in the art. It is further preferred that the air or gas is cooled or chilled with one or more chill coils or refrigerated air systems (770) that are known to those skilled in the art. The means (770) to chill or cool the air or gas can be, without limitation, attached to the apparatus (215) in the present invention, be separate from the apparatus (215) and connect with one or more pipe(s) (810) or outbound cooled air pipe(s) (780) or inbound air pipe(s) (785) that connect with the targeted area(s) (210), or it can be part of or positioned anywhere within the space(s) or targeted area(s) (210) to be treated, and it can be controlled by one or more PLC(s) (315) or remote PLC(s). Without limitation, any pipe(s) that lead to (780) or from (785) the source of the refrigerated or cooled air can be separated from the targeted area (210) with one or more valve(s) (815) that can be controlled by one or more PLC(s) (315) or remote PLC(s). Without limitation, one or more valve(s) (815) may also be positioned at any location between the location where the administered air/gas or aerosol enters any pipe(s) (780) (785) or targeted area(s) (210) and the aerosol generating apparatus (215), and can be controlled by one or more PLC(s) (315) or remote PLC(s). The said valve(s) (815)(775), pipe(s) (220), or other related part(s) or component(s) can all be constructed from any material that is compatible, and suitable for use with the liquid (30). Without limitation, the amount or duration of air or gas that is flowed into or recirculated through the targeted area(s) (210), the locations that the air or gas is flowed into our out of the targeted area(s) (210), the temperature of the air or gas, as well as the temperature of the surfaces within the targeted area(s) (210) can vary depending on variables such as, but not limited to, the application, the level of performance that is desired, desired application time, as well as the volume of the targeted area(s) (210). Without limitation, the temperature of the atmosphere, surfaces, or space(s) in the targeted area(s) (210) can be cooled to at least nine degrees Fahrenheit below the temperature of the applied liquid (30). It is preferred, without limitation, that the temperature of the atmosphere, surfaces, or space(s) in the targeted area(s) (210) be cooled to at least nine to twenty-five degrees Fahrenheit below the temperature of the applied liquid (30). However, it is more preferred, without limitation, that the temperature of the atmosphere, surfaces, or space(s) in the targeted area(s) (210) be cooled to at least forty degrees Fahrenheit or lower. It is further preferred, without limitation, that the temperature of the atmosphere, surfaces, or space(s) in the targeted area(s) (210) be cooled to at least thirty-two degrees Fahrenheit or lower. The temperature of the applied liquid (30) of which the aerosol (200) is created or the temperature to which the aerosol (200) is heated with other means, can also vary. It is also preferred, without limitation, that the aerosol (200) is administered or deployed into an environment or targeted area(s) (210) where all heat emanating lights and/or machinery are turned off before or during the administering or deployment of the aerosol (200).

According to an embodiment, the apparatus (215) can be designed and constructed so that it can administer the generated aerosol (200) to a plurality of separate enclosed targeted areas (210). This can be accomplished, without limitation, through the use of one or more pipes (220) that emanate from or connect to the apparatus (215) and administer the aerosol (200) to the said enclosed areas (210). The flow of air or gas and aerosol (200) that emanates from the apparatus (215) may also, without limitation, be split various times, with one or more, or to one or more pipes (220), and the various pipes (220) can interface, or connect with one or more enclosed areas (210) in which the piped air/gas and aerosol (200) is administered. The one or more pipes (220) that emanate from the apparatus (215) can connect with one or more valve(s) (775) that can open or close one or more pipe(s) (220) that can be connected to one or more pipe(s) (220) or pipe junction(s) (790). The valve(s) (775) can be electronically opened or closed by one or more PLC(s) (315) connected to the apparatus (215), or one or more control PLC(s) external to the apparatus (215), all in a manner known to those skilled in the art. The said valve(s) (775), pipe(s) (220), or other related part(s) or component(s) can all be constructed from any material that is compatible, and suitable for use with the liquid (30). This embodiment does not encompass any configuration(s) or application(s) where the plurality of targeted areas (210) or areas where the aerosol (200) is deployed is within the same room, since this is already known to those skilled in the art. This embodiment may, without limitation, be used with any anti-pathogen/toxin/fungal/sporicidal agent(s) or substance(s) that may be in the form including but not limited to any liquid, gas, vapor, plasma, or aerosol, which is generated, delivered, moved, or administered, by any means.

According to an embodiment, the apparatus (215) can, without limitation, be designed and constructed so that the drive electronics (645), or any part of the drive electronics (645) that includes, but is not limited to, one or more signal generator(s), that emit or send electrical signal (herein referred to as "signal" or "signals") to energize the transducer(s) (10), causing it to emit pressure (energy) of a desired character, can have the capability to emit or send various defined signal or signal range(s) for various defined period(s) of time during the lifespan of the transducer(s) (10) in order to, without limitation, continue to operate or energize the transducer(s) (10) at a frequency or within a frequency range in which the transducer(s) (10) are able to have an effective or functional output and/or operate at a frequency or in a frequency range where the transducer(s) (10) are able to operate at or within a range close to or at their maximum performance or aerosol (200) output. It is preferred, without limitation, that this embodiment pertains only to the new aerosol producing transducers (10) taught or claimed in co-owned and co-pending U.S. patent application Ser. No. 11/915,524 titled "Method And Apparatus For Optimizing Aerosol Generation With Ultrasonic Transducers". However, it is more preferred, without limitation, that this embodiment pertain not only to the aerosol (200) producing transducers (10) taught in co-owned and co-pending U.S. patent application Ser. No. 11/915,524 titled "Method And Apparatus For Optimizing Aerosol Generation With Ultrasonic Transducers", but also to other transducers (10) intended for aerosol (200) production, except for those that operate at the resonant frequency of the transducer (10). It is even more preferred, without limitation, that this embodiment pertains not only to the aerosol (200) producing transducers taught in co-owned and co-pending U.S. patent application Ser. No. 11/915,524 titled "Method And Apparatus For Optimizing Aerosol Generation With Ultrasonic Transducers", but also to other transducers (10) intended for aerosol (200) production, except for those that operate at or near the resonant frequency of the transducer (10). The aforementioned exclusions to the preferences are needed since the current art, without limitation, encompasses the operation of a transducer (10) at its resonant frequency, as well as the design of the drive electronics (645) or ancillary components to sense any changes in the resonant frequency of the transducer (10), and to automatically adjust the frequency of the signal to the transducer (10) by way of the drive electronics (645) in order to compensate for, or match the transducer's (10) resonant frequency change. However, the prior art does not address the adjustment of the signal output from the drive electronics (645) to an aerosol (200) producing transducer (10) that has an effective or optimum operational frequency(s) above or below its resonant frequency that changes over time. One reason for this includes, without limitation, the complexity or difficulty to detect the optimum or effective operating frequency(s) for a transducer (10) at frequencies outside of the resonant frequency of a transducer (10), especially as it changes. This can be appreciated by those skilled in the art.

Aerosol (200) producing transducer(s) (10) in the present invention can have, without limitation, one or more frequency(s), group(s) of frequencies, or frequency range(s) in which they produce an aerosol (200) that can be characterized as effective, functional, or productive. The transducer(s) (10) utilized in the present invention can, without limitation, operate at one or more specific frequency(s), group(s) of frequencies, or frequency range(s), where the transducer(s) (10) are able to generate a greater amount of aerosol when compared to other frequency(s), group(s) of frequencies, or frequency range(s). Furthermore, the transducer(s) (10) utilized in the present invention can, without limitation, have or exhibit one or more specific frequency(s), group(s) of frequencies, or frequency range(s), where the transducer(s) (10) are able to generate not only an effective or functional output of aerosol (200), but generate the maximum amount of aerosol (200) or close to the maximum amount of aerosol (200) for each transducer(s) (10). Without limitation, for any frequency(s), group(s) of frequencies, or frequency range(s), where the transducer(s) (10) produce an effective, functional, or even maximum amount of aerosol (200) that is effective or functional, the aerosol output will decrease as the frequency of the signal sent to the transducer(s) (10) either increases or decreases from these established frequency(s), group(s) of frequencies, or frequency range(s).

Without being limited, any transducer (10) utilized in the present invention, may exhibit or have one or more additional frequency range(s) that encompasses the frequency(s), group(s) of frequencies, or frequency range(s) that will produce an effective, functional, or even maximum amount of aerosol. The magnitude of this frequency range can vary greatly, however, it is preferred without limitation, that this frequency range be within at least plus or minus 0.03 MHz (+/−0.03 MHz) from the frequency where the transducer(s) (10) generates the maximum amount of aerosol (200) or close to the maximum amount of aerosol (200) for a particular group of frequencies or frequency range, and is surrounded by frequency(s), group(s) of frequencies, or frequency range(s), where the transducer(s) (10) do not produce an effective or functional aerosol (200) output. It is more preferred, without limitation, that this frequency range is within at least plus or minus 0.05 MHz (+/−0.05 MHz) from the frequency where the transducer(s) (10) are able to generate the maximum amount of aerosol (200) or close to the maximum amount of aerosol (200) for a particular frequency, group of frequencies or frequency range, and is surrounded by frequency(s), group(s) of frequencies, or frequency range(s), where the transducer(s) (10) do not produce an effective or functional aerosol (200) output. It is even more preferred, without limitation, that this frequency range is within at least plus or minus (+/−0.08 MHz) from the frequency that the transducer(s) (10) are able to generate the maximum amount of aerosol (200) or close to the maximum amount of aerosol (200) for a particular frequency, group of frequencies, or frequency range, and is surrounded by frequency(s), group(s) of frequencies, or frequency range(s), where the transducer(s) (10) do not produce an effective or functional aerosol (200) output.

It has been observed, without limitation, that the transducer(s) (10) in the present invention, can have multiple, separate, or independent, frequency(s), group(s) of frequencies, or frequency range(s), where the transducer(s) (10) are able to generate an effective, functional, or productive aerosol (200) output. In addition, and without limitation, it has been further observed that in between these frequency(s), group(s) of frequencies, or frequency range(s), the transducer(s) (10) do not produce an effective or functional amount of aerosol (200).

It is important to note that the frequency or frequency range(s) in which the transducer(s) (10) produces either the maximum amount of aerosol (200) and/or an effective or functional amount of aerosol (200) can, without limitation, vary, and that it can be at or close to the resonant frequency of the transducer(s) (10) or anywhere above or below the resonant frequency of the transducer(s) (10). Resonant frequency can refer in this embodiment to either the resonant frequency of a free unmounted transducer(s) (10) or a transducer(s) (10) that has been mounted or assembled.

The resonant frequency of a transducer(s) (10) can, without limitation, increase due to age or other variables known to those skilled in the art. The nature of this change in resonant frequency can vary depending on variables known to those skilled in the art. As the resonant frequency of the transducer(s) (10) increases, the frequency range(s) in which the transducer(s) (10) would produce either the maximum amount of aerosol (200) and/or an effective or functional amount of aerosol (200) can, without limitation, also increase.

Referring now to FIGS. 42-45, the drive electronics (645), or any part of the drive electronics (645) that includes, but is not limited to, one or more signal generator(s) or ancillary components, used in the present invention can, without limitation, compensate for this shift or increase in frequency, and continue to operate the transducer(s) (10) at a frequency or frequency range where they produce either the maximum amount of aerosol (200) and/or an effective or functional amount of aerosol (200). This does not pertain to the prior art that encompasses the operation of a transducer (10) at its resonant frequency, as well as the design of the drive electronics (645) or ancillary components to sense any changes in the resonant frequency of the transducer (10), and to automatically adjust the frequency of the signal to the transducer (10) by the drive electronics (645) in order to compensate for, or match the transducer's (10) resonant frequency change. However, due to, without limitation, the complexities or limitations involved with this mode of operation or its successful execution or implementation, the following techniques can also be applied to aerosol (200) producing transducer(s) (10) that operates at or near its resonant frequency. This may be accomplished in ways including, but not limited to: (a) switching from one or more crystal(s) (825) that is initially used to generate one specific frequency or specific frequency range, to one or more different crystal(s) (830) that is used to generate other specific frequency(s) or specific frequency range(s). This can, without limitation, occur numerous times, for various durations of time, over a period of time; or (b) switching from one or more signal generator(s) (835) that is initially used to generate one specific frequency or specific frequency range, to one or more different signal generator(s) (840) that is used to generate other specific frequency(s) or specific frequency range(s). This can, without limitation, occur numerous times, for various durations of time, over a period of time. Without limitation, this switching from one or more crystal(s) or signal generator(s) to another can also be performed multiple times or in multiple series with one or a plurality of crystal(s) or signal generator(s) with any frequency or frequency range output. Also, and without limitation, if a plurality of crystal(s) or signal generator(s) is initially used, they as well as any subsequent set of crystal(s) or signal generator(s) that are utilized may have any, similar, different, identical, approximately identical, frequency or frequency range output. Each of the one or more crystal(s) or signal generator(s) can, without limitation, be utilized to emit or send either a specific frequency, or a range of frequency(s) that is amplified by one or more amplifier(s) (230), drive electronics (645), or other electronics known in the art, and is used to power or operate one or more transducer(s) (10), all in a manner known to those skilled in the art. It is preferred, without limitation, that the crystal(s) (845) is a direct or indirect part(s) or component(s) of the signal generator(s) (850). Each crystal(s) or signal generator(s) is, of a type, design, and construction, known to those skilled in the art. Any type of crystal(s) (845) or signal generator(s) (850) can be used that is effective. However, it is preferred, without limitation, that the crystal(s) (845) is made from quartz and resonates at a frequency that can be used by a signal generator(s) (850) to create a waveform(s) that is then amplified by an amplifier (230), drive electronics (645) or other electronics known in the art, to operate or energize the transducer(s) (10) at a frequency where the one or more transducer(s) (10) can produce either the maximum amount of aerosol (200) and/or an effective or functional amount of aerosol (200); or (c) utilizing, one or more of, without limitation, drive electronics (645), signal generator(s) (850), or other component(s) or circuit board, that has the means, ability, or capacity, to electronically produce the various frequency(s) or frequency range(s) that are needed or desired, and is known to those skilled in the art. It is preferred, without limitation, that these electronics or circuitry has the ability or capacity to be programmed so that various frequencies or frequency ranges may be created or generated, for various durations of time, over a period of time.

The specific resonant frequency(s) for a free unmounted transducer(s) (10) or a transducer(s) (10) that has been mounted or assembled, as well as the specific frequency(s) or frequency range(s) in which the transducer(s) (10) produce either the maximum amount of aerosol (200) and/or an effective or functional amount of aerosol (200), can be determined, planned, calculated, plotted, or projected, over time, in a manner known to those skilled in the art.

This data can be used, without limitation, to program one or more components such as, but not limited to, a signal generator or other related components, or PLC(s) (315) which is, without limitation, either a dedicated part of the signal generator(s) (850), amplifier(s) (230), drive electronics (645), or other components that are used to generate and send signal to energize the transducer(s) (10), or the PLC(s) (315) that is used to control and operate the apparatus in the present invention, to cause the switching from a crystal(s) (845) or signal generator(s) (850) to another in order to operate the transducer(s) (10) at a frequency or frequency range where they produce either the maximum amount of aerosol (200) and/or an effective or functional amount of aerosol (200).

Figure 46:
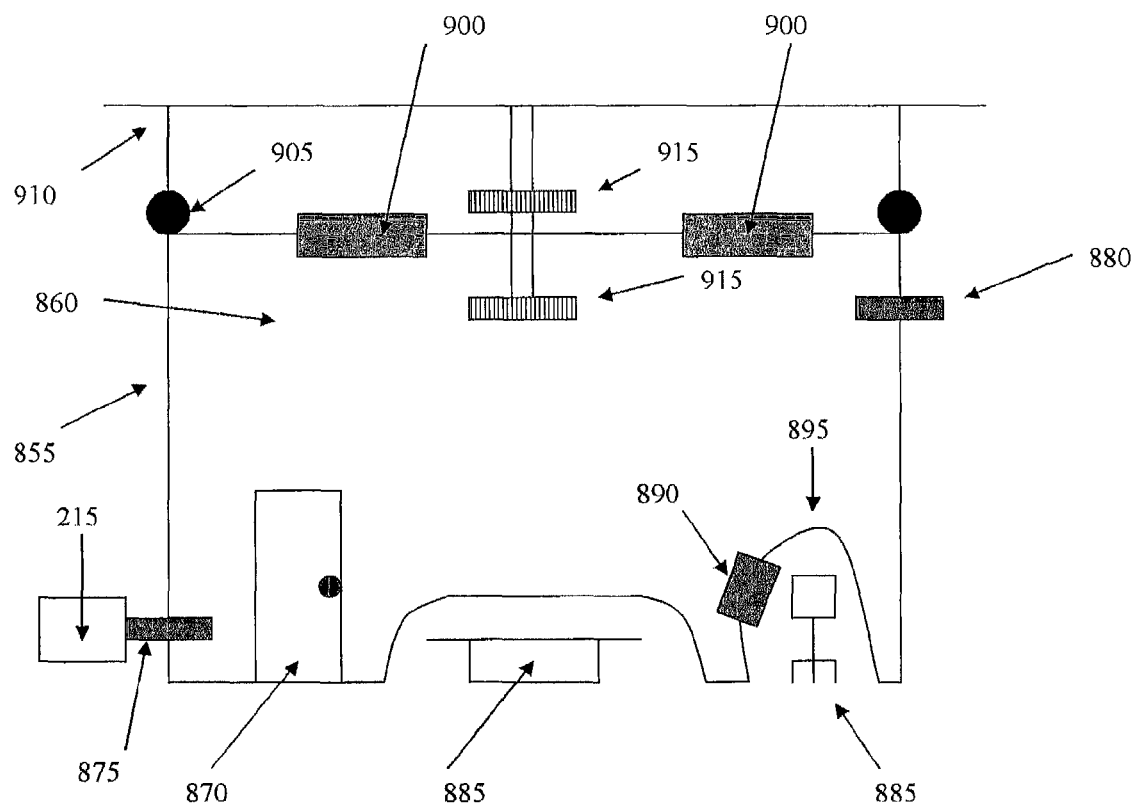
FIG. 46 is a schematic view of an embodiment of an enclosure that is connected to an aerosol generating apparatus, the enclosure having various features, parts, and components, according to the present invention.

As shown in FIG. 46, according to an embodiment, the aerosol (200) generating apparatus (215) in the present invention, can be, without limitation, connected, interfaced, or attached, to one or more sealed, semi-sealed, or semi-open, enclosure(s) or areas (herein referred to as "target enclosure(s)") (855), that is erected, established, constructed, or positioned at any place or within any area that is, without limitation, enclosed, not enclosed, semi-enclosed, sealed, semi-sealed, or unsealed. The said target enclosure(s) (855) can be without limitation, any size, shape, or dimension, and constructed of any material, and can be designed to be disposable or so that it can undergo multiple cycles of having the aerosol (200) applied to the interior of the target enclosure(s) (855) during, after, or both during and after, the use of the interior space of the enclosure(s) (860). The target enclosure(s) (855) can, without limitation, be designed in a manner known in the art so that they can be connected, interconnected, or interfaced, with one or more target enclosures(s) (855). The target enclosure(s) (855) can, without limitation, be supported with a frame that is designed and interfaced with the target enclosure(s) (855) in a manner known to those skilled in the art. Without being limited, the target enclosure(s) (855) can also have one or more doors (870) of various sizes, shapes, and locations, through which objects and people can pass through, and can be designed to be opened, closed, and effectively sealed multiple times in a manner known in the art. Without limitation, the door (870) can be designed and function as an airlock. It is preferred, without limitation, that the enclosure has at least one door (870). The target enclosure(s) (855) can be made from any material. However, it is preferred, without limitation, that the material is at least transparent or translucent. The target enclosure(s) (855) can have one or more inbound air/gas ports (875) or outbound air/gas ports (880) interfaced anywhere with the target enclosure (855), through which air and aerosol (200) may be administered or exhausted. The said ports may connect, in a manner known to those skilled in the art, to one or more aerosol generator(s) (215).

The target enclosure(s) (855) in this embodiment can have at least, but is not limited to, six features that distinguish it from chambers, tents, or bags, which have been used or have been proposed in the prior art. First, any wall(s), floor(s), or ceiling(s), of the target enclosure(s) (855) can be, without limitation, pre-formed, pre-constructed, pre-laminated, pre-seam sealed, or pre-molded, so that the chamber can effectively or functionally follow or fit over or under one or more of any, object(s), fixture(s), architectural feature(s), or equipment or fixture(s) such as, but not limited to, exam tables, x-ray equipment, anesthesia equipment, heart rate monitors, cardiopulmonary equipment, operating room theatre lights, laboratory equipment, or industrial equipment (Herein referred to as "structure(s)" (885). Second, any wall(s), floor(s), or ceiling(s), of the target enclosure(s) (855), including any material (895) that fits over the said objects, fixtures, architectural features, or equipment or fixtures (885), can, without limitation, have various openings (890) of various shapes, sizes, and locations, to allow a person to access, without limitation, any objects, various human machine interfaces, tools, or move any objects in and out of the target enclosure(s) (855). The openings (890) can also have a means so that they can be opened, closed, and effectively sealed multiple times. The openings may be designed or function as an airlock. Third, any wall(s), ceiling(s), or floor(s), of the target enclosure (855) may have one or more holes or openings of any size, shape, or dimension, and be interfaced with one or more of any plastic or glass panels, panes, or pieces (herein referred to as "panels") (900) of any size, shape, or dimension. The panels can be effectively interfaced and sealed with or into the wall(s), ceiling(s), or floor(s), of the target enclosure (855) in a manner known in the art. Any openings (890) may also interface with any plastic or glass panels (900), and the interface can be effectively sealed in a manner known in the art. The plastic or glass panels (900) can, without limitation, offer to: (a) allow light into the target enclosure(s) (855) in situations where the wall(s), floors, or ceiling(s) of the target enclosure (855) are opaque, (b) improve light transmittance or the quality of light that is transmitted into the target enclosure(s) (855), (c) decrease any diffraction of light entering the target enclosure(s) (855). Fourth, the target enclosure(s) (855) can utilize, without limitation, any means known in the art to connect, interface, hang, or suspend the target enclosure(s) (855) within the area in which it is placed, so that the target enclosure(s) (855) is erected or positioned so that its interior space (860) can be effectively or efficiently used. It is preferred without limitation, that the ceiling(s) of the target enclosure(s) (855) is suspended from at least one hook(s) (905) or other means of attachment that is effectively connected or attached to the ceiling (910) or other location(s) in the area in which the target enclosure(s) (855) is located. The various components and designs utilized for this purpose are known those skilled in the art. Fifth, the target enclosure(s) (855) can, without limitation, be constructed with or utilize any means known to those skilled in the art so that the floor(s) of the target enclosure(s) (855) do not present a slip hazard for any people working inside the target enclosure(s) (855). It is preferred, without limitation, that the floor(s) of the target enclosure (855) be textured to reduce any potential slip hazards. Sixth, the target enclosure(s) (855) can, without limitation, be interfaced with one or more means for fire suppression (915) outside or within the target enclosure(s) (855), and can be designed and built for this feature in a manner known in the art. In addition, the components and materials utilized in this embodiment are constructed from any material that is compatible, and suitable for use with the liquid (30), and may also be fireproof or fire resistant. This embodiment may, without limitation, be used with any anti-pathogen/toxin/fungal/sporicidal agent(s) or substance(s) that may be in the form including but not limited to any liquid, gas, vapor, plasma, or aerosol, which is generated, delivered, moved, or administered, by any means.

Figure 47:
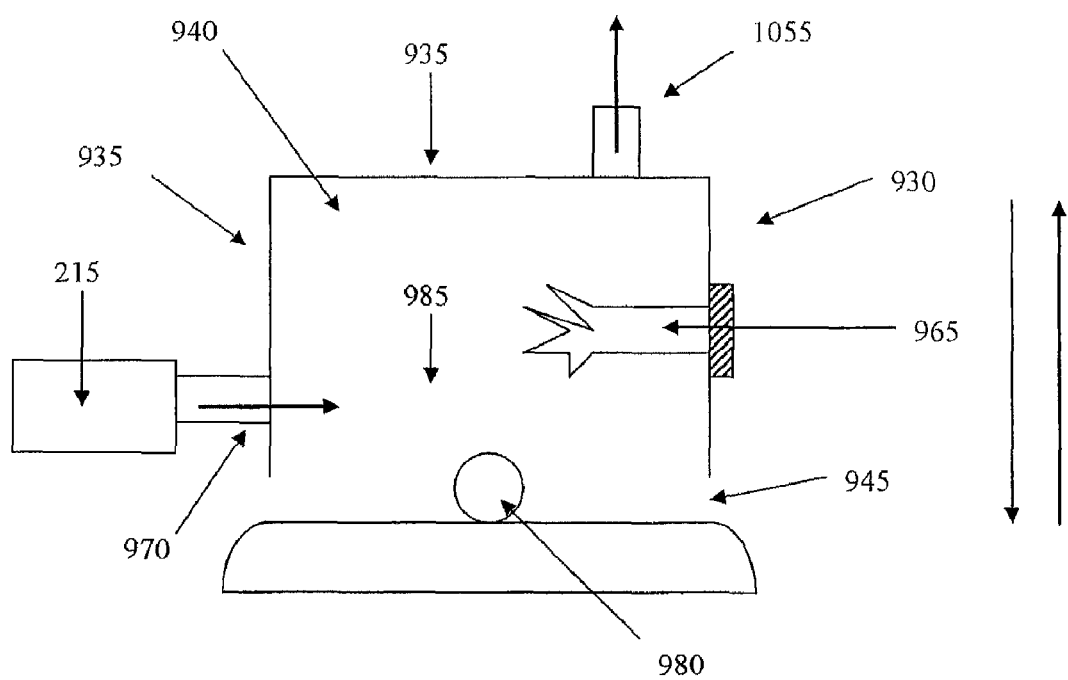
FIG. 47 is a schematic view of an embodiment of an enclosure that is connected to an aerosol generating apparatus, where the surfaces that it interfaces with effectively forms a missing wall, and the enclosure can have various features, parts, and components such as a glove sealed to the wall of the enclosure, according to the present invention.
Figure 48:
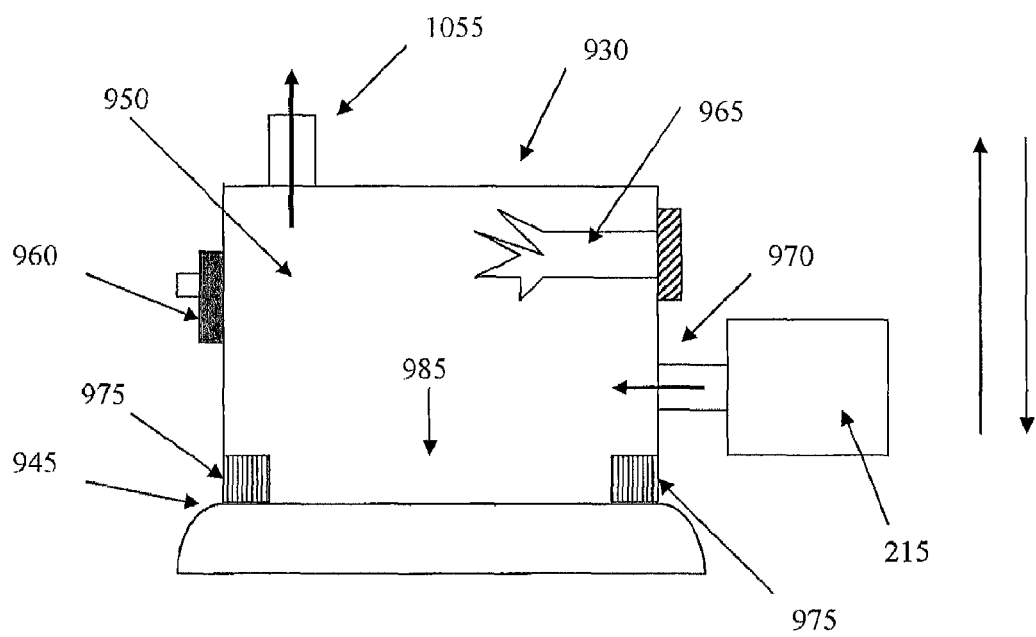
FIG. 48 is a schematic view of an embodiment of an enclosure that is connected to an aerosol generating apparatus, where the surfaces that it interfaces with effectively forms a missing wall, and the enclosure can have various features, parts, and components such as a glove sealed to the wall of the enclosure, seal material that connects with the enclosure and any surfaces with which the enclosure interfaces, according to the present invention.
Figure 49:
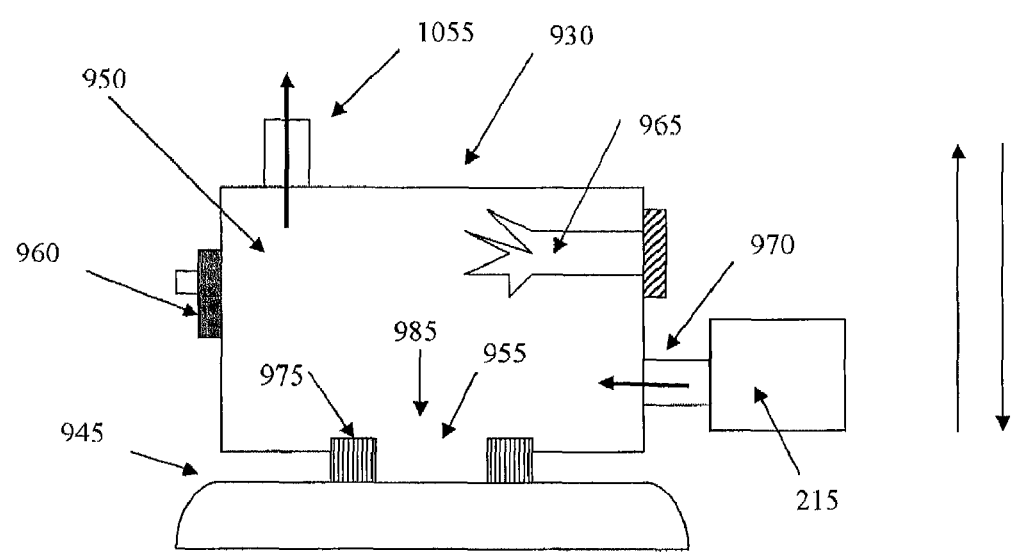
FIG. 49 is a schematic view of an embodiment of an enclosure that is connected to an aerosol generating apparatus, where the surfaces that it interfaces with effectively forms a missing wall, effectively covers or seals a hole, and the enclosure can have various features, parts, and components such as a glove sealed to the wall of the enclosure, seal material that connects with the enclosure and any surfaces with which the enclosure interfaces, and an airlock or access door, according to the present invention.

Looking now at FIGS. 47-49, according to an embodiment, the aerosol (200) generating apparatus (215) in the present invention, can be, without limitation, connected, interfaced, or attached, to one or more specially designed enclosure(s) (herein referred to as "application enclosure(s)") (930) that consists of, one or more wall(s) (935) that form one or more semi-enclosed or unenclosed area(s) (940) and where, without limitation, the interface, connection, or attachment, of any part of these wall(s) (935) with any surface(s) (945), forms one or more enclosed area(s) (950). The one or more wall(s) (935) of the application enclosure(s) (930) may also have one or more openings or holes (herein referred to as hole(s)) (955) of any size, shape, or dimension, and the interface of these hole(s) (955) with any surface(s) (945), forms one or more enclosed area(s) (950). The wall(s) (935) of the application enclosure(s) (930) can be, without limitation, constructed from any, stainless steel, metal, glass, cellulose, cloth, gauze, polyolefin, polymer, natural or manufactured fibers or materials that may be coated or uncoated, combinations of these materials, or other materials known to those skilled in the art. The wall(s) (935) of the application enclosure(s) (930) can be, without limitation, flexible, rigid, semi-rigid, opaque, translucent, or transparent.

The enclosed area(s) formed by the interface or contact of the said wall(s) (935) or hole(s) (955) with any surface(s) (945) can be, without limitation, sealed, fully sealed, semi-sealed, or unsealed, in a manner known to those skilled in the art. Any material that can form or create an effective seal or interface (herein referred to as "seal material") (975) can also be, without limitation, glued, cemented, molded, laminated, adhered, or otherwise attached, to any part of the wall(s) (935) or hole(s) (955) that can come in contact with any surface(s) (945). Without limitation, the seal material (975) can be porous, permeable, semi-permeable, or impermeable, rigid, semi-rigid, or flexible, and can be constructed from materials including, but not limited to any, stainless steel, steel, glass, cellulose, cloth, gauze, polyolefin, polymer, natural or manufactured fibers or materials that may be coated or uncoated, combinations of these materials, or other materials known to those skilled in the art. The seal material (975) or parts of the seal material (975) may also, without limitation, have absorbent characteristics to improve its efficacy. The seal material (975) or wall(s) (935) can have, without limitation, various thicknesses, as well as lengths or heights, or it may even be designed to have the ability to vary its length(s), height(s), or thickness(s), in a manner that is known to those skilled in the art. The walls(s) (935) of the application enclosure(s) (930) can be constructed from the seal material (975).

In addition, the application enclosure(s) (930) can have, without limitation, one or more port(s), opening(s), or airlock(s) (960) of various sizes and shapes, which can be effectively sealed closed, or be in an open, semi-sealed, or unsealed state, in a manner known to those skilled in the art. The enclosure may also, without limitation, have one or more gloves (965) attached to any of the port(s), opening(s), or airlock(s) (960) and be hermitically sealed to the application enclosure(s) (930), all in a manner known to those skilled in the art. This can, without limitation, allow an operator to handle any object(s) in the application enclosure(s) (930) without being exposed to anything in the application enclosure(s) (930) or introducing anything into the application enclosure(s) (930).

The application enclosure(s) (930) can have one or more port(s) (970) at various locations through which inbound air/gas and aerosol, or filtered inbound air/gas from outside of the application enclosure(s) (930), can be administered or moved into the application enclosure(s) (930). The application enclosure(s) (930) can also have one or more port(s) (1055) at various locations through which outbound air/gas or aerosol, can move out of the application enclosure(s) (930). Without limitation, any outbound air/gas or air/gas that is laden with aerosol can be filtered at any port (1055) or at any location after it has been removed from the application enclosure (930), with any means known to those skilled in the art. The application enclosure(s) (930) can have various uses, including, but not limited to, being interfaced, strapped, positioned, or placed, over, with, or onto one or more object(s) or substance(s) (980), or targeted surfaces (985), at any angle or orientation, in order to apply an aerosol (200) onto the various surfaces. This embodiment may, without limitation, be used with any anti-pathogen/toxin/fungal/sporicidal agent(s) or substance(s) that may be in the form including but not limited to any liquid, gas, vapor, plasma, or aerosol, which is generated, delivered, moved, or administered, by any means.

According to an embodiment, any objects or items such as, but not limited to, hose(s), wire(s), pipe(s), or cord(s) (herein referred to as "cord(s)") (990), which are present in the targeted area(s) (210) in which the aerosol (200) is administered or deployed, can be, without limitation, held, lifted, or supported, by one or more holder(s) (995), that prevents the cord(s) (990) from touching or contacting the floor or surface(s) (1000) on which the holder(s) (995) are placed, but can also insure that all of the surfaces of the cord(s) (990) which interact with or contact the holder(s) (995) can also have contact, without limitation, with the same liquid (30) that is aerosolized or deployed by the apparatus in the present invention. Without limitation, surfaces that contact one another are often difficult to reach or contact with an administered aerosol (200) or other deployed substance(s), and this embodiment, without further limitation, helps to reduce or eliminate an incomplete treatment or administration of the aerosol (200), or other treatment product(s), to all of the desired or needed surfaces in a targeted area (210). In addition, the holder(s) (995) may also be used with any other chemical or agent delivery systems or apparatuses that can deliver any, without limitation, chemical(s), agent(s), or compound(s) in the form including, but not limited to, any aerosol(s), gas(s), or vapor(s), for various purposes.

Figure 50:
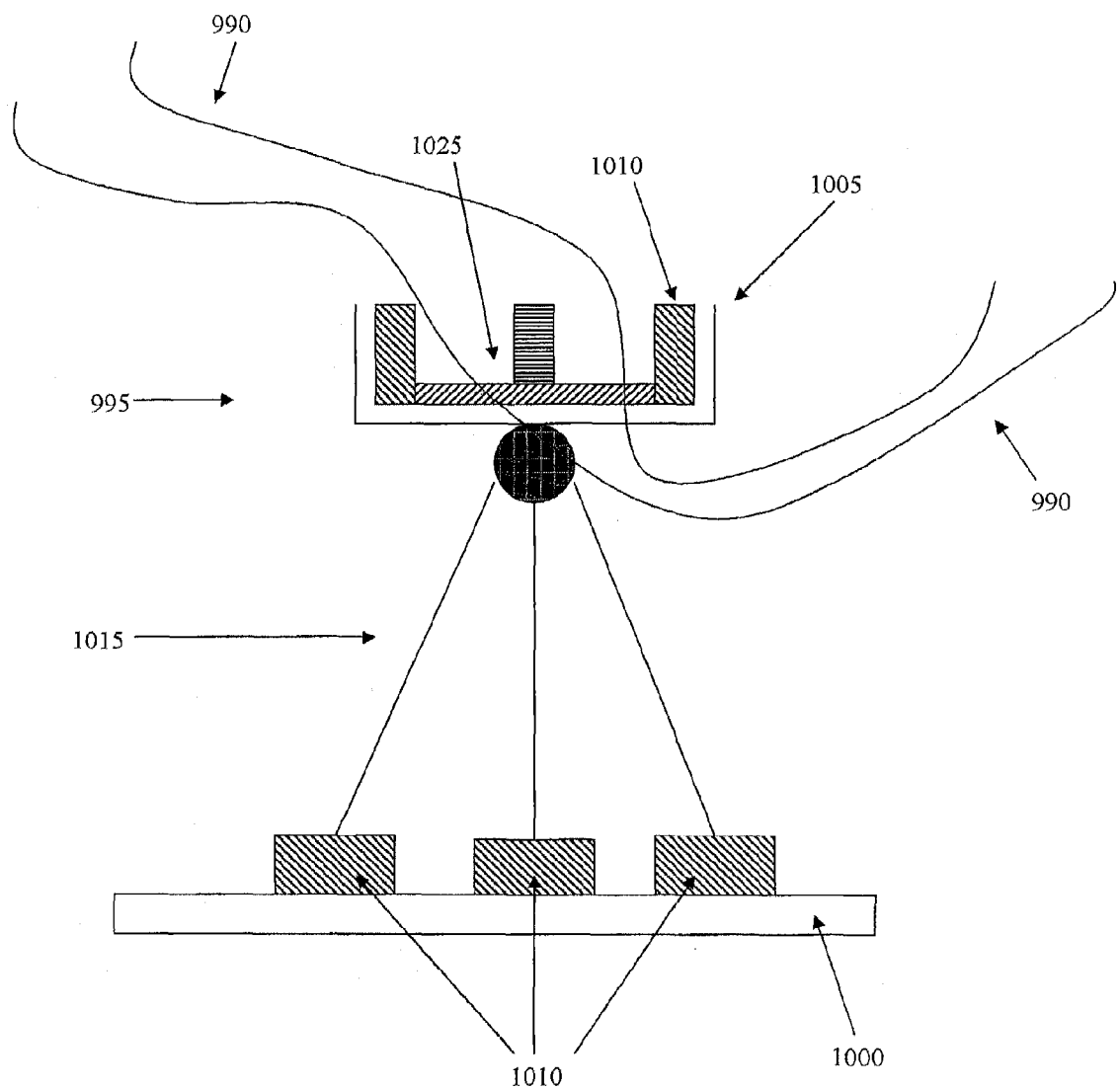
FIG. 50 is a schematic view of an embodiment of a holder that interfaces with one or a plurality of objects, and the said holder incorporates absorbent material that is positioned between the holder and any surfaces with which it interfaces including the said objects it holds and any surface on which it is placed.

Without limitation, the said holder(s) (995), as shown in FIG. 50, can consist of at least, but not limited to, the following components: (a) one or more cradle(s) or other means (herein referred to as "cradle(s)") (1005), to hold or support the cord(s) (990), (b) absorbent material(s) (1010) that is interfaced, attached, or connected to the cradle(s) (1005), (c) one or more legs or supports (1010) that extend from or are interfaced or attached to the cradle(s) (1005) or part(s) connected to the cradle(s) (1005), (d) absorbent material(s) (1010) that is interfaced, attached, applied, or connected in such a way so that it is positioned between any parts or components of the holder(s) (995) and any surfaces (1000) on which the holder(s) (995) is placed or interfaces with. Without limitation, the one or more legs or supports (1015) that extend from or are directly or indirectly interfaced or attached to the cradle(s) (1005), can be of various number and lengths, and can be designed in a manner known to those skilled in the art.

The cradle(s) (1005) or absorbent material(s) (1010) can have one or more slot(s) or a rippled shape of one or more ripple(s) (1025) so that one or more cord(s) (990) can nest or lay in or interface with the cradle(s) (1005) or absorbent material(s) (1010). The holder(s) (995) is designed and constructed in a manner known to those skilled in the art so that the cord(s) (990) cannot easily twist, fall, or move out of the cradle(s) (1005) or absorbent material(s) (1010). An absorbent material(s) (1010) is interfaced, attached, applied, or connected to the cradle(s) (1005) or holder(s) (995) in various ways known to those skilled in the art. The cradle(s) (1005) can also be constructed from any absorbent material (1010). The cradle(s) (1005) and absorbent material(s) (1010) can also be designed so that either the absorbent material(s) (1010) or even the cradle(s) (1005) can be disposable. The one or more legs or supports (1015) can also be constructed from any absorbent material (1010). The interface, attachment, application, or connection, of any absorbent material(s) (1010) to the one or more legs or supports (1015) can be accomplished in various ways known to those skilled in the art.

The absorbent material(s) (1010) that is utilized, can be made of any absorbent materials, or combinations of absorbent materials, including, but not limited to, gauze, cellulose, any sponge like material, or any material with absorbent qualities that is known to those skilled in the art. The absorbent material(s) (1010) is of a sufficient quality, thickness, density, size, shape, construction, consistency, and design, to complete its task at least once in an effective manner.

Any of the absorbent material(s) (1010) can also, without limitation, be soaked, saturated, or contacted, with any desired chemical, compound, agent, additive, or otherwise liquid (30), that would be used for various purposes. It is preferred, without limitation, that this is performed before the cord(s) (990) are interfaced or positioned in or on the cradle(s) (1005) or absorbent material(s) (1010), or the holder(s) (995) are placed on any floor or surface(s) (1000). This can, without limitation, further increase the probability that all surfaces of the cord(s) (990), holder(s) (995), or surface(s) (1000) on which the holder(s) (995) is placed, have contact with the aforementioned chemical, compound, agent, additive, or otherwise liquid (30). It is preferred, without limitation that the absorbent material(s) (1010) is saturated with the same liquid (30) that is generated into aerosol (200) in the present invention. This same absorbent material(s) (1010) can also be positioned under the wheels of the aerosol generating apparatus(s) (215). Any parts or components utilized to construct the holder(s) can be constructed from any material that is compatible, and suitable for use with the liquid (30). This embodiment may, without limitation, be used with any anti-pathogen/toxin/fungal/sporicidal agent(s) or substance(s) that may be in the form including but not limited to any liquid, gas, vapor, plasma, or aerosol, which is generated, delivered, moved, or administered, by any means.

Figure 56:
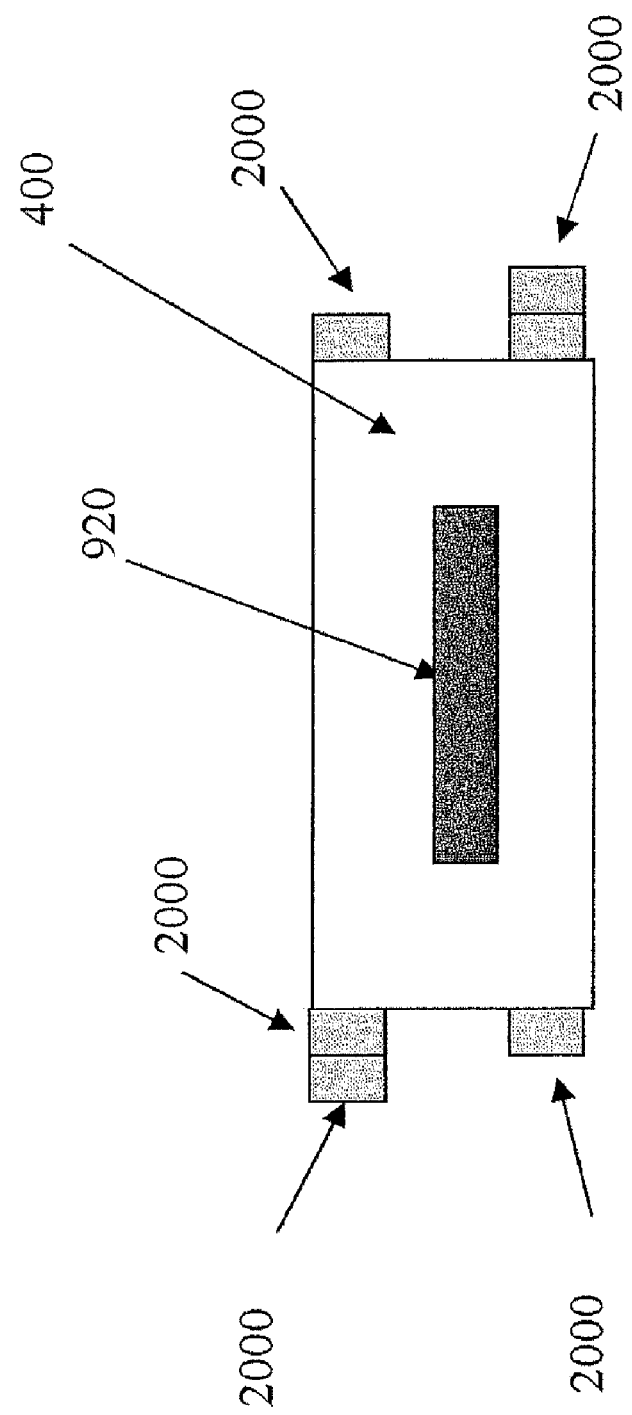
FIG. 56 is a schematic view of a float device employed within the aerosol generator.
Figure 57:
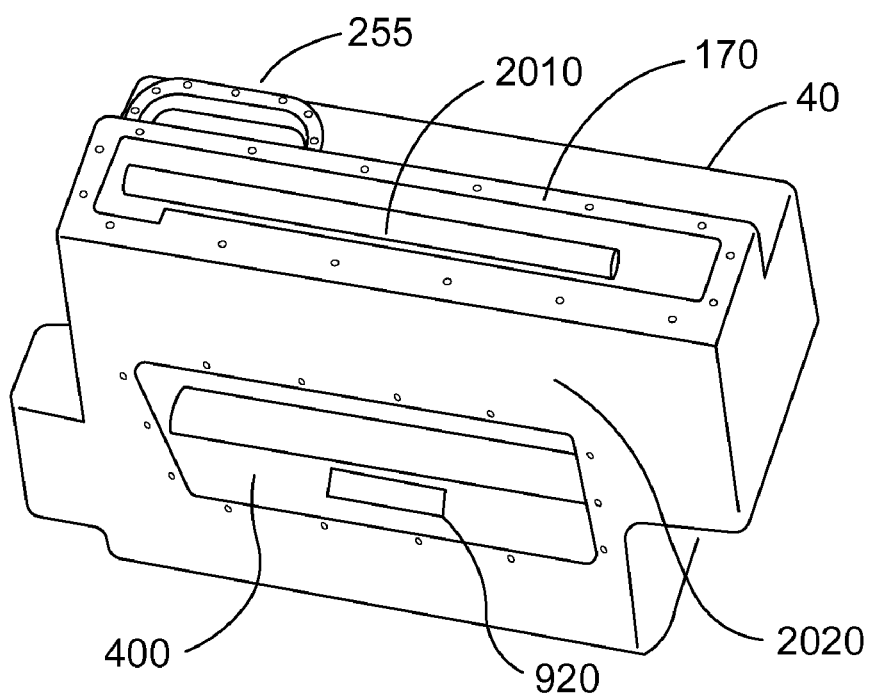
FIG. 57 is an isometric view of another embodiment of the fluid reservoir including an air dividing channel.

According to embodiments, as best shown in FIGS. 56-57, the apparatus (215) can, without limitation, be designed and constructed so weight or mass can be added or removed from any parts or components in order to maintain a specific level of liquid (30), or at least an effective amount of liquid (30), that covers all of the aerosol producing transducer(s) (10). Weight or mass (2000) can be can be added or removed from any parts that are directly or indirectly connected to any of the buoyant object(s) (400), or the transducer assembly(s) (100) themselves. It is preferred, without limitation, that the weight or mass (2000) takes the form of one or more stainless steel weights (2000) that are attached to the buoyant object(s) (400) in a manner known to those skilled in the art, and the various weight(s) (2000) are added to numerous positions or locations on the buoyant object(s) (400) in order to maintain a specific and/or effective liquid level (30) above each of the one or more aerosol producing transducer(s) (10).

Figure 64:
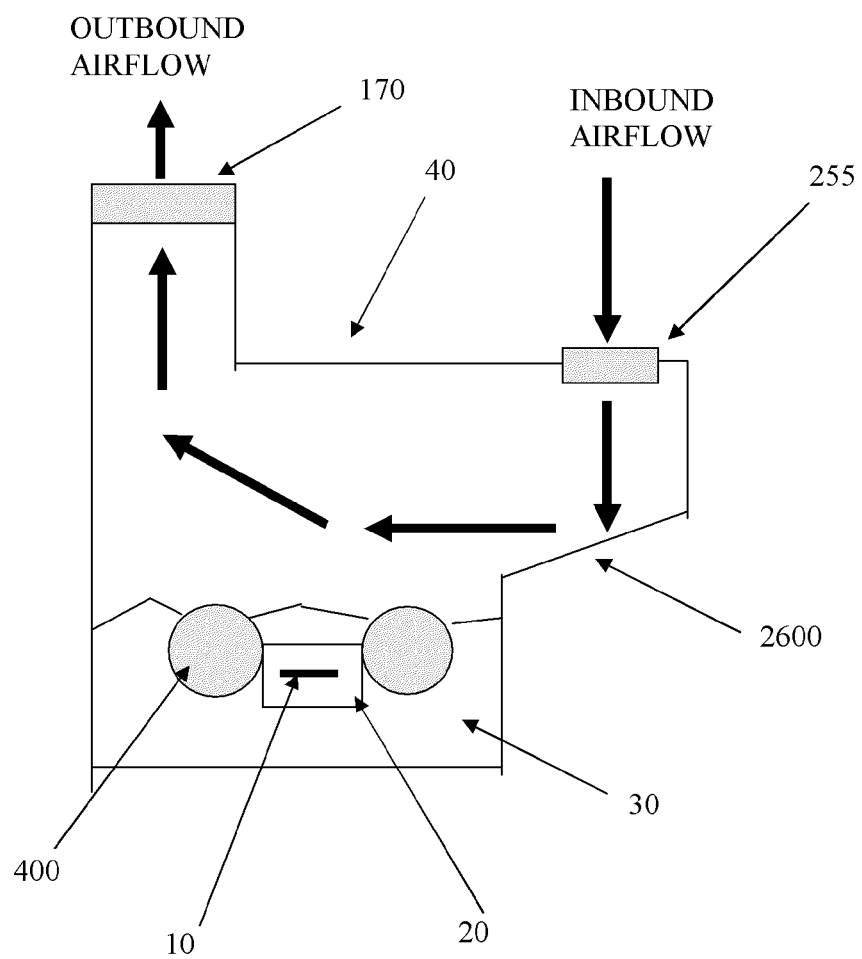
FIG. 64 is a schematic view of another embodiment of the liquid reservoir for the aerosol generator.

According to an embodiment shown in FIG. 64, the apparatus (215) can, without limitation, be designed and constructed so that the one or more buoyant object(s) (400), or even the transducer assembly(s) (100) themselves may freely float within the liquid (30) in the reservoir (40). It is preferred, without limitation, the one or more transducer assembly(s) (100) is attached to only one buoyant object (400) and the transducers are centered in connecting holes (920) cut in the buoyant object (400). The buoyant object (400), and one or more transducer assembly(s) (100) are connected to any wall of the reservoir (40). It is preferred, without limitation, that the one or more pieces of flexible tubing (375) that contains the wiring from the drive electronics (645) or amplifier(s) (230), emanates from a common wall of the reservoir (40), and connects to the side of each respective transducer housing (20) in order to power the one or more of the aerosol producing transducer(s) (10).

Figure 58:
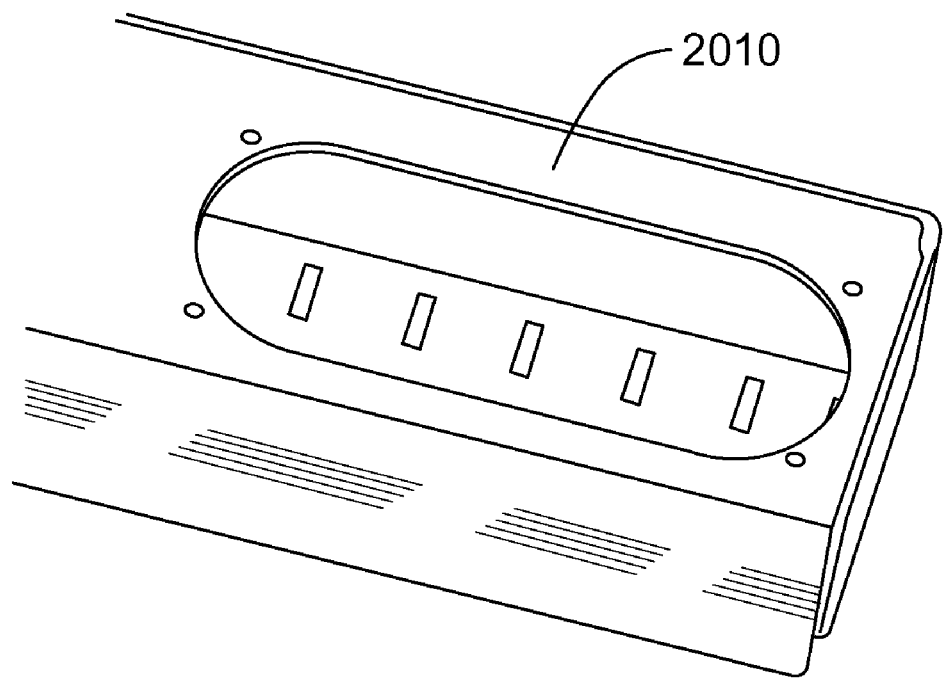
FIG. 58 is a partially broken away isometric view of the air dividing channel of FIG. 57
Figure 59:
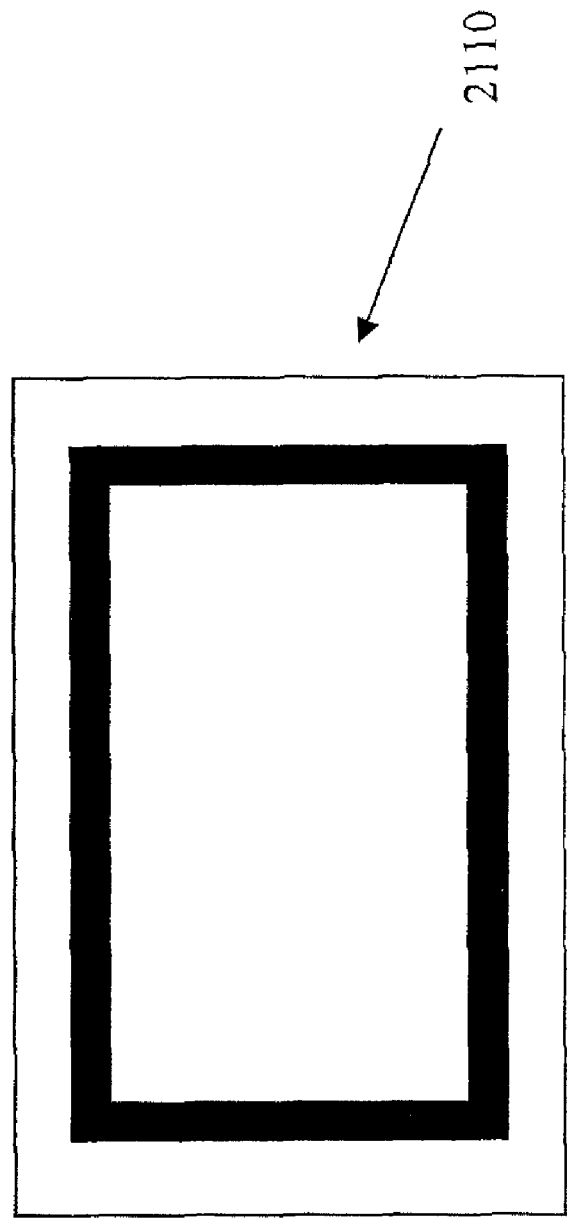
FIG. 59 is a schematic view of a vent cover for use with the aerosol generator.

According to an embodiment shown in FIGS. 57-58, the apparatus (215) can, without limitation, be designed and constructed so that air, or any combination of gas(es), enters the fog tank or reservoir (40) through one or more inlets or intake orifices (255), located opposite from the one or more air outlets, exit orifices, or openings (170) that are located on the top, roof, or ceiling of the reservoir (40). It is preferred, without limitation, that the one or more air outlets, exit orifices, or openings (170), consists of only one opening and the air outlet is formed or positioned at the end of a chimney (2020). Both the air inlets and air outlets can be any shape or size. It is also preferred, without limitation, that the inbound air or gas is directed downward at various angles, including vertically, into the fog tank or reservoir (40). According to another embodiment, the downward moving air stream may, without limitation, strike one or more surfaces that cause the inbound airflow to be redirected in various directions and angles inside of the reservoir (40). It is preferred, without limitation, that one or more redistribution surfaces are located near the bottom of the reservoir, but at least above the highest possible liquid (30) level. The fog tank or reservoir(s) (40) can be any, without limitation, size, shape, or geometry, and it can have any height of air space or volume above the liquid (30) that is located in the bottom of the reservoir (40). The liquid (30) in the bottom of the reservoir (40) can be, without limitation, any effective depth.

Figure 69:
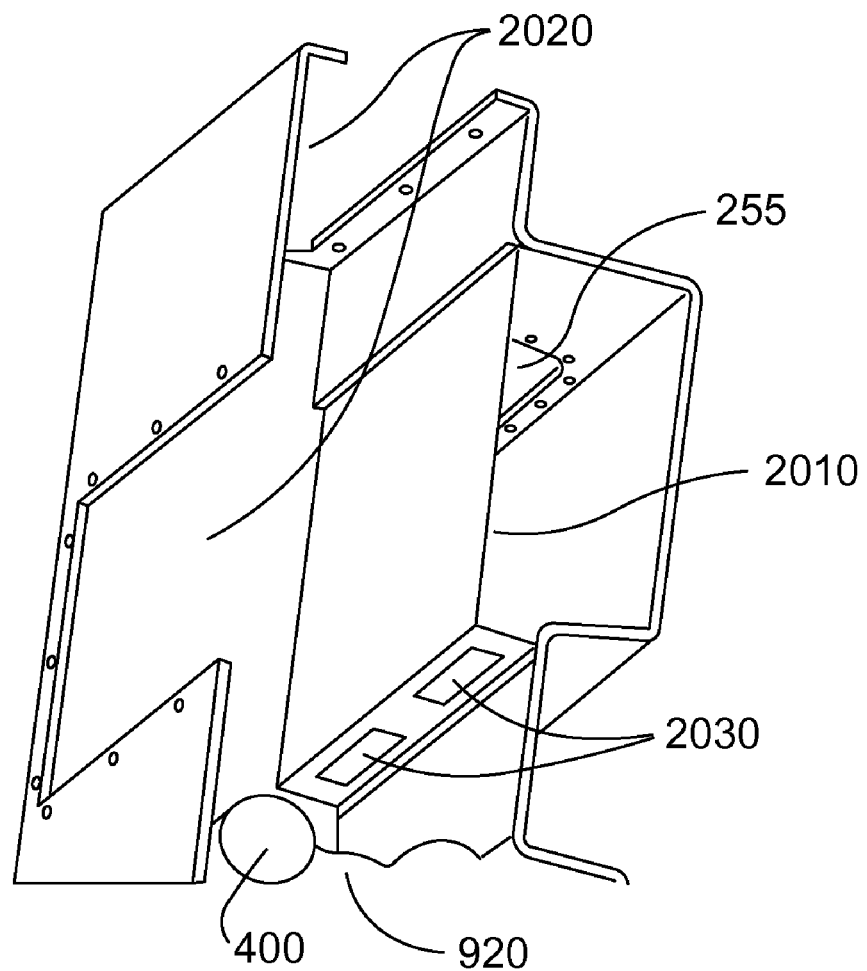
FIG. 69 is a partially broken away, cross-sectional view of the air dividing channel of FIG. 57.
Figure 70:
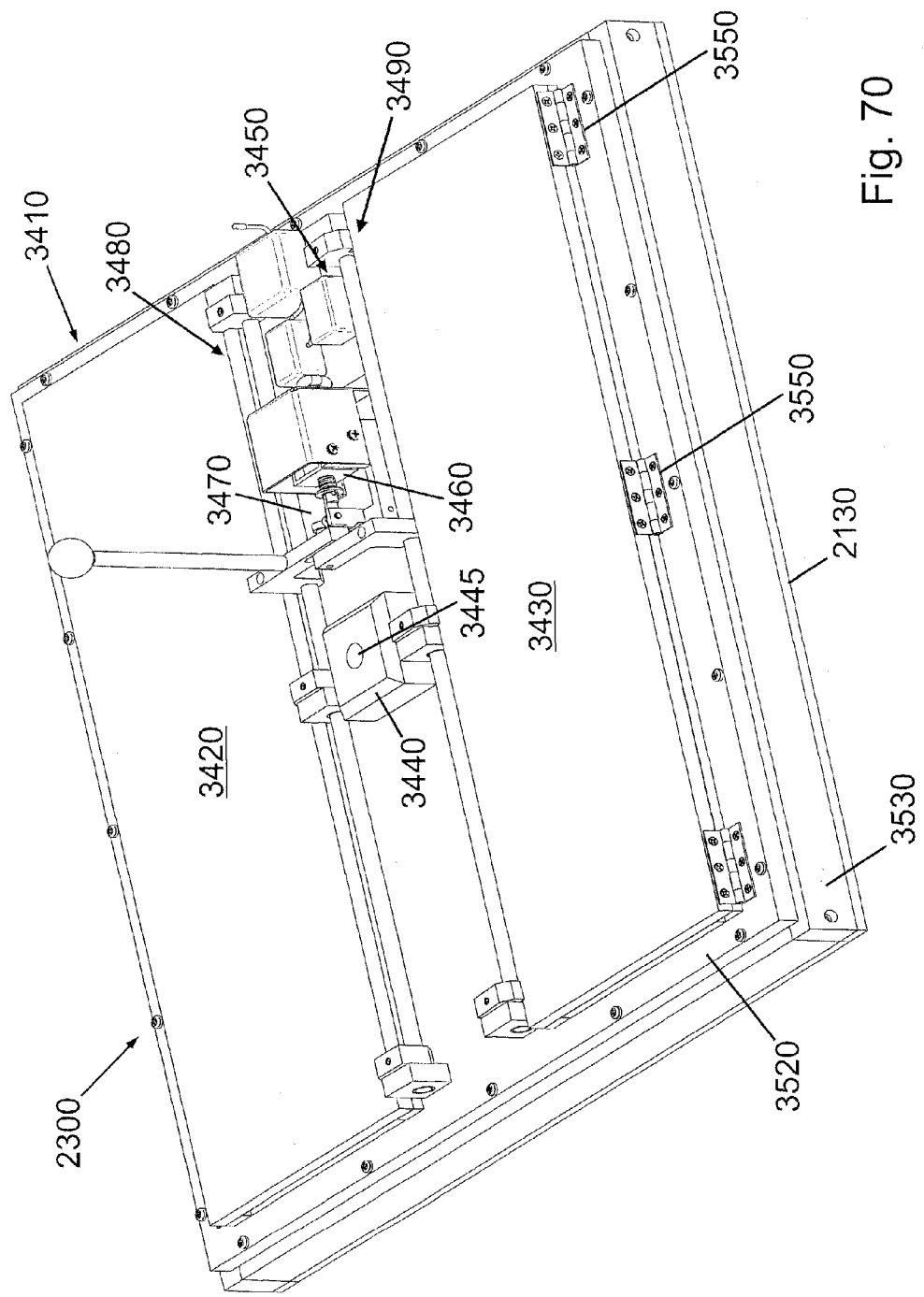
FIG. 70 is a bottom perspective view of a vent cover with a pair of doors in a closed orientation.
Figure 71:
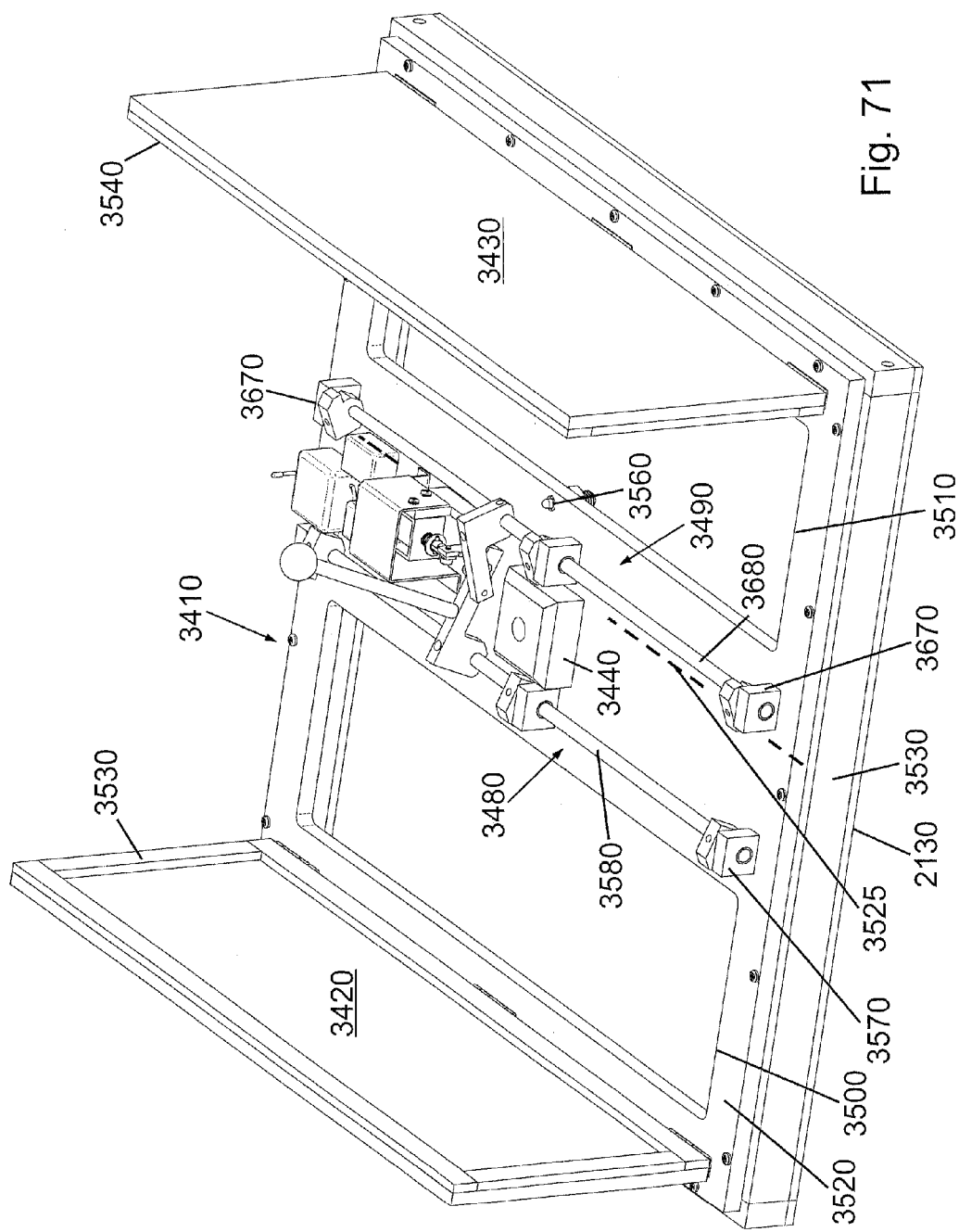
FIG. 71 is a bottom perspective view of a vent cover with a pair of doors in an open orientation.
Figure 72:
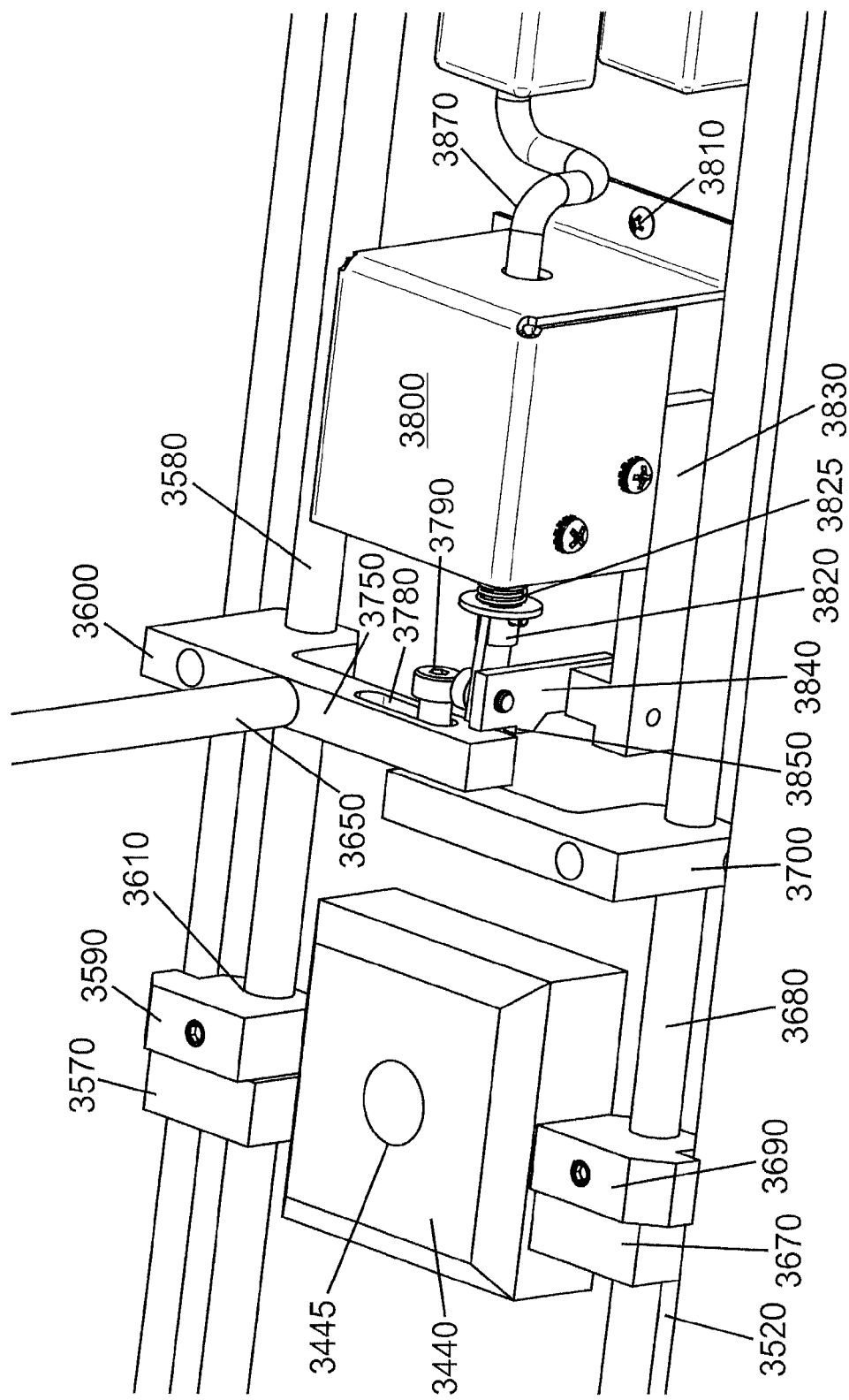
FIG. 72 is an enlarged perspective view of a latching mechanism in a latched orientation of a vent cover to keep both pair of doors in a closed.
Figure 73:
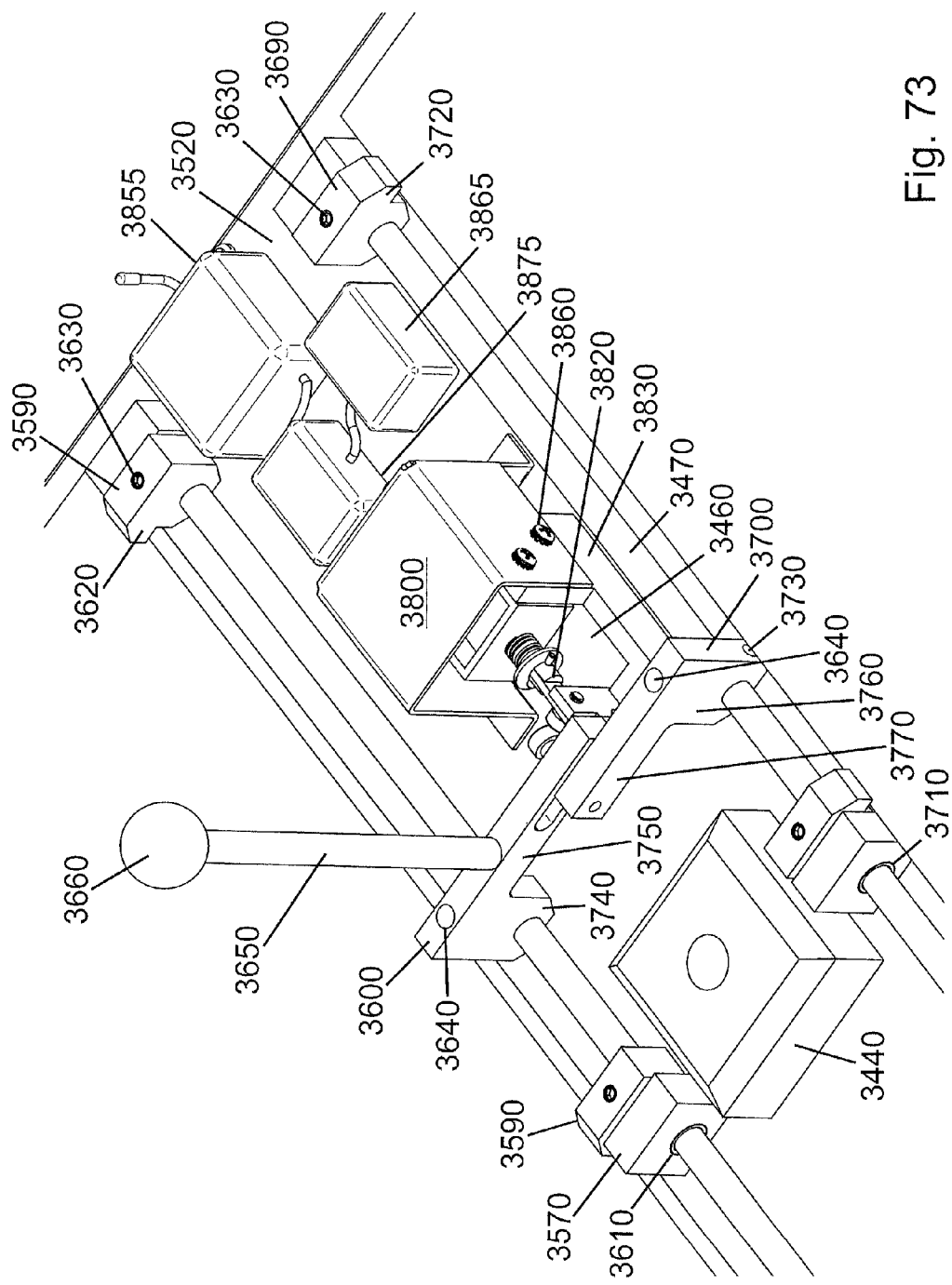
FIG. 73 is an enlarged perspective view of a latching mechanism in an unlatched orientation of a vent cover to allow keep both pair of doors to open.

According to an embodiment shown in FIGS. 57-58 and 69, the apparatus (215) can, without limitation, be designed and constructed so that the air entering the reservoir (40) is distributed to one or more locations inside of the reservoir (40) via means such as, but not limited to, conduit, piping, tubing, channels (2010). According to an embodiment, these means to move the air can be easily removed for cleaning. According to another embodiment, this means to move, channel, or distribute the inbound air to one or more locations throughout the fog tank or reservoir (40) can have various lengths, shapes, and geometries, and can have one or more holes or perforations (2030) of various sizes and shapes in various orientations, as best shown in FIG. 69. They can also be partially or completely enclosed. These embodiments can reduce, diminish, or eliminate, unwanted air patterns or airflow in the reservoir and/or fog tank (40) such as, but not limited to, stagnant airflow, uneven or unbalanced airflow, turbulent airflow, or vortices. It is preferred, without limitation, that the air exiting these holes or perforations (2030), is directed downward toward the liquid in the reservoir (40). It is even more preferred that the air is directed downward toward the bottom of the reservoir (40), and the bottom of the reservoir (40), or any area near the bottom of the reservoir (40), is designed so that the inbound air flow strikes a shelf (2600) (FIG. 64) or area that is not covered with liquid (30). The shelf (2600) can be canted at any angle. It is preferred, without limitation, the shelf (2600) is sloped downward at a forty-five degree angle toward the part of the reservoir (40) where the liquid (30) is held. It is very preferred that the air is directed along the wall of the tank or reservoir (40) opposite from the wall closest to the one or more orifices (170) though which the air and aerosol (20) exits the apparatus (215).

According to an embodiment, the apparatus (215) can, without limitation, be designed and constructed so that the velocity and/or volume of air exiting from the reservoir (40) or apparatus (215) can be reduced at any time during the aerosol generation and output cycle. It is preferred without limitation, this process occurs at or near the end of the aerosol generation and output cycle. It is also preferred, without limitation, that the velocity and/or volume of air or gas exiting from the reservoir (40) or apparatus (215) is reduced to at least 150 cubic feet or more per minute, and more preferred to at least 100 cubic feet or more per minute, and even more preferred that the air velocity be reduced to 10 cubic feet or more per minute. The decrease in the velocity and/or volume of air or gas and aerosol (200) exiting from the reservoir (40) or apparatus (215) can, without limitation, promote a more rapid build up of aerosol (200) in the area surrounding the apparatus.

According to an embodiment, the apparatus (215) can, without limitation, be designed and constructed so that it is connected to one or more sensors or has communication with one or more sensors to determine when an effective or sufficient amount of aerosol (200) is applied to the treated or targeted area. This embodiment includes configurations in which the sensor(s) may be directly or indirectly attached to the apparatus, or that one or more sensors may be remotely located and operated in any location where the aerosol (200) may be administered. The sensor(s) can be positioned in any orientation and communicate directly or indirectly with the aerosol generating apparatus (215) in various ways such as, but not limited to, radio, sound, wire, or fiber optics.

According to an embodiment in FIGS. 52-55, a means to dehumidify (2040) an area in which the aerosol (200) is administered can be operated, without limitation, at any time during or after the apparatus (215) has stopped administering the aerosol (200). The dehumidification cycle time can vary for reasons including, but not limited to, the size of the targeted area being dehumidified, the amount of aerosol (200) that is deployed into the targeted area, the specific level of humidity that is desired or chosen for the dehumidification process or the targeted area.

According to an embodiment, the means to dehumidify (2040) can delay starting the dehumidification process for any period of time after, without limitation, receiving a signal or command to begin the dehumidification process, receiving any humidity level information, or detecting a certain humidity level. This time delay can be impacted by inputs or factors such as, but not limited to, the size of the treated space, the temperature of the treated area, or the desired level of disinfection or efficacy of the process.

The means to dehumidify (2040) can be any means or apparatus known to those skilled in the art. The means to dehumidify (2040) may also, without limitation, include or implement any catalytic technology known to those skilled in the art. The means to dehumidify can also be directly or remotely programmed or controlled by any means known to those skilled in the art such as, but not limited to any, software, relays, timers, programmable logic circuits, or integrated circuits.

Figure 52:
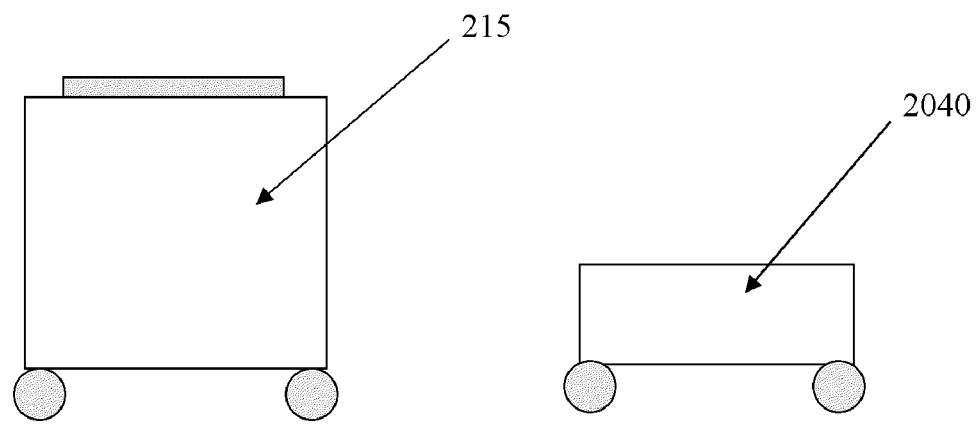
FIG. 52 is a schematic view of a dehumidifier for use with the aerosol generator.
Figure 53:
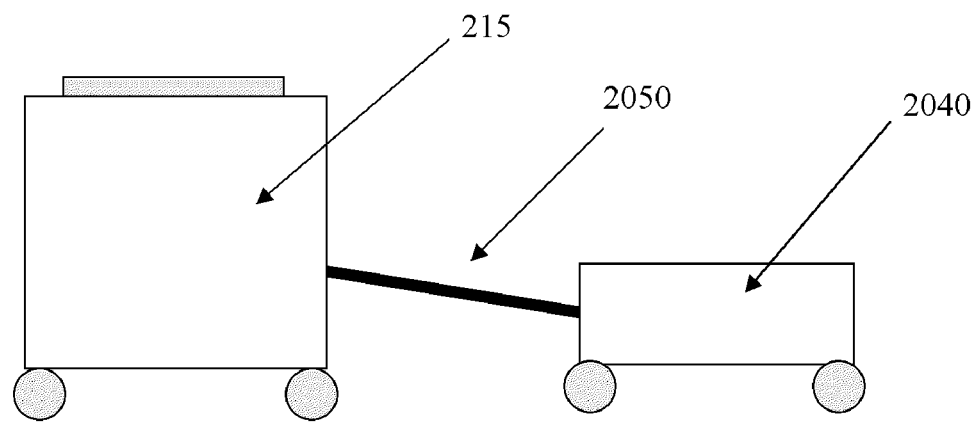
FIG. 53 is a schematic view of another embodiment of a dehumidifier for use with the aerosol generator.

In one embodiment shown in FIG. 52, the means to dehumidify (2040) an area in which the aerosol (200) is administered is an independent apparatus that is "not" connected to the aerosol generating apparatus (215), and it is remote controlled or programmed by the operator, all in a manner all known to those skilled in the art. In another embodiment shown in FIG. 53, the means to dehumidify (2040) an area in which the aerosol (200) is administered, is also an independent apparatus, but in this particular embodiment its operation is electrically controlled by, and electrically connected to, the aerosol generating apparatus (215) via connection (2050). In still another embodiment, the means to dehumidify (2040) an area in which the aerosol (200) is administered, is also an independent apparatus, but in this particular embodiment its operation is controlled by the aerosol generating apparatus (215) via radio in a manner known to those skilled in the art. However, it is electrically independent in this particular embodiment.

Figure 54:
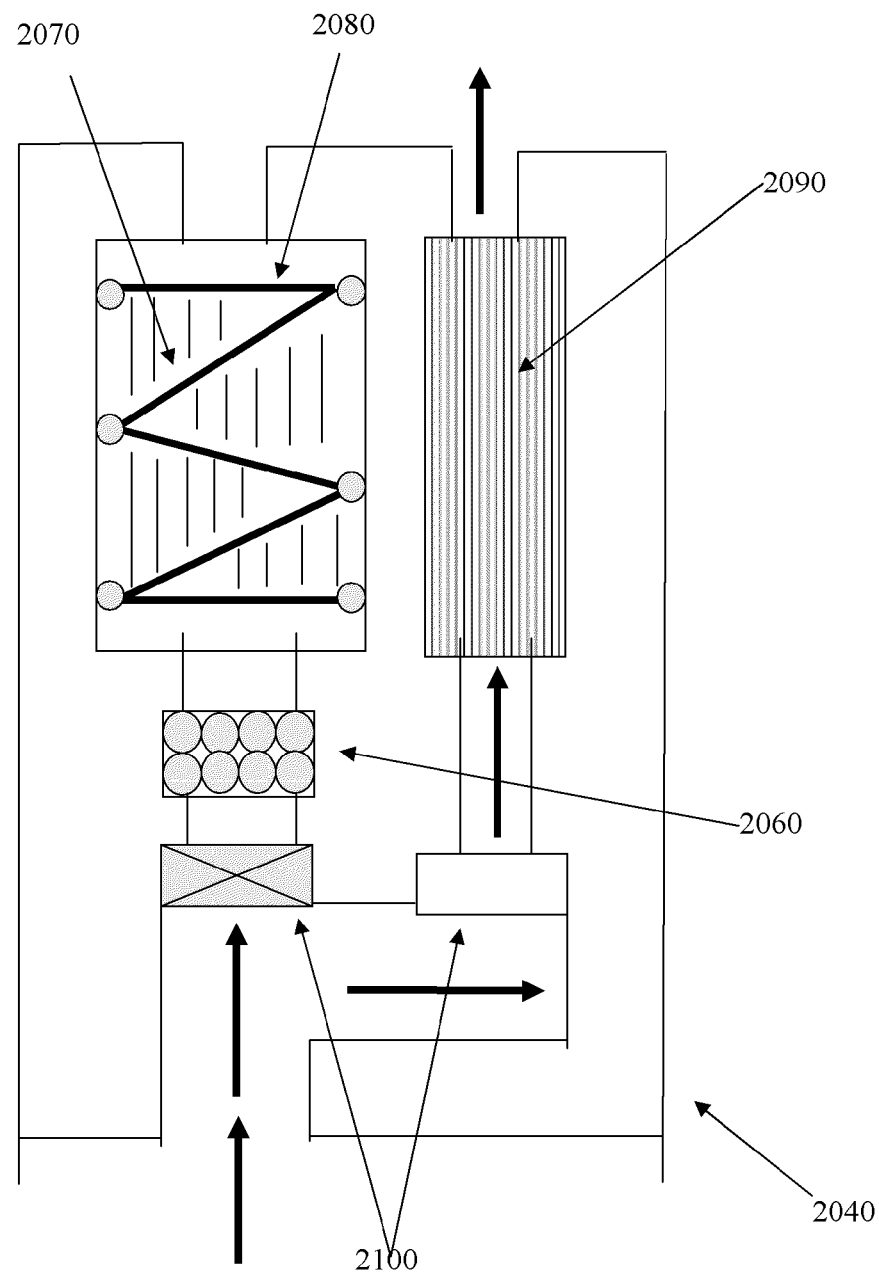
FIG. 54 is a schematic view of another embodiment of a dehumidifier for use with the aerosol generator.
Figure 55:
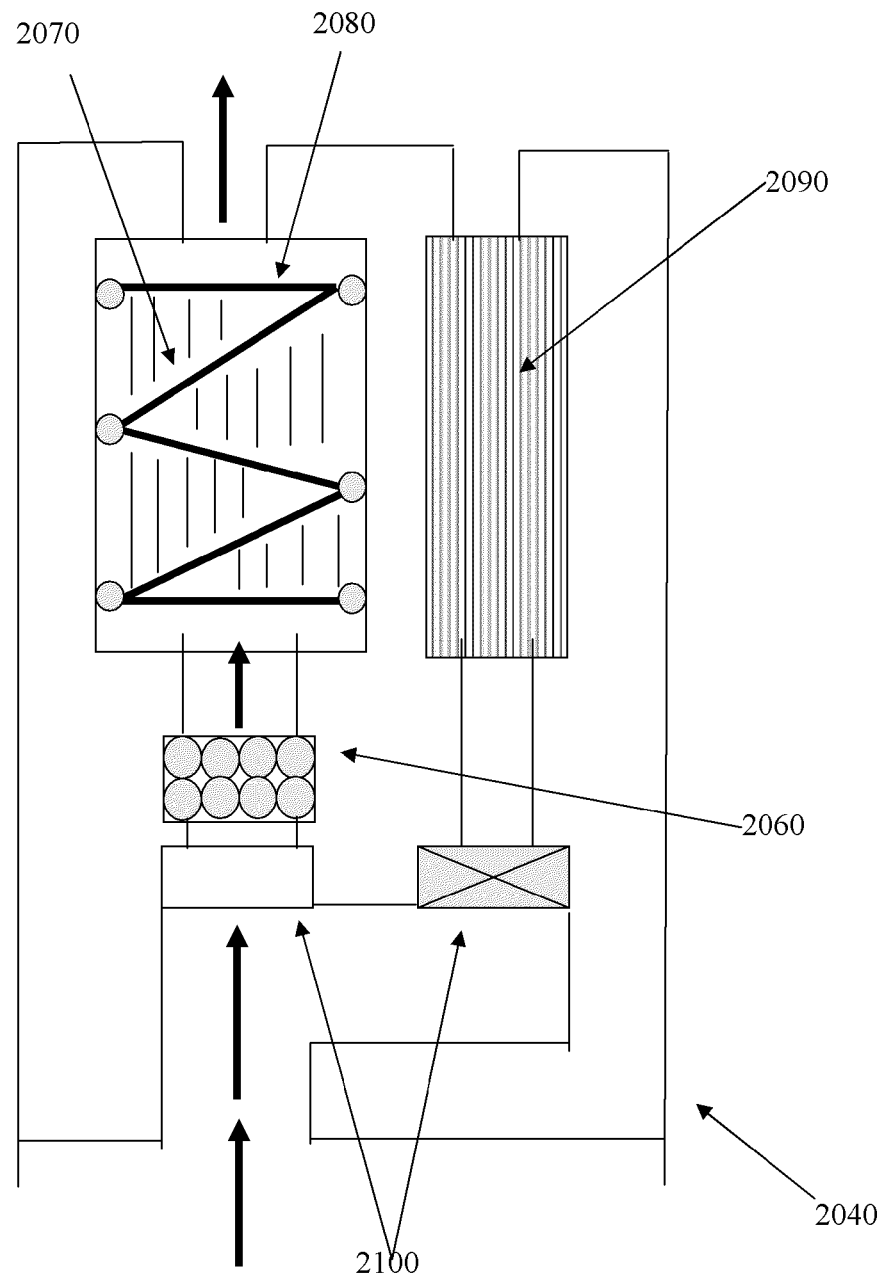
FIG. 55 is a schematic view of another embodiment of a dehumidifier for use with the aerosol generator.

In an embodiment shown in FIGS. 54-55, the means to dehumidify (2040) an area in which the aerosol (200) is administered contains one or more filter media to filter the aerosol from the air during, or after it passes over the chill coils. The filter media can be any filter known in the art, but it is preferred, without limitation, that the filter media or mechanism consists of one or more separation cones (2060) that separates the aerosol (200) from the air as the air moves through the separation cone(s) (2060).

In another embodiment, the means to dehumidify (2040) an area in which the aerosol (200) is administered is designed and manufactured so that stainless steel filter material or metal mesh of any porosity size, number, and shape (2070) connects with, spans between, or is interwoven with the one or more chill coils (2080) of various size and shape, that are used by the means to dehumidify (2040). This construction may, without limitation, increase the cooling efficiency of the means to dehumidify (2040) by increasing the cooled surface area.

In another embodiment, any liquid filtered from the air, or condensed by the chill coil(s) (2080) or any connecting metal filter material or mesh, can without limitation, be collected in a common collection container.

In another embodiment, the means to dehumidify (2040) an area in which the aerosol (200) is administered is without limitation, designed and built so it can receive any type of signal known to those skilled in the art, and this signal may cause the means to dehumidify (2040) to switch or direct the air flowing into or through any filter known to those skilled in the art, that is able to effectively remove any chosen or selected gas(s) or vapor(s) (2090) from the air in the treated area(s). It is preferred, without limitation, that this filter (2090) is constructed from activated charcoal in a manner that is known to those skilled in the art, and one or more valves (2100), or other means known to those skilled in the art, closes thus forcing air through a separate channel that leads to the filtering (2090) means.

In another embodiment, the means to dehumidify (2040) an area in which the aerosol (200) is administered or deployed, can be, without limitation, designed and built so the operator can program or select various options including, but not limited to, (a) any time delay between when a certain humidity level or range of humidity is detected and when the dehumidifier would commence the dehumidification process, (b) any humidity level where the means to dehumidify (2040) would stop the dehumidification process, (c) any duration of time for moving, switching, or directing the air flowing into or through any filter (2090) that is able to effectively remove any targeted gas(s) or vapor(s) from the treated area(s), (d) any duration of time that the means to dehumidify (2040) would operate and dehumidify the room.

According to an embodiment shown in FIGS. 59-63, a means to effectively or efficaciously cover various types of inbound or outbound air vents and/or any surrounding area or surfaces of the vents (2120), in the treated area can, without limitation, be used in concert with the aerosol generating apparatus (215) or any aerosol or vapor generating apparatus, and prevent or limit the movement of air, gas, aerosol (200) and vapor(s) through these vents (2120). This vent covering assembly (2300) consists of parts including, but not limited to, a means to cover the vent (2110), any material extensions (2160) that are needed to directly or indirectly attach to the cover (2110) so that it will have sufficient clearance and cover any protruding vent (2120) parts (3010), sealing material (2130) that can seal the cover (2110) to the vent (2120) or any surface(s) surrounding the vent, any one or more pole(s) (2140) which can, without limitation, be adjusted or modified for length by the operator, a means to directly or indirectly connect the pole(s) to the vent cover (2150), one or more means to directly or indirectly connect (2500) the pole(s) (2140) to the floor or any other surface (2400). This assembly of parts can be made of any mechanically, structural, and chemically suitable materials that are known to those skilled in the art for this application.

Any parts used to construct the vent covering assembly (2300) can be constructed from various materials such as, but not limited to, stainless steel, glass, polymer, polyolefin, cellulose, or even natural or manufactured fibers that are either coated or uncoated. It is preferred, without limitation, that the vent covering assembly (2300) is constructed from one or more polymers that can include, but is not limited to, PVC, polycarbonate, polypropylene, and HDPE. The materials used to construct the vent cover (2110) or extension(s) (2160) may be rigid, semi-rigid, flexible, or pliable. It is preferred, without limitation, that the vent cover (2110) and any needed extension(s) (2160) are constructed from rigid PVC. The seal material (2130) can be any material that can create an effective seal with/against any materials that it contacts. It is preferred, without limitation, that the seal material (2130) is constructed from materials such as, but not limited to, Viton, or EPDM, with a durometer of at least 10. The seal material can be, without limitation, any foam, open or closed cell material, and any shape or construction known in the art. The sealing material (2130) can also vary with variables including but not limited to its, size, shape, width, surface area, geometry, fit, thickness, density, hardness, elasticity, porosity, permeability, mechanical properties, physical properties, and other variables known to those skilled in the art. One or more strips or layers of various seal material(s) (2130) may also be utilized and can be used in various orientations, including, but not limited to, parallel to one another. It is preferred, without limitation, that the seal material consists of a single row of closed cell EPDM foam. Any of the surfaces of the vent covering assembly (2300) can, without limitation, be electrically or electrostatically charged in order to attract the "applied agent". The vent covering assembly (2300) can be designed and constructed for single or multiple uses.

According to another embodiment, the vent cover (2110) and/or its extensions (2160) can, without limitation, be constructed from, or be molded with, any material that can create an effective seal, or otherwise function as the seal, which negates the use of a separate seal material and/or seal layer (2130). This represents the vent cover (2110) in its simplest form. In this case, the vent cover (2110) and/or its extensions (2160) is designed and constructed so that it incorporates the purpose, performance, traits, attributes, and characteristics of both the seal material and/or seal layer (2130) and the vent cover (2110) and/or extensions (2160).

In another embodiment, any parts connected directly or indirectly to the means to cover the vent (2110) can be adjusted for height in order to create or maintain effective compression on any seal that is formed to effectively or efficaciously seal or cover the air or gas vents (2120). It is preferred, without limitation, that the one or more pole(s) (2140) is constructed in a manner known to those skilled in the art, so that its length can be adjusted and locked into position once sufficient or effective force is exerted onto any part of the vent covering assembly (2300) such as, but not limited to, a means to cover the vent (2110) and/or the seal material (2130).

It is preferred, without limitation, that the means to cover the vent (2110) is any shape, size, construction, or geometry that is sufficiently large enough so that the sealing means and/or seal material (2130) can effectively seal to or around any air vents (2120). It is even more preferred, without limitation, that the means to cover the vent (2110) is in the shape of a plate or bowl. This means to cover the vent (2110) can, without limitation, have one or more structural supports that are positioned in a manner known in the art to prevent any unwanted flexing of the means to cover the vent (2110) during use. The means to cover the vent (2110) can also, without limitation, have extensions (2160) directly or indirectly attached to allow the various vent cover components (2170) to effectively fit over the vent (2120) and any protruding vent parts (3010). The extensions (2160) can be made of the same materials as the means to cover the vent (2110), and have any thickness, width, length, height, geometry, or construction. The extensions (2160) can, without limitation, follow the outline of the means to cover the vent (2110).

The seal material (2130) can be attached to the vent cover (2110) or its extensions (2160) in various ways known to those skilled in the art. The seal material (2130) can be made from any compatible and suitable material. However, it is preferred, without limitation, that the seal material (2130) consists of any suitable material and design that has sufficient compression and/or compliance to form an effective seal when it is compressed or contacts between the vent cover (2110) and/or extension(s) (2160) and the vent (2120) or any surface surrounding the vent. It is even more preferred that the seal material (2130) has absorbent properties. A lip or other effective means can also be built or formed around the seal material (2130) to catch or hold any liquid if it is compressed out of the seal material (2130).

Any pole (2140) known to those skilled in the art, can be used in the present invention, but it is preferred, without limitation, that the pole (2140) has an adjustable length, and a locking means (3020) (FIG. 61) known in the art to maintain the effective or chosen pole length. Any method known to those skilled in the art can be used to incorporate a pole (2140) adjustable for length into the present invention. It is preferred, without limitation, that the pole (2140) consists of two parts, and the length of the combined poles can either gain length or loose length depending on which way the operator screws or ratchets the two pole pieces. The pole (2140) connects either directly or indirectly to the means to cover the vent (2110) and this connection can, without limitation, swivel. It is preferred, without limitation, that the pole screws into a bracket or threaded block that is directly mounted to the means to cover the vent (2110). The end of the pole that contacts the floor or other surface, can also without limitation, be adjustable for length, and have the ability to swivel. The end of the pole or support mechanism (2800) can be, without limitation, formed from, molded, coated, adhered, or covered, with any absorbent material so that the surface and/or area below the pole can be treated with any liquid. The end of the pole or support mechanism (2800) can also, without limitation, be manufactured with any material that will decrease the movement or slipping of the pole.

According to an embodiment, installation includes, but is not limited to, pressing the means to cover the vent (2110) and its accompanying seal material (2130), up against or around the vent (2110) and extending the pole until sufficient pressure is formed against or around the vent (2110), and the end of the pole (2140). Before, during, or after installation, the seals (2130) and end of the pole (2140) can be, without limitation, soaked with or saturated with any liquid consisting of any anti-pathogen, toxin, fungal, sterilization, disinfection, or sporicidal agent(s) or mixtures thereof (herein collectively "agent(s)").

Figure 63:
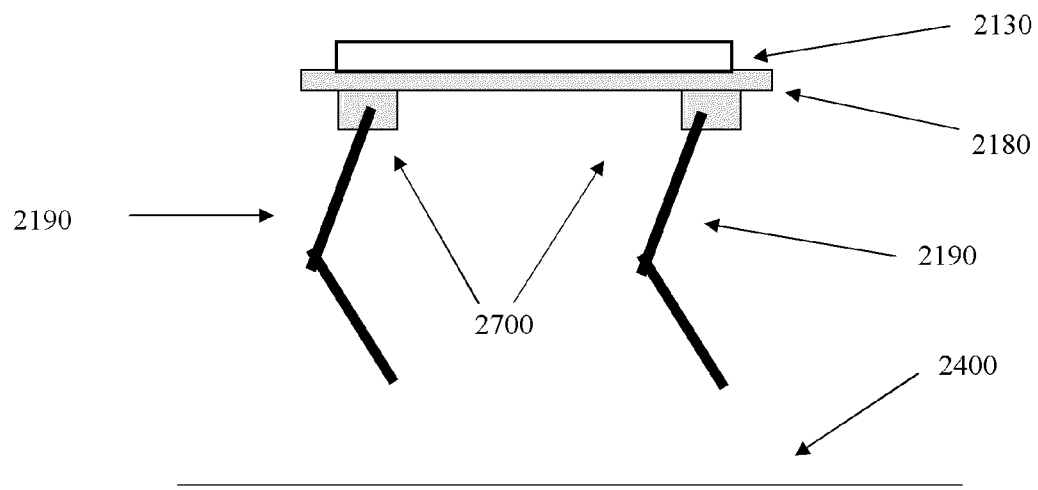
FIG. 63 is a schematic view of another embodiment of the vent cover for use with the aerosol generator.

According to an embodiment shown in FIG. 63, one or more attachment points (2700) can be added to the design of a magnetic vent cover (2180) so that a means (2190), can be attached to the vent cover to pull it from the ceiling vent without the need for a person to use a means such as, but not limited to, a ladder to reach it. This means (2190) used for pulling can include, but is not limited to, rope, cord, thread, wire, cable, twine, tube, that can be various, size, length, materials, and construction. Protruding objects (2200) of various lengths, shapes, and construction, can also, without limitation, be attached to the magnetic vent cover (2180) in various ways known in the art, for the same purposes. The protruding objects can include, but is not limited to, any dowel, pipe, or conduit, and can also be constructed from any suitable materials, and have various flexibility or rigidity. The construction of the magnetic vent cover (2180) is known to those skilled in the art, but it can, without limitation, be made by laminating a sheet of magnetic material between two or more polymer layers. The magnetic material can have any thickness, power, or strength, and the polymer coatings or laminations, can be any suitable polymer. According to another embodiment, the magnetic vent cover (2180) can, without limitation, incorporate any deformable seal material (2130), which can increase the ability of the magnetic vent cover (2180) to effectively seal the vent (2120). The seal material (2130) can without limitation, contact the vent (2120), surround the vent (2120), or contact any area near the vent (2120). The seal material (2130) can be encompassed or enclosed on one or more sides by any magnetic material (2900) of any strength. The seal material (2130) can be, without limitation, separated from the magnetic material (2900) by one or more layers of any suitable polymer of any thickness.

According to an embodiment shown in FIGS. 60-61, one or more chemical contact or biological indicators (hereinafter "indicator(s)") (3000) of any size, type, or construction, may be mounted, held, hung, positioned, or placed, on any part including, but not limited to, the vent covering assembly (2300), or any part directly or indirectly connected to the vent covering assembly (2300) or magnetic vent cover (2180). It is preferred, without limitation, that the indicator (3000) is attached to a surface that faces the treated area. The vent covering assembly (2300) can be designed for the addition as well as removal of these accessories, in a manner known to those skilled in the art. The indicator (3000) provides a means for communicating or assuring that proper sanitization, detoxification, disinfection, high level disinfection, or sterilization has occurred, without limitation, on surfaces on or surrounding the vent covering assembly (2300). A detailed description of the indicator (3000) is not specifically set forth, but is known to those skilled in the art.

According to embodiment shown in FIGS. 65-68, the "application enclosure(s)" (930) can include, without limitation, one or more wall(s) (935), of any material, that form one or more enclosed, semi-enclosed, or unenclosed area(s) (940). The one or more wall(s) (935) of the application enclosure(s) (930) may also have one or more openings or holes (herein referred to as hole(s)) (955) of any size, shape, or dimension, and the interface of these hole(s) (955) with any surface(s) (945), or any object(s) (3030), forms one or more enclosed area(s) (950) which can vary with respect to variables such as, but not limited to any, size, shape, or geometry.

According to an embodiment, the application enclosure (930) can also, without limitation, be designed and constructed so that it has one or more opening(s) or orifice(s) ("hole(s)") (955), and one or more object(s) (3030) with one or more various surfaces (945) can be positioned or inserted through these hole(s) (955), and the direct or indirect contact or interface of the object(s) (3030) with these hole(s) (955) results or causes the enclosed area(s) (950) to become, without limitation, effectively sealed. The hole(s) (955) can also be formed around one or object(s) (3030). The object(s) (3030) can, without limitation, be oriented, located, or inserted, completely through the enclosed area (950) in any orientation, through the one or more hole(s) (955). The hole(s) (955) can be any size, geometry, orientation, or in any location. The holes(s) (955) and/or any parts of the application enclosure (930) can, without limitation, be of any construction, and be adjusted by various means known in the art, to accommodate any object(s)'s attributes including, but not limited to size, width, length, shape, and/or geometry. The application enclosure (930) can also, without limitation, be designed and constructed in a manner known to those skilled in the art, so that it can be temporarily or permanently mounted, strapped, or connected to any table, bench, or other surface.

Figure 65:
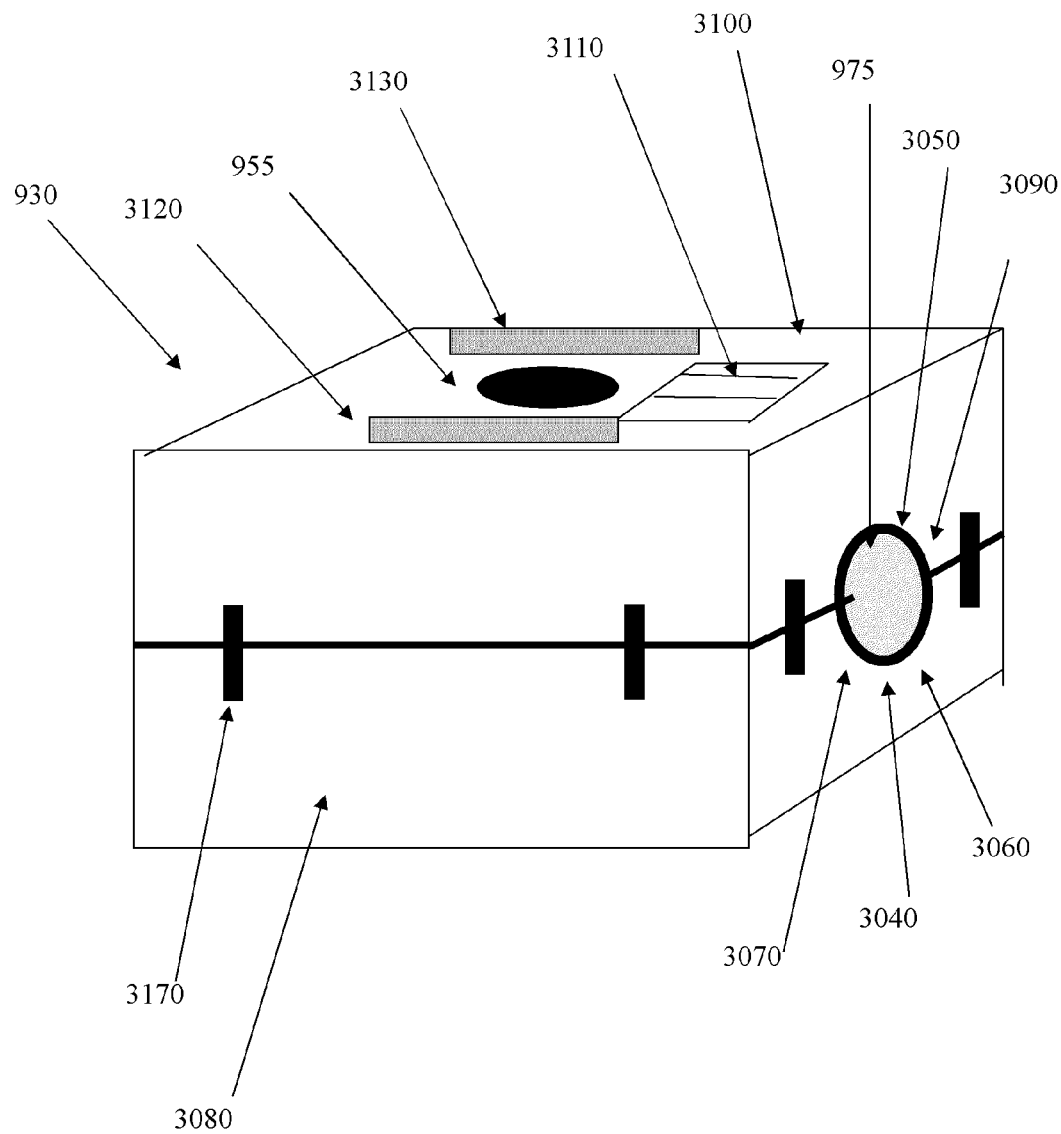
FIG. 65 is a schematic view of another alternative embodiment of the enclosure for the aerosol generator.
Figure 66:
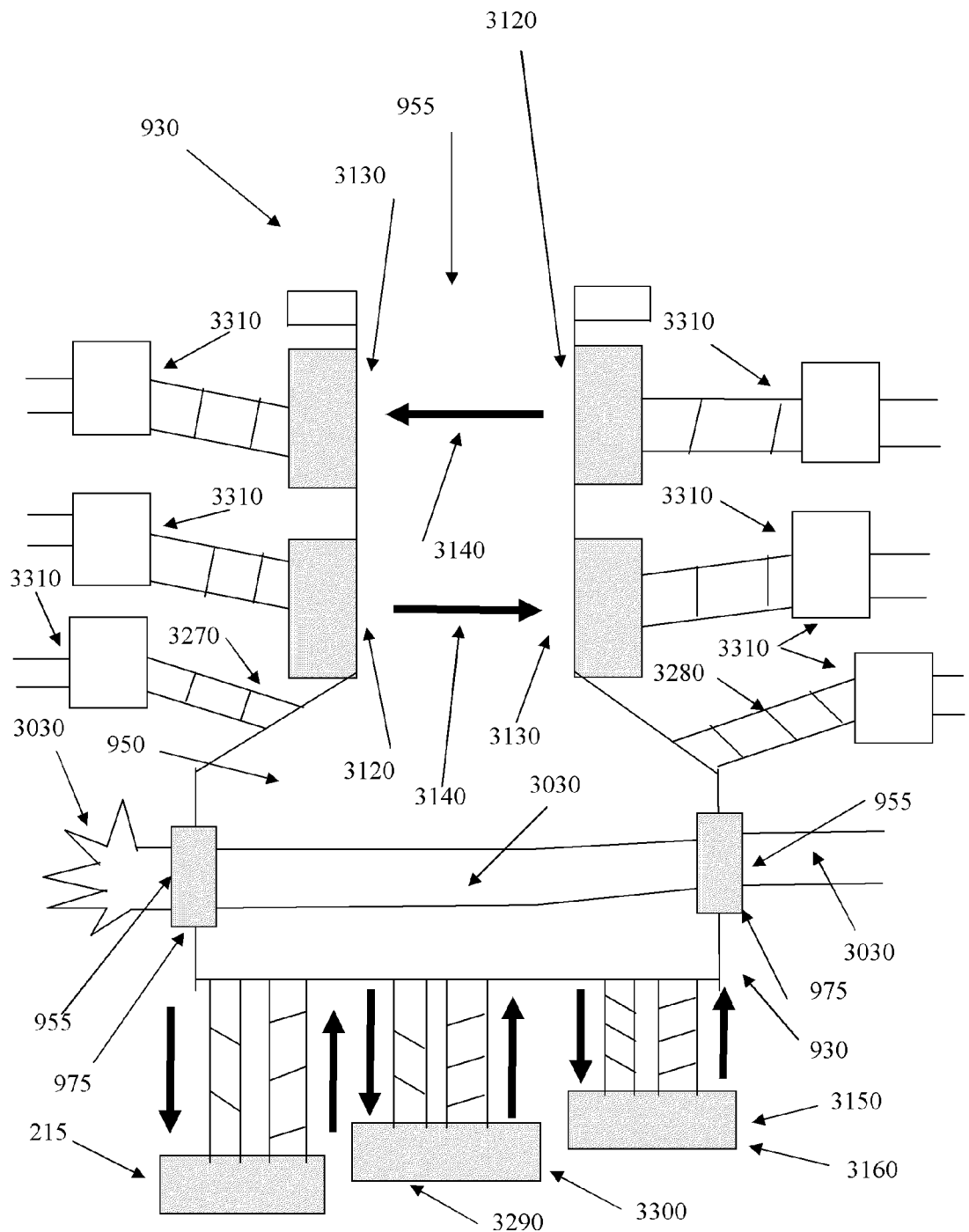
FIG. 66 is a schematic view of another alternative embodiment of the enclosure for the aerosol generator.
Figure 67:
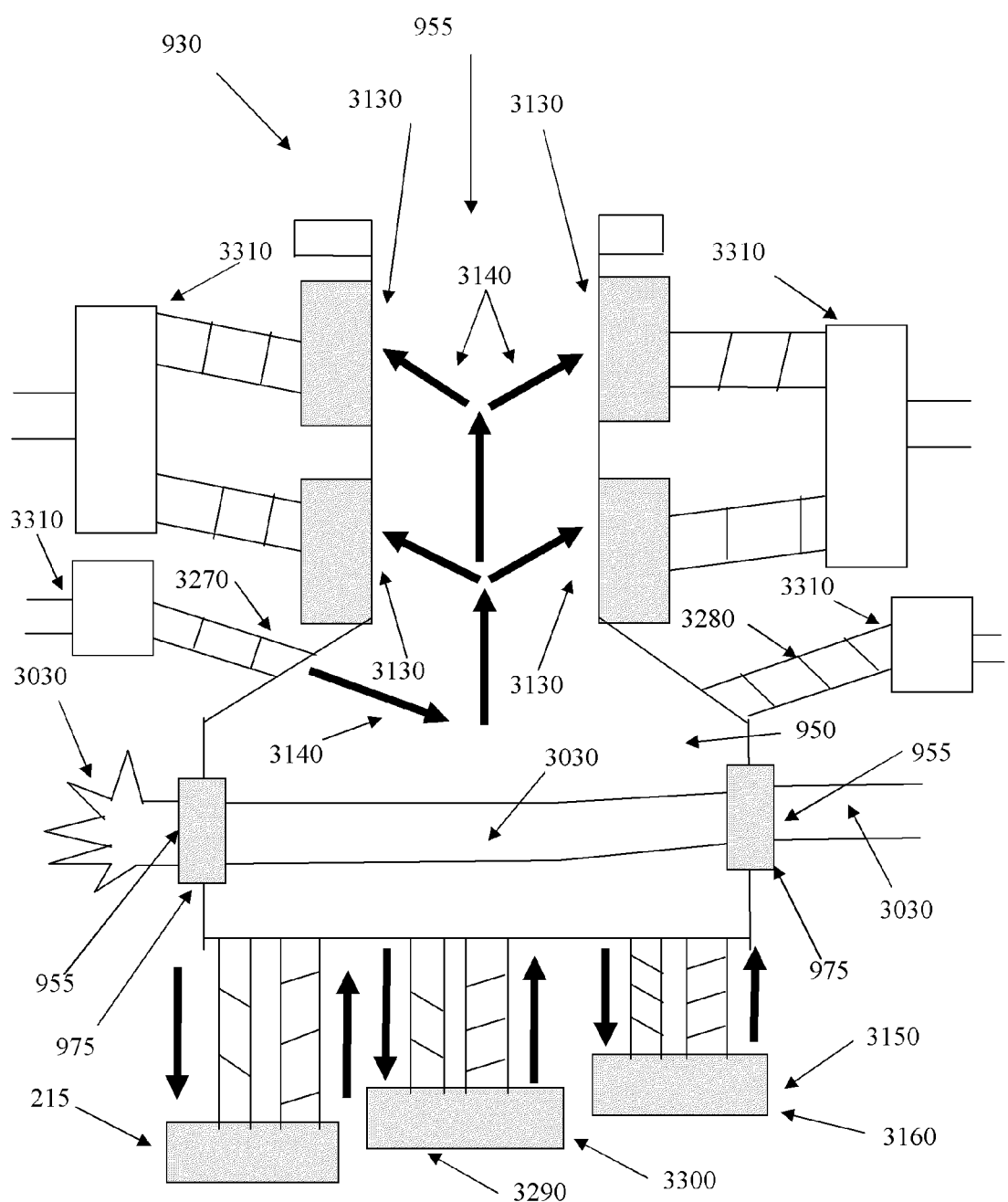
FIG. 67 is a schematic view of another alternative embodiment of the enclosure for the aerosol generator.
Figure 68:
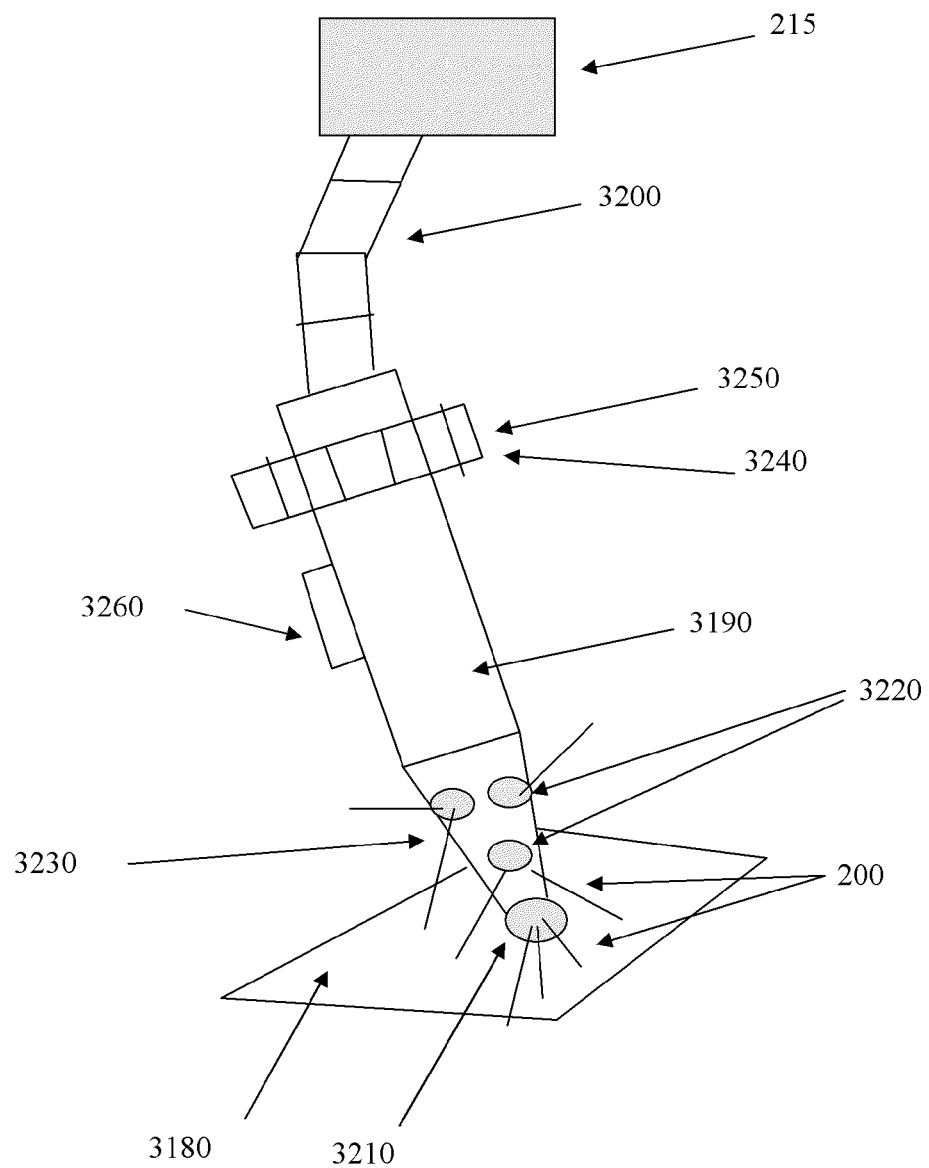
FIG. 68 is a schematic view of another alternative embodiment of the enclosure for the aerosol generator.

Looking now at FIGS. 65-67, according to an embodiment, the application enclosure (930) can, without limitation, be designed and constructed so that one or more object(s) (3030) or any combination of objects (3030) can be positioned in or onto one or more section(s) (3040) of the one or more hole(s) (955) and/or their seal material (975), and the one or more opposing section(s) (3050) of each hole(s) (955) and/or their seal material (975), is then brought together by connecting the one or more component(s) (3060) that create an effectively sealed enclosed area(s) (950) when joined. It is preferred, without limitation, that this is accomplished by placing any number or combination of object(s) (3030) such as, but not limited to any legs, head, feet, hands, arms, or torso, inside or onto any part of the lower half (3070) of the section of hole(s) (955) and/or any seal material (975) directly or indirectly connected to any parts constituting the lower half (3080) of the enclosed area (950), and then enabling contact of these object(s) (3030) with any part of the upper half (3090) of the section of the hole(s) (955) and/or any seal material (975) that is directly or indirectly connected to any parts constituting the upper half (3100) of the enclosed area (950). It is preferred, without limitation, that the upper half and lower half of the enclosed area (950) are connected. It is even more preferred that upper (3100) and lower (3080) halves are able to hinge open and closed in a manner known in the art. The various application enclosure (930) parts, such as but not limited to the upper (3100) and lower (3080) halves can also, without limitation, be connected with one or more of any mechanical means (3170) known to those skilled in the art, to apply pressure to areas such as, but not limited to any seal between the upper (3100) and lower (3080) halves, and the one or more seals or interfaces between the object(s) and any part of the lower half (3070) and upper half (3090) sections, or any other sealing segments, of any hole(s) (955).

Any segments or parts of the hole(s) (955) can, without limitation, interface with the object(s) (3030) with one or more of any materials of any construction. It is preferred, without limitation, that this material is any seal forming material (975) or combination of materials (975), or any other means to form an effective seal (975), and is known to those skilled in the art. It is even more preferred, without limitation, that the seal (975) or any seal that interfaces with the object(s) (3030) can be directly or indirectly adjusted in any way, for effectiveness and fit and/or integrity, and can accommodate and effectively seal to objects (3030) of various size, shape, width, length, and geometry, and is known to those skilled in the art. The application enclosure (930) can, without limitation, seal or effectively interface with one or more of any object(s) (3030) in a manner known in the art, but it can be as simple as inserting the object(s) (3030) such as, but not limited to, any or all parts of a patient's body through any of the one or more hole(s) (955), and tightening or sealing any part connected to the object (3030) interfacing seal material (975), or interface material, that is directly or indirectly in contact with each or all of the object(s) (3030) or body part(s), to form, without limitation, an effective seal that can effectively seal the hole(s) (955). This can also be utilized, without limitation, for the hands or arms of any surgeons, nurses, technicians, or other personnel or operators, that need to access the inside of the application enclosure(s) (930) for any reason. Any pneumatic means consisting of any materials, any sealing materials (975), and construction, known to those skilled in the art, may also, without limitation, be used to effectively seal directly or indirectly around any object(s), or hand(s) or arm(s) of one or more of any personnel that interface with the application enclosure (930) in any way for any reason. One or more gloves (965) can also attach to any port(s), opening(s), or airlock(s) (960) or hole(s) (955) and be hermetically sealed to the application enclosure(s) (930). Furthermore, the gloves or gauntlets (965), and or any interface they may have with the application enclosure (930) can, without limitation, be designed in a manner known to those skilled in the art, so that they may be easily or quickly removed and replaced. It is preferred, without limitation, that the gloves or gauntlets (965) are disposable, and they can be replaced after each use of the application enclosure (930).

According to an embodiment, the application enclosure (930) can, without limitation, have one or more sources of pressurized or moving air or any gas, and these resulting flows or streams (herein referred to as "stream") of air or gas (3140) can move in various ways over, under, or across (herein referred to as "across") any door or hole (955) which personnel or robotics may use to access the inside of the application enclosure (930). The supplied air or gas stream (3140) can move, without limitation, completely or partially across any part or entirety of any door or hole (955) opening, at any angle, and at any velocity or volume. It is preferred, without limitation, that the air or gas stream is active or enabled for any door or hole (955) that is open or unsealed in any way, and the air or gas stream (3140) completely covers the door or hole (955) area and/or any area in close proximity to the door or hole (955). The one or more source(s) (3120) of the air or gas stream (3140) can be, without limitation, any size, shape, length, width, geometry, orientation, or construction, and can be positioned in any locations in various effective proximity to any door, opening, or hole (955). The air or gas can, without limitation, be directed with any form of baffles located anywhere within the application enclosure (930). It is also preferred, without limitation, that the outlet orifice for the source(s) (3120) of the air or gas stream (3140) is rectangular in shape and spans at least the width of the door or hole (955). The one or more sources (3120) of the air or gas stream (3140) can be, without limitation, located above one another, directly or indirectly opposed to one another, and separated by any distance. The one or more source(s) (3120) of the air or gas stream (3140) can also be, without limitation, perforated, and the perforations can be, without limitation, any number, size, shape, or orientation. Any air or gas that is used to form the air or gas stream (3140) can be, without limitation, filtered before being deployed or flowed, by any type of filter or filtering method (3310) including, but not limited to, a HEPA filter, all in a manner known by those skilled in the art.

It is also preferred, without limitation, that one or more door(s) or hole (955) cover(s) (Herein called "door(s)" (3110) can slide open and out of the way of the one or more human operator(s) or any robotic arms or tools, when access is needed to reach through the one or more hole(s) to work or perform any tasks anywhere inside of the enclosed area (950). The design and construction of the sliding door(s) (3110) is known to those skilled in the art. The hole(s) (955) as well as any door(s) (3110) can be any, size, width, length, depth, shape, thickness, construction, and material, and the door(s) (3110) can move via any means, and any construction, known to those skilled in the art. It is preferred without limitation that the sliding door(s) (3110) possesses sufficient attributes known in the art so that it can effectively seal the application enclosure (930) when it is closed. Any number of door(s) (3110) can be located at any location on the application enclosure (930). It is preferred, without limitation, that at least one door(s) (3110) is located on the top of the application enclosure (930). The application enclosure (930), any structures inside of the enclosed area(s) (950), and any hole(s) (955), are designed and constructed so that the hole(s) (955) are positioned or located, without limitation, at any height, distance, or location, from any objects located inside of the application enclosure (930).

According to another embodiment, an object (3030) can, without limitation, be placed completely inside the application enclosure (930), and all hole(s) (955) are either closed with door(s) (3110), or at least one hole (955) is kept open or partially open to enable personnel access into the application enclosure (930) to conduct work or tasks.

Any parts used to construct the application enclosure (930), or any door(s) (3110), can be constructed from various materials such as, but not limited to, stainless steel, glass, polymer, polyolefin, cellulose, or even natural or manufactured fibers that are either coated or uncoated. It is preferred, without limitation, that these parts or components are constructed from one or more polymers that can include, but is not limited to, PVC, polycarbonate, polypropylene, and HDPE. The application enclosure (930), or any door(s) (3110), can be, without limitation, flexible, rigid, semi-rigid, opaque, translucent, or transparent. It is preferred, without limitation, that rigid transparent materials are utilized.

According to an embodiment, one or more sources of vacuum (3130) (herein called "door vacuum") located near the door(s) (955) can be, without limitation, located anywhere in front of or opposed from the one or more outlet orifice(s) for the source(s) (3120) of the air or gas stream (3140) that can move various ways over, under, or across any door or hole (955). Any strength, velocity, volume, or amount of vacuum can, without limitation, be used. The orifice(s) for the door vacuum(s) (3130) can be, without limitation, any size, shape, length, width, geometry, orientation, or construction, and can be positioned in any locations in close proximity to any door, opening, or hole (955). It is preferred, without limitation, that the inlet orifice(s) for the door vacuum(s) (3130) can be rectangular in shape and span at least the width of the door or hole (955). The door vacuum(s) (3130) can be, without limitation, located above one another and separated by any distance, and be perforated with perforations that can be any, number, size, shape, or orientation. It is preferred, without limitation that the door vacuum(s) (3130) is active or enabled whiles the door or hole (955) is open or unsealed in any way, or one or more air or gas streams (3140) are present. Any air or gas that is pulled via vacuum can be, without limitation, filtered by any type of filter or filtering method (3310) including, but not limited to, a HEPA filter, all in a manner known by those skilled in the art.

The combination of the one or more stream(s) of air or gas (3140) moving in various ways over, under, or across any door or hole (955) and opposing door vacuum(s) (3130) can, create a synergistic effect that can, without limitation, reduce the chance of introducing contamination into the application enclosure (930) through any door or hole (955).

According to an embodiment, any positive pressure can, without limitation, be established or maintained inside of the application enclosure (930) at any time, and for any duration, or during any part of any cycle, by flowing air or any gas into the application enclosure (930). This positive pressure can, without limitation, be turned on or off at any time, and for any duration, before, during, or after any number of procedures or treatments are conducted inside of the application enclosure(s) (930). Furthermore, any or all doors (3110) can, without limitation, be opened or closed at any time and for any duration, during use of the application enclosure (930). Any positive pressure can, without limitation, be established or maintained inside of the application enclosure (930) whether any door(s) (3110) are open or closed. One or more means or outlets utilized to supply (3270) the air or gas under positive pressure can, without limitation, be located at any location within the application enclosure (930). The supplied (3270) air or gas can also, without limitation, be filtered before being deployed or flowed into the application enclosure (930), by any type of filter or filtering method (3310) including, but not limited to, a HEPA filter, all in a manner known by those skilled in the art. The air or gas can be supplied or flowed (3270) into the application enclosure (930) at any rate, speed or volume, and via means such as, but not limited to, one or more fan(s) or blower(s).

According to another embodiment, one or more of the door vacuum(s) (3130) sources can also operate while a positive pressure is established or maintained inside of the application enclosure (930). Any strength, velocity, volume, or amount of vacuum can, without limitation, be used. It is preferred, without limitation, that the door vacuum(s) (3130) are active or enabled while any door or hole (955) is open or unsealed in any way, or one or more supplied air or gas streams (3140) are present. Any supplied air or gas stream (3140) may also, without limitation, be active near any door(s) (955) at any time while a positive pressure is established or maintained inside of the application enclosure (930). The supplied air or gas (3270) and the vacuum can, without limitation, vary in order to maintain a desired level of positive pressure inside of the application enclosure (930). This is especially important when openings such as, but not limited to, one or more door or hole(s) (955) is open or unsealed.

According to an embodiment, the application enclosure (930) can also be designed and constructed so that it has, without limitation, (a) any means to filter (3150) and/or dehumidify (3160) the atmosphere within the application enclosure to any humidity level at any time and for any duration, (b) any means to either heat (3290) or cool (3300) the atmosphere inside the application enclosure at any time and for any duration, (c) any means, located anywhere inside of the application enclosure (930), to either increase or decrease the pressure (3270) inside of the application enclosure at any time and for any duration, (d) a means to create an additional vacuum (3280) located anywhere inside of the application enclosure (930) to remove materials such as, but not limited to, any unwanted fumes, vapors or aerosols. Any air or gas that is supplied into, or pulled via vacuum inside, the application enclosure (930), can be, without limitation, filtered by any type of filter or filtering method (3310) including, but not limited to, a HEPA filter, all in a manner known by those skilled in the art. In certain circumstances, the various filters may, without limitation, be shared by similar equipment or processes, in a manner known to those skilled in the art.

According to an embodiment, the application enclosure (930) as described in the present invention, can be used in various ways including, but not limited to, the following brief description of steps, activities, and/or or procedures, that can, without limitation, be undertaken: (a) locate the object (3030) or patient's body, torso, or other parts of the body, in the application enclosure (930), (b) seal the application enclosure (930), (c) if desired or necessary, condition the atmosphere for temperature within the application enclosure (930), (d) deploy, for any time period, the aerosol and/or vapor (200) into the application enclosure (930), (e) terminate the deployment of the aerosol and/or vapor (200) once a sufficient time has passed to effectively fill the application enclosure (930), (f) expose the surfaces inside the application enclosure (930) to the aerosol and/or vapor (200) for a sufficient amount of time to achieve an efficacious outcome, (g) dehumidify, to any desired humidity range, and/or remove the remaining aerosol and/or vapor (200) from inside the application enclosure (930), (h) conduct surgery on the patient, (i) if necessary or desired, redeploy, for any time period, the aerosol and/or vapor (200) into the application enclosure (930) during surgery and remove any humidity and/or aerosol as needed, (j) complete surgery, (k) if needed or desired, terminate the surgery with a final redeployment of the aerosol and/or vapor (200), for any time period, into the application enclosure (930) (l) dehumidify, to any desired humidity range, and/or remove the remaining aerosol and/or vapor (200) from inside the application enclosure (930), (m) remove the patient from the application enclosure (930). These steps or procedures are only a small and incomplete example of the numerous combinations of various steps, activities, and/or procedures, that can take place within the application enclosure (930).

According to another embodiment, the application enclosure (930) can have various equipment located inside, such as, but not limited to any, lights, robotic apparatus(s) used for any purpose, imaging equipment, means to support or hold any objects, surgical or medical equipment or accessories, and manufacturing equipment.

Looking now at FIG. 68, according to an embodiment, an aerosol and/or vapor is generated by a means such as, but not limited to, the aerosol (200) generating apparatus (215) in the present invention, and the aerosol and/or vapor (200) is delivered into one or more targeted areas such as, but not limited to, any wound, any body cavity, surgical plain or surgical incision (3180). Any aerosol (200) or vapor generating means can be used in this embodiment. The aerosol and/or vapor is delivered via one or more tube, pipe, or conduit (herein called "application wand" or "woundwand") (3190) which can be any, without limitation, angle, size, length, orientation, diameter, width, or geometry. The woundwand (3190) can be connected to the aerosol (200) generating apparatus (215) in various ways knows to those skilled in the art. The woundwand (3190) can also be designed and constructed so that it can be easily connected or disconnected from any aerosol and/or vapor (200) supply line(s) (3200), and it can be effectively cleaned, sterilized, or disinfected, in a manner known to those skilled in the art. Various types of flexible pipe or tubing (3200) can, without limitation, connect to the application wand (3190) in a manner known to those skilled in the art.

It is further preferred, without limitation, that one or more perforations (3220) can be located at any location(s) on the application wand (3190). The perforations (3220) can be, without limitation, any size, pattern, shape, angle, geometry, and any orientation. The application wand (3190) can also be designed to interface with interchangeable tips (3230) that vary in attributes such as, but not limited to, length, diameter, any exit orifice (3210) attributes, number or size of perforations (3220), angle of perforations (3220). The interchangeable tips (3230) can connect to the application wand (3190) in a manner known to those skilled in the art. The exit orifice (3210) can be, without limitation, any shape, size, geometry, in order to develop an effective and efficacious device.

According to an embodiment, the application wand (3190) can, without limitation, incorporate any means anywhere on its surface which when actuated or activated (3240), controls and/or stops the flow of aerosol (200) and/or vapor that emanates from the application wand (3190) or any of its interchangeable tips (3230). These control functions can be separate or combined control interfaces. These means (3240) can, without limitation, be any mechanical/electrical means known to those skilled in the art.

According to an embodiment, any parts used to construct the application wand (3190) can be constructed from various materials such as, but not limited to, stainless steel, glass, polymer, polyolefin, cellulose, or even natural or manufactured fibers that are either coated or uncoated. It is preferred, without limitation, that the application wand (3190) is constructed from one or more polymers that can include, but is not limited to, PVC, polycarbonate, polypropylene, and HDPE. The materials used to construct the application wand (3190) may have any rigidity. Any surfaces of the application wand (3190) may have any electrical charge.

According to another embodiment, the application wand (3190) can, without limitation, incorporate any means, known to those skilled in the art, to mount or attach to, integrate, attach, or combine, either temporarily or permanently, any devices or to any devices, such as, but not limited to any, source of light, means to present or create suction, camera or any other imaging or video device, cauterization, robotic grips or hands, scalpel, means for suture application or removal, or any means for applying electrical shock or pulses.

With reference to FIGS. 70-73, the one or more means to effectively or efficaciously cover various types of inbound or outbound air vents (2120) and/or any surrounding area or surfaces of the vents (2120), in the treated area can, without limitation, be modified so that it has, without limitation, one or more of any door(s), cover(s), gill(s), shudder(s), slat(s), louver(s), fin(s), grate(s), or other opening(s) (herein collectively "vent door(s)" (3420, 3430), that can open and allow the passage of any air, gas, vapor, or aerosol. The vent door(s) (3420, 3430) can open any amount, and allow any quantity of air or gas per unit of time to flow through the vent door(s) (3420, 3430), but it is preferred, without limitation, that it is at least able to allow an effective quantity per unit of time. It is preferred, without limitation, that the vent door(s) (3420, 3430) are kept closed when the targeted area is being filled with any aerosol, gas, or vapor. It is also preferred, without limitation, that the door(s) are opened any time after the targeted area has been efficaciously filled, or filled with any aerosol, gas, or vapor, for the desired amount of time. However, the door(s) can be opened at any time and for any reason known to those skilled in the art.

According to an embodiment, any part that directly or indirectly connects to the vent cover (2110) or vent cover assembly (2300) can be, without limitation, directly or indirectly connected to one or more of any pole(s), tube (s), rod(s), beam(s), support structure(s), or any other structure(s) (herein collectively "pole(s)") (2140), used to transmit or exert sufficient force(s) to facilitate a sufficient seal between the vent cover (2110) or vent cover assembly (2300) and the various surfaces these part(s) are intended to have contact with, in order to effectively seal the vent(s) (2120).

According to an embodiment, the one or more vent doors (3420, 3430) can be attached to any part of the vent cover (2110), vent cover assembly (2300), magnetic vent cover (2180), or any magnetic vent cover assembly, in a manner known to those skilled in the art. Seal material (2130) may, without limitation, be positioned between the door(s) (3800) and the various parts of the vent cover assembly (2300) so that a sufficient or at least effective seal is created by the whole vent cover assembly (2300), including the vent door(s) (3420, 3430), and the vent (2120). It is preferred, without limitation, that the vent door(s) (3420, 3430) are inset into the vent cover assembly (2300) frame with an effective interface of seal material (2130) on certain vertical and horizontal surfaces, or contact the top of the cover (2110) with effective interface of the seal material (2130). It is preferred, without limitation, that the vent door(s) (3420, 3430) are connected using one or more hinge(s) (3550) constructed from any compatible material. One or more of various spring(s), detent(s), hydraulics, or other source of force (herein collectively "spring(s)") (3560), can, without limitation, be positioned under the vent door(s) (3420, 3430) or connect to the vent door(s) (3420, 3430) to assist with the opening of the doors. It is preferred, without limitation, that the springs(s) (3560) are located opposite from the one or more hinge(s) (3550).

According to another embodiment, the vent door(s) (3420, 3430) can be opened by one or more of any servo-motor, solenoid, or any other electromechanical means (herein collectively "solenoid(s)") (3460) known to those skilled in the art. It is preferred, without limitation, that upon receipt of any signal or command, a servo motor or solenoid (3460) is actuated and its movement results in the direct or indirect mechanical opening of the vent door(s) (3420, 3430). It is even more preferred that upon receipt of any signal or command, a servo motor or solenoid (3460) is actuated and this results in the movement of one or more latch(s) (3840) that holds the door closed. The vent door(s) (3420, 3430) can also, without limitation, be held closed as well as opened with the use of magnetics or electrically induced magnetic fields, all in a manner known to those skilled in the art. The power and communications necessary to conduct these operations can be provided either directly or indirectly. It is preferred, without limitation, that the vent cover assembly (2300) and the various attached components are connected via wire or cable to the vapor generating, or aerosol generating apparatus (215), PLC (315) or HMI (320) that controls the one or more aerosol or vapor generator(s), for power control and/or power supply, and communications. It is even more preferred, without limitation, that the vent cover assembly (2300) and the various attached components are battery powered, and the various electromechanical components are controlled via commands received by an integrated radio and associated electronics, all in a manner known to those skilled in the art.

With further reference to FIGS. 70-73, the vent cover (2300) preferably includes a vent base 3410, a first vent door 3420, a second vent door (3430) and a release mechanism (3450). The release mechanism (3450) preferably includes a solenoid (3460), a pivot release (3470), a first latch device (3480) and a second latch device (3490). However, other actuation devices may be used, besides the solenoid (3460). The vent base (3410) preferably includes at least one first vent opening (3500), at least one second opening (3510), a base plate (3520), a tubular boss (3530) and the vent seal (2130). A pole boss (3440) includes a pole hole (3445) and is attached to a bottom of the base plate (3520). The tubular boss (3530) is attached to a top of the base plate (3520) and the vent seal (2130) is attached to a top of the tubular boss (3530). The vent seal (2130) makes contact with a vent. The first and second vent openings are formed through the base plate (3520). Preferably, a first peripheral seal is attached to an inside perimeter of the first vent door (3420) and preferably a second peripheral seal (3540) is attached to an inside perimeter of the second vent door (3430). The first and second peripheral seals seal the first and second vent doors to the base plate (3520) to prevent leakage through the first and second vent openings, respectively. The first vent door (3420) is pivotal attached to one end of the base plate (3520) preferably with at least two hinges (3550) (not shown). The second vent door (3430) is pivotally attached to the other end of the base plate (3520) preferably with the at least two hinges (3550). Two springs (3560) or the like preferably aid in opening of the first and second vent doors. However, the vent cover (2300) may also include only one vent door. The at least one vent opening (3500) would be formed through the base plate (3520). However, the base plate (3520) would be cutoff along a dashed line (3525), eliminating the second latch device (3490), the second vent door (3420) and the second vent opening (3510).

The first latch device (3480) preferably includes at least two first pivot blocks (3570), a first pivot rod (3580), at least two first latches (3590) and a first lever arm (3600). Each first pivot block (3570) includes a first rod bore (3610), which is sized to rotatably receive an outer diameter of the first pivot rod (3580). The at least two first pivot blocks (3570) are attached to the base plate (3520), adjacent an edge of the first vent door (3420). Each first latch (3590) includes a lip extension (3620), which is sized to receive and retain the edge of the first vent door (3420). The first pivot rod (3580) is inserted through the at least two first latches (3590). The at least two first latches (3590) are secured to the first pivot rod (3580) with a set screw (3630) or the like. The first pivot rod (3580) is inserted through the first lever arm (3600) and the first lever arm (3600) is secured to the first pivot rod (3580) with a fastener (3640) or the like. An end of a manual actuation rod (3650) is retained in the first lever arm (3600). The other end of the manual actuation rod (3650) is preferably terminated with a knob (3660). The manual actuation rod (3650) allows the first and second vent doors to be opened, if the solenoid (3460) should fail.

The second latch device (3490) preferably includes at least two second pivot blocks (3670), a second pivot rod (3680), at least two second latches (3690) and a second lever arm (3700). Each second pivot block (3670) includes a second rod bore (3710), which is sized to rotatably receive an outer diameter of the second pivot rod (3680). The at least two second pivot blocks (3670) are attached to the base plate (3520), adjacent an edge of the second vent door (3430). Each second latch (3690) includes a lip extension (3720), which is sized to receive and retain the edge of the second vent door (3430). The second pivot rod (3680) is inserted through the at least two second latches (3690). The at least two second latches (3690) are secured to the second pivot rod (3680) with the set screw (3630) or the like. The second pivot rod (3680) is inserted through the second lever arm (3700) and the second lever arm (3700) is secured to the second pivot rod (3680) with the fastener (3640) or the like. A set screw (3730) may be additionally used to secure both the first and second lever arms to their respective pivot rods.

The first lever arm (3600) further includes a first base member (3740) and a first extension leg (3750) that extends from the first base member (3740). The second lever arm (3700) further includes a second base member (3760) and a second extension leg (3770) that extends from the second base member (3760). A slot (3780) is formed through an end of the first extension leg (3750). A shoulder bolt (3790) or the like is inserted through the slot (3780) and threaded into an end of the second extension leg (3770). The first extension leg (3750) pivots and slides relative to the second extension leg (3770). A solenoid shield (3800) is preferably attached to the base plate (3520) with at least one fastener (3810). The solenoid (3460) includes an actuation rod (3820). The pivot release (3470) preferably includes a release base (3830) and a release latch (3840).

A support lip (3850) extends from a side of the release latch (3840). The release base (3830) is attached to the base plate (3520) with fasteners (not shown) or the like. The solenoid (3460) and the solenoid shield (3800) are preferably secured to the release base (3830) with at least one fastener (3860). One end of the release latch (3840) is pivotally retained by an end of the release base (3830). The other end of the release latch (3840) is pivotally retained by an end of the actuation rod (3820) of the solenoid (3460). The end of one or more cable(s), communication line(s), or electrical line(s) (3870)

extends from the solenoid (3460) and the other end(s) is connectable either directly or indirectly to the PLC (315) of the aerosol generating system (110).

However, the one or more cable(s), communication line(s), or electrical power line(s) (Herein referred to as electrical line(s)) (3870), providing hard wire connection to the PLC (315) may be replaced with a wireless transceiver (3855), at least one battery (3865) and a power switching device (3875). The wireless transceiver (3855) preferably communicates through radio frequency, but could use any suitable wireless communication technology or protocol. Electrical power would be supplied by the at least one battery (3865). The at least one battery (3865) would preferably be two 9 volt transistor batteries, but other batterie(s) may also be used. The switching device (3875) is preferably a FET switch or a relay, but could be any other suitable switching device. The wireless transceiver (3855) controls the operation of the switching device (3875). The wireless transceiver (3855) receives a wireless signal from the transceiver (340) to activate the solenoid (3460). The electrical line(s) (3870) may also be connected to the switching device (3875).

Figure 60:
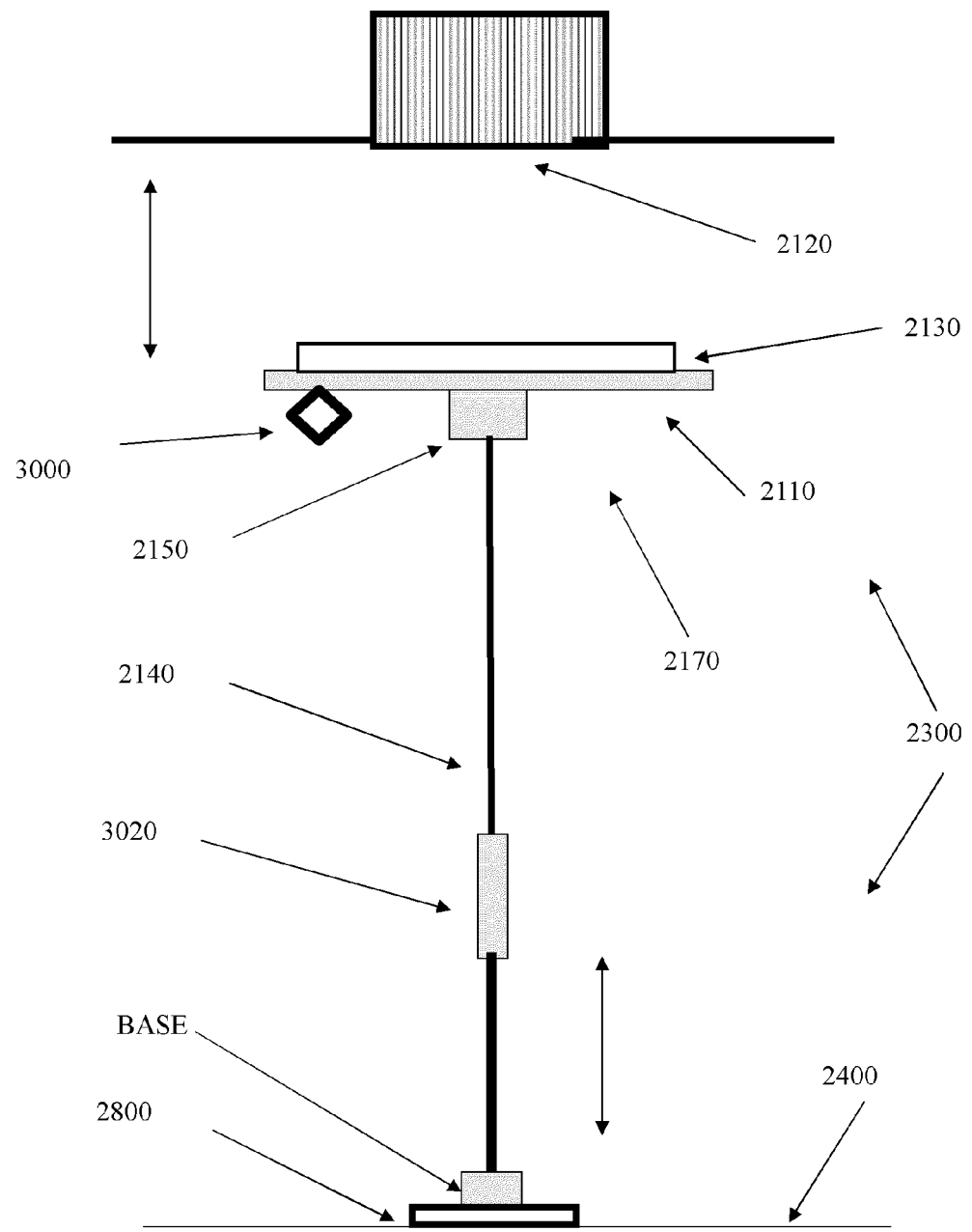
FIG. 60 is a schematic view of another embodiment of the vent cover for use with the aerosol generator.
Figure 61:
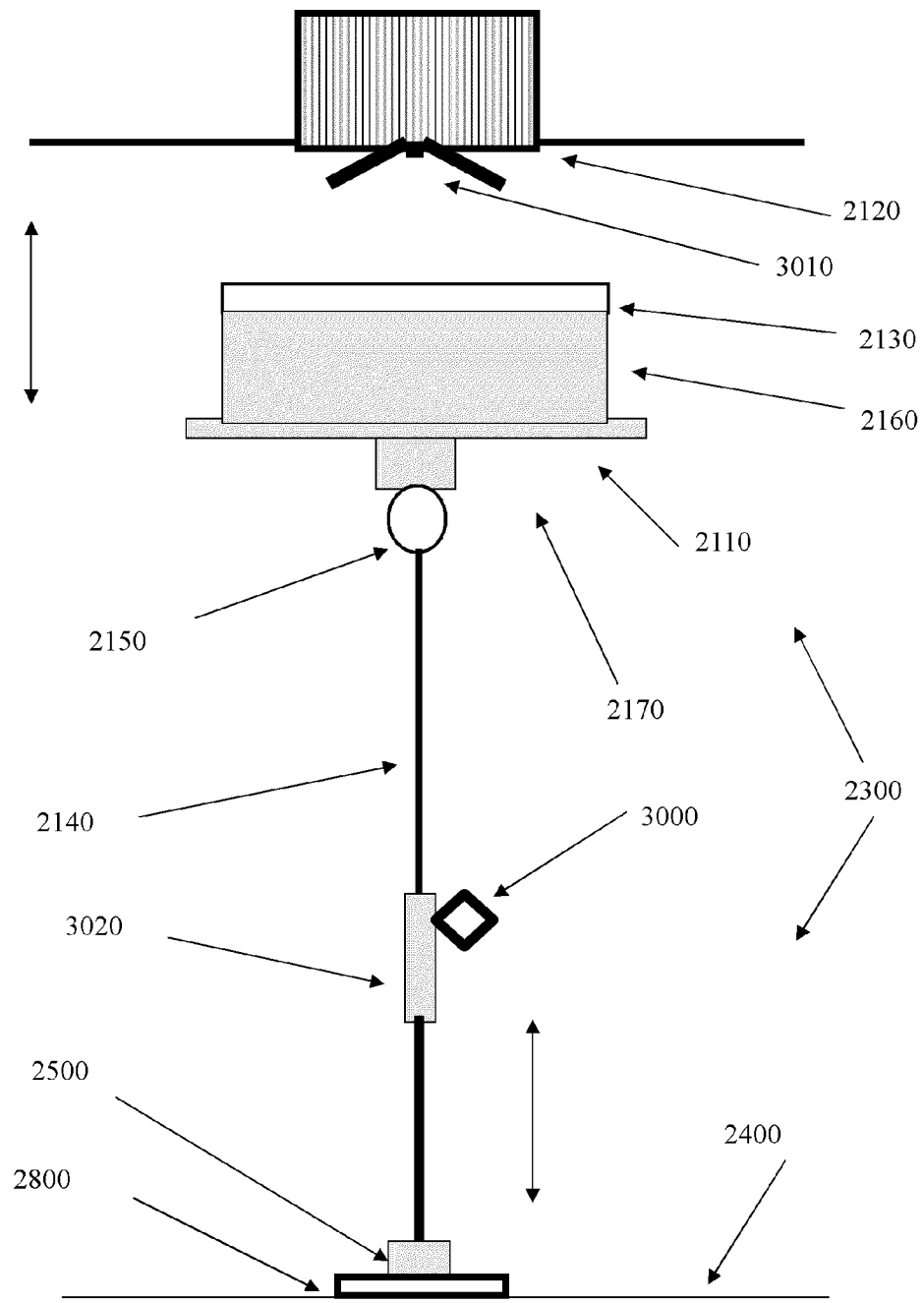
FIG. 61 is a schematic view of another embodiment of the vent cover for use with the aerosol generator.
Figure 62:
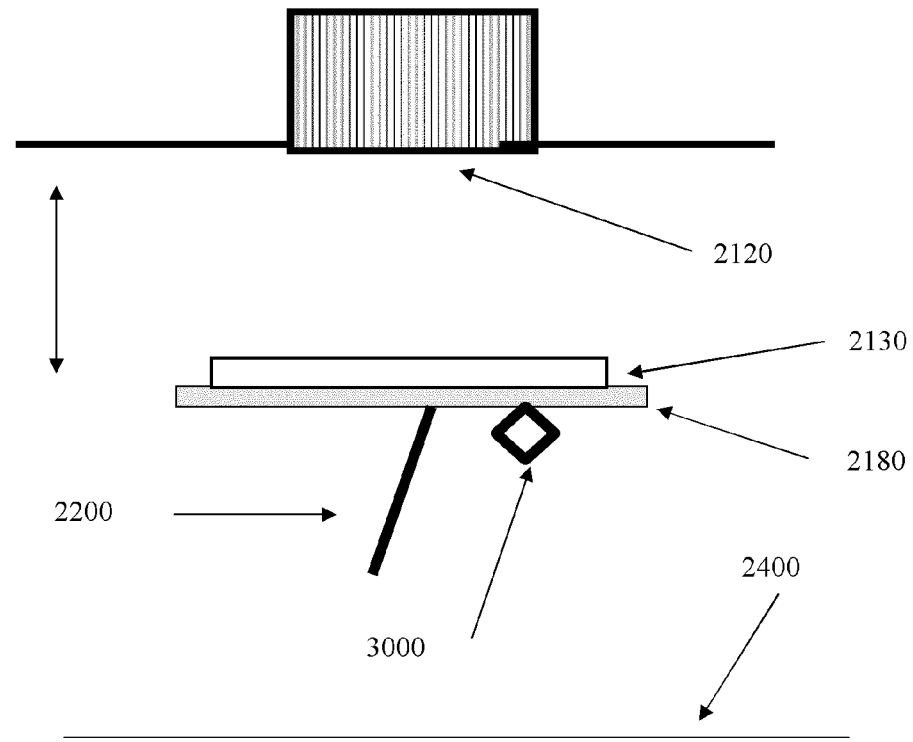
FIG. 62 is a schematic view of another embodiment of the vent cover for use with the aerosol generator.

With reference to FIG. 60, the pole (2140) is inserted into the pole hole (3445). The pole (2140) is raised, or otherwise effectively positioned, until the vent cover (2300) seals the vents (2120). The electrical line(s) (3870) is connected to the PLC (315). If a wireless transceiver (3855) is used, no connection is required. The aerosol generating system (110) is activated and treats an enclosed area. When the treatment is finished, the PLC (315) or the switching device (3875) provides electrical power to the solenoid (3460) for a set period of time, which results in the actuation rod (3820) being retracted into the solenoid (3460). The actuation rod (3820) is normally extended with the aid of a compression spring (3825). The retraction of the solenoid (3460) pulls the support lip (3850) of the release latch (3840) backward from under the first extension leg (3750). The refraction of the solenoid (3460) results in the pivotal connection of the first and second extension legs moving toward the base plate (3520). However, with a vent cover only having the first vent door (3420), only the first extension leg moves toward the base plate (3520). The inward movement of the first and second extension legs causes the first pivot rod (3580) to rotate and pull the first lip extension (3620) of the first latch (3590) away from the first vent door (3420) and the second pivot rod (3680) to rotate and pull the second lip extension (3720) of the second latch (3690) away from the second vent door (3430). Both the first and second vent doors open. The linear motion of the actuation rod (3820) is translated to rotational motion through the pivot release (3470), the first latch device (3480) and the second latch device (3490). After use, the pivotal connection of the first and second extension legs is manually pulled away from the base plate (3520), such that the support lip (3850) supports the first extension leg (3750).

Any, (a) liquid, (b) mixture or solids suspended in any liquid, (c) solution, (d) medication, (e) organisms, (f) anti-pathogen/toxin/fungal/sporicidal agent(s) or substance(s), (g) micro machine(s) or structure(s), (h) nano machine(s) or structure(s), may also, without limitation, be used in these embodiments.

Various alternatives are contemplated as being within the scope of the following claims particularly pointing out and distinctly claiming the subject matter regarded as the invention.

We claim:

1. A vent cover comprising:

a first vent door and a second vent door;

a base plate having at least one first opening and at least one second opening formed therethrough, said first vent door is pivotally attached to said base plate to cover said at least one first opening, said second vent door is pivotally attached to said base plate to cover said at least one second opening;

a first latch device for retaining said first vent door in a closed orientation, said first latch device includes a first lever arm;

a second latch device for retaining said second vent door in a closed orientation, said second latch device includes a second lever arm, an end of said first lever arm is slidably engaged with said second lever arm;

an actuation device includes an actuation rod; and a release latch includes a support lip extending from a side thereof, said support lip is located under one of said first and second lever arms, said release latch is engaged with an end of said actuation rod, wherein withdrawal of said release latch by said actuation device causes said first and second lever arms to release said first and second latch devices to open said first and second vent doors.

2. The vent cover of claim 1, further comprising:

means for retaining said vent cover against a vent.

3. The vent cover of claim 2, further comprising:

said means for retaining said vent cover against a vent is a telescoping pole having one end is inserted into a bottom of said base plate.

4. The vent cover of claim 1, further comprising:

said actuation device is activated through a wireless connection to an aerosol generating system.

5. The vent cover of claim 1, further comprising:

a vent seal extends around a perimeter of a top of said base plate for sealing to a vent.

6. The vent cover of claim 1, further comprising:

a tubular boss is attached to a top of said base plate, a vent seal is attached to a top of said tubular boss.

7. The vent cover of claim 1, further comprising:

said first latch device further includes a first pivot rod and at least two first latches, said first lever arm is secured to said first pivot rod, said at least two first latches are secured to said first pivot rod, wherein said at least two first latches retain said first vent door in the closed orientation.

8. A vent cover comprising:

a first vent door and a second vent door;

a base plate having at least one first opening and at least one second opening formed therethrough, said first vent door is pivotally attached to said base plate to cover said at least one first opening, said second vent door is pivotally attached to said base plate to cover said at least one second opening;

a first latch device for retaining said first vent door in a closed orientation, said first latch device includes a first extension leg;

a second latch device for retaining said second vent door in a closed orientation, said second latch device includes a second extension leg, an end of said first extension, said first extension leg is slidably engaged with said second extension leg;

a linear actuation device includes an actuation rod; and a release latch includes a support lip extending from a side thereof, said support lip is located under one of said first and second extension legs, one end of said release latch is pivotally retained relative to said base plate, the other end of said release latch is pivotally engaged with an end of said actuation rod, wherein withdrawal of said release latch causes said first and second extension legs to release said first and second latch devices to open said first and second vent doors.

9. The vent cover of claim 8, further comprising:
means for retaining said vent cover against a vent.

10. The vent cover of claim 9, further comprising:
said means for retaining said vent cover against a vent is a telescoping pole having one end is inserted into a bottom of said base plate.

11. The vent cover of claim 8, further comprising:
said actuation device is activated through a wireless connection to an aerosol generating system.

12. The vent cover of claim 8, further comprising:
a vent seal extends around a perimeter of a top of said base plate for sealing to a vent.

13. The vent cover of claim 8, further comprising:

a tubular boss is attached to a top of said base plate, a vent seal is attached to a top of said tubular boss.

14. The vent cover of claim 8, further comprising:

said second latch device further includes a second pivot rod and at least two second latches, said second lever arm is secured to said second pivot rod, said at least two second latches are secured to said second pivot rod, wherein said at least two second latches retain said second vent door in the closed orientation.

15. A vent cover comprising:

a vent door;

a base plate having at least one opening formed therethrough, said vent door is pivotally attached to said base plate to cover said at least one opening;

a latch device for retaining said vent door in a closed orientation, said latch device includes a lever arm;

an actuation device includes an actuation rod;

a release latch includes a support lip extending from a side thereof, said support lip is located under said lever arm, said release latch is engaged with an end of said actuation rod, wherein withdrawal of said release latch by said actuation device causes said lever arm to release said latch device to open said vent door; and a telescoping pole for retaining said vent cover against a vent.

16. The vent cover of claim 15, further comprising:

said actuation device is activated through a wireless connection to an aerosol generating system.

17. The vent cover of claim 15, further comprising:

a vent seal extends around a perimeter of a top of said base plate for sealing to a vent.

18. The vent cover of claim 15, further comprising:

a tubular boss is attached to a top of said base plate, a vent seal is attached to a top of said tubular boss.

* * * * *